US008889387B2

(12) United States Patent
Beck et al.

(10) Patent No.: US 8,889,387 B2

(45) Date of Patent: Nov. 18, 2014

(54) USE OF RECOMBINANT PGL FOR INCREASED PRODUCTION OF ISOPRENE

(71) Applicants: Danisco US Inc., Palo Alto, CA (US); The Goodyear Tire & Rubber Company, Akron, OH (US)

(72) Inventors: Zachary Q. Beck, Palo Alto, CA (US); Marguerite A. Cervin, Redwood City, CA (US); Alex T. Nielsen, Kokkedal (DK); Caroline M. Peres, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/888,248

(22) Filed: May 6, 2013

(65) Prior Publication Data

US 2013/0295633 A1 Nov. 7, 2013

Related U.S. Application Data

(62) Division of application No. 12/978,324, filed on Dec. 23, 2010, now Pat. No. 8,455,236.

(60) Provisional application No. 61/289,959, filed on Dec. 23, 2009.

(51) Int. Cl.

| | |
|---|---|
| ***C12P 7/42*** | (2006.01) |
| ***C12P 5/02*** | (2006.01) |
| ***C12N 9/00*** | (2006.01) |
| ***C12N 1/20*** | (2006.01) |
| ***C12N 15/00*** | (2006.01) |
| ***C07H 21/04*** | (2006.01) |
| ***C12N 15/70*** | (2006.01) |
| ***C12P 5/00*** | (2006.01) |
| ***C12N 15/52*** | (2006.01) |
| ***C12N 15/63*** | (2006.01) |

(52) U.S. Cl.

CPC ................. *C12P 5/007* (2013.01); *C12N 15/70* (2013.01); *C12P 7/42* (2013.01); *C12N 15/52* (2013.01); *C12N 15/635* (2013.01)

USPC ........ 435/167; 435/146; 435/183; 435/252.3; 435/320.1; 536/23.2

(58) Field of Classification Search

None

See application file for complete search history.

(56) References Cited

U.S. PATENT DOCUMENTS

| | | | |
|---|---|---|---|
| 7,132,527 | B2 | 11/2006 | Payne et al. |
| 8,455,236 | B2 | 6/2013 | Beck et al. |
| 2008/0038805 | A1 | 2/2008 | Melis |
| 2009/0203102 | A1 | 8/2009 | Cervin et al. |
| 2010/0003716 | A1 | 1/2010 | Cervin et al. |
| 2010/0048964 | A1 | 2/2010 | Calabria et al. |
| 2010/0086978 | A1 | 4/2010 | Beck et al. |
| 2010/0113846 | A1 | 5/2010 | McAuliffe et al. |
| 2010/0167370 | A1 | 7/2010 | Chotani et al. |
| 2010/0167371 | A1 | 7/2010 | Chotani et al. |
| 2010/0184178 | A1 | 7/2010 | Beck et al. |
| 2010/0196977 | A1 | 8/2010 | Chotani et al. |

FOREIGN PATENT DOCUMENTS

| | | | |
|---|---|---|---|
| EP | 1 510 583 | A1 | 3/2005 |
| SG | 181828 | A1 | 8/2012 |
| WO | WO-96/35796 | A1 | 11/1996 |
| WO | WO-98/02550 | A2 | 1/1998 |
| WO | WO-98/02550 | A3 | 1/1998 |
| WO | WO-2004/003175 | A2 | 1/2004 |
| WO | WO-2004/003175 | A3 | 1/2004 |
| WO | WO-2004/033646 | A2 | 4/2004 |
| WO | WO-2004/033646 | A3 | 4/2004 |
| WO | WO-2005/080583 | A2 | 9/2005 |
| WO | WO-2005/080583 | A3 | 9/2005 |
| WO | WO-2009/076676 | A2 | 6/2009 |
| WO | WO-2009/076676 | A3 | 6/2009 |
| WO | WO-2009/132220 | A9 | 10/2009 |
| WO | WO-2010/003007 | A2 | 1/2010 |
| WO | WO-2010/003007 | A3 | 1/2010 |
| WO | WO-2010/014825 | A1 | 2/2010 |
| WO | WO-2010/078457 | A2 | 7/2010 |
| WO | WO-2010/078457 | A3 | 7/2010 |
| WO | WO-2010/124146 | A2 | 10/2010 |
| WO | WO-2010/124146 | A3 | 10/2010 |
| WO | WO-2010/148144 | A1 | 12/2010 |
| WO | WO-2011/075748 | A1 | 6/2011 |

OTHER PUBLICATIONS

Chica et al. Curr Opin Biotechnol. Aug. 2005;16(4):378-84.*

Sen et al. Appl Biochem Biotechnol. Dec. 2007;143(3):212-23.*

Anderson, M.S. et al., (1989). "Isopentenyl Diphosphate: Dimethlallyl Diphosphate Isomerare. An Improved Purification of the Enzyme andn Isolation of the Gen From *Saccharomyces cerevisia,*" *J. Biol. Chem.* 264(32):19169-19175.

Aon, J. et al., (2008) "Suppressing Posttranslational Gluconoylation of Heterologous Proteins by Metabolic Engineering of *Escherichia coli,*" *Appl. Environ. Microbiol.* 74:950-958.

Baba, T. et al., (2006) "Construction of *Escherichia coli* K-12 In-Frame, Single-Gene Knockout Mutants: The Keio Collection," *Mol. Syst. Biol.* 2: 2006.0008.

(Continued)

*Primary Examiner* — Christian Fronda

(74) *Attorney, Agent, or Firm* — Morrison & Foerster LLP

(57) ABSTRACT

Provided herein are improved compositions and methods for the increased production of isoprene. Also provided herein are improved compositions and methods for the increased production of heterologous polypeptides capable of biological activity.

16 Claims, 66 Drawing Sheets

(56) References Cited

OTHER PUBLICATIONS

Balbas et al. (Jun. 12, 1996). Gene 172(1):65-69.
Bouvier, F. et al., (2005) "Biogenesis, Moleculars Regulation and Function of Plant Isoprenoids," *Progress in Lipid Res*. 44:357-429.
Campbell, E. et al., (1989) "Improved Transformation Efficiency of *Aspregillus niger* Using Homologous niaD Gene for Nitrate Reductase," *Curr. Genet.* 16:53-56.
Cherepanov, P.P. et al., (1995) "Gene Disruption in *Escherichia coli*: TcR and KmR Cassettes with the Option of Flp-Catalyzed Excision of the Antibiotic-Resistance Determinant," *Gene* 158(1):9-14.
Datsenko, K., et al., (2000) "One-Step Inactivation of Chromosomal Genes in *Escherichia coli* K-12 Using PCR Products," *Proc. Nat. Acad. Sci.USA* 97:6640-6645.
Dhe-Paganon, S. et al., (1994). "Mechanism of Mevalonate Pyrophosphate Decarboxylase: Evidence for a Carbocationic Transition State," *Biochemistry* 33(45):13355-13362.
EcoGene Accession No. EG13231, located at <www.ecogene.org>, last visited on Jun. 25, 2012, 1 page.
GenBank Accession No. AAG06570.1, located at < http://www.ncbi.nlm.nih.gov>, last visited on Jun. 25, 2012, 2 pages.
GenBank Accession No. AE004091, located at < http://www.ncbi.nlm.nih.gov>, last visited on Jun. 25, 2012, 908 pages.
GenBank Accession No. NC_001140, located at < http://www.ncbi.nlm.nih.gov>, last visited on Jun. 25, 2012, 204 pages.
GenBank Accession No. 000096, located at < http://www.ncbi.nlm.nih.gov>, last visited on Jun. 25, 2012, 352 pages.
Grawert, T. et al., (2004). "IspH Protein of *Escherichia coli*: Studies on Iron-Sulfur Cluster Implementation and Catalysis," *Journal American Chemistry Society*, 126(40):12847-12855.
Grunden, A.M. et al., (1997). "Molybdate Transport and Regulation in Bacteria," *Arch Microbiol.* 168:345-354.
Hedl, M. et al., (2002). "*Enterococcus* Taecalis Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol.* 184(8):2116-2122.
Hoeffler, J-F. et al., (2002). "Isoprenoid Biosynthesis via the Methylerythritol Phosphate Pathway. Mechanistic Investigations of the 1-Deox Y-D-Xylulose 5-Phosphate D Reductiosimerase," *Eur. J. Biochem.* 269:4446-4457.
Koga, et al., (2007). "Biosyntheseis of Ester-Type Polar Lipids in Archea and Evolutionary Consideration," *Microbiology and Mol. Biology Reviews* 71(1):97-120.
Kutsche, M. et al. (1996). "Promoters Controlling Expression of the Alternative Nitrogenase and the Molybdenum Uptake System in *Rhodobacter* Capsulatus are Activated by NtrC, Independent of Sigma-54, and Repressed by Molybdenum," *Journal of Bacteriology* 178(1):2010-2017.
Luttgen, H. et al., (2000). "Biosynthesis of Terpenoids: YchB Protein *Escherichia coli* Phosphorylates the 2-Hydrozy Group of 4-Diphosphocytidyl-2C-Methyl-o-Erythritol," *PNAS* 97(3):1062-1067.
Martin et al. (Jul. 2003, e-published Jun. 1, 2003). *Nat Biotechnol.* 21(7):796-802.
Miclet, E. et al., (Sep. 14, 2001). "NMR Spectroscopic Analysis of the First Two Steps of the Pentose-Phosphate Pathway Elucidates the Role of 6-Phosphogluconolactonase," *J. Biol. Chem.* 276(37):34840-34846.
Miller, B. et al., (2001). "First Isolation of an Isoprene Synthase Gene From Poplar and Successful Expression of the Gene in *Escherichia coli," Planta* 213:483-487.
Oulmouden, A. et al., (1991). "Nucleotide Sequence of the ERG 12 Gene of *Saccharomyces cerevisiae* EncodinQ Mevalonate Kinase," Curr Genet. 19:9-14.
Rohdich, F. et al., (1999). "Cytidine 5'-Triphosphate-Dependent Biosynthesis of Isoprenoids: YgbP Protein of *Escherichia coli* Catalyzes the Formation of 4-Diphosphocytidyl-D-2-C-Methylerythritol," *PNAS* 96(21):11758-11763.
Rohdich, F. et al., (2000). "Biosynthesis of Terpenoids: 4-Diphosphocytidly-2C-Methyl-o-Erythritol Synthase of *Arabidopsis thaliana*," PNAS 97(12):6451-6456.
Self, W.T. et al., (2001). "Molybdate Transport," *Res Microbiol.* 152:311-321.
Sasaki et al. (Apr. 25, 2005). *FEBS Lett.* 579(11):2514-2518.
Sharkey, T. et al., (2005). "Evolution of the Isoprene Biosynthetic Pathway in Kudza," *Plant Physiology* 137:700-712.
Silver, G. et al., (1995). "Characterization of Aspen Isoprene Synthase, An Enzyme Responsible for Leaf Isoprene Emission to the Atmosphere," *JBC* 270(22):13010-1316.
Sinha, A. et al., (1992). "Induction of Specific Enzymes of the Oxidative Pentose Phosphate Pathway by Glucono-δ-Lactone in *Saccharomyces cerevisiae," J. Gen. Microbiol.* 138:1865-1873.
Sprenger, G.A. et al., (1997). "Identification of a Thiamin-Dependent Synthase in *Escherichia coli* Required for the Formation of the 1-DeoxY-o-Xylulose 5-Phosphate Precursor to Isoprenoids, Thiamin, and Pyridoxol," *PNAS* 94:12857-12862.
Studier, F.W., et al., (2009). "Understanding the Differences Between Genome Sequences of *Escherichia coli* B Strains REL606 and BL21(DE3) and Comparison of the *E. coli* B and K12 Genomes," *J. Mol. Biol.* 394(4):653-680.
Sutherlin, A. et al., (2002). "Enterococcus Taecalis 3-Hydrozy-3-Methylglutaryl Coenzyme A Synthase, an Enzyme of Isopentenyl Diphosphate Biosynthesis," *J. Bacteriol.* 184(15):4065-4070.
Thomason, L.C. et al., (Dec. 2004). "Identification of the *Escherichia coli* K-12 ybhE Gene as pgl, Encoding 6-Phosphogluconolactonase," *J. Bact.* 186(24):8248-8253.
Thomason, L.C. (Jul. 2007). "*E. coli* Genome Manipulation by P1 Transduction," *Curr. Protocols Mol. Biol.* Chapter 1, Unit 1.17.
Tsay, Y.H. et al., (1991). "Cloning and Characterization of ERG8, An Essential Gene of *Saccharomyces cerevisiae* That Encodes Phosphomevalonate Kinase," *Mol Cell Biol.* 11(2):620-631.
UniProtKB/Swiss-Prot Accession No. P38858 (PGL polypeptide), located at < http://www.ncbi.nlm.nih.gov>, last visited on Jun. 25, 2012, 3 pages.
UniProtKB/Swiss-Prot Accession No. P52697 (PGL polypeptide), located at < http://www.ncbi.nlm.nih.gov>, last visited on Jun. 25, 2012, 7 pages.
Yuan, L.Z. et al. (2006, e-pub. Oct. 28, 2005). "Chromosomal Promoter Replacement of the Isoprenoid Pathway for Enhancing Carotenoid Production in *E. coli," Metabolic Engineering* 8:79-90.
Zepeck, F. et al., (2005). "Biosynthesis of Isoprenoids. Purification and Properties of IspG Protein from *Escherichia coli," J. Org. Chem.* 70:9168 -9174.
International Search Report mailed on Jun. 15, 2011, for PCT Patent Application No. PCT/US2010/062099, filed on Dec. 23, 2010, 3 pages.

* cited by examiner

Figure 3A.

1- tggcgaatgggacgcgccctgtagcggcgcattaagcgcggcgggtgtggtggttacgcgcagcgtgaccgctacacttgccagcgccc
tagcgcccgctcctttcgctttcttcccttcctttctcgccacgttcgccggctttccccgtcaagctctaaatcgggggctccctttagggttcc
gatttagtgctttacggcacctcgaccccaaaaaacttgattagggtgatggttcacgtagtgggccatcgccctgatagacggtttttcgccc
tttgacgttggagtccacgttctttaatagtggactcttgttccaaactggaacaacactcaaccctatctcggtctattcttttgatttataagggat
tttgccgatttcggcctattggttaaaaaatgagctgatttaacaaaaatttaacgcgaattttaacaaaatattaacgtttacaatttcaggtggca
cttttcggggaaatgtgcgcggaacccctatttgtttatttttctaaatacattcaaatatgtatccgctcatgaattaattcttagaaaaactcatcg
agcatcaaatgaaactgcaatttattcatatcaggattatcaataccatatttttgaaaaagccgtttctgtaatgaaggagaaaactcaccgag
gcagttccataggatggcaagatcctggtatcggtctgcgattccgactcgtccaacatcaatacaacctattaatttcccctcgtcaaaaataa
ggttatcaagtgagaaatcaccatgagtgacgactgaatccggtgagaatggcaaaagtttatgcatttctttccagacttgttcaacaggcca
gccattacgctcgtcatcaaaatcactcgcatcaaccaaaccgttattcattcgtgattgcgcctgagcgagacgaaatacgcgatcgctgtta
aaaggacaattacaaacaggaatcgaatgcaaccggcgcaggaacactgccagcgcatcaacaatattttcacctgaatcaggatattcttc
taatacctggaatgctgttttcccggggatcgcagtggtgagtaaccatgcatcatcaggagtacggataaaatgcttgatggtcggaagag
gcataaattccgtcagccagtttagtctgaccatctcatctgtaacatcattggcaacgctacctttgccatgtttcagaaacaactctggcgcat
cgggcttcccatacaatcgatagattgtcgcacctgattgcccgacattatcgcgagcccatttatacccatataaatcagcatccatgttggaa
tttaatcgcggcctagagcaagacgtttcccgttgaatatggctcataacaccccttgtattactgtttatgtaagcagacagttttattgttcatga
ccaaaatcccttaacgtgagttttcgttccactgagcgtcagaccccgtagaaaagatcaaaggatcttcttgagatcctttttttctgcgcgtaa
tctgctgcttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacatacctcgc
tctgctaatcctgttaccagtggctgctgccagtggcgataagtcgtgtcttaccgggttggactcaagacgatagttaccggataaggcgca
gcggtcgggctgaacggggggttcgtgcacacagcccagcttggagcgaacgacctacaccgaactgagatacctacagcgtgagctat
gagaaagcgccacgcttcccgaagggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgttatcccct
gattctgtggataaccgtattaccgcctttgagtgagctgataccgctcgccgcagccgaacgaccgagcgcagcgagtcagtgagcgag
gaagcggaagagcgcctgatgcggtattttctccttacgcatctgtgcggtatttcacaccgcatatggtgcactctcagtacaatctgctct
gatgccgcatagttaagccagtatacactccgctatcgctacgtgactgggtcatggctgcgccccgacacccgccaacacccgctgacgc
gccctgacgggcttgtctgctcccggcatccgcttacagacaagctgtgaccgtctccgggagctgcatgtgtcagaggttttcaccgtcatc
accgaaacgcgcgaggcagctgcggtaaagctcatcagcgtggtcgtgaagcgattcacagatgtctgcctgttcatccgcgtccagctcg
ttgagtttctccagaagcgttaatgtctggcttctgataaagcgggccatgttaagggcggttttttcctgtttggtcactgatgcctccgtgtaag
ggggatttctgttcatgggggtaatgataccgatgaaacgagagaggatgctcacgatacgggttactgatgatgaacatgcccggttactg
gaacgttgtgagggtaaacaactggcggtatggatgcggcgggaccagagaaaaatcactcagggtcaatgccagcgcttcgttaataca
gatgtaggtgttccacagggtagccagcagcatcctgcgatgcagatccggaacataatggtgcagggcgctgacttccgcgtttccagac
tttacgaaacacggaaaccgaagaccattcatgttgttgctcaggtcgcagacgttttgcagcagcagtcgcttcacgttcgctcgcgtatcg
gtgattcattctgctaaccagtaaggcaaccccgccagcctagccgggtcctcaacgacaggagcacgatcatgcgcacccgtggggcc
gccatgccggcgataatggcctgcttctcgccgaaacgtttggtggcgggaccagtgacgaaggcttgagcgagggcgtgcaagattccg
aataccgcaagcgacaggccgatcatcgtcgcgctccagcgaaagcggtcctcgccgaaaatgacccagagcgctgccggcacctgtc
ctacgagttgcatgataaagaagacagtcataagtgcggcgacgatagtcatgccccgcgcccaccggaaggagctgactgggttgaag
gctctcaagggcatcggtcgagatcccggtgcctaatgagtgagctaacttacattaattgcgttgcgctcactgcccgctttccagtcggga
aacctgtcgtgccagctgcattaatgaatcggccaacgcgcggggagaggcggtttgcgtattgggcgccagggtggtttttcttttcacca
gtgagacgggcaacagctgattgcccttcaccgcctggccctgagagagttgcagcaagcggtccacgctggtttgccccagcaggcga
aaatcctgtttgatggtggttaacggcgggatataacatgagctgtcttcggtatcgtcgtatcccactaccgagatatccgcaccaacgcgc
agcccggactcggtaatggcgcgcattgcgcccagcgccatctgatcgttggcaaccagcatcgcagtgggaacgatgccctcattcagc
atttgcatggtttgttgaaaaccggacatggcactccagtcgccttcccgttccgctatcggctgaattgattgcgagtgagatatttatgccag

Figure 3B.

ccagccagacgcagacgcgccgagacagaacttaatgggcccgctaacagcgcgatttgctggtgacccaatgcgaccagatgctccac
gcccagtcgcgtaccgtcttcatgggagaaaataatactgttgatgggtgtctggtcagagacatcaagaaataacgccggaacattagtgc
aggcagcttccacagcaatggcatcctggtcatccagcggatagttaatgatcagcccactgacgcgttgcgcgagaagattgtgcaccgc
cgctttacaggcttcgacgccgcttcgttctaccatcgacaccaccacgctggcacccagttgatcggcgcgagatttaatcgccgcgacaa
tttgcgacggcgcgtgcagggccagactggaggtggcaacgccaatcagcaacgactgtttgcccgccagttgttgtgccacgcggttgg
gaatgtaattcagctccgccatcgccgcttccactttttcccgcgttttcgcagaaacgtggctggcctggttcaccacgcgggaaacggtct
gataagagacaccggcatactctgcgacatcgtataacgttactggtttcacattcaccaccctgaattgactctcttccgggcgctatcatgc
cataccgcgaaaggttttgcgccattcgatggtgtccgggatctcgacgctctcccttatgcgactcctgcattaggaagcagcccagtagta
ggttgaggccgttgagcaccgccgccgcaaggaatggtgcatgcaaggagatggcgcccaacagtcccccggccacggggcctgcca
ccatacccacgccgaaacaagcgctcatgagcccgaagtggcgagcccgatcttccccatcggtgatgtcggcgatataggcgccagca
accgcacctgtggcgccggtgatgccggccacgatgcgtccggcgtagaggatcgagatctcgatcccgcgaaattaatacgactcacta
taggggaattgtgagcggataacaattcccctctagaaataattttgtttaactttaagaaggagatatacatatgcgttgtagcgtgtccaccg
aaaatgtgtctttcaccgaaactgaaaccgaagctcgtcgttctgcgaactacgaacctaacagctgggactatgattacctgctgtcctccga
cacggacgagtccatcgaagtatacaaagacaaagcgaaaaagctggaagccgaagttcgtcgcgagattaataacgaaaaagcagaat
ttctgaccctgctggaactgattgacaacgtccagcgcctgggcctgggttaccgtttcgagtctgatatccgtggtgcgctggatcgcttcgt
ttcctccggcggcttcgatgcggtaaccaagacttccctgcacggtacggcactgtctttccgtctgctgcgtcaacacggttttgaggtttctc
aggaagcgttcagcggcttcaaagaccaaaacggcaacttcctggagaacctgaaggaagatatcaaagctatcctgagcctgtacgagg
ccagcttcctggctctggaaggcgaaaacatcctggacgaggcgaaggttttcgcaatctctcatctgaaagaactgtctgaagaaaagatc
ggtaaagagctggcagaacaggtgaaccatgcactggaactgccactgcatcgccgtactcagcgtctggaagcagtatggtctatcgag
gcctaccgtaaaaaggaggacgcgaatcaggttctgctggagctggcaattctggattacaacatgatccagtctgtataccagcgtgatct
gcgtgaaacgtcccgttggtggcgtcgtgtgggtctggcgaccaaactgcactttgctcgtgaccgcctgattgagagcttctactgggccg
tgggtgtagcattcgaaccgcaatactccgactgccgtaactccgtcgcaaaaatgtttcttcgtaaccattatcgacgatatctacgatgtat
acggcaccctggacgaactggagctgtttactgatgcagttgagcgttgggacgtaaacgccatcaacgacctgccggattacatgaaact
gtgctttctggctctgtataacactattaacgaaatcgcctacgacaacctgaaagataaaggtgagaacatcctgccgtatctgaccaaagc
ctgggctgacctgtgcaacgctttcctgcaagaagccaagtggctgtacaacaaatctactccgacctttgacgactacttcggcaacgcatg
gaaatcctcttctggcccgctgcaactggtgttcgcttacttcgctgtcgtgcagaacattaaaaaggaagagatcgaaaacctgcaaaaata
ccatgacaccatctctcgtccttcccatatcttccgtctgtgcaatgacctggctagcgcgtctgcggaaattgcgcgtggtgaaaccgcaaat
agcgtttcttgttacatgcgcactaaaggtatctccgaagaactggctaccgaaagcgtgatgaatctgatcgatgaaacctggaaaaagatg
aacaaggaaaaactgggtggtagcctgttcgcgaaaccgttcgtggaaaccgcgatcaacctggcacgtcaatctcactgcacttatcataa
cggcgacggcgcatacctctccggatgagctgacccgcaaacgcgttctgtctgtaatcactgaaccgattctgccgtttgaacgctaaggat
ccgaattcgagctccgtcgacaagcttgcggccgcactcgagcaccaccaccaccaccactgagatccggctgctaacaaagcccgaaa
ggaagctgagttggctgctgccaccgctgagcaataactagcataaccccttggggcctctaaacgggtcttgaggggttttttgctgaaag
gaggaactatatccggat (SEQ ID NO:1)

Figure 6A.

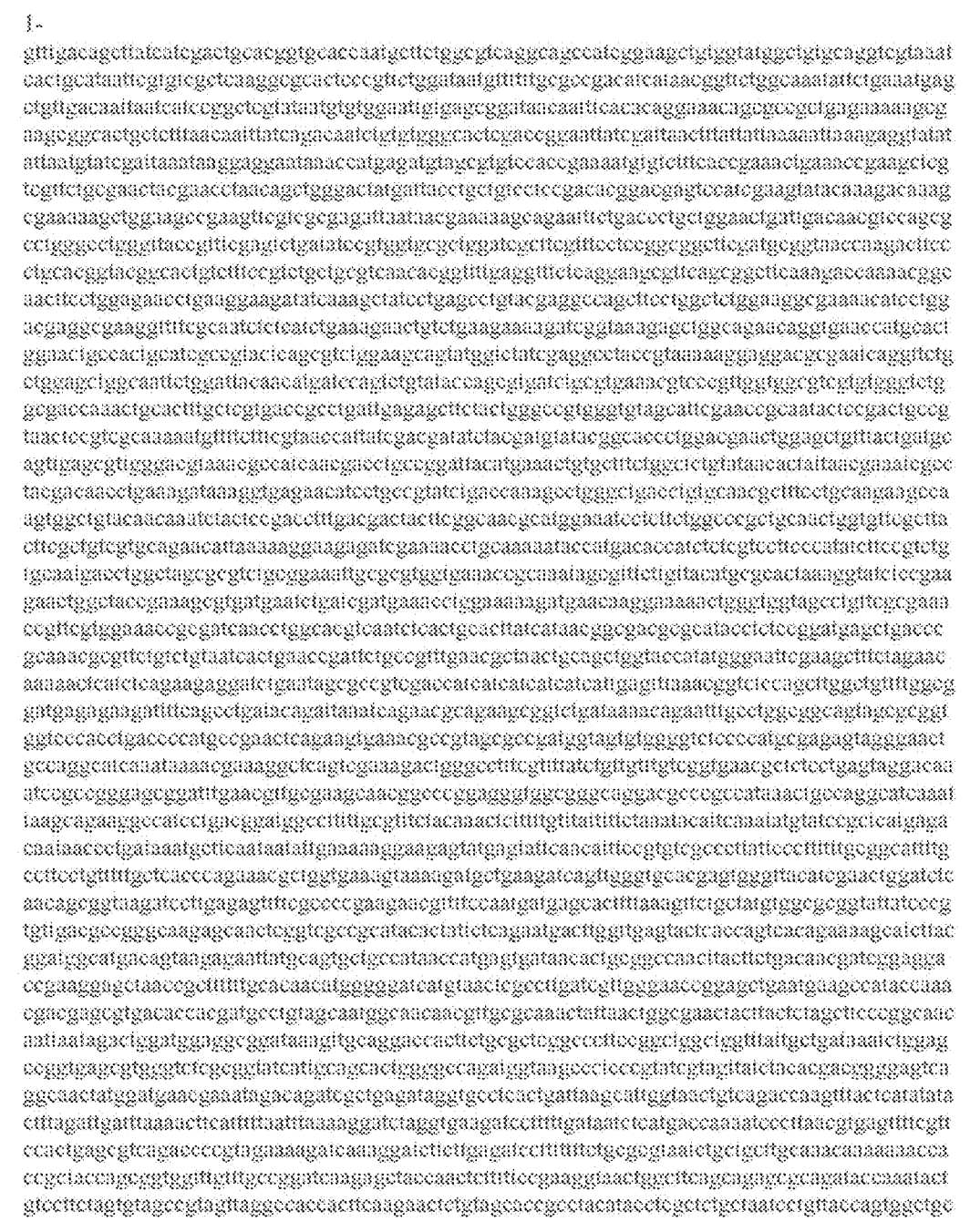

1- gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgtttcctccggcggcttcgatgcggtaaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggttttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgtttcttcgtaaccattatcgacgatatctacgatgtatacggcaccctggacgaactggagctgtttactgatgc
agttgagcgttgggacgtaaacgccatcaacgacctgccggattacatgaaactgtgcttcctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcagctggtaccatatgggaattcgaagctttctagaac
aaaaactcatctcagaagaggatctgaatagcgccgtcgaccatcatcatcatcatcattgagtttaaacggtctccagcttggctgttttggcg
gatgagagaagattttcagcctgatacagattaaatcagaacgcagaagcggtctgataaaacagaatttgcctggcggcagtagcgcggt
ggtcccacctgaccccatgccgaactcagaagtgaaacgccgtagcgccgatggtagtgtggggtctccccatgcgagagtagggaact
gccaggcatcaaataaaacgaaaggctcagtcgaaagactgggcctttcgttttatctgttgtttgtcggtgaacgctctcctgagtaggacaa
atccgccgggagcggatttgaacgttgcgaagcaacggcccggagggtggcgggcaggacgcccgccataaactgccaggcatcaaat
taagcagaaggccatcctgacggatggcctttttgcgtttctacaaactctttttgtttatttttctaaatacattcaaatatgtatccgctcatgaga
caataaccctgataaatgcttcaataatattgaaaaaggaagagtatgagtattcaacatttccgtgtcgcccttattcccttttttgcggcattttg
ccttcctgtttttgctcacccagaaacgctggtgaaagtaaaagatgctgaagatcagttgggtgcacgagtgggttacatcgaactggatctc
aacagcggtaagatccttgagagttttcgccccgaagaacgttttccaatgatgagcacttttaaagttctgctatgtggcgcggtattatcccg
tgttgacgccgggcaagagcaactcggtcgccgcatacactattctcagaatgacttggttgagtactcaccagtcacagaaaagcatcttac
ggatggcatgacagtaagagaattatgcagtgctgccataaccatgagtgataacactgcggccaacttacttctgacaacgatcggagga
ccgaaggagctaaccgcttttttgcacaacatgggggatcatgtaactcgccttgatcgttgggaaccggagctgaatgaagccataccaaa
cgacgagcgtgacaccacgatgcctgtagcaatggcaacaacgttgcgcaaactattaactggcgaactacttactctagcttcccggcaac
aattaatagactggatggaggcggataaagttgcaggaccacttctgcgctcggcccttccggctggctggtttattgctgataaatctggag
ccggtgagcgtgggtctcgcggtatcattgcagcactggggccagatggtaagccctcccgtatcgtagttatctacacgacggggagtca
ggcaactatggatgaacgaaatagacagatcgctgagataggtgcctcactgattaagcattggtaactgtcagaccaagtttactcatata
ctttagattgatttaaaacttcatttttaatttaaaaggatctaggtgaagatcctttttgataatctcatgaccaaaatcccttaacgtgagttttcgtt
ccactgagcgtcagaccccgtagaaaagatcaaaggatcttcttgagatcctttttttctgcgcgtaatctgctgcttgcaaacaaaaaaacca
ccgctaccagcggtggtttgtttgccggatcaagagctaccaactctttttccgaaggtaactggcttcagcagagcgcagataccaaatact
gtccttctagtgtagccgtagttaggccaccacttcaagaactctgtagcaccgcctacatacctcgctctgctaatcctgttaccagtggctgc

Figure 6B.

tgccagtggcgataagtcgtgtcttaccgggttggactcaagacgatagttaccggataaggcgcagcggtcgggctgaacggggggttc
gtgcacacagcccagcttggagcgaacgacctacaccgaactgagatacctacagcgtgagctatgagaaagcgccacgcttcccgaag
ggagaaaggcggacaggtatccggtaagcggcagggtcggaacaggagagcgcacgagggagcttccagggggaaacgcctggtat
ctttatagtcctgtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgtattaccgcct
ttgagtgagctgataccgctcgccgcagccgaacgaccgagcgcagcgagtcagtgagcgaggaagcggaagagcgcctgatgcggt
attttctccttacgcatctgtgcggtatttcacaccgcatatggtgcactctcagtacaatctgctctgatgccgcatagttaagccagtatacact
ccgctatcgctacgtgactgggtcatggctgcgccccgacacccgccaacacccgctgacgcgccctgacgggcttgtctgctcccggca
tccgcttacagacaagctgtgaccgtctccgggagctgcatgtgtcagaggttttcaccgtcatcaccgaaacgcgcgaggcagcagatca
attcgcgcgcgaaggcgaagcggcatgcatttacgttgacaccatcgaatggtgcaaaacctttcgcggtatggcatgatagcgcccggaa
gagagtcaattcagggtggtgaatgtgaaaccagtaacgttatacgatgtcgcagagtatgccggtgtctcttatcagaccgtttcccgcgtg
gtgaaccaggccagccacgtttctgcgaaaacgcgggaaaaagtggaagcggcgatggcggagctgaattacattcccaaccgcgtggc
acaacaactggcgggcaaacagtcgttgctgattggcgttgccacctccagtctggccctgcacgcgccgtcgcaaattgtcgcggcgatt
aaatctcgcgccgatcaactgggtgccagcgtggtggtgtcgatggtagaacgaagcggcgtcgaagcctgtaaagcggcggtgcacaa
tcttctcgcgcaacgcgtcagtgggctgatcattaactatccgctggatgaccaggatgccattgctgtggaagctgcctgcactaatgttccg
gcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcg
caatcaaattcagccgatagcggaacgggaaggcgactggagtgccatgtccggttttcaacaaaccatgcaaatgctgaatgagggcatc
gttcccactgcgatgctggttgccaacgatcagatggcgctgggcgcaatgcgcgccattaccgagtccgggctgcgcgttggtgcggat
atctcggtagtgggatacgacgataccgaagacagctcatgttatatcccgccgtcaaccaccatcaaacaggattttcgcctgctggggca
aaccagcgtggaccgcttgctgcaactctctcagggccaggcggtgaagggcaatcagctgttgcccgtctcactggtgaaaagaaaaac
caccctggcgcccaatacgcaaaccgcctctccccgcgcgttggccgattcattaatgcagctggcacgacaggtttcccgactggaaagc
gggcagtgagcgcaacgcaattaatgtgagttagcgcgaattgatctg (SEQ ID NO:2)

Figure 9A.

1- gtttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatgagatgtagcgtgtccaccgaaaatgtgtctttcaccgaaactgaaaccgaagctcg
tcgttctgcgaactacgaacctaacagctgggactatgattacctgctgtcctccgacacggacgagtccatcgaagtatacaaagacaaag
cgaaaaagctggaagccgaagttcgtcgcgagattaataacgaaaaagcagaatttctgaccctgctggaactgattgacaacgtccagcg
cctgggcctgggttaccgtttcgagtctgatatccgtggtgcgctggatcgcttcgttcctccggcggcttcgatgcggttaccaagacttcc
ctgcacggtacggcactgtctttccgtctgctgcgtcaacacggttttgaggtttctcaggaagcgttcagcggcttcaaagaccaaaacggc
aacttcctggagaacctgaaggaagatatcaaagctatcctgagcctgtacgaggccagcttcctggctctggaaggcgaaaacatcctgg
acgaggcgaaggtttcgcaatctctcatctgaaagaactgtctgaagaaaagatcggtaaagagctggcagaacaggtgaaccatgcact
ggaactgccactgcatcgccgtactcagcgtctggaagcagtatggtctatcgaggcctaccgtaaaaaggaggacgcgaatcaggttctg
ctggagctggcaattctggattacaacatgatccagtctgtataccagcgtgatctgcgtgaaacgtcccgttggtggcgtcgtgtgggtctg
gcgaccaaactgcactttgctcgtgaccgcctgattgagagcttctactgggccgtgggtgtagcattcgaaccgcaatactccgactgccg
taactccgtcgcaaaaatgtttctttcgtaaccattatcgacgatatctacgatgtatacggcaccctggacgaactggagctgtttactgatgc
agttgagcgttgggacgtaaacgccatcaacgacctgccggattacatgaaactgtgctttctggctctgtataacactattaacgaaatcgcc
tacgacaacctgaaagataaaggtgagaacatcctgccgtatctgaccaaagcctgggctgacctgtgcaacgctttcctgcaagaagcca
agtggctgtacaacaaatctactccgacctttgacgactacttcggcaacgcatggaaatcctcttctggcccgctgcaactggtgttcgctta
cttcgctgtcgtgcagaacattaaaaaggaagagatcgaaaacctgcaaaaataccatgacaccatctctcgtccttcccatatcttccgtctg
tgcaatgacctggctagcgcgtctgcggaaattgcgcgtggtgaaaccgcaaatagcgtttcttgttacatgcgcactaaaggtatctccgaa
gaactggctaccgaaagcgtgatgaatctgatcgatgaaacctggaaaaagatgaacaaggaaaaactgggtggtagcctgttcgcgaaa
ccgttcgtggaaaccgcgatcaacctggcacgtcaatctcactgcacttatcataacggcgacgcgcatacctctccggatgagctgaccc
gcaaacgcgttctgtctgtaatcactgaaccgattctgccgtttgaacgctaactgcataaaggaggtaaaaaacatggtatcctgttctgcg
ccgggtaagatttacctgttcggtgaacacgccgtagtttatggcgaaactgcaattgcgtgtgcggtggaactgcgtacccgtgttcgcgcg
gaactcaatgactctatcactattcagagccagatcggccgcaccggtctggatttcgaaaagcacccttatgtgtctgcggtaattgagaaa
atgcgcaaatctattcctattaacggtgttttcttgaccgtcgattccgacatcccggtgggctccggtctgggtagcagcgcagccgttactat
cgcgtctattggtgcgctgaacgagctgttcggctttggcctcagcctgcaagaaatcgctaaactgggccacgaaatcgaaattaaagtac
aggggtgccggcgtcccaaccgatacgtatgtttctacctcgggcggcgtggttaccatcccggaacgtcgcaaactgaaaactccggactg
cggcattgtgattggcgataccggcgtttctcctccaccaaagagttagtagctaacgtacgtcagctgcgcgaaagctacccggatttgat
cgaaccgctgatgacctctattggcaaaatctctcgtatcggcgaacaactggttctgtctggcgactacgcatccatcggccgcctgatgaa
cgtcaaccagggtctcctggacgccctgggcgttaacatcttagaactgagccagctgatctattccgctcgtgcggcaggtgcgtttggcg
ctaaaatcacgggcgctggcggcggtggctgtatggttgcgctgaccgctccggaaaaatgcaaccaagtggcagaagcggtagcaggc
gctggcggtaaagtgactatcactaaaccgaccgagcaaggtctgaaagtagattaaagtctagttaaagtttaaacggtctccagcttggct
gttttggcggatgagagaagattttcagcctgatacagattaaatcagaacgcagaagcggtctgataaaacagaatttgcctggcggcagt
agcgcggtggtcccacctgaccccatgccgaactcagaagtgaaacgccgtagcgccgatggtagtgtggggtctccccatgcgagagt
agggaactgccaggcatcaaataaaacgaaaggctcagtcgaaagactgggcctttcgttttatctgttgtttgtcggtgaacgctctcctgag
taggacaaatccgccgggagcggatttgaacgttgcgaagcaacggcccggagggtggcgggcaggacgcccgccataaactgccag
gcatcaaattaagcagaaggccatcctgacggatggcctttttgcgtttctacaaactctttttgtttatttttctaaatacattcaaatatgtatccg
ctcatgagacaataaccctgataaatgcttcaataatattgaaaaaggaagagtatgagtattcaacatttccgtgtcgcccttattcccttttttg
cggcattttgccttcctgtttttgctcacccagaaacgctggtgaaagtaaaagatgctgaagatcagttgggtgcacgagtgggttacatcga
actggatctcaacagcggtaagatccttgagagttttcgccccgaagaacgttttccaatgatgagcacttttaaagttctgctatgtggcgcg
gtattatcccgtgttgacgccgggcaagagcaactcggtcgccgcatacactattctcagaatgacttggttgagtactcaccagtcacagaa
aagcatcttacggatggcatgacagtaagagaattatgcagtgctgccataaccatgagtgataacactgcggccaacttacttctgacaacg

Figure 9B.

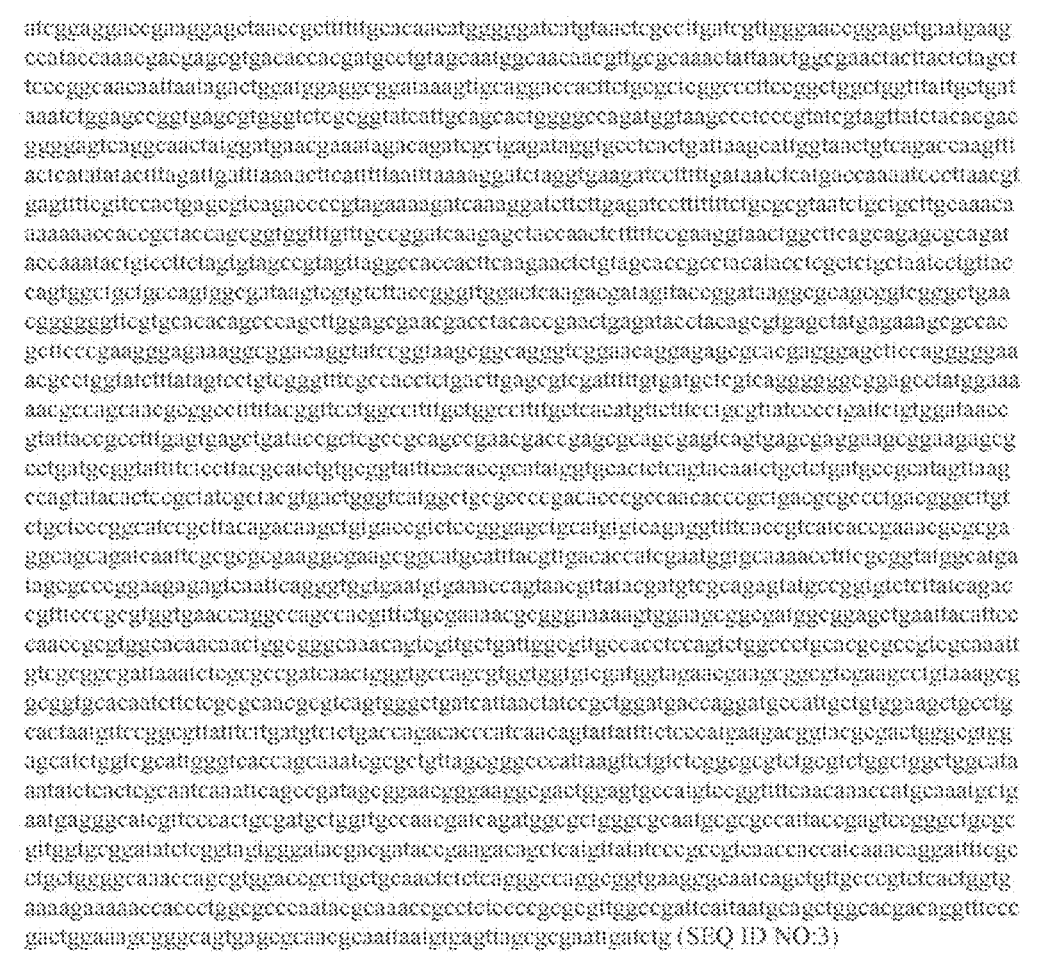

atcggaggaccgaaggagctaaccgcttttttgcacaacatgggggatcatgtaactcgccttgatcgttgggaaccggagctgaatgaag
ccataccaaacgacgagcgtgacaccacgatgcctgtagcaatggcaacaacgttgcgcaaactattaactggcgaactacttactctagct
tcccggcaacaattaatagactggatggaggcggataaagttgcaggaccacttctgcgctcggcccttccggctggctggtttattgctgat
aaatctggagccggtgagcgtgggtctcgcggtatcattgcagcactggggccagatggtaagccctcccgtatcgtagttatctacacgac
ggggagtcaggcaactatggatgaacgaaatagacagatcgctgagataggtgcctcactgattaagcattggtaactgtcagaccaagttt
actcatatatactttagattgatttaaaacttcatttttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctgcttgcaaaca
aaaaaaccaccgctaccagcggtggtttgtttgccggatcaagagctaccaactctttttccgaaggtaactggcttcagcagagcgcagat
accaaatactgtccttctagtgtagccgtagttaggccaccacttcaagaactctgtagcaccgcctacatacctcgctctgctaatcctgttac
cagtggctgctgccagtggcgataagtcgtgtcttaccgggttggactcaagacgatagttaccggataaggcgcagcggtcgggctgaa
cggggggttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttccagggggaa
acgcctggtatctttatagtcctgtcgggtttcgccacctctgacttgagcgtcgatttttgtgatgctcgtcaggggggcggagcctatggaaa
aacgccagcaacgcggcctttttacggttcctggccttttgctggccttttgctcacatgttctttcctgcgttatcccctgattctgtggataacc
gtattaccgcctttgagtgagctgataccgctcgccgcagccgaacgaccgagcgcagcgagtcagtgagcgaggaagcggaagagcg
cctgatgcggtattttctccttacgcatctgtgcggtatttcacaccgcatatggtgcactctcagtacaatctgctctgatgccgcatagttaag
ccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcga
ggcagcagatcaattcgcgcgcgaaggcgaagcggcatgcatttacgttgacaccatcgaatggtgcaaaacctttcgcggtatggcatga
tagcgcccggaagagagtcaattcagggtggtgaatgtgaaaccagtaacgttatacgatgtcgcagagtatgccggtgtctcttatcagac
cgtttcccgcgtggtgaaccaggccagccacgtttctgcgaaaacgcgggaaaaagtggaagcggcgatggcggagctgaattacattcc
caaccgcgtggcacaacaactggcgggcaaacagtcgttgctgattggcgttgccacctccagtctggccctgcacgcgccgtcgcaaatt
gtcgcggcgattaaatctcgcgccgatcaactgggtgccagcgtggtggtgtcgatggtagaacgaagcggcgtcgaagcctgtaaagcg
gcggtgcacaatcttctcgcgcaacgcgtcagtgggctgatcattaactatccgctggatgaccaggatgccattgctgtggaagctgcctg
cactaatgttccggcgttatttcttgatgtctctgaccagacacccatcaacagtattattttctcccatgaagacggtacgcgactgggcgtgg
agcatctggtcgcattgggtcaccagcaaatcgcgctgttagcgggcccattaagttctgtctcggcgcgtctgcgtctggctggctggcata
aatatctcactcgcaatcaaattcagccgatagcggaacgggaaggcgactggagtgccatgtccggttttcaacaaaccatgcaaatgctg
aatgagggcatcgttcccactgcgatgctggttgccaacgatcagatggcgctgggcgcaatgcgcgccattaccgagtccgggctgcgc
gttggtgcggatatctcggtagtgggatacgacgataccgaagacagctcatgttatatcccgccgtcaaccaccatcaaacaggattttcgc
ctgctggggcaaaccagcgtggaccgcttgctgcaactctctcagggccaggcggtgaagggcaatcagctgttgcccgtctcactggtg
aaaagaaaaaccaccctggcgcccaatacgcaaaccgcctctccccgcgcgttggccgattcattaatgcagctggcacgacaggtttccc
gactggaaagcgggcagtgagcgcaacgcaattaatgtgagttagcgcgaattgatctg (SEQ ID NO:3)

Figure 10B.

gcggccgcgcccttgacgatgccacatcctgagcaaataattcaaccactaattgtgagcggataacacaaggaggaaacagc
catggtatcctgttctgcgccgggtaagatttacctgttcggtgaacacgccgtagtttatggcgaaactgcaattgcgtgtgcggt
ggaactgcgtacccgtgttcgcgcggaactcaatgactctatcactattcagagccagatcggccgcaccggtctggatttcgaa
aagcacccttatgtgtctgcggtaattgagaaaatgcgcaaatctattcctattaacggtgttttcttgaccgtcgattccgacatccc
ggtgggctccggtctgggtagcagcgcagccgttactatcgcgtctattggtgcgctgaacgagctgttcggctttggcctcagc
ctgcaagaaatcgctaaactgggccacgaaatcgaaattaaagtacagggtgccgcgtccccaaccgatacgtatgtttctacct
tcggcggcgtggttaccatcccggaacgtcgcaaactgaaaactccggactgcggcattgtgattggcgataccggcgtttctc
ctccaccaaagagttagtagctaacgtacgtcagctgcgcgaaagctacccggatttgatcgaaccgctgatgacctctattggc
aaaatctctcgtatcggcgaacaactggttctgtctggcgactacgcatccatcggccgcctgatgaacgtcaaccagggtctcct
ggacgccctgggcgttaacatcttagaactgagccagctgatctattccgctcgtgcggcaggtgcgtttggcgctaaaatcacg
ggcgctggcggcggtggctgtatggttgcgctgaccgctccggaaaaatgcaaccaagtggcagaagcggtagcaggcgct
ggcggtaaagtgactatcactaaaccgaccgagcaaggtctgaaagtagattaagcctgacttaatagctgcttatttcgcccta
tggtacctagtaggaggaaaaaaacatggaaatgcgtcaaccggctgtcgcaggtcaattctacccactgcgttgcgagaacct
ggaaaacgaactgaaacgctgcttcgaaggcctggagatccgcgaacaagaagtgctgggcgcagtctgtccgcacgccggt
tatatgtactctggcaaagttgcggcgcacgtctatgccactctgccggaagctgatacctacgtaatcttcggccccgaaccacac
cggctacggtagccctgtctctgtgagccgtgaaacttggaagaccccgttgggcaatatcgatgttgacctggaactggcgga
cggcttcctgggttccatcgtagatgcggatgaactcggtcacaaatacgaacactctatcgaagttcagctgccgtttctgcaata
ccgttttgaacgcgatttcaaaatctgccaatctgcatgggtatgcaagacgaagaaaccgcggtcgaagtaggtaacctgctg
gcggatctgatcagcgagtccggtaaacgtgctgtgatcatcgcaagctctgatttcacccactatgagacggctgaacgtgcca
aagaaatcgatccgaagttattgattctatcctgaacttgacatctctggcatgtacgatcgcctgtatcgccgtaacgccctctgtt
gcggttacggcccgatcaccgctatgctgacggcaagcaaaaagctgggcggctctcgtgcgacttgctgaaatacgcaaac
agcgtgtgacgtgtccggtgataaagacgctgtggtgggctacgccgccatcatcgttgagtaagctgattaaaggttgaacagat
aggatttcgtcatggatcctacaaggaggaaaaaaacatgaatgcttctaatgaaccggtgattctgaaactgggtggctctgcta
ttaccgacaaaggtgcctacgaaggcgtagttaaggaagctgatttgctgcgcatcgcacaggaagttagcggtttccgtggca
agatgatcgtggttcatggtgctggtagcttcggccatacgtacgcgaagaaatacggcctggaccgtaccttcgacccagagg
gcgcaattgttactcatgaatctgttaaaagctcgcctccaaagttgtaggtgctctgaatagcttcggcgtgcgtgctatcgcgg
tgcatcctatggactgcgcagtatgccgtaacggtcgtatcgaaacgatgtatctggactccatcaagttaatgctggaaaaaggt
ctggtgccggttctgcacggcgacgtcgcaatggatattgaactgggcacttgtatcctgtccggtgatcaaatcgtccttacctg
gccaaagaactgggtatctcccgcctcggcctgggcagcgcagaggatggtgtgctggatatggagggcaaacctgtaccgg
aaatcacccagaaactttcgaagagttccgccactgcatcggtggttctggttctactgatgtaaccggtggcatgctgggcaaa
gtgctggaacttctggaattgagcaaaaattcttccattactagctacatttcaacgctggtaaagcagacaacatctaccgctttct
gaatggtgagtccatcggcactcgcatcagcccggacaagcgtgttaagctagttattaacctaaatgctctaaaccagttatga
gctctacaaggaggaaaaaaacatgattaacactaccagccgccgcaaaattgaacacctgaaactctgcgcagaatccccgg
ttgaagcgcgtcaggtatctgccggctttgaagacgttactctgatccaccgcgctttaccggagctgaacatggatgaactgga
cctcagcgttgatttcctgggtaaacgcatcaaagcgccgttcctgattgcgtctatcacgggtggtcacccagataccatcccgg
ttaacgctgcgctggcagctgctgctgaggagctgggtgttggcatcggcgttggctctcagcgcgcggccattgatgatccga
gccaggaagacagcttccgtgtagtgcgtgatgaagccccagatgcgtttgtttatggcaacgtcggcgcagcacagatccgtc
agtatggtgttgaaggtgttgaaaaactgatcgaaatgattgacgcagatgccttggcaatccacctgaactttctgcaagaagcg
gtccaaccggaaggtgaccgcgacgcgaccggttgcctggacatgattaccgaaatttgctctcagattaaaactccggtaatcg
tgaaagaaaccggtgcaggcattagccgtgaagatgcgattctgtccagaaagctggcgtgagcgcaatcgacgttggcggc
gcgggcggcacctcctgggctggcgtcgaggtctaccgtgctaagaaagccgtgactctgttagcgagcgtttaggtgagct
gtttgggatttcggcattccgacggtagcttctctgattgaatcccgcgtttcctgccgctgatcgcaaccggcggtatccgtaac
ggtctggacattgctaaagcattgctctcggcgcaagcgctgccagcgccgctctgccgttcgttggtccgtccctggagggc
aaagaatccgttgtacgtgtgctgagctgcatgctggaagaatttaaagcagcaatgtttttgtgcggttgcggcaacatcaaaga

Figure 10C.

cctgcacaactctccagtagtggtaactggttggacccgcgaatacctggagcagcgcggttttaacgttaaggacctctcccctg
ccgggcaacgctctgtaagcttcaacgcgtctacaaataaaaaaggcacgtcagatgacgtgcctttttttcttgtctaga
(SEQ ID NO:4)

MCM376 - MVK from M. mazei archeal Lowerin pET200D
6647 bp

Figure 11B.

aagggcgagctcaacgatccggctgctaacaaagcccgaaaggaagctgagttggctgctgccaccgctgagcaataactag
cataaccccttggggcctctaaacgggtcttgaggggttttttgctgaaaggaggaactatatccggatatcccgcaagaggccc
ggcagtaccggcataaccaagcctatgcctacagcatccagggtgacggtgccgaggatgacgatgagcgcattgttagatttc
atacacggtgcctgactgcgttagcaatttaactgtgataaactaccgcattaaagcttatcgatgataagctgtcaaacatgagaa
ttaattcttgaagacgaaagggcctcgtgatacgcctatttttataggttaatgtcatgataataatggtttcttagacgtcaggtggca
cttttcggggaaatgtgcgcggaacccctatttgtttatttttctaaatacattcaaatatgtatccgctcatgagacaataaccctgat
aaatgcttcaataatattgaaaaaggaagagtatgattgaacaagatggattgcacgcaggttctccggccgcttgggtggagag
gctattcggctatgactgggcacaactgacaatcggctgctctgatgccgccgtgttccggctgtcagcgcaggggcgcccggt
tctttttgtcaagaccgacctgtccggtgccctgaatgaactgcaggacgaggcagcgcggctatcgtggctggccacgacgg
gcgttccttgcgcagctgtgctcgacgttgtcactgaagcgggaagggactggctgctattgggcgaagtgccggggcaggat
ctcctgtcatctcaccttgctcctgccgagaaagtatccatcatggctgatgcaatgcggcggctgcatacgcttgatccggctac
ctgcccattcgaccaccaagcgaaacatcgcatcgagcgggcacgtactcggatggaagccggtcttgtcgatcaggatgatct
ggacgaagagcatcaggggctcgcgccagccgaactgttcgccaggctcaaggcgcgcatgcccgacggcgaggatctcgt
cgtgacacatggcgatgcctgcttgccgaatatcatggtggaaaatggccgcttttctggattcatcgactgtggccggctgggtg
tggcggaccgctatcaggacatagcgttggctacccgtgatattgctgaagagcttggcggcgaatgggctgaccgcttcctcgt
gctttacggtatcgccgctcccgattcgcagcgcatcgccttctatcgccttcttgacgagttcttctgagcgggactctggggttc
gaaatgaccgaccaagcgacgcctaactgtcagaccaagtttactcatatatactttagattgatttaaaacttcatttttaatttaaaa
ggatctaggtgaagatcctttttgataatctcatgaccaaaatcccttaacgtgagttttcgttccactgagcgtcagaccccgtaga
aaagatcaaaggatcttcttgagatcctttttttctgcgcgtaatctgctgcttgcaaacaaaaaaaccaccgctaccagcggtggtt
tgtttgccggatcaagagctaccaactctttttccgaaggtaactggcttcagcagagcgcagataccaaatactgtccttctagtgt
agccgtagttaggccaccacttcaagaactctgtagcaccgcctacatacctcgctctgctaatcctgttaccagtggctgctgcc
agtggcgataagtcgtgtcttaccgggttggactcaagacgatagttaccggataaggcgcagcggtcgggctgaacgggggg
ttcgtgcacacagcccagcttggagcgaacgacctacaccgaactgagatacctacagcgtgagctatgagaaagcgccac
gcttcccgaagggagaaaggcggacaggtatccggtaagcggcagggtcggaacaggagagcgcacgagggagcttcca
gggggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctgcgtt
atcccctgattctgtggataaccgtattaccgcctttgagtgagctgataccgctcgccgcagccgaacgaccgagcgcagcga
gtcagtgagcgaggaagcggaagagcgcctgatgcggtattttctccttacgcatctgtgcggtatttcacaccgcaatggtgca
ctctcagtacaatctgctctgatgccgcatagttaagccagtatacactccgctatcgctacgtgactgggtcatggctgcgcccc
gacacccgccaacacccgctgacgcgccctgacgggcttgtctgctcccggcatccgcttacagacaagctgtgaccgtctcc
gggagctgcatgtgtcagaggttttcaccgtcatcaccgaaacgcgcgaggcagctgcggtaaagctcatcagcgtggtcgtg
aagcgattcacagatgtctgcctgttcatccgcgtccagctcgttgagtttctccagaagcgttaatgtctggcttctgataaagcgg
gccatgttaagggcggttttttcctgtttggtcactgatgcctccgtgtaagggggatttctgttcatgggggtaatgataccgatga
aacgagagaggatgctcacgatacgggttactgatgatgaacatgcccggttactggaacgttgtgagggtaaacaactggcg
gtatggatgcggcgggaccagagaaaaatcactcagggtcaatgccagcgcttcgttaatacagatgtaggtgttccacagggt
agccagcagcatcctgcgatgcagatccggaacataatggtgcagggcgctgacttccgcgtttccagactttacgaaacacgg
aaaccgaagaccattcatgttgttgctcaggtcgcagacgttttgcagcagcagtcgcttcacgttcgctcgcgtatcggtgattca
ttctgctaaccagtaaggcaaccccgccagcctagccgggtcctcaacgacaggagcacgatcatgcgcacccgtggccagg
acccaacgctgcccgagatgcgccgcgtgcggctgctggagatggcggacgcgatggatatgttctgccaagggttggtttgc
gcattcacagttctccgcaagaattgattggctccaattcttggagtggtgaatccgttagcgaggtgccgccggcttccattcagg
tcgaggtggcccggctccatgcaccgcgacgcaacgcggggaggcagacaaggtatagggcggcgcctacaatccatgcc
aacccgttccatgtgctcgccgaggcggcataaatcgccgtgacgatcagcggtccaatgatcgaagttaggctggtaagagc
cgcgagcgatccttgaagctgtccctgatggtcgtcatctacctgcctggacagcatggcctgcaacgcgggcatcccgatgcc
gccggaagcgagaagaatcataatggggaaggccatccagcctcgcgtcgcgaacgccagcaagacgtagcccagcgcgt

Figure 11C.

cggccgccatgccggcgataatggcctgcttctcgccgaaacgtttggtggcgggaccagtgacgaaggcttgagcgagggc
gtgcaagattccgaataccgcaagcgacaggccgatcatcgtcgcgctccagcgaaagcggtcctcgccgaaaatgacccag
agcgctgccggcacctgtcctacgagttgcatgataaagaagacagtcataagtgcggcgacgatagtcatgccccgcgccca
ccggaaggagctgactgggttgaaggctctcaagggcatcggtcgagatcccggtgcctaatgagtgagctaacttacattaatt
gcgttgcgctcactgcccgctttccagtcgggaaacctgtcgtgccagctgcattaatgaatcggccaacgcgcggggagagg
cggtttgcgtattgggcgccagggtggtttttcttttcaccagtgagacgggcaacagctgattgcccttcaccgcctggccctga
gagagttgcagcaagcggtccacgctggtttgccccagcaggcgaaaatcctgtttgatggtggttaacggcgggatataacat
gagctgtcttcggtatcgtcgtatcccactaccgagatatccgcaccaacgcgcagcccggactcggtaatggcgcgcattgcg
cccagcgccatctgatcgttggcaaccagcatcgcagtgggaacgatgccctcattcagcatttgcatggtttgttgaaaaccgg
acatggcactccagtcgccttcccgttccgctatcggctgaatttgattgcgagtgagatatttatgccagccagccagacgcaga
cgcgccgagacagaacttaatgggcccgctaacagcgcgatttgctggtgacccaatgcgaccagatgctccacgcccagtcg
cgtaccgtcttcatgggagaaaataatactgttgatgggtgtctggtcagagacatcaagaaataacgccggaacattagtgcag
gcagcttccacagcaatggcatcctggtcatccagcggatagttaatgatcagcccactgacgcgttgcgcgagaagattgtgc
accgccgctttacaggcttcgacgccgcttcgttctaccatcgacaccaccacgctggcacccagttgatcggcgcgagatttaa
tcgccgcgacaatttgcgacggcgcgtgcagggccagactggaggtggcaacgccaatcagcaacgactgtttgcccgccag
ttgttgtgccacgcggttgggaatgtaattcagctccgccatcgccgcttccactttttcccgcgttttcgcagaaacgtggctggc
ctggttcaccacgcgggaaacggtctgataagagacaccggcatactctgcgacatcgtataacgttactggtttcacattcacca
ccctgaattgactctcttccgggcgctatcatgccataccgcgaaaggttttgcgccattcgatggtgtccgggatctcgacgctct
cccttatgcgactcctgcattaggaagcagcccagtagtaggttgaggccgttgagcaccgccgccgcaaggaatggtgcatg
caaggagatggcgcccaacagtcccccggccacggggcctgccaccatacccacgccgaaacaagcgctcatgagcccga
agtggcgagcccgatcttccccatcggtgatgtcggcgatataggcgccagcaaccgcacctgtggcgccggtgatgccggc
cacgatgcgtccggcgtagaggatcgagatctcgatcccgcgaaattaatacgactcactataggggaattgtgagcggataac
aattcccctctagaaataattttgtttaactttaagaaggagatatacatatgcggggttctcatcatcatcatcatcatggtatggcta
gcatgactggtggacagcaaatgggtcgggatctgtacgacgatgacgataaggatcatcccttcaccatggtatcctgttctgc
gccgggtaagattacctgttcggtgaacacgccgtagtttatggcgaaactgcaattgcgtgtgcggtggaactgcgtacccgt
gttcgcgcggaactcaatgactctatcactattcagagccagatcggccgcaccggtctggatttcgaaaagcacccttatgtgtc
tgcggtaattgagaaaatgcgcaaatctattcctattaacggtgttttcttgaccgtcgattccgacatcccggtgggctccggtctg
ggtagcagcgcagccgttactatcgcgtctattggtgcgctgaacgagctgttcggctttggcctcagcctgcaagaaatcgcta
aactgggccacgaaatcgaaattaaagtacagggtgccgcgtccccaaccgatacgtatgtttctaccttcggcggcgtggttac
catcccggaacgtcgcaaactgaaaactccggactgcggcattgtgattggcgataccggcgtttctcctccaccaaagagtta
gtagctaacgtacgtcagctgcgcgaaagctacccggatttgatcgaaccgctgatgacctctattggcaaaatctctcgtatcgg
cgaacaactggttctgtctggcgactacgcatccatcggccgcctgatgaacgtcaaccagggtctcctggacgccctgggcgt
taacatcttagaactgagccagctgatctattccgctcgtgcggcaggtgcgtttggcgctaaaatcacgggcgctggcggcggt
ggctgtatggttgcgctgaccgctccggaaaaatgcaaccaagtggcagaagcggtagcaggcgctggcggtaaagtgactat
cactaaaccgaccgagcaaggtctgaaagtagattaa
(SEQ ID NO:5)

CDS2: Gentamycin resistance gene; CDS1: *E. coli* replication protein

Figure 13A.

1- ctcgggccgtctcttgggcttgatcggccttcttgcgcatctcacgcgctcctgcggcggcctgtagggcaggctcatacccctgccgaacc
gctttgtcagccggtcggccacggcttccggcgtctcaacgcgctttgagattcccagcttttcggccaatccctgcggtgcataggcgcgt
ggctcgaccgcttgcgggctgatggtgacgtggcccactggtggccgctccagggcctcgtagaacgcctgaatgcgcgtgtgacgtgc
cttgctgccctcgatgccccgttgcagccctagatcggccacagcggccgcaaacgtggtctggtcgcgggtcatctgcgcttgttgccga
tgaactccttggccgacagcctgccgtcctgcgtcagcggcaccacgaacgcggtcatgtgcgggctggtttcgtcacggtggatgctggc
cgtcacgatgcgatccgccccgtacttgtccgccagccacttgtgcgccttctcgaagaacgccgcctgctgttcttggctggccgacttcca
ccattccgggctggccgtcatgacgtactcgaccgccaacacagcgtccttgcgccgcttctctggcagcaactcgcgcagtcggcccatc
gcttcatcggtgctgctggccgcccagtgctcgttctctggcgtcctgctggcgtcagcgttgggcgtctcgcgctcgcggtaggcgtgctt
gagactggccgccacgttgcccattttcgccagcttcttgcatcgcatgatcgcgtatgccgccatgcctgcccctcccttttggtgtccaacc
ggctcgacgggggcagcgcaaggcggtgcctccggcgggccactcaatgcttgagtatactcactagactttgcttcgcaaagtcgtgac
cgcctacggcggctgcggcgccctacgggcttgctctccgggcttcgccctgcgcggtcgctgcgctcccttgccagcccgtggatatgtg
gacgatggccgcgagcggccaccggctggctcgcttcgctcggcccgtggacaaccctgctggacaagctgatggacaggctgcgcct
gcccacgagcttgaccacagggattgcccaccggctacccagccttcgaccacatacccaccggctccaactgcgcggcctgcggcctt
gccccatcaattttttaatttctctggggaaaagcctccggcctgcggcctgcgcgcttcgcttgccggttggacaccaagtggaaggcgg
gtcaaggctcgcgcagcgaccgcgcagcggcttggccttgacgcgcctggaacgacccaagcctatgcgagtgggggcagtcgaagg
cgaagcccgcccgcctgccccccgagcctcacggcggcgagtgcgggggttccaagggggcagcgccaccttgggcaaggccgaag
gccgcgcagtcgatcaacaagccccggaggggccactttttgccggagggggagccgcgccgaaggcgtgggggaacccgcaggg
gtgcccttctttgggcaccaaagaactagatatagggcgaaatgcgaaagacttaaaaatcaacaacttaaaaaagggggggtacgcaacag
ctcattgcggcaccccccgcaatagctcattgcgtaggttaaagaaaatctgtaattgactgccacttttacgcaacgcataattgttgtcgcgc
tgccgaaaagttgcagctgattgcgcatggtgccgcaaccgtgcggcacccctaccgcatggagataagcatggccacgcagtccagaga
aatcggcattcaagccaagaacaagcccggtcactgggtgcaaacggaacgcaaagcgcatgaggcgtgggccgggcttattgcgagg
aaacccacggcggcaatgctgctgcatcacctcgtggcgcagatgggccaccagaacgccgtggtggtcagccagaagacactttccaa
gctcatcggacgttctttgcggacggtccaatacgcagtcaaggacttggtggccgagcgctggatctccgtcgtgaagctcaacggcccc
ggcaccgtgtcggcctacgtggtcaatgaccgcgtggcgtggggccagccccgcgaccagttgcgcctgtcggtgttcagtgccgccgt
ggtggttgatcacgacgaccaggacgaatcgctgttggggcatggcgacctgcgccgcatcccgaccctgtatccgggcgagcagcaac
taccgaccggccccggcggaggagccgcccagccagcccggcattccgggcatggaaccagacctgccagccttgaccgaaacggag
gaatgggaacggcgcgggcagcagcgcctgccgatgcccgatgagccgtgttttctggacgatggcgagccgttggagccgccgacac
gggtcacgctgccgcgccggtagcacttgggttgcgcagcaacccgtaagtgcgctgttccagactatcggctgtagccgcctcgccgcc
ctataccttgtctgcctccccgcgttgcgtcgcggtgcatggagccgggccacctcgacctgaatggaagccggcggcacctcgctaacg
gattcaccgtttttatcaggctctgggaggcagaataaatgatcatatcgtcaattattacctccacggggagagcctgagcaaactggccca
ggcatttgagaagcacacggtcacactgcttccggtagtcaataaaccggtaaaccagcaatagacataagcggctatttaacgaccctgcc
ctgaaccgacgaccgggtcgaatttgctttcgaatttctgccattcatccgcttattatcacttattcaggcgtagcaccaggcgtttaagggca
ccaataactgccttaaaaaaattacgccccgccctgccactcatcgcagtcggcctattggttaaaaaatgagctgatttaacaaaaatttaac
gcgaattttaacaaaatattaacgcttacaatttccattcgccattcaggctgcgcaactgttgggaagggcgatcggtgcgggcctcttcgct
attacgccagctggcgaaagggggatgtgctgcaaggcgattaagttgggtaacgccagggttttcccagtcacgacgttgtaaaacgacg
gccagtgagcgcgcgtaatacgactcactatagggcgaattggagctccaccgcggtggcggccgctctagaactagtggatcccccgg
gctgcatgctcgagcggccgccagtgtgatggatatctgcagaattcgcccttcttgatatcttagtgtgcgttaaccaccacccacattggtc
cctgcccgaccgcatagcggccttttcatgcagtagcccctgctcgccaacaatttcgtataccgagatgtggtgagatttttgcccggcgg
caatcagatacttgccgctgtgatcaacattgaagccgcgcggctgggtttccgttggctggaagccttctttactcaacacgctgccatcttc
cgaaacgctgaaaacggtaatcaggctggcggtacggtcgcaggcgtataaatggcgaccatccggggtgatatgaatatcagccgccc
aacgggtgtcggagaagtttcccggcatcatatccagcgtctggacacattcgatattaccgtgcggatctttcagttcccagacatccactga
gctgttaactcattgacgcaatacgcatattgttcgtttggatggaataccatatgacgcgggccggccccttcaacggtggtcacttccgca
gggtcctgcgccacgagatgaccatcatcgctgaccgtaaacaggcaaatgcgatcctgcttaatgccggaacccacagcgtacggttgt

Figure 13B.

ccggtgagatattggcggaatggcaaccgtccagcccctcgaccacatcgacgacgcccactggcaggccatcttccagacgcggtacgc
tcacgtacccgcattgtaagaacctacaaagacaaactgcccctggtgatcggtggaatatgcgtcggactacccggcagcgcagactc
tgcggcaaaggtcagtgcgccatcgtccggggcgatacgatacgccaggacgcgaaactcagggcgaacaccaacatagagataacgt
ttgtccgggctgaccaccatcggctgcacctgccccggcacatcgacaacctgtgtcagcgtcagtgcgccttcatgattcagattccagac
gtgaattgctggctctcagggctgggatataaactgtttgcttcatgaatgctccttttgggttacctccgggaaacgcggttgatttgtttagtg
gttgaattatttgctcaggatgtggcatagtcaagggcgtgacggctcgctaatacaactcactatagggctcgaggaagttcctatactttcta
gagaataggaacttccgcggccgcacacaaaaaccaacacacagatcatgaaaataaagctcttttattggtaccgaatcgccagggagct
ctcagacgtcgcttggtcggtctttattcgaaccccagagtcccgcttacgccccgccctgccactcatcgcagtactgttgtaattcattaagc
attctgccgacatggaagccatcacaaacggcatgatgaacctgaatcgccagcggcatcagcaccttgtcgccttgcgtataatatttgccc
atggtgaaaacgggggcgaagaagttgtccatattggccacgtttaaatcaaaactggtgaaactcacccagggattggctgagacgaaa
aacatattctcaataaaccctttagggaaataggccaggttttcaccgtaacacgccacatcttgcgaatatatgtgtagaaactgccggaaatc
gtcgtggtattcactccagagcgatgaaaacgtttcagtttgctcatggaaaacggtgtaacaagggtgaacactatcccatatcaccagctc
accgtctttcattgccatacggaattccggatgagcattcatcaggcgggcaagaatgtgaataaaggccggataaaacttgtgcttatttttct
ttacggtctttaaaaaggccgtaatatccagctgaacggtctggttataggtacattgagcaactgactgaaatgcctcaaaatgttctttacgat
gccattgggatatatcaacggtggtatatccagtgatttttttctccatggtttagttcctcaccttgtcgtattatactatgccgatatactatgccg
atgattaattgtcaacacgtgctgctgcaggtcgaaaggcccggagatgaggaagaggagaacagcgcggcagacgtgcgcttttgaag
cgtgcagaatgccgggcctccggaggaccttcgggcgcccgccccgcccctgagcccgcccctgagcccgcccccggacccaccccttc
ccagcctctgagcccagaaagcgaaggagcaaagctgctattggccgctgccccaaaggcctacccgcttccattgctcagcggtgctg
tccatctgcacgagactagtgagacgtgctacttccatttgtcacgtcctgcacgacgcgagctgcggggcgggggggaacttcctgacta
ggggaggagtggaaggtggcgcgaagggggccaccaaagaacggagccggttggcgcctaccggtggatgtggaatgtgtgcgaggc
cagaggccacttgtgtagcgccaagtgcccagcggggctgctaaagcgcatgctccagactgccttgggaaaagcgcctcccctacccg
gtagaatgaagttcctatactttctagagaataggaacttcgcggccgcccttagtgagggttaattcaactgactgtaacagctaaaattagt
cgctttggcggtaagggcgaattccagcacactggcggccgttactagtggatccgagctcggtaccaagcttgatgcaggaattcgatat
caagcttatcgataccgtcgacctcgagggggggcccggtacccagcttttgttccctttagtgagggttaattgcgcgcttggcgtaatcatg
gtcatagctgtttcctgtgtgaaattgttatccgctcacaattccacacaacatacgagccggaagcataaagtgtaaagcctggggtgcctaa
tgagtgagctaactcacattaattgcgttgcgctcactgcccgctttccagtcgggaaacctgtcgtgccagctgcattaatgaatcggccaac
gcgcggggagaggcggtttgcgtattgggcgcatgcataaaaactgttgtaattcattaagcattctgccgacatggaagccatcacaaacg
gcatgatgaacctgaatcgccagcggcatcagcaccttgtcgccttgcgtataatatttgcccatggacgcacaccgtggaaacggatgaa
ggcacgaacccagttgacataagcctgttcggttcgtaaactgtaatgcaagtagcgtatgcgctcacgcaactggtccagaaccttgaccg
aacgcagcggtggtaacggcgcagtggcggttttcatggcttgttatgactgtttttttgtacagtctatgcctcgggcatccaagcagcaagc
gcgttacgccgtgggtcgatgtttgatgttatggagcagcaacgatgttacgcagcagcaacgatgttacgcagcagggcagtcgccctaa
aacaaagttaggtggctcaagtatgggcatcattcgcacatgtaggctcggccctgaccaagtcaaatccatgcgggctgctcttgatctttt
cggtcgtgagttcggagacgtagccacctactcccaacatcagccggactccgattacctcgggaacttgctccgtagtaagacattcatcgc
gcttgctgccttcgaccaagaagcggttgttggcgctctcgcggcttacgttctgcccaggtttgagcagccgcgtagtgagatctatatctat
gatctcgcagtctccggcgagcaccggaggcagggcattgccaccgcgctcatcaatctcctcaagcatgaggccaacgcgcttggtgct
tatgtgatctacgtgcaagcagattacggtgacgatcccgcagtggctctctatacaaagttgggcatacgggaagaagtgatgcactttgat
atcgacccaagtaccgccacctaacaattcgttcaagccgagatcggcttcccggccgcggagttgttcggtaaattgtcacaacgccgcc
aggtggcacttttcggggaaatgtgcgcgcccgcgttcctgctggcgctgggcctgtttctggcgctggacttcccgctgttccgtcagcag
ctttcgcccacggccttgatgatcgcggcggccttggcctgcatatcccgattcaacggccccagggcgtccagaacgggcttcaggcgc
tcccgaaggt (SEQ ID NO:6).

Abundance 280000
260000
240000
220000
200000
180000
160000
140000
120000
100000
80000
60000
40000
20000
Time-->
6.00 8.00 10.00 12.00 14.00 16.00 18.00 20.00 22.00 24.00 26.00

100000
80000
60000
40000
20000
Time-->
6.00 8.00 10.00 12.00 14.00 16.00 18.00 20.00 22.00 24.00 26.00

100000
80000
60000
40000
20000
Time-->
6.00 8.00 10.00 12.00 14.00 16.00 18.00 20.00 22.00 24.00 26.00

Figure 19A. Map of plasmid pDW34
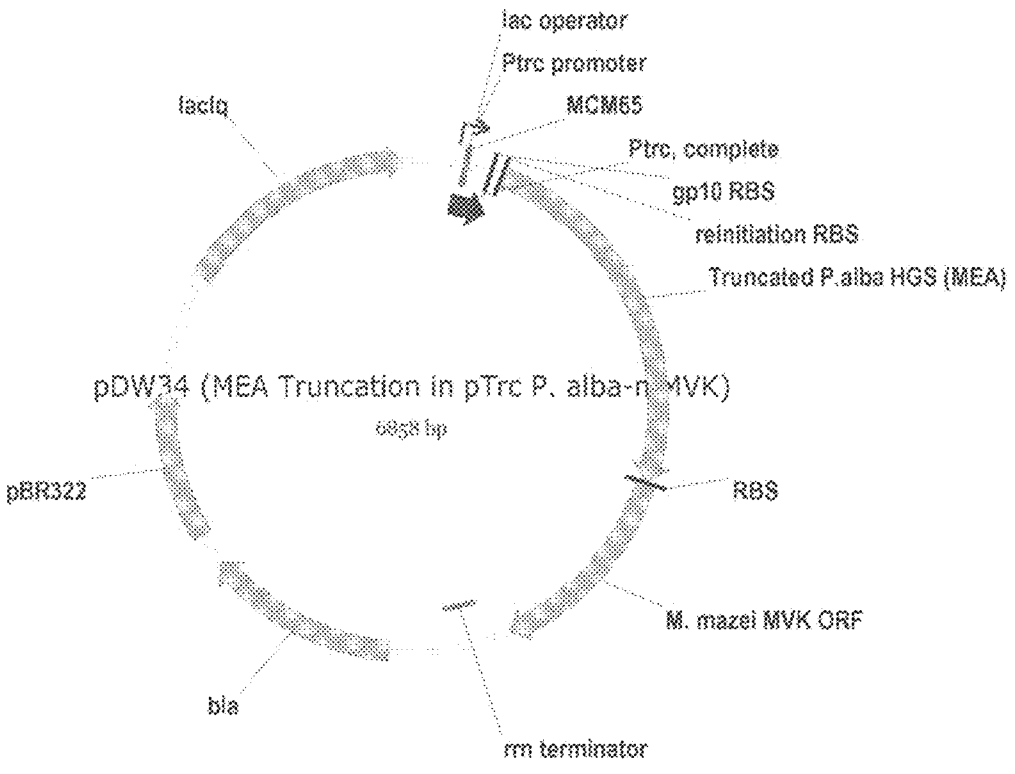

Figure 19B. Sequence of pDW34

5'- gttgacagcttatcatcgactgcacggtgcaccaatgcttctggcgtcaggcagccatcggaagctgtggtatggctgtgcaggtcgtaaat
cactgcataattcgtgtcgctcaaggcgcactcccgttctggataatgttttttgcgccgacatcataacggttctggcaaatattctgaaatgag
ctgttgacaattaatcatccggctcgtataatgtgtggaattgtgagcggataacaatttcacacaggaaacagcgccgctgagaaaaagcg
aagcggcactgctctttaacaatttatcagacaatctgtgtgggcactcgaccggaattatcgattaactttattattaaaaattaaagaggtatat
attaatgtatcgattaaataaggaggaataaaccatggaagctcgtcgttctgcgaactacgaacctaacagctgggactatgattacctgctg
tcctccgacacggacgagtccatcgaagtatacaaagacaaagcgaaaaagctggaagccgaagttcgtcgcgagattaataacgaaaaa
gcagaatttctgaccctgctggaactgattgacaacgtccagcgcctgggcctgggttaccgtttcgagtctgatatccgtggtgcgctggat
cgcttcgtttcctccggcggcttcgatgcggtaaccaagacttccctgcacggtacggcactgtctttccgtctgctgcgtcaacacggttttg
aggtttctcaggaagcgttcagcggcttcaaagaccaaaacggcaacttcctggagaacctgaaggaagatatcaaagctatcctgagcct
gtacgaggccagcttcctggctctggaaggcgaaaacatcctggacgaggcgaaggttttcgcaatctctcatctgaaagaactgtctgaag
aaaagatcggtaaagagctggcagaacaggtgaaccatgcactggaactgccactgcatcgccgtactcagcgtctggaagcagtatggt
ctatcgaggcctaccgtaaaaaggaggacgcgaatcaggttctgctggagctggcaattctggattacaacatgatccagtctgtataccag
cgtgatctgcgtgaaacgtcccgttggtggcgtcgtgtgggtctggcgaccaaactgcactttgctcgtgaccgcctgattgagagcttctac
tgggccgtgggtgtagcattcgaaccgcaatactccgactgccgtaactccgtcgcaaaaatgtttctttcgtaaccattatcgacgatatcta
cgatgtatacggcaccctggacgaactggagctgttactgatgcagttgagcgttgggacgtaaacgccatcaacgacctgccggattaca
tgaaactgtgctttctggctctgtataacactattaacgaaatcgcctacgacaacctgaaagataaaggtgagaacatcctgccgtatctgac
caaagcctgggctgacctgtgcaacgctttcctgcaagaagccaagtggctgtacaacaaatctactccgacctttgacgactacttcggca
acgcatggaaatcctcttctggcccgctgcaactggtgttcgcttacttcgctgtcgtgcagaacattaaaaaggaagagatcgaaaacctgc
aaaaataccatgacaccatctctcgtccttcccatatcttccgtctgtgcaatgacctggctagcgcgtctgcggaaattgcgcgtggtgaaac
cgcaaatagcgtttcttgttacatgcgcactaaaggtatctccgaagaactggctaccgaaagcgtgatgaatctgatcgatgaaacctggaa
aaagatgaacaaggaaaaactgggtggtagcctgttcgcgaaaccgttcgtggaaaccgcgatcaacctggcacgtcaatctcactgcact
tatcataacggcgacgcgcatacctctccggatgagctgacccgcaaacgcgttctgtctgtaatcactgaaccgattctgccgtttgaacgc
taactgcataaaggaggtaaaaaacatggtatcctgttctgcgccgggtaagatttacctgttcggtgaacacgccgtagtttatggcgaaa
ctgcaattgcgtgtgcggtggaactgcgtacccgtgttcgcgcggaactcaatgactctatcactattcagagccagatcggccgcaccggt
ctggatttcgaaaagcacccttatgtgtctgcggtaattgagaaaatgcgcaaatctattcctattaacggtgttttcttgaccgtcgattccgac
atcccggtgggctccggtctgggtagcagcgcagccgttactatcgcgtctattggtgcgctgaacgagctgttcggctttggcctcagcct
gcaagaaatcgctaaactgggccacgaaatcgaaattaaagtacagggtgccgcgtccccaaccgatacgtatgtttctaccttcggcggc
gtggttaccatcccggaacgtcgcaaactgaaaactccggactgcggcattgtgattggcgataccggcgtttctcctccaccaaagagtta
gtagctaacgtacgtcagctgcgcgaaagctacccggatttgatcgaaccgctgatgacctctattggcaaaatctctcgtatcggcgaaca

Figure 19C. Sequence of pDW34 actggttctgtctggcgactacgcatccatcggccgcctgatgaacgtcaaccagggtctcctggacgccctgggcgttaacatcttagaact
gagccagctgatctattccgctcgtgcggcaggtgcgtttggcgctaaaatcacgggcgctggcggcggtggctgtatggttgcgctgacc
gctccggaaaaatgcaaccaagtggcagaagcggtagcaggcgctggcggtaaagtgactatcactaaaccgaccgagcaaggtctga
aagtagattaaagtctagttaaagtttaaacggtctccagcttggctgttttggcggatgagagaagattttcagcctgatacagattaaatcag
aacgcagaagcggtctgataaaacagaatttgcctggcggcagtagcgcggtggtcccacctgaccccatgccgaactcagaagtgaaa
cgccgtagcgccgatggtagtgtggggtctccccatgcgagagtagggaactgccaggcatcaaataaaacgaaaggctcagtcgaaag
actgggcctttcgttttatctgttgtttgtcggtgaacgctctcctgagtaggacaaatccgccgggagcggatttgaacgttgcgaagcaacg
gcccggagggtggcgggcaggacgcccgccataaactgccaggcatcaaattaagcagaaggccatcctgacggatggcctttttgcgtt
tctacaaactctttttgtttatttttctaaatacattcaaatatgtatccgctcatgagacaataaccctgataaatgcttcaataatattgaaaaagga
agagtatgagtattcaacatttccgtgtcgcccttattcccttttttgcggcattttgccttcctgtttttgctcacccagaaacgctggtgaaagta
aaagatgctgaagatcagttgggtgcacgagtgggttacatcgaactggatctcaacagcggtaagatccttgagagttttcgccccgaaga
acgttttccaatgatgagcacttttaaagttctgctatgtggcgcggtattatcccgtgttgacgccgggcaagagcaactcggtcgccgcata
cactattctcagaatgacttggttgagtactcaccagtcacagaaaagcatcttacggatggcatgacagtaagagaattatgcagtgctgcc
ataaccatgagtgataacactgcggccaacttacttctgacaacgatcggaggaccgaaggagctaaccgcttttttgcacaacatggggga
tcatgtaactcgccttgatcgttgggaaccggagctgaatgaagccataccaaacgacgagcgtgacaccacgatgcctgtagcaatggca
acaacgttgcgcaaactattaactggcgaactacttactctagcttcccggcaacaattaatagactggatggaggcggataaagttgcagg
accacttctgcgctcggcccttccggctggctggtttattgctgataaatctggagccggtgagcgtgggtctcgcggtatcattgcagcact
ggggccagatggtaagccctcccgtatcgtagttatctacacgacggggagtcaggcaactatggatgaacgaaatagacagatcgctga
gataggtgcctcactgattaagcattggtaactgtcagaccaagtttactcatatatactttagattgatttaaaacttcatttttaatttaaaaggat
ctaggtgaagatcctttttgataatctcatgaccaaaatcccttaacgtgagttttcgttccactgagcgtcagaccccgtagaaaagatcaaag
gatcttcttgagatcctttttttctgcgcgtaatctgctgcttgcaaacaaaaaaaccaccgctaccagcggtggtttgtttgccggatcaagagc
taccaactctttttccgaaggtaactggcttcagcagagcgcagataccaaatactgtccttctagtgtagccgtagttaggccaccacttcaa
gaactctgtagcaccgcctacatacctcgctctgctaatcctgttaccagtggctgctgccagtggcgataagtcgtgtcttaccgggttggac
tcaagacgatagttaccggataaggcgcagcggtcgggctgaacggggggttcgtgcacacagcccagcttggagcgaacgacctaca
ccgaactgagatacctacagcgtgagctatgagaaagcgccacgcttcccgaagggagaaaggcggacaggtatccggtaagcggcag
ggtcggaacaggagagcgcacgagggagcttccagggggaaacgcctggtatctttatagtcctgtcgggtttcgccacctctgacttgag
cgtcgatttttgtgatgctcgtcaggggggcggagcctatggaaaaacgccagcaacgcggcctttttacggttcctggccttttgctggcctt
ttgctcacatgttctttcctgcgttatcccctgattctgtggataaccgtattaccgcctttgagtgagctgataccgctcgccgcagccgaacga
ccgagcgcagcgagtcagtgagcgaggaagcggaagagcgcctgatgcggtattttctccttacgcatctgtgcggtatttcacaccgcat
atggtgcactctcagtacaatctgctctgatgccgcatagttaagccagtatacactccgctatcgctacgtgactgggtcatggctgcgcccc

Figure 19D. Sequence of pDW34 gacacccgccaacacccgctgacgcgccctgacgggcttgtctgctcccggcatccgcttacagacaagctgtgaccgtctccgggagct
gcatgtgtcagaggttttcaccgtcatcaccgaaacgcgcgaggcagcagatcaattcgcgcgcgaaggcgaagcggcatgcatttacgtt
gacaccatcgaatggtgcaaaacctttcgcggtatggcatgatagcgcccggaagagagtcaattcagggtggtgaatgtgaaaccagtaa
cgttatacgatgtcgcagagtatgccggtgtctcttatcagaccgtttcccgcgtggtgaaccaggccagccacgtttctgcgaaaacgcgg
gaaaaagtggaagcggcgatggcggagctgaattacattcccaaccgcgtggcacaacaactggcgggcaaacagtcgttgctgattgg
cgttgccacctccagtctggccctgcacgcgccgtcgcaaattgtcgcggcgattaaatctcgcgccgatcaactgggtgccagcgtggtg
gtgtcgatggtagaacgaagcggcgtcgaagcctgtaaagcggcggtgcacaatcttctcgcgcaacgcgtcagtgggctgatcattaact
atccgctggatgaccaggatgccattgctgtggaagctgcctgcactaatgttccggcgttatttcttgatgtctctgaccagacacccatcaa
cagtattattttctcccatgaagacggtacgcgactgggcgtggagcatctggtcgcattgggtcaccagcaaatcgcgctgttagcgggcc
cattaagttctgtctcggcgcgtctgcgtctggctggctggcataaatatctcactcgcaatcaaattcagccgatagcggaacgggaaggc
gactggagtgccatgtccggttttcaacaaaccatgcaaatgctgaatgagggcatcgttcccactgcgatgctggttgccaacgatcagat
ggcgctgggcgcaatgcgcgccattaccgagtccgggctgcgcgttggtgcggatatctcggtagtgggatacgacgataccgaagaca
gctcatgttatatcccgccgtcaaccaccatcaaacaggattttcgcctgctggggcaaaccagcgtggaccgcttgctgcaactctctcagg
gccaggcggtgaagggcaatcagctgttgcccgtctcactggtgaaaagaaaaaccaccctggcgcccaatacgcaaaccgcctctccc
cgcgcgttggccgattcattaatgcagctggcacgacaggtttcccgactggaaagcgggcagtgagcgcaacgcaattaatgtgagttag
cgcgaattgatctg -3' (SEQ ID NO:7)

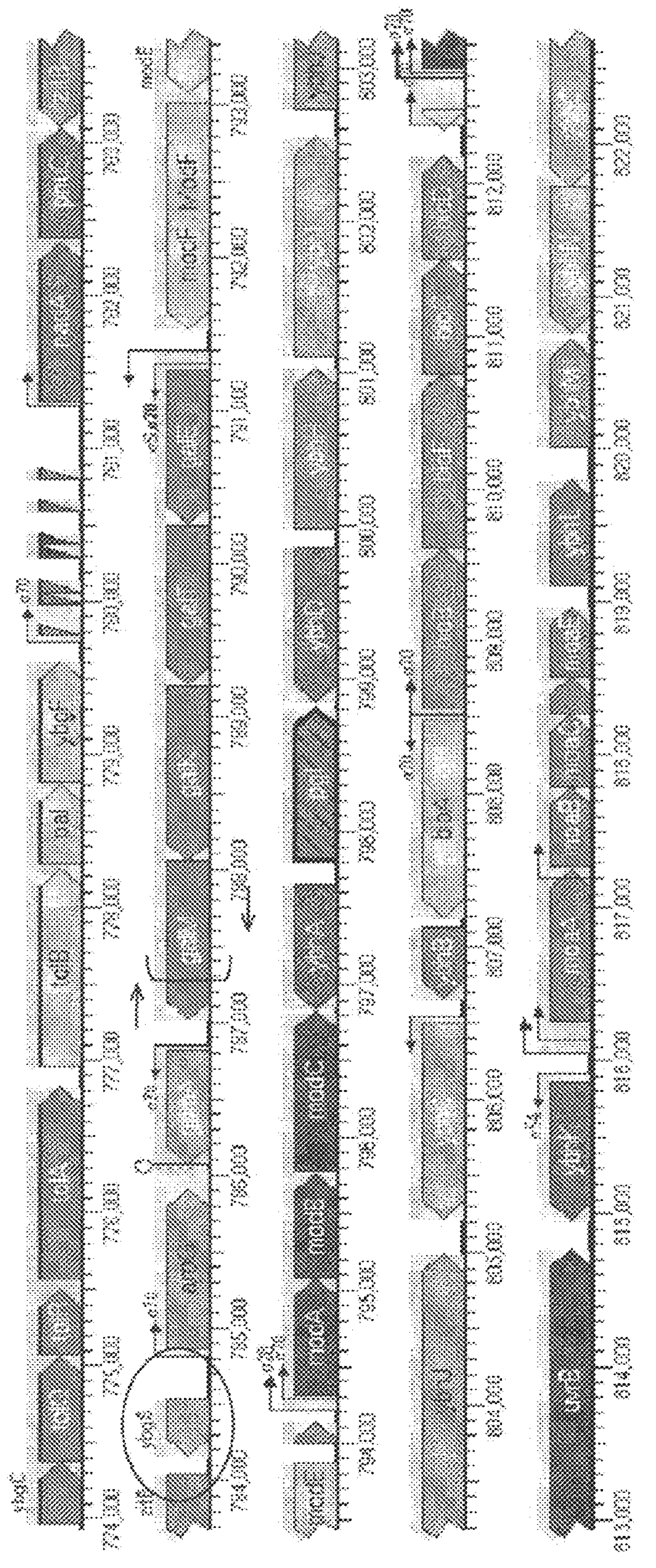
Figure 20. Chromosomal organization of *Escherichia coli* K-12 MG1655 around *pgl*.

Figure 34A. Map of plasmid pDW15.

Figure 34B. Sequence of plasmid pDW15.

5'-
accttcgggagcgcctgaagcccgttctggacgccctggggccgttgaatcgggatatgcaggccaaggccgccgcgatcatcaaggcc
gtgggcgaaaagctgctgacggaacagcgggaagtccagcgccagaaacaggcccagcgccagcaggaacgcgggcgcgcacattt
ccccgaaaagtgccacctggcggcgttgtgacaatttaccgaacaactccgcggccgggaagccgatctcggcttgaacgaattgttaggt
ggcggtacttgggtcgatatcaaagtgcatcacttcttcccgtatgcccaactttgtatagagagccactgcgggatcgtcaccgtaatctgctt
gcacgtagatcacataagcaccaagcgcgttggcctcatgcttgaggagattgatgagcgcggtggcaatgccctgcctccggtgctcgcc
ggagactgcgagatcatagatatagatctcactacgcggctgctcaaacctgggcagaacgtaagccgcgagagcgccaacaaccgcttc
ttggtcgaaggcagcaagcgcgatgaatgtcttactacggagcaagttcccgaggtaatcggagtccggctgatgttgggagtaggtggct
acgtctccgaactcacgaccgaaaagatcaagagcagcccgcatggatttgacttggtcagggccgagcctacatgtgcgaatgatgccc
atacttgagccacctaactttgttttagggcgactgccctgctgcgtaacatcgttgctgctgcgtaacatcgttgctgctccataacatcaaac
atcgacccacggcgtaacgcgcttgctgcttggatgcccgaggcatagactgtacaaaaaaacagtcataacaagccatgaaaaccgcca
ctgcgccgttaccaccgctgcgttcggtcaaggttctggaccagttgcgtgagcgcatacgctacttgcattacagtttacgaaccgaacag
gcttatgtcaactgggttcgtgccttcatccgtttccacggtgtgcgtccatgggcaaatattatacgcaaggcgacaaggtgctgatgccgct
ggcgattcaggttcatcatgccgtttgtgatggcttccatgtcggcagaatgcttaatgaattacaacagtttttatgcatgcgcccaatacgca
aaccgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaatttca
cacaggaaacagctatgaccatgattacgccaagcgcgcaattaaccctcactaaagggaacaaaagctgggtaccgggccccccctcg
agctgttgacaattaatcatccggctcgtataatgtgtggaattgtgagcggataacaatttcacacaggaaacagcgccgctgagaaaaag
cgaagcggcactgctctttaacaatttatcagacaatctgtgtgggcactcgaccggaattatcgattaactttattattaaaaattaaagaggta
tatattaatgtatcgattaaataaggaggaataaaccatggatccgagctcaggaggtaaaaaacatgaaaacagtagttattattgatgcatt
acgaacaccaattggaaaatataaaggcagcttaagtcaagtaagtgccgtagacttaggaacacatgttacaacacaactttaaaaagac
attccactatttctgaagaaattgatcaagtaatctttggaaatgttttacaagctggaaatggccaaaatcccgcacgacaaatagcaataaac
agcggtttgtctcatgaaattcccgcaatgacggttaatgaggtctgcggatcaggaatgaaggccgttattttggcgaaacaattgattcaatt
aggagaagcggaagttttaaatgctggcgggattgagaatatgtcccaagcacctaaattacaacgttttaattacgaaacagaaagctacga
tgcgcctttttctagtatgatgtatgatggattaacggatgccttagtggtcaggcaatgggcttaactgctgaaaatgtggccgaaaagtatc
atgtaactagagaagagcaagatcaatttctgtacattcacaattaaaagcagctcaagcacaagcagaaggatatttcgctgacgaaata
gccccattagaagtatcaggaacgcttgtggagaaagatgaagggattcgccctaattcgagcgttgagaagctaggaacgcttaaaacag
tttttaaagaagacggtactgtaacagcagggaatgcatcaaccattaatgatggggcttctgctttgattattgcttcacaagaatatgccgaa
gcacacggtcttccttatttagctattattcgagacagtgtggaagtcggtattgatccagcctatatgggaatttcgccgattaaagccattcaa
aaactgttagcgcgcaatcaacttactacggaagaaattgatctgtatgaaatcaacgaagcatttgcagcaacttcaatcgtggtccaaaga
gaactggctttaccagaggaaaaggtcaacatttatggtggcggtatttcattaggtcatgcgattggtgccacaggtgctcgtttattaacga
gtttaagtatcaattaaatcaaaaagaaaagaaatatggagtggcttctttatgtatcggcggtggcttaggactcgctatgctactagagaga
cctcagcaaaaaaaaaacagccgattttatcaaatgagtcctgaggaacgcctggcttctcttcttaatgaaggccagatttctgctgatacaa
aaaaagaatttgaaaatacggctttatcttcgcagattgccaatcatatgattgaaaatcaaatcagtgaaacagaagtgccgatgggcgttgg
cttacatttaacagtggacgaaactgattatttggtaccaatggcgacagaagagccctcagttattgcggctttgagtaatggtgcaaaaata
gcacaaggatttaaaacagtgaatcaacaacgcttaatgcgtggacaaatcgttttttacgatgttgcagatcccgagtcattgattgataaact
acaagtaagagaagcggaagtttttcaacaagcagagttaagttatccatctatcgttaaacggggcggcggcttaagagatttgcaatatcg
tactttgatgaatcatttgtatctgtcgacttttagtagatgttaaggatgcaatgggggcaaatatcgttaacgctatgttggaaggtgtggcc
gagttgttccgtgaatggtttgcggagcaaaagattttattcagtattttaagtaatttatgccacggagtcggttgttacgatgaaaacggctattc
cagtttcacgtttaagtaaggggagcaatggccgggaaattgctgaaaaaattgtttttagcttcacgctatgcttcattagatccttatcgggca
gtcacgcataacaaaggaatcatgaatggcattgaagctgtagttttagctacaggaaatgatacacgcgctgttagcgcttctgtcatgcttt
tgcgggtgaaggaaggtcgctaccaaggcttgactagttggacgctggatggcgaacaactaattggtgaaatttcagttccgcttgcttagc
cacggttggcggtgccacaaaagtcttacctaaatctcaagcagctgctgatttgttagcagtgacggatgcaaaagaactaagtcgagtagt
agcggctgttggtttggcacaaaatttagcggcgttacgggccttagtctctgaaggaattcaaaaaggacacatggctctacaagcacgttc Figure 34C. Sequence of plasmid pDW15.

Figure 34C:
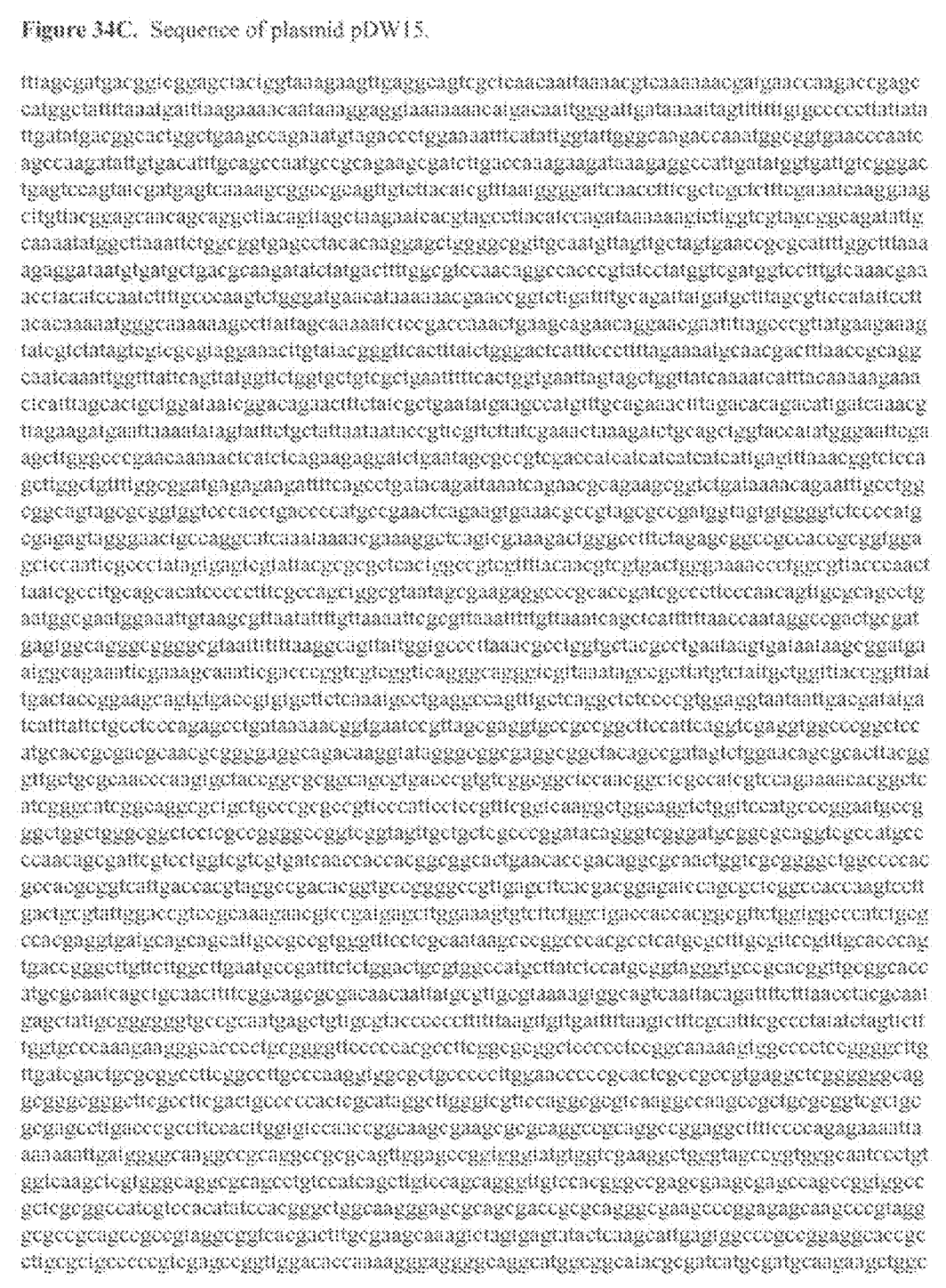

tttagcgatgacggtcggagctactggtaaagaagttgaggcagtcgctcaacaattaaacgtcaaaaaacgatgaaccaagaccgagc
catggctatttttaaatgatttaagaaaacaataaaggaggtaaaaaaacatgacaattgggattgataaaattagttttttgtgcccccttattata
ttgatatgacggcactggctgaagccagaaatgtagaccctggaaaatttcatattggtattgggcaagaccaaatggcggtgaaccccaatc
agccaagatattgtgacatttgcagccaatgccgcagaagcgatcttgaccaaagaagataaagaggccattgatatggtgattgtcgggac
tgagtccagtatcgatgagtcaaaagcggccgcagttgtcttacatcgtttaatggggattcaacctttcgctcgctctttcgaaatcaaggaag
cttgttacggagcaacagcaggcttacagttagctaagaatcacgtagccttacatccagataaaaagtctggtcgtagcggcagatattg
caaaatatggcttaaattctggcggtgagcctacacaaggagctgggcggttgcaatgttagttgctagtgaaccgcgcatttggctttaaa
agaggataatgtgatgctgacgcaagatatctatgacttttggcgtccaacaggccacccgtatcctatggtcgatggtcctttgtcaaacgaa
acctacatccaatctttgcccaagtctgggatgaacataaaaaacgaaccggtctgatttgcagattatgatgctttagcgttccatattcctt
acacaaaaatgggcaaaaaagccttattagcaaaaatctccgaccaaactgaagcagaacaggaacgtatttagcccgttatgaagaaag
tatcgtctatagtcgtcgcgtaggaaacttgtatacgggttcactttatctgggactcatttccctttagaaaatgcaacgactttaaccgcagg
caatcaaattggtttattcagttatggttctggtgctgtcgctgaatttttcactggtgaattagtagctggttatcaaaatcatttacaaaaagaaa
ctcatttagcactgctggataatcggacagaactttctatcgctgaaatatgaagccatgtttgcagaaacttagacacagacattgatcaaacg
ttagaagatgaatttaaaatatagtatttctgctattaataatacgttcgttcttatcgaaactaaagatctgcagctggtaccatatgggaattcga
agcttgggcccgaacaaaaactcatctcagaagaggatctgaatagcgccgtcgaccatcatcatcatcatcattgagtttaaacggtctcca
gcttggctgttttggcggatgagagaagattttcagcctgatacagattaaatcagaacgcagaagcggtctgataaaacagaatttgcctgg
cggcagtagcgcggtggtcccacctgaccccatgccgaactcagaagtgaaacgccgtagcgccgatggtagtgtggggtctccccatg
cgagagtagggaactgccaggcatcaaataaaacgaaaggctcagtcgaaagactgggcctttctagagcggccgccaccgcggtgga
gctccaattcgccctatagtgagtcgtattacgcgcgctcactggccgtcgttttacaacgtcgtgactgggaaaaccctggcgttacccaact
taatcgccttgcagcacatccccctttcgccagctggcgtaatagcgaagaggcccgcaccgatcgcccttcccaacagttgcgcagcctg
aatggcgaatggaaattgtaagcgttaatattttgttaaaattcgcgttaaatttttgttaaatcagctcattttttaaccaataggccgactgcgat
gagtggcagggcggggcgtaatttttttaaggcagttattggtgcccttaaacgcctggtgctacgcctgaataagtgataataagcggatga
atggcagaaattcgaaagcaaattcgacccggtcgtcggttcagggcagggtcgttaaatagccgcttatgtctattgctggtttaccggttat
tgactaccggaagcagtgtgaccgtgtgcttctcaaatgcctgaggccagtttgctcaggctctccccgtggaggtaataattgacgatatga
tcatttattctgcctcccagagcctgataaaaacggtgaatccgttagcgaggtgccgccggcttccattcaggtcgaggtggcccggctcc
atgcaccgcgacgcaacgcggggaggcagacaaggtatagggcggcgaggcggctacagccgatagtctggaacagcgcacttacgg
gttgctgcgcaacccaagtgctaccggcgcggcagcgtgacccgtgtcggcggctccaacggctcgccatcgtccagaaaacacggctc
atcgggcatcggcaggcgctgctgcccgcgccgttcccattcctccgtttcggtcaaggctggcaggtctggttccatgcccggaatgccg
ggctggctgggcggctcctcgccggggccggtcggtagttgctgctcgcccggatacagggtcgggatgcggcgcaggtcgccatgcc
ccaacagcgattcgtcctggtcgtcgtgatcaaccaccacggcggcactgaacaccgacaggcgcaactggtcgcggggctggccccac
gccacgcggtcattgaccacgtaggccgacacggtgccggggccgttgagcttcacgacggagatccagcgctcggccaccaagtcctt
gactgcgtattggaccgtccgcaaagaacgtccgatgagcttggaaagtgtcttctggctgaccaccacggcgttctggtggcccatctgcg
ccacgaggtgatgcagcagcattgccgccgtgggtttcctcgcaataagcccggcccacgcctcatgcgcttgcgttccgtttgcacccag
tgaccgggcttgttcttggcttgaatgccgatttctctggactgcgtggccatgcttatctccatgcggtagggtgccgcacggttgcggcacc
atgcgcaatcagctgcaactttcggcagcgcgacaacaattatgcgttgcgtaaaagtggcagtcaattacagattttctttaacctacgcaat
gagctattgcggggggtgccgcaatgagctgttgcgtacccccctttttaagttgttgatttttaagtctttcgcatttcgccctatatctagttctt
tggtgcccaaagaagggcacccctgcggggttcccccacgccttcggcgcggctccccctccggcaaaaagtggcccctccggggcttg
ttgatcgactgcgcggccttcggccttgcccaaggtggcgctgcccccttggaaccccgcactcgccgccgtgaggctcggggggcag
gcgggcgggcttcgccttcgactgcccccactcgcataggcttgggtcgttccaggcgcgtcaaggccaagccgctgcgcggtcgctgc
gcgagccttgacccgccttccacttggtgtccaaccggcaagcgaagcgcgcaggccgcaggccggaggcttttccccagagaaaatta
aaaaaattgatggggcaaggccgcaggccgcgcagttggagccggtggtatgtggtcgaaggctgggtagccggtggcaatccctgt
ggtcaagctcgtgggcaggcgcagcctgtccatcagcttgtccagcagggttgtccacgggccgagcgaagcgagccagccggtggcc
gctcgcggccatcgtccacatatccacgggctggcaagggagcgcagcgaccgcgcagggcgaagcccggagagcaagcccgtagg
gcgccgcagccgccgtaggcggtcacgactttgcgaagcaaagtctagtgagtatactcaagcattgagtggcccgccggaggcaccgc
cttgcgctgcccccgtcgagccggttggacaccaaaagggaggggcaggcatggcggcatacgcgatcatgcgatgcaagaagctggc

Figure 34D. Sequence of plasmid pDW15.

gaaaatgggcaacgtggcggccagtctcaagcacgcctaccgcgagcgcgagacgcccaacgctgacgccagcaggacgccagaga
acgagcactgggcggccagcagcaccgatgaagcgatgggccgactgcgcgagttgctgccagagaagcggcgcaaggacgctggt
tggcggtcgagtacgtcatgacggccagcccggaatggtggaagtcggccagccaagaacagcaggcggcgttcttcgagaaggcgca
caagtggctggcggacaagtacggggcggatcgcatcgtgacggccagcatccaccgtgacgaaaccagcccgcacatgaccgcgttc
gtggtgccgctgacgcaggacggcaggctgtcggccaaggagttcatcggcaacaaagcgcagatgacccgcgaccagaccacgttg
cggccgctgtggccgatctagggctgcaacggggcatcgagggcagcaaggcacgtcacacgcgcattcaggcgttctacgaggccct
ggagcggccaccagtgggccacgtcaccatcagcccgcaagcggtcgagccacgcgcctatgcaccgcagggattggccgaaaagct
gggaatctcaaagcgcgttgagacgcccggaagccgtggccgacccggctgacaaaagcggttcggcaggggtatgagcctgccctacag
gccgccgcaggagcgcgtgagatgcgcaagaaggccgatcaagcccaagagacggcccgag-3'
(SEQ ID NO:10)

Figure 40A.: Amino acid sequence of PGL from *E. coli* K12 MG1655 (SEQ ID NO:11).

MKQTVYIASPESQQIHVWNLNHEGALTLTQVVDVPGQVQPMVVSPDKRYLYVGVRPEF
RVLAYRIAPDDGALTFAAESALPGSPTHISTDHQGQFVFVGSYNAGNVSVTRLEDGLPV
GVVDVVEGLDGCHSANISPDNRTLWVPALKQDRICLFTVSDDGHLVAQDPAEVTTVEG
AGPRHMVFHPNEQYAYCVNELNSSVDVWELKDPHGNIECVQTLDMMPENFSDTRWAA
DIHITPDGRHLYACDRTASLITVFSVSEDGSVLSKEGFQPTETQPRGFNVDHSGKYLIAAG
QKSHHISVYEIVGEQGLLHEKGRYAVGQGPMWVVVNAH

Figure 40B. Amino acid sequence of PGL from *P. aeruginosa* (SEQ ID NO:12).

MAISELKLPAGVGLQVWGSAAEQARGLAAEVAGRLRSALAEQGQALLVVSGGRSPVA
FLEALSEEPLDWSRITVSLADERWVPESHADSNAGLVRRHLLRGEAAKARFIGLYQPAA
SLEEAAELADHHLHELPLPIDVLVLGMGDDGHTASLFPNSPGLDLAMDPQGTRRCLPM
WAPSVPHQRLTLPRAVLAAAKVQLLAIQGQSKLATLNAALAVEDERRMPVRAFLRAPL
TIHWYP

Figure 40C. Amino acid sequence of PGL from *S. cerevisiae* (SEQ ID NO:13).

MVTVGVFSERASLTHQLGEFIVKKQDEALQKKSDFKVSVSGGSLIDALYESLVADESLSS
RVQWSKWQIYFSDERIVPLTDADSNYGAFKRAVLDKLPSTSQPNVYPMDESLIGSDAES
NNKIAAEYERIVPQVLDLVLLGCGPDGHTCSLFPGETHRYLLNETTKRVAWCHDSPKPP
SDRITFTLPVLKDAKALCFVAEGSSKQNIMHEIFDLKNDQLPTALVNKLFGEKTSWFVNE
EAFGKVQTKTF

Identity 9.7%; Similarity 17.8%
Vector Nti Align X

*E. coli* MG1655 pgl
*Pseudomonas aeruginosa* pgl

SEQUENCE LISTING

<160> NUMBER OF SEQ ID NOS: 66

<210> SEQ ID NO 1
<211> LENGTH: 6957
<212> TYPE: DNA
<213> ORGANISM: Artificial Sequence
<220> FEATURE:
<223> OTHER INFORMATION: Synthetic Construct

<400> SEQUENCE: 1

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
```

-continued

```
cgtcgatttt tgtgatgctc gtcagggggg cggagcctat ggaaaaacgc cagcaacgcg   2100
gcctttttac ggttcctggc cttttgctgg ccttttgctc acatgttctt tcctgcgtta   2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
```

-continued

```
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatctc gatcccgcga   4980
aattaatacg actcactata ggggaattgt gagcggataa caattcccct ctagaaataa   5040
ttttgtttaa ctttaagaag gagatataca tatgcgttgt agcgtgtcca ccgaaaatgt   5100
gtctttcacc gaaactgaaa ccgaagctcg tcgttctgcg aactacgaac ctaacagctg   5160
ggactatgat tacctgctgt cctccgacac ggacgagtcc atcgaagtat acaaagacaa   5220
agcgaaaaag ctggaagccg aagttcgtcg cgagattaat aacgaaaaag cagaatttct   5280
gaccctgctg gaactgattg acaacgtcca gcgcctgggc ctgggttacc gtttcgagtc   5340
tgatatccgt ggtgcgctgg atcgcttcgt ttcctccggc ggcttcgatg cggtaaccaa   5400
gacttccctg cacggtacgg cactgtcttt ccgtctgctg cgtcaacacg gttttgaggt   5460
ttctcaggaa gcgttcagcg gcttcaaaga ccaaaacggc aacttcctgg agaacctgaa   5520
ggaagatatc aaagctatcc tgagcctgta cgaggccagc ttcctggctc tggaaggcga   5580
aaacatcctg gacgaggcga aggttttcgc aatctctcat ctgaaagaac tgtctgaaga   5640
aaagatcggt aaagagctgg cagaacaggt gaaccatgca ctggaactgc cactgcatcg   5700
ccgtactcag cgtctggaag cagtatggtc tatcgaggcc taccgtaaaa aggaggacgc   5760
gaatcaggtt ctgctggagc tggcaattct ggattacaac atgatccagt ctgtatacca   5820
gcgtgatctg cgtgaaacgt cccgttggtg gcgtcgtgtg ggtctggcga ccaaactgca   5880
ctttgctcgt gaccgcctga ttgagagctt ctactgggcc gtgggtgtag cattcgaacc   5940
gcaatactcc gactgccgta actccgtcgc aaaaatgttt tctttcgtaa ccattatcga   6000
cgatatctac gatgtatacg gcaccctgga cgaactggag ctgtttactg atgcagttga   6060
gcgttgggac gtaaacgcca tcaacgacct gccggattac atgaaactgt gctttctggc   6120
tctgtataac actattaacg aaatcgccta cgacaacctg aaagataaag gtgagaacat   6180
cctgccgtat ctgaccaaag cctgggctga cctgtgcaac gctttcctgc aagaagccaa   6240
gtggctgtac aacaaatcta ctccgacctt tgacgactac ttcggcaacg catggaaatc   6300
ctcttctggc ccgctgcaac tggtgttcgc ttacttcgct gtcgtgcaga acattaaaaa   6360
ggaagagatc gaaaacctgc aaaaatacca tgacaccatc tctcgtcctt cccatatctt   6420
ccgtctgtgc aatgacctgg ctagcgcgtc tgcggaaatt gcgcgtggtg aaaccgcaaa   6480
tagcgtttct tgttacatgc gcactaaagg tatctccgaa gaactggcta ccgaaagcgt   6540
gatgaatctg atcgatgaaa cctggaaaaa gatgaacaag gaaaaactgg gtggtagcct   6600
gttcgcgaaa ccgttcgtgg aaaccgcgat caacctggca cgtcaatctc actgcactta   6660
tcataacggc gacgcgcata cctctccgga tgagctgacc cgcaaacgcg ttctgtctgt   6720
aatcactgaa ccgattctgc cgtttgaacg ctaaggatcc gaattcgagc tccgtcgaca   6780
```

agcttgcggc cgcactcgag caccaccacc accaccactg agatccggct gctaacaaag 6840
cccgaaagga agctgagttg gctgctgcca ccgctgagca ataactagca taaccccttg 6900
gggcctctaa acgggtcttg aggggttttt tgctgaaagg aggaactata tccggat 6957

<210> SEQ ID NO 2
<211> LENGTH: 6068
<212> TYPE: DNA
<213> ORGANISM: Artificial Sequence
<220> FEATURE:
<223> OTHER INFORMATION: Synthetic Construct

<400> SEQUENCE: 2
gtttgacagc ttatcatcga ctgcacggtg caccaatgct tctggcgtca ggcagccatc 60
ggaagctgtg gtatggctgt gcaggtcgta aatcactgca taattcgtgt cgctcaaggc 120
gcactcccgt tctggataat gtttttttgcg ccgacatcat aacggttctg gcaaatattc 180
tgaaatgagc tgttgacaat taatcatccg gctcgtataa tgtgtggaat tgtgagcgga 240
taacaatttc acacaggaaa cagcgccgct gagaaaaagc gaagcggcac tgctctttaa 300
caatttatca gacaatctgt gtgggcactc gaccggaatt atcgattaac tttattatta 360
aaaattaaag aggtatatat taatgtatcg attaaataag gaggaataaa ccatgagatg 420
tagcgtgtcc accgaaaatg tgtctttcac cgaaactgaa accgaagctc gtcgttctgc 480
gaactacgaa cctaacagct gggactatga ttacctgctg tcctccgaca cggacgagtc 540
catcgaagta tacaaagaca aagcgaaaaa gctggaagcc gaagttcgtc gcgagattaa 600
taacgaaaaa gcagaatttc tgaccctgct ggaactgatt gacaacgtcc agcgcctggg 660
cctgggttac cgtttcgagt ctgatatccg tggtgcgctg gatcgcttcg tttcctccgg 720
cggcttcgat gcggtaacca agacttccct gcacggtacg gcactgtctt tccgtctgct 780
gcgtcaacac ggttttgagg tttctcagga agcgttcagc ggcttcaaag accaaaacgg 840
caacttcctg gagaacctga aggaagatat caaagctatc ctgagcctgt acgaggccag 900
cttcctggct ctggaaggcg aaaacatcct ggacgaggcg aaggttttcg caatctctca 960
tctgaaagaa ctgtctgaag aaaagatcgg taaagagctg gcagaacagg tgaaccatgc 1020
actggaactg ccactgcatc gccgtactca gcgtctggaa gcagtatggt ctatcgaggc 1080
ctaccgtaaa aaggaggacg cgaatcaggt tctgctggag ctggcaattc tggattacaa 1140
catgatccag tctgtatacc agcgtgatct gcgtgaaacg tcccgttggt ggcgtcgtgt 1200
gggtctggcg accaaactgc actttgctcg tgaccgcctg attgagagct tctactgggc 1260
cgtgggtgta gcattcgaac cgcaatactc cgactgccgt aactccgtcg caaaaatgtt 1320
ttctttcgta accattatcg acgatatcta cgatgtatac ggcaccctgg acgaactgga 1380
gctgtttact gatgcagttg agcgttggga cgtaaacgcc atcaacgacc tgccggatta 1440
catgaaactg tgctttctgg ctctgtataa cactattaac gaaatcgcct acgacaacct 1500
gaaagataaa ggtgagaaca tcctgccgta tctgaccaaa gcctgggctg acctgtgcaa 1560
cgctttcctg caagaagcca agtggctgta caacaaatct actccgacct ttgacgacta 1620
cttcggcaac gcatggaaat cctcttctgg cccgctgcaa ctggtgttcg cttacttcgc 1680
tgtcgtgcag aacattaaaa aggaagagat cgaaaacctg caaaaatacc atgacaccat 1740
ctctcgtcct tcccatatct tccgtctgtg caatgacctg gctagcgcgt ctgcggaaat 1800
tgcgcgtggt gaaaccgcaa atagcgtttc ttgttacatg cgcactaaag gtatctccga 1860

-continued

```
agaactggct accgaaagcg tgatgaatct gatcgatgaa acctggaaaa agatgaacaa   1920
ggaaaaactg ggtggtagcc tgttcgcgaa accgttcgtg gaaaccgcga tcaacctggc   1980
acgtcaatct cactgcactt atcataacgg cgacgcgcat acctctccgg atgagctgac   2040
ccgcaaacgc gttctgtctg taatcactga accgattctg ccgtttgaac gctaactgca   2100
gctggtacca tatgggaatt cgaagctttc tagaacaaaa actcatctca gaagaggatc   2160
tgaatagcgc cgtcgaccat catcatcatc atcattgagt ttaaacggtc tccagcttgg   2220
ctgttttggc ggatgagaga agattttcag cctgatacag attaaatcag aacgcagaag   2280
cggtctgata aaacagaatt tgcctggcgg cagtagcgcg gtggtcccac ctgaccccat   2340
gccgaactca gaagtgaaac gccgtagcgc cgatggtagt gtggggtctc cccatgcgag   2400
agtagggaac tgccaggcat caaataaaac gaaaggctca gtcgaaagac tgggcctttc   2460
gttttatctg ttgtttgtcg gtgaacgctc tcctgagtag gacaaatccg ccgggagcgg   2520
atttgaacgt tgcgaagcaa cggcccggag ggtggcgggc aggacgcccg ccataaactg   2580
ccaggcatca aattaagcag aaggccatcc tgacggatgg cctttttgcg tttctacaaa   2640
ctctttttgt ttatttttct aaatacattc aaatatgtat ccgctcatga gacaataacc   2700
ctgataaatg cttcaataat attgaaaaag gaagagtatg agtattcaac atttccgtgt   2760
cgcccttatt cccttttttg cggcattttg ccttcctgtt tttgctcacc cagaaacgct   2820
ggtgaaagta aaagatgctg aagatcagtt gggtgcacga gtgggttaca tcgaactgga   2880
tctcaacagc ggtaagatcc ttgagagttt tcgccccgaa gaacgttttc caatgatgag   2940
cacttttaaa gttctgctat gtggcgcggt attatcccgt gttgacgccg ggcaagagca   3000
actcggtcgc cgcatacact attctcagaa tgacttggtt gagtactcac cagtcacaga   3060
aaagcatctt acggatggca tgacagtaag agaattatgc agtgctgcca taaccatgag   3120
tgataacact gcggccaact tacttctgac aacgatcgga ggaccgaagg agctaaccgc   3180
ttttttgcac aacatggggg atcatgtaac tcgccttgat cgttgggaac cggagctgaa   3240
tgaagccata ccaaacgacg agcgtgacac cacgatgcct gtagcaatgg caacaacgtt   3300
gcgcaaacta ttaactggcg aactacttac tctagcttcc cggcaacaat taatagactg   3360
gatggaggcg gataaagttg caggaccact tctgcgctcg gcccttccgg ctggctggtt   3420
tattgctgat aaatctggag ccggtgagcg tgggtctcgc ggtatcattg cagcactggg   3480
gccagatggt aagccctccc gtatcgtagt tatctacacg acggggagtc aggcaactat   3540
ggatgaacga aatagacaga tcgctgagat aggtgcctca ctgattaagc attggtaact   3600
gtcagaccaa gtttactcat atatacttta gattgattta aaacttcatt tttaatttaa   3660
aaggatctag gtgaagatcc tttttgataa tctcatgacc aaaatccctt aacgtgagtt   3720
ttcgttccac tgagcgtcag accccgtaga aaagatcaaa ggatcttctt gagatccttt   3780
ttttctgcgc gtaatctgct gcttgcaaac aaaaaaacca ccgctaccag cggtggtttg   3840
tttgccggat caagagctac caactctttt tccgaaggta actggcttca gcagagcgca   3900
gataccaaat actgtccttc tagtgtagcc gtagttaggc caccacttca agaactctgt   3960
agcaccgcct acatacctcg ctctgctaat cctgttacca gtggctgctg ccagtggcga   4020
taagtcgtgt cttaccgggt tggactcaag acgatagtta ccggataagg cgcagcggtc   4080
gggctgaacg gggggttcgt gcacacagcc cagcttggag cgaacgacct acaccgaact   4140
gagataccta cagcgtgagc tatgagaaag cgccacgctt cccgaaggga gaaaggcgga   4200
caggtatccg gtaagcggca gggtcggaac aggagagcgc acgagggagc ttccaggggg   4260
```

```
aaacgcctgg tatctttata gtcctgtcgg gtttcgccac ctctgacttg agcgtcgatt   4320

tttgtgatgc tcgtcagggg ggcggagcct atggaaaaac gccagcaacg cggccttttt   4380

acggttcctg gccttttgct ggccttttgc tcacatgttc tttcctgcgt tatcccctga   4440

ttctgtggat aaccgtatta ccgcctttga gtgagctgat accgctcgcc gcagccgaac   4500

gaccgagcgc agcgagtcag tgagcgagga agcggaagag cgcctgatgc ggtattttct   4560

ccttacgcat ctgtgcggta tttcacaccg catatggtgc actctcagta caatctgctc   4620

tgatgccgca tagttaagcc agtatacact ccgctatcgc tacgtgactg ggtcatggct   4680

gcgccccgac acccgccaac acccgctgac gcgccctgac gggcttgtct gctcccggca   4740

tccgcttaca gacaagctgt gaccgtctcc gggagctgca tgtgtcagag gttttcaccg   4800

tcatcaccga aacgcgcgag gcagcagatc aattcgcgcg cgaaggcgaa gcggcatgca   4860

tttacgttga caccatcgaa tggtgcaaaa cctttcgcgg tatggcatga tagcgcccgg   4920

aagagagtca attcagggtg gtgaatgtga aaccagtaac gttatacgat gtcgcagagt   4980

atgccggtgt ctcttatcag accgtttccc gcgtggtgaa ccaggccagc cacgtttctg   5040

cgaaaacgcg ggaaaaagtg gaagcggcga tggcggagct gaattacatt cccaaccgcg   5100

tggcacaaca actggcgggc aaacagtcgt tgctgattgg cgttgccacc tccagtctgg   5160

ccctgcacgc gccgtcgcaa attgtcgcgg cgattaaatc tcgcgccgat caactgggtg   5220

ccagcgtggt ggtgtcgatg gtagaacgaa gcggcgtcga agcctgtaaa gcggcggtgc   5280

acaatcttct cgcgcaacgc gtcagtgggc tgatcattaa ctatccgctg gatgaccagg   5340

atgccattgc tgtggaagct gcctgcacta atgttccggc gttatttctt gatgtctctg   5400

accagacacc catcaacagt attattttct cccatgaaga cggtacgcga ctgggcgtgg   5460

agcatctggt cgcattgggt caccagcaaa tcgcgctgtt agcgggccca ttaagttctg   5520

tctcggcgcg tctgcgtctg gctggctggc ataaatatct cactcgcaat caaattcagc   5580

cgatagcgga acgggaaggc gactggagtg ccatgtccgg ttttcaacaa accatgcaaa   5640

tgctgaatga gggcatcgtt cccactgcga tgctggttgc caacgatcag atggcgctgg   5700

gcgcaatgcg cgccattacc gagtccgggc tgcgcgttgg tgcggatatc tcggtagtgg   5760

gatacgacga taccgaagac agctcatgtt atatcccgcc gtcaaccacc atcaaacagg   5820

attttcgcct gctggggcaa accagcgtgg accgcttgct gcaactctct cagggccagg   5880

cggtgaaggg caatcagctg ttgcccgtct cactggtgaa aagaaaaacc accctggcgc   5940

ccaatacgca aaccgcctct ccccgcgcgt tggccgattc attaatgcag ctggcacgac   6000

aggtttcccg actggaaagc gggcagtgag cgcaacgcaa ttaatgtgag ttagcgcgaa   6060

ttgatctg                                                           6068
```

<210> SEQ ID NO 3
<211> LENGTH: 6906
<212> TYPE: DNA
<213> ORGANISM: Artificial Sequence
<220> FEATURE:
<223> OTHER INFORMATION: Synthetic Construct

<400> SEQUENCE: 3

```
gtttgacagc ttatcatcga ctgcacggtg caccaatgct tctggcgtca ggcagccatc     60

ggaagctgtg gtatggctgt gcaggtcgta aatcactgca taattcgtgt cgctcaaggc    120

gcactcccgt tctggataat gtttttttgcg ccgacatcat aacggttctg gcaaatattc    180
```

-continued

```
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatgagatg    420
tagcgtgtcc accgaaaatg tgtctttcac cgaaactgaa accgaagctc gtcgttctgc    480
gaactacgaa cctaacagct gggactatga ttacctgctg tcctccgaca cggacgagtc    540
catcgaagta tacaaagaca aagcgaaaaa gctggaagcc gaagttcgtc gcgagattaa    600
taacgaaaaa gcagaatttc tgaccctgct ggaactgatt gacaacgtcc agcgcctggg    660
cctgggttac cgtttcgagt ctgatatccg tggtgcgctg gatcgcttcg tttcctccgg    720
cggcttcgat gcggtaacca agacttccct gcacggtacg gcactgtctt tccgtctgct    780
gcgtcaacac ggttttgagg tttctcagga agcgttcagc ggcttcaaag accaaaacgg    840
caacttcctg gagaacctga aggaagatat caaagctatc ctgagcctgt acgaggccag    900
cttcctggct ctggaaggcg aaaacatcct ggacgaggcg aaggttttcg caatctctca    960
tctgaaagaa ctgtctgaag aaaagatcgg taaagagctg gcagaacagg tgaaccatgc   1020
actggaactg ccactgcatc gccgtactca gcgtctggaa gcagtatggt ctatcgaggc   1080
ctaccgtaaa aaggaggacg cgaatcaggt tctgctggag ctggcaattc tggattacaa   1140
catgatccag tctgtatacc agcgtgatct gcgtgaaacg tcccgttggt ggcgtcgtgt   1200
gggtctggcg accaaactgc actttgctcg tgaccgcctg attgagagct tctactgggc   1260
cgtgggtgta gcattcgaac cgcaatactc cgactgccgt aactccgtcg caaaaatgtt   1320
ttctttcgta accattatcg acgatatcta cgatgtatac ggcaccctgg acgaactgga   1380
gctgtttact gatgcagttg agcgttggga cgtaaacgcc atcaacgacc tgccggatta   1440
catgaaactg tgctttctgg ctctgtataa cactattaac gaaatcgcct acgacaacct   1500
gaaagataaa ggtgagaaca tcctgccgta tctgaccaaa gcctgggctg acctgtgcaa   1560
cgctttcctg caagaagcca agtggctgta caacaaatct actccgacct ttgacgacta   1620
cttcggcaac gcatggaaat cctcttctgg cccgctgcaa ctggtgttcg cttacttcgc   1680
tgtcgtgcag aacattaaaa aggaagagat cgaaaacctg caaaaatacc atgacaccat   1740
ctctcgtcct tcccatatct tccgtctgtg caatgacctg gctagcgcgt ctgcggaaat   1800
tgcgcgtggt gaaaccgcaa atagcgtttc ttgttacatg cgcactaaag gtatctccga   1860
agaactggct accgaaagcg tgatgaatct gatcgatgaa acctggaaaa agatgaacaa   1920
ggaaaaactg ggtggtagcc tgttcgcgaa accgttcgtg gaaaccgcga tcaacctggc   1980
acgtcaatct cactgcactt atcataacgg cgacgcgcat acctctccgg atgagctgac   2040
ccgcaaacgc gttctgtctg taatcactga accgattctg ccgtttgaac gctaactgca   2100
taaaggaggt aaaaaaacat ggtatcctgt tctgcgccgg gtaagattta cctgttcggt   2160
gaacacgccg tagtttatgg cgaaactgca attgcgtgtg cggtggaact gcgtacccgt   2220
gttcgcgcgg aactcaatga ctctatcact attcagagcc agatcggccg caccggtctg   2280
gatttcgaaa agcaccctta tgtgtctgcg gtaattgaga aaatgcgcaa atctattcct   2340
attaacggtg ttttcttgac cgtcgattcc gacatcccgg tgggctccgg tctgggtagc   2400
agcgcagccg ttactatcgc gtctattggt gcgctgaacg agctgttcgg ctttggcctc   2460
agcctgcaag aaatcgctaa actgggccac gaaatcgaaa ttaaagtaca gggtgccgcg   2520
tccccaaccg atacgtatgt ttctaccttc ggcggcgtgg ttaccatccc ggaacgtcgc   2580
```

aaactgaaaa ctccggactg cggcattgtg attggcgata ccggcgtttt ctcctccacc 2640
aaagagttag tagctaacgt acgtcagctg cgcgaaagct acccggattt gatcgaaccg 2700
ctgatgacct ctattggcaa aatctctcgt atcggcgaac aactggttct gtctggcgac 2760
tacgcatcca tcggccgcct gatgaacgtc aaccagggtc tcctggacgc cctgggcgtt 2820
aacatcttag aactgagcca gctgatctat tccgctcgtg cggcaggtgc gtttggcgct 2880
aaaatcacgg gcgctggcgg cggtggctgt atggttgcgc tgaccgctcc ggaaaaatgc 2940
aaccaagtgg cagaagcggt agcaggcgct ggcggtaaag tgactatcac taaaccgacc 3000
gagcaaggtc tgaaagtaga ttaaagtcta gttaaagttt aaacggtctc cagcttggct 3060
gttttggcgg atgagagaag attttcagcc tgatacagat taaatcagaa cgcagaagcg 3120
gtctgataaa acagaatttg cctggcggca gtagcgcggt ggtcccacct gaccccatgc 3180
cgaactcaga agtgaaacgc cgtagcgccg atggtagtgt ggggtctccc catgcgagag 3240
tagggaactg ccaggcatca aataaaacga aaggctcagt cgaaagactg ggcctttcgt 3300
tttatctgtt gtttgtcggt gaacgctctc ctgagtagga caaatccgcc gggagcggat 3360
ttgaacgttg cgaagcaacg gcccggaggg tggcgggcag gacgcccgcc ataaactgcc 3420
aggcatcaaa ttaagcagaa ggccatcctg acggatggcc tttttgcgtt tctacaaact 3480
ctttttgttt atttttctaa atacattcaa atatgtatcc gctcatgaga caataaccct 3540
gataaatgct tcaataatat tgaaaaagga agagtatgag tattcaacat ttccgtgtcg 3600
cccttattcc cttttttgcg gcattttgcc ttcctgtttt tgctcaccca gaaacgctgg 3660
tgaaagtaaa agatgctgaa gatcagttgg gtgcacgagt gggttacatc gaactggatc 3720
tcaacagcgg taagatcctt gagagttttc gccccgaaga acgttttcca atgatgagca 3780
cttttaaagt tctgctatgt ggcgcggtat tatcccgtgt tgacgccggg caagagcaac 3840
tcggtcgccg catacactat tctcagaatg acttggttga gtactcacca gtcacagaaa 3900
agcatcttac ggatggcatg acagtaagag aattatgcag tgctgccata accatgagtg 3960
ataacactgc ggccaactta cttctgacaa cgatcggagg accgaaggag ctaaccgctt 4020
ttttgcacaa catgggggat catgtaactc gccttgatcg ttgggaaccg gagctgaatg 4080
aagccatacc aaacgacgag cgtgacacca cgatgcctgt agcaatggca acaacgttgc 4140
gcaaactatt aactggcgaa ctacttactc tagcttcccg gcaacaatta atagactgga 4200
tggaggcgga taaagttgca ggaccacttc tgcgctcggc ccttccggct ggctggttta 4260
ttgctgataa atctggagcc ggtgagcgtg ggtctcgcgg tatcattgca gcactggggc 4320
cagatggtaa gccctcccgt atcgtagtta tctacacgac ggggagtcag gcaactatgg 4380
atgaacgaaa tagacagatc gctgagatag gtgcctcact gattaagcat tggtaactgt 4440
cagaccaagt ttactcatat atactttaga ttgatttaaa acttcatttt taatttaaaa 4500
ggatctaggt gaagatcctt tttgataatc tcatgaccaa aatcccttaa cgtgagtttt 4560
cgttccactg agcgtcagac cccgtagaaa agatcaaagg atcttcttga gatccttttt 4620
ttctgcgcgt aatctgctgc ttgcaaacaa aaaaaccacc gctaccagcg gtggtttgtt 4680
tgccggatca agagctacca actctttttc cgaaggtaac tggcttcagc agagcgcaga 4740
taccaaatac tgtccttcta gtgtagccgt agttaggcca ccacttcaag aactctgtag 4800
caccgcctac atacctcgct ctgctaatcc tgttaccagt ggctgctgcc agtggcgata 4860
agtcgtgtct taccgggttg gactcaagac gatagttacc ggataaggcg cagcggtcgg 4920

-continued

```
gctgaacggg gggttcgtgc acacagccca gcttggagcg aacgacctac accgaactga   4980

gatacctaca gcgtgagcta tgagaaagcg ccacgcttcc cgaagggaga aaggcggaca   5040

ggtatccggt aagcggcagg gtcggaacag gagagcgcac gagggagctt ccagggggaa   5100

acgcctggta tctttatagt cctgtcgggt ttcgccacct ctgacttgag cgtcgatttt   5160

tgtgatgctc gtcagggggg cggagcctat ggaaaaacgc cagcaacgcg gcctttttac   5220

ggttcctggc cttttgctgg ccttttgctc acatgttctt tcctgcgtta tcccctgatt   5280

ctgtggataa ccgtattacc gcctttgagt gagctgatac cgctcgccgc agccgaacga   5340

ccgagcgcag cgagtcagtg agcgaggaag cggaagagcg cctgatgcgg tattttctcc   5400

ttacgcatct gtgcggtatt tcacaccgca tatggtgcac tctcagtaca atctgctctg   5460

atgccgcata gttaagccag tatacactcc gctatcgcta cgtgactggg tcatggctgc   5520

gccccgacac ccgccaacac ccgctgacgc gccctgacgg gcttgtctgc tcccggcatc   5580

cgcttacaga caagctgtga ccgtctccgg gagctgcatg tgtcagaggt tttcaccgtc   5640

atcaccgaaa cgcgcgaggc agcagatcaa ttcgcgcgcg aaggcgaagc ggcatgcatt   5700

tacgttgaca ccatcgaatg gtgcaaaacc tttcgcggta tggcatgata gcgcccggaa   5760

gagagtcaat tcagggtggt gaatgtgaaa ccagtaacgt tatacgatgt cgcagagtat   5820

gccggtgtct cttatcagac cgtttcccgc gtggtgaacc aggccagcca cgtttctgcg   5880

aaaacgcggg aaaaagtgga agcggcgatg gcggagctga attacattcc caaccgcgtg   5940

gcacaacaac tggcgggcaa acagtcgttg ctgattggcg ttgccacctc cagtctggcc   6000

ctgcacgcgc cgtcgcaaat tgtcgcggcg attaaatctc gcgccgatca actgggtgcc   6060

agcgtggtgg tgtcgatggt agaacgaagc ggcgtcgaag cctgtaaagc ggcggtgcac   6120

aatcttctcg cgcaacgcgt cagtgggctg atcattaact atccgctgga tgaccaggat   6180

gccattgctg tggaagctgc ctgcactaat gttccggcgt tatttcttga tgtctctgac   6240

cagacaccca tcaacagtat tattttctcc catgaagacg gtacgcgact gggcgtggag   6300

catctggtcg cattgggtca ccagcaaatc gcgctgttag cgggcccatt aagttctgtc   6360

tcggcgcgtc tgcgtctggc tggctggcat aaatatctca ctcgcaatca aattcagccg   6420

atagcggaac gggaaggcga ctggagtgcc atgtccggtt ttcaacaaac catgcaaatg   6480

ctgaatgagg gcatcgttcc cactgcgatg ctggttgcca acgatcagat ggcgctgggc   6540

gcaatgcgcg ccattaccga gtccgggctg cgcgttggtg cggatatctc ggtagtggga   6600

tacgacgata ccgaagacag ctcatgttat atcccgccgt caaccaccat caaacaggat   6660

tttcgcctgc tggggcaaac cagcgtggac cgcttgctgc aactctctca gggccaggcg   6720

gtgaagggca atcagctgtt gcccgtctca ctggtgaaaa gaaaaaccac cctggcgccc   6780

aatacgcaaa ccgcctctcc ccgcgcgttg gccgattcat taatgcagct ggcacgacag   6840

gtttcccgac tggaaagcgg gcagtgagcg caacgcaatt aatgtgagtt agcgcgaatt   6900

gatctg                                                              6906
```

<210> SEQ ID NO 4
<211> LENGTH: 3913
<212> TYPE: DNA
<213> ORGANISM: Artificial Sequence
<220> FEATURE:
<223> OTHER INFORMATION: Synthetic Construct

<400> SEQUENCE: 4

```
gcggccgcgc ccttgacgat gccacatcct gagcaaataa ttcaaccact aattgtgagc     60
```

-continued

```
ggataacaca aggaggaaac agccatggta tcctgttctg cgccgggtaa gatttacctg    120
ttcggtgaac acgccgtagt ttatggcgaa actgcaattg cgtgtgcggt ggaactgcgt    180
acccgtgttc gcgcggaact caatgactct atcactattc agagccagat cggccgcacc    240
ggtctggatt tcgaaaagca cccttatgtg tctgcggtaa ttgagaaaat gcgcaaatct    300
attcctatta acggtgtttt cttgaccgtc gattccgaca tcccggtggg ctccggtctg    360
ggtagcagcg cagccgttac tatcgcgtct attggtgcgc tgaacgagct gttcggcttt    420
ggcctcagcc tgcaagaaat cgctaaactg ggccacgaaa tcgaaattaa agtacagggt    480
gccgcgtccc caaccgatac gtatgtttct accttcggcg gcgtggttac catcccggaa    540
cgtcgcaaac tgaaaactcc ggactgcggc attgtgattg gcgataccgg cgttttctcc    600
tccaccaaag agttagtagc taacgtacgt cagctgcgcg aaagctaccc ggatttgatc    660
gaaccgctga tgacctctat tggcaaaatc tctcgtatcg gcgaacaact ggttctgtct    720
ggcgactacg catccatcgg ccgcctgatg aacgtcaacc agggtctcct ggacgccctg    780
ggcgttaaca tcttagaact gagccagctg atctattccg ctcgtgcggc aggtgcgttt    840
ggcgctaaaa tcacgggcgc tggcggcggt ggctgtatgg ttgcgctgac cgctccggaa    900
aaatgcaacc aagtggcaga agcggtagca ggcgctggcg gtaaagtgac tatcactaaa    960
ccgaccgagc aaggtctgaa agtagattaa gccttgactt aatagctgct tatttcgccc   1020
ttatggtacc tagtaggagg aaaaaaacat ggaaatgcgt caaccggctg tcgcaggtca   1080
attctaccca ctgcgttgcg agaacctgga aaacgaactg aaacgctgct tcgaaggcct   1140
ggagatccgc gaacaagaag tgctgggcgc agtctgtccg cacgccggtt atatgtactc   1200
tggcaaagtt gcggcgcacg tctatgccac tctgccggaa gctgatacct acgtaatctt   1260
cggcccgaac cacaccggct acggtagccc tgtctctgtg agccgtgaaa cttggaagac   1320
cccgttgggc aatatcgatg ttgacctgga actggcggac ggcttcctgg gttccatcgt   1380
agatgcggat gaactcggtc acaaatacga acactctatc gaagttcagc tgccgtttct   1440
gcaataccgt tttgaacgcg atttcaaaat tctgccaatc tgcatgggta tgcaagacga   1500
agaaaccgcg gtcgaagtag gtaacctgct ggcggatctg atcagcgagt ccggtaaacg   1560
tgctgtgatc atcgcaagct ctgatttcac ccactatgag acggctgaac gtgccaaaga   1620
aatcgattcc gaagttattg attctatcct gaactttgac atctctggca tgtacgatcg   1680
cctgtatcgc cgtaacgcct ctgtttgcgg ttacggcccg atcaccgcta tgctgacggc   1740
aagcaaaaag ctgggcggct ctcgtgcgac tttgctgaaa tacgcaaaca gcggtgacgt   1800
gtccggtgat aaagacgctg tggtgggcta cgccgccatc atcgttgagt aagctgatta   1860
aaggttgaac agataggatt tcgtcatgga tcctacaagg aggaaaaaaa catgaatgct   1920
tctaatgaac cggtgattct gaaactgggt ggctctgcta ttaccgacaa aggtgcctac   1980
gaaggcgtag ttaaggaagc tgatttgctg cgcatcgcac aggaagttag cggtttccgt   2040
ggcaagatga tcgtggttca tggtgctggt agcttcggcc atacgtacgc gaagaaatac   2100
ggcctggacc gtaccttcga cccagagggc gcaattgtta ctcatgaatc tgttaaaaag   2160
ctcgcctcca aagttgtagg tgctctgaat agcttcggcg tgcgtgctat cgcggtgcat   2220
cctatggact gcgcagtatg ccgtaacggt cgtatcgaaa cgatgtatct ggactccatc   2280
aagttaatgc tggaaaaagg tctggtgccg gttctgcacg gcgacgtcgc aatggatatt   2340
gaactgggca cttgtatcct gtccggtgat caaatcgttc cttacctggc caaagaactg   2400
```

ggtatctccc gcctcggcct gggcagcgca gaggatggtg tgctggatat ggagggcaaa 2460
cctgtaccgg aaatcacccc agaaactttc gaagagttcc gccactgcat cggtggttct 2520
ggttctactg atgtaaccgg tggcatgctg ggcaaagtgc tggaacttct ggaattgagc 2580
aaaaattctt ccattactag ctacattttc aacgctggta aagcagacaa catctaccgc 2640
tttctgaatg gtgagtccat cggcactcgc atcagcccgg acaagcgtgt ttaagctagt 2700
tattaaccta aatgctctaa accagttatg agctctacaa ggaggaaaaa aacatgatta 2760
acactaccag ccgccgcaaa attgaacacc tgaaactctg cgcagaatcc ccggttgaag 2820
cgcgtcaggt atctgccggc tttgaagacg ttactctgat ccaccgcgct ttaccggagc 2880
tgaacatgga tgaactggac ctcagcgttg atttcctggg taaacgcatc aaagcgccgt 2940
tcctgattgc gtctatcacg ggtggtcacc cagataccat cccggttaac gctgcgctgg 3000
cagctgctgc tgaggagctg ggtgttggca tcggcgttgg ctctcagcgc gcggccattg 3060
atgatccgag ccaggaagac agcttccgtg tagtgcgtga tgaagcccca gatgcgtttg 3120
tttatggcaa cgtcggcgca gcacagatcc gtcagtatgg tgttgaaggt gttgaaaaac 3180
tgatcgaaat gattgacgca gatgccttgg caatccacct gaactttctg caagaagcgg 3240
tccaaccgga aggtgaccgc gacgcgaccg gttgcctgga catgattacc gaaatttgct 3300
ctcagattaa aactccggta atcgtgaaag aaaccggtgc aggcattagc cgtgaagatg 3360
cgattctgtt ccagaaagct ggcgtgagcg caatcgacgt tggcggcgcg ggcggcacct 3420
cctgggctgg cgtcgaggtc taccgtgcta aagaaagccg tgactctgtt agcgagcgtt 3480
taggtgagct gttttgggat ttcggcattc cgacggtagc ttctctgatt gaatcccgcg 3540
tttccttgcc gctgatcgca accggcggta tccgtaacgg tctggacatt gctaaaagca 3600
ttgctctcgg cgcaagcgct gccagcgccg ctctgccgtt cgttggtccg tccctggagg 3660
gcaaagaatc cgttgtacgt gtgctgagct gcatgctgga agaatttaaa gcagcaatgt 3720
ttttgtgcgg ttgcggcaac atcaaagacc tgcacaactc tccagtagtg gtaactggtt 3780
ggacccgcga atacctggag cagcgcggtt ttaacgttaa ggacctctcc ctgccgggca 3840
acgctctgta agcttcaacg cgtctacaaa taaaaaaggc acgtcagatg acgtgccttt 3900
tttcttgtct aga 3913

<210> SEQ ID NO 5
<211> LENGTH: 6647
<212> TYPE: DNA
<213> ORGANISM: Artificial Sequence
<220> FEATURE:
<223> OTHER INFORMATION: Synthetic Construct

<400> SEQUENCE: 5
aagggcgagc tcaacgatcc ggctgctaac aaagcccgaa aggaagctga gttggctgct 60
gccaccgctg agcaataact agcataaccc cttggggcct ctaaacgggt cttgaggagt 120
tttttgctga aaggaggaac tatatccgga tatcccgcaa gaggcccggc agtaccggca 180
taaccaagcc tatgcctaca gcatccaggg tgacggtgcc gaggatgacg atgagcgcat 240
tgttagattt catacacggt gcctgactgc gttagcaatt taactgtgat aaactaccgc 300
attaaagctt atcgatgata agctgtcaaa catgagaatt aattcttgaa gacgaaaggg 360
cctcgtgata cgcctatttt tataggttaa tgtcatgata ataatggttt cttagacgtc 420
aggtggcact tttcggggaa atgtgcgcgg aacccctatt tgtttatttt tctaaataca 480
ttcaaatatg tatccgctca tgagacaata accctgataa atgcttcaat aatattgaaa 540

```
aaggaagagt atgattgaac aagatggatt gcacgcaggt tctccggccg cttgggtgga    600
gaggctattc ggctatgact gggcacaact gacaatcggc tgctctgatg ccgccgtgtt    660
ccggctgtca gcgcaggggc gcccggttct ttttgtcaag accgacctgt ccggtgccct    720
gaatgaactg caggacgagg cagcgcggct atcgtggctg gccacgacgg gcgttccttg    780
cgcagctgtg ctcgacgttg tcactgaagc gggaagggac tggctgctat tgggcgaagt    840
gccggggcag gatctcctgt catctcacct tgctcctgcc gagaaagtat ccatcatggc    900
tgatgcaatg cggcggctgc atacgcttga tccggctacc tgcccattcg accaccaagc    960
gaaacatcgc atcgagcggg cacgtactcg gatggaagcc ggtcttgtcg atcaggatga   1020
tctggacgaa gagcatcagg ggctcgcgcc agccgaactg ttcgccaggc tcaaggcgcg   1080
catgcccgac ggcgaggatc tcgtcgtgac acatggcgat gcctgcttgc cgaatatcat   1140
ggtggaaaat ggccgctttt ctggattcat cgactgtggc cggctgggtg tggcggaccg   1200
ctatcaggac atagcgttgg ctacccgtga tattgctgaa gagcttggcg gcgaatgggc   1260
tgaccgcttc ctcgtgcttt acggtatcgc cgctcccgat tcgcagcgca tcgccttcta   1320
tcgccttctt gacgagttct tctgagcggg actctggggt tcgaaatgac cgaccaagcg   1380
acgcctaact gtcagaccaa gtttactcat atatacttta gattgattta aaacttcatt   1440
tttaatttaa aaggatctag gtgaagatcc tttttgataa tctcatgacc aaaatccctt   1500
aacgtgagtt ttcgttccac tgagcgtcag accccgtaga aaagatcaaa ggatcttctt   1560
gagatccttt ttttctgcgc gtaatctgct gcttgcaaac aaaaaaacca ccgctaccag   1620
cggtggtttg tttgccggat caagagctac caactctttt tccgaaggta actggcttca   1680
gcagagcgca gataccaaat actgtccttc tagtgtagcc gtagttaggc caccacttca   1740
agaactctgt agcaccgcct acatacctcg ctctgctaat cctgttacca gtggctgctg   1800
ccagtggcga taagtcgtgt cttaccgggt tggactcaag acgatagtta ccggataagg   1860
cgcagcggtc gggctgaacg gggggttcgt gcacacagcc cagcttggag cgaacgacct   1920
acaccgaact gagataccta cagcgtgagc tatgagaaag cgccacgctt cccgaaggga   1980
gaaaggcgga caggtatccg gtaagcggca gggtcggaac aggagagcgc acgagggagc   2040
ttccaggggg aaacgcctgg tatctttata gtcctgtcgg gtttcgccac ctctgacttg   2100
agcgtcgatt tttgtgatgc tcgtcagggg ggcggagcct atggaaaaac gccagcaacg   2160
cggccttttt acggttcctg gccttttgct ggccttttgc tcacatgttc tttcctgcgt   2220
tatcccctga ttctgtggat aaccgtatta ccgcctttga gtgagctgat accgctcgcc   2280
gcagccgaac gaccgagcgc agcgagtcag tgagcgagga agcggaagag cgcctgatgc   2340
ggtattttct ccttacgcat ctgtgcggta tttcacaccg caatggtgca ctctcagtac   2400
aatctgctct gatgccgcat agttaagcca gtatacactc cgctatcgct acgtgactgg   2460
gtcatggctg cgccccgaca cccgccaaca cccgctgacg cgccctgacg ggcttgtctg   2520
ctcccggcat ccgcttacag acaagctgtg accgtctccg ggagctgcat gtgtcagagg   2580
ttttcaccgt catcaccgaa acgcgcgagg cagctgcggt aaagctcatc agcgtggtcg   2640
tgaagcgatt cacagatgtc tgcctgttca tccgcgtcca gctcgttgag tttctccaga   2700
agcgttaatg tctggcttct gataaagcgg gccatgttaa gggcggtttt ttcctgtttg   2760
gtcactgatg cctccgtgta agggggattt ctgttcatgg gggtaatgat accgatgaaa   2820
cgagagagga tgctcacgat acgggttact gatgatgaac atgcccggtt actggaacgt   2880
```

-continued

```
tgtgagggta aacaactggc ggtatggatg cggcgggacc agagaaaaat cactcagggt   2940
caatgccagc gcttcgttaa tacagatgta ggtgttccac agggtagcca gcagcatcct   3000
gcgatgcaga tccggaacat aatggtgcag ggcgctgact tccgcgtttc cagactttac   3060
gaaacacgga aaccgaagac cattcatgtt gttgctcagg tcgcagacgt tttgcagcag   3120
cagtcgcttc acgttcgctc gcgtatcggt gattcattct gctaaccagt aaggcaaccc   3180
cgccagccta gccgggtcct caacgacagg agcacgatca tgcgcacccg tggccaggac   3240
ccaacgctgc ccgagatgcg ccgcgtgcgg ctgctggaga tggcggacgc gatggatatg   3300
ttctgccaag ggttggtttg cgcattcaca gttctccgca agaattgatt ggctccaatt   3360
cttggagtgg tgaatccgtt agcgaggtgc cgccggcttc cattcaggtc gaggtggccc   3420
ggctccatgc accgcgacgc aacgcgggga ggcagacaag gtatagggcg gcgcctacaa   3480
tccatgccaa cccgttccat gtgctcgccg aggcggcata aatcgccgtg acgatcagcg   3540
gtccaatgat cgaagttagg ctggtaagag ccgcgagcga tccttgaagc tgtccctgat   3600
ggtcgtcatc tacctgcctg gacagcatgg cctgcaacgc gggcatcccg atgccgccgg   3660
aagcgagaag aatcataatg gggaaggcca tccagcctcg cgtcgcgaac gccagcaaga   3720
cgtagcccag cgcgtcggcc gccatgccgg cgataatggc ctgcttctcg ccgaaacgtt   3780
tggtggcggg accagtgacg aaggcttgag cgagggcgtg caagattccg aataccgcaa   3840
gcgacaggcc gatcatcgtc gcgctccagc gaaagcggtc ctcgccgaaa atgacccaga   3900
gcgctgccgg cacctgtcct acgagttgca tgataaagaa gacagtcata agtgcggcga   3960
cgatagtcat gccccgcgcc caccggaagg agctgactgg gttgaaggct ctcaagggca   4020
tcggtcgaga tcccggtgcc taatgagtga gctaacttac attaattgcg ttgcgctcac   4080
tgcccgcttt ccagtcggga aacctgtcgt gccagctgca ttaatgaatc ggccaacgcg   4140
cggggagagg cggtttgcgt attgggcgcc agggtggttt ttcttttcac cagtgagacg   4200
ggcaacagct gattgccctt caccgcctgg ccctgagaga gttgcagcaa gcggtccacg   4260
ctggtttgcc ccagcaggcg aaaatcctgt ttgatggtgg ttaacggcgg gatataacat   4320
gagctgtctt cggtatcgtc gtatcccact accgagatat ccgcaccaac gcgcagcccg   4380
gactcggtaa tggcgcgcat tgcgcccagc gccatctgat cgttggcaac cagcatcgca   4440
gtgggaacga tgccctcatt cagcatttgc atggtttgtt gaaaaccgga catggcactc   4500
cagtcgcctt cccgttccgc tatcggctga atttgattgc gagtgagata tttatgccag   4560
ccagccagac gcagacgcgc cgagacagaa cttaatgggc ccgctaacag cgcgatttgc   4620
tggtgaccca atgcgaccag atgctccacg cccagtcgcg taccgtcttc atgggagaaa   4680
ataatactgt tgatgggtgt ctggtcagag acatcaagaa ataacgccgg aacattagtg   4740
caggcagctt ccacagcaat ggcatcctgg tcatccagcg gatagttaat gatcagccca   4800
ctgacgcgtt gcgcgagaag attgtgcacc gccgctttac aggcttcgac gccgcttcgt   4860
tctaccatcg acaccaccac gctggcaccc agttgatcgg cgcgagattt aatcgccgcg   4920
acaatttgcg acggcgcgtg cagggccaga ctggaggtgg caacgccaat cagcaacgac   4980
tgtttgcccg ccagttgttg tgccacgcgg ttgggaatgt aattcagctc cgccatcgcc   5040
gcttccactt tttcccgcgt tttcgcagaa acgtggctgg cctggttcac cacgcgggaa   5100
acggtctgat aagagacacc ggcatactct gcgacatcgt ataacgttac tggtttcaca   5160
ttcaccaccc tgaattgact ctcttccggg cgctatcatg ccataccgcg aaaggttttg   5220
cgccattcga tggtgtccgg gatctcgacg ctctccctta tgcgactcct gcattaggaa   5280
```

gcagcccagt agtaggttga ggccgttgag caccgccgcc gcaaggaatg gtgcatgcaa 5340
ggagatggcg cccaacagtc ccccggccac ggggcctgcc accataccca cgccgaaaca 5400
agcgctcatg agcccgaagt ggcgagcccg atcttcccca tcggtgatgt cggcgatata 5460
ggcgccagca accgcacctg tggcgccggt gatgccggcc acgatgcgtc cggcgtagag 5520
gatcgagatc tcgatcccgc gaaattaata cgactcacta taggggaatt gtgagcggat 5580
aacaattccc ctctagaaat aattttgttt aactttaaga aggagatata catatgcggg 5640
gttctcatca tcatcatcat catggtatgg ctagcatgac tggtggacag caaatgggtc 5700
gggatctgta cgacgatgac gataaggatc atcccttcac catggtatcc tgttctgcgc 5760
cgggtaagat ttacctgttc ggtgaacacg ccgtagttta tggcgaaact gcaattgcgt 5820
gtgcggtgga actgcgtacc cgtgttcgcg cggaactcaa tgactctatc actattcaga 5880
gccagatcgg ccgcaccggt ctggatttcg aaaagcaccc ttatgtgtct gcggtaattg 5940
agaaaatgcg caaatctatt cctattaacg gtgttttctt gaccgtcgat tccgacatcc 6000
cggtgggctc cggtctgggt agcagcgcag ccgttactat cgcgtctatt ggtgcgctga 6060
acgagctgtt cggctttggc ctcagcctgc aagaaatcgc taaactgggc cacgaaatcg 6120
aaattaaagt acagggtgcc gcgtccccaa ccgatacgta tgtttctacc ttcggcggcg 6180
tggttaccat cccggaacgt cgcaaactga aaactccgga ctgcggcatt gtgattggcg 6240
ataccggcgt tttctcctcc accaaagagt tagtagctaa cgtacgtcag ctgcgcgaaa 6300
gctacccgga tttgatcgaa ccgctgatga cctctattgg caaaatctct cgtatcggcg 6360
aacaactggt tctgtctggc gactacgcat ccatcggccg cctgatgaac gtcaaccagg 6420
gtctcctgga cgccctgggc gttaacatct tagaactgag ccagctgatc tattccgctc 6480
gtgcggcagg tgcgtttggc gctaaaatca cgggcgctgg cggcggtggc tgtatggttg 6540
cgctgaccgc tccggaaaaa tgcaaccaag tggcagaagc ggtagcaggc gctggcggta 6600
aagtgactat cactaaaccg accgagcaag gtctgaaagt agattaa 6647

<210> SEQ ID NO 6
<211> LENGTH: 7519
<212> TYPE: DNA
<213> ORGANISM: Artificial Sequence
<220> FEATURE:
<223> OTHER INFORMATION: Synthetic Construct

<400> SEQUENCE: 6
ctcgggccgt ctcttgggct tgatcggcct tcttgcgcat ctcacgcgct cctgcggcgg 60
cctgtagggc aggctcatac ccctgccgaa ccgcttttgt cagccggtcg gccacggctt 120
ccggcgtctc aacgcgcttt gagattccca gcttttcggc caatccctgc ggtgcatagg 180
cgcgtggctc gaccgcttgc gggctgatgg tgacgtggcc cactggtggc cgctccaggg 240
cctcgtagaa cgcctgaatg cgcgtgtgac gtgccttgct gccctcgatg ccccgttgca 300
gccctagatc ggccacagcg gccgcaaacg tggtctggtc gcgggtcatc tgcgctttgt 360
tgccgatgaa ctccttggcc gacagcctgc cgtcctgcgt cagcggcacc acgaacgcgg 420
tcatgtgcgg gctggtttcg tcacggtgga tgctggccgt cacgatgcga tccgccccgt 480
acttgtccgc cagccacttg tgcgccttct cgaagaacgc cgcctgctgt tcttggctgg 540
ccgacttcca ccattccggg ctggccgtca tgacgtactc gaccgccaac acagcgtcct 600
tgcgccgctt ctctggcagc aactcgcgca gtcggcccat cgcttcatcg gtgctgctgg 660

-continued

```
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg gacaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380
tgccccccga gcctcacggc ggcgagtgcg ggggttccaa gggggcagcg ccaccttggg   1440
caaggccgaa ggccgcgcag tcgatcaaca agccccggag gggccacttt ttgccggagg   1500
gggagccgcg ccgaaggcgt gggggaaccc cgcaggggtg cccttctttg ggcaccaaag   1560
aactagatat agggcgaaat gcgaaagact taaaaatcaa caacttaaaa aagggggggta   1620
cgcaacagct cattgcggca ccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg gccacctcga   2580
cctgaatgga agccggcggc acctcgctaa cggattcacc gtttttatca ggctctggga   2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
```

-continued atcggtgcgg gcctcttcgc tattacgcca gctggcgaaa gggggatgtg ctgcaaggcg 3120
attaagttgg gtaacgccag ggttttccca gtcacgacgt tgtaaaacga cggccagtga 3180
gcgcgcgtaa tacgactcac tatagggcga attggagctc caccgcggtg gcggccgctc 3240
tagaactagt ggatcccccg ggctgcatgc tcgagcggcc gccagtgtga tggatatctg 3300
cagaattcgc ccttcttgat atcttagtgt gcgttaacca ccacccacat tggtccctgc 3360
ccgaccgcat agcggccttt ttcatgcagt agcccctgct cgccaacaat ttcgtatacc 3420
gagatgtggt gagatttttg cccggcggca atcagatact tgccgctgtg atcaacattg 3480
aagccgcgcg gctgggtttc cgttggctgg aagccttctt tactcaacac gctgccatct 3540
tccgaaacgc tgaaaacggt aatcaggctg gcggtacggt cgcaggcgta taaatggcga 3600
ccatccgggg tgatatgaat atcagccgcc caacgggtgt cggagaagtt ttccggcatc 3660
atatccagcg tctggacaca ttcgatatta ccgtgcggat ctttcagttc ccagacatcc 3720
actgagctgt ttaactcatt gacgcaatac gcatattgtt cgtttggatg gaataccata 3780
tgacgcgggc cggccccttc aacggtggtc acttccgcag ggtcctgcgc cacgagatga 3840
ccatcatcgc tgaccgtaaa caggcaaatg cgatcctgct ttaatgccgg aacccacagc 3900
gtacggttgt ccggtgagat attggcggaa tggcaaccgt ccagcccctc gaccacatcg 3960
acgacgccca ctggcaggcc atcttccaga cgcgttacgc tcacgttacc cgcattgtaa 4020
gaacctacaa agacaaactg cccctggtga tcggtggaaa tatgcgtcgg actacccggc 4080
agcgcagact ctgcggcaaa ggtcagtgcg ccatcgtccg ggcgatacgg atacgccagg 4140
acgcgaaact cagggcgaac accaacatag agataacgtt tgtccgggct gaccaccatc 4200
ggctgcacct gccccggcac atcgacaacc tgtgtcagcg tcagtgcgcc ttcatgattc 4260
agattccaga cgtgaatttg ctggctctca gggctggcga tataaactgt ttgcttcatg 4320
aatgctcctt tgggttacct ccgggaaacg cggttgattt gtttagtggt tgaattattt 4380
gctcaggatg tggcatagtc aagggcgtga cggctcgcta atacaactca ctatagggct 4440
cgaggaagtt cctatacttt ctagagaata ggaacttccg cgccgcacac aaaaaccaac 4500
acacagatca tgaaaataaa gctcttttat tggtaccgaa ttcgccaggg agctctcaga 4560
cgtcgcttgg tcggtcttta ttcgaacccc agagtcccgc ttacgccccg ccctgccact 4620
catcgcagta ctgttgtaat tcattaagca ttctgccgac atggaagcca tcacaaacgg 4680
catgatgaac ctgaatcgcc agcggcatca gcaccttgtc gccttgcgta taatatttgc 4740
ccatggtgaa aacgggggcg aagaagttgt ccatattggc cacgtttaaa tcaaaactgg 4800
tgaaactcac ccagggattg gctgagacga aaaacatatt ctcaataaac cctttaggga 4860
aataggccag gttttcaccg taacacgcca catcttgcga atatatgtgt agaaactgcc 4920
ggaaatcgtc gtggtattca ctccagagcg atgaaaacgt ttcagtttgc tcatggaaaa 4980
cggtgtaaca agggtgaaca ctatcccata tcaccagctc accgtctttc attgccatac 5040
ggaattccgg atgagcattc atcaggcggg caagaatgtg aataaaggcc ggataaaact 5100
tgtgcttatt tttctttacg gtctttaaaa aggccgtaat atccagctga acggtctggt 5160
tataggtaca ttgagcaact gactgaaatg cctcaaaatg ttctttacga tgccattggg 5220
atatatcaac ggtggtatat ccagtgattt ttttctccat ggtttagttc ctcaccttgt 5280
cgtattatac tatgccgata tactatgccg atgattaatt gtcaacacgt gctgctgcag 5340
gtcgaaaggc ccggagatga ggaagaggag aacagcgcgg cagacgtgcg cttttgaagc 5400

-continued

```
gtgcagaatg ccgggcctcc ggaggacctt cgggcgcccg ccccgcccct gagcccgccc   5460
ctgagcccgc ccccggaccc accccttccc agcctctgag cccagaaagc gaaggagcaa   5520
agctgctatt ggccgctgcc ccaaaggcct acccgcttcc attgctcagc ggtgctgtcc   5580
atctgcacga gactagtgag acgtgctact tccatttgtc acgtcctgca cgacgcgagc   5640
tgcggggcgg gggggaactt cctgactagg ggaggagtgg aaggtggcgc gaaggggcca   5700
ccaaagaacg gagccggttg gcgcctaccg gtggatgtgg aatgtgtgcg aggccagagg   5760
ccacttgtgt agcgccaagt gcccagcggg gctgctaaag cgcatgctcc agactgcctt   5820
gggaaaagcg cctcccctac ccggtagaat gaagttccta tactttctag agaataggaa   5880
cttcgcggcc gccctttagt gagggttaat tcaactgact gtaacagcta aaattagtcg   5940
cttttggcgg taagggcgaa ttccagcaca ctggcggccg ttactagtgg atccgagctc   6000
ggtaccaagc ttgatgcagg aattcgatat caagcttatc gataccgtcg acctcgaggg   6060
ggggcccggt acccagcttt tgttcccttt agtgagggtt aattgcgcgc ttggcgtaat   6120
catggtcata gctgtttcct gtgtgaaatt gttatccgct cacaattcca cacaacatac   6180
gagccggaag cataaagtgt aaagcctggg gtgcctaatg agtgagctaa ctcacattaa   6240
ttgcgttgcg ctcactgccc gctttccagt cgggaaacct gtcgtgccag ctgcattaat   6300
gaatcggcca acgcgcgggg agaggcggtt tgcgtattgg gcgcatgcat aaaaactgtt   6360
gtaattcatt aagcattctg ccgacatgga agccatcaca aacggcatga tgaacctgaa   6420
tcgccagcgg catcagcacc ttgtcgcctt gcgtataata tttgcccatg gacgcacacc   6480
gtggaaacgg atgaaggcac gaacccagtt gacataagcc tgttcggttc gtaaactgta   6540
atgcaagtag cgtatgcgct cacgcaactg gtccagaacc ttgaccgaac gcagcggtgg   6600
taacggcgca gtggcggttt tcatggcttg ttatgactgt ttttttgtac agtctatgcc   6660
tcgggcatcc aagcagcaag cgcgttacgc cgtgggtcga tgtttgatgt tatggagcag   6720
caacgatgtt acgcagcagc aacgatgtta cgcagcaggg cagtcgccct aaaacaaagt   6780
taggtggctc aagtatgggc atcattcgca catgtaggct cggccctgac caagtcaaat   6840
ccatgcgggc tgctcttgat cttttcggtc gtgagttcgg agacgtagcc acctactccc   6900
aacatcagcc ggactccgat tacctcggga acttgctccg tagtaagaca ttcatcgcgc   6960
ttgctgcctt cgaccaagaa gcggttgttg gcgctctcgc ggcttacgtt ctgcccaggt   7020
ttgagcagcc gcgtagtgag atctatatct atgatctcgc agtctccggc gagcaccgga   7080
ggcagggcat tgccaccgcg ctcatcaatc tcctcaagca tgaggccaac gcgcttggtg   7140
cttatgtgat ctacgtgcaa gcagattacg gtgacgatcc cgcagtggct ctctatacaa   7200
agttgggcat acgggaagaa gtgatgcact ttgatatcga cccaagtacc gccacctaac   7260
aattcgttca agccgagatc ggcttcccgg ccgcggagtt gttcggtaaa ttgtcacaac   7320
gccgccaggt ggcacttttc ggggaaatgt gcgcgcccgc gttcctgctg gcgctgggcc   7380
tgtttctggc gctggacttc ccgctgttcc gtcagcagct tttcgcccac ggccttgatg   7440
atcgcggcgg ccttggcctg catatcccga ttcaacggcc ccagggcgtc cagaacgggc   7500
ttcaggcgct cccgaaggt                                                7519
```

<210> SEQ ID NO 7
<211> LENGTH: 6858
<212> TYPE: DNA
<213> ORGANISM: Artificial Sequence
<220> FEATURE:
<223> OTHER INFORMATION: Synthetic Construct -continued

<400> SEQUENCE: 7

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gtttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggaagc     420
tcgtcgttct gcgaactacg aacctaacag ctgggactat gattacctgc tgtcctccga     480
cacggacgag tccatcgaag tatacaaaga caaagcgaaa aagctggaag ccgaagttcg     540
tcgcgagatt aataacgaaa aagcagaatt tctgaccctg ctggaactga ttgacaacgt     600
ccagcgcctg ggcctgggtt accgtttcga gtctgatatc cgtggtgcgc tggatcgctt     660
cgtttcctcc ggcggcttcg atgcggtaac caagacttcc ctgcacggta cggcactgtc     720
tttccgtctg ctgcgtcaac acggttttga ggtttctcag gaagcgttca gcggcttcaa     780
agaccaaaac ggcaacttcc tggagaacct gaaggaagat atcaaagcta tcctgagcct     840
gtacgaggcc agcttcctgg ctctggaagg cgaaaacatc ctggacgagg cgaaggtttt     900
cgcaatctct catctgaaag aactgtctga agaaaagatc ggtaaagagc tggcagaaca     960
ggtgaaccat gcactggaac tgccactgca tcgccgtact cagcgtctgg aagcagtatg    1020
gtctatcgag gcctaccgta aaaaggagga cgcgaatcag gttctgctgg agctggcaat    1080
tctggattac aacatgatcc agtctgtata ccagcgtgat ctgcgtgaaa cgtcccgttg    1140
gtggcgtcgt gtgggtctgg cgaccaaact gcactttgct cgtgaccgcc tgattgagag    1200
cttctactgg gccgtgggtg tagcattcga accgcaatac tccgactgcc gtaactccgt    1260
cgcaaaaatg ttttctttcg taaccattat cgacgatatc tacgatgtat acggcaccct    1320
ggacgaactg gagctgttta ctgatgcagt tgagcgttgg gacgtaaacg ccatcaacga    1380
cctgccggat tacatgaaac tgtgctttct ggctctgtat aacactatta acgaaatcgc    1440
ctacgacaac ctgaaagata aaggtgagaa catcctgccg tatctgacca aagcctgggc    1500
tgacctgtgc aacgctttcc tgcaagaagc caagtggctg tacaacaaat ctactccgac    1560
ctttgacgac tacttcggca acgcatggaa atcctcttct ggcccgctgc aactggtgtt    1620
cgcttacttc gctgtcgtgc agaacattaa aaaggaagag atcgaaaacc tgcaaaaata    1680
ccatgacacc atctctcgtc cttcccatat cttccgtctg tgcaatgacc tggctagcgc    1740
gtctgcggaa attgcgcgtg gtgaaaccgc aaatagcgtt tcttgttaca tgcgcactaa    1800
aggtatctcc gaagaactgg ctaccgaaag cgtgatgaat ctgatcgatg aaacctggaa    1860
aaagatgaac aaggaaaaac tgggtggtag cctgttcgcg aaaccgttcg tggaaaccgc    1920
gatcaacctg gcacgtcaat ctcactgcac ttatcataac ggcgacgcgc atacctctcc    1980
ggatgagctg acccgcaaac gcgttctgtc tgtaatcact gaaccgattc tgccgtttga    2040
acgctaactg cataaaggag gtaaaaaaac atggtatcct gttctgcgcc gggtaagatt    2100
tacctgttcg gtgaacacgc cgtagtttat ggcgaaactg caattgcgtg tgcggtggaa    2160
ctgcgtaccc gtgttcgcgc ggaactcaat gactctatca ctattcagag ccagatcggc    2220
cgcaccggtc tggatttcga aaagcaccct tatgtgtctg cggtaattga gaaaatgcgc    2280
```

-continued

```
aaatctattc ctattaacgg tgttttcttg accgtcgatt ccgacatccc ggtgggctcc   2340
ggtctgggta gcagcgcagc cgttactatc gcgtctattg gtgcgctgaa cgagctgttc   2400
ggctttggcc tcagcctgca agaaatcgct aaactgggcc acgaaatcga aattaaagta   2460
cagggtgccg cgtccccaac cgatacgtat gtttctacct tcggcggcgt ggttaccatc   2520
ccggaacgtc gcaaactgaa aactccggac tgcggcattg tgattggcga taccggcgtt   2580
ttctcctcca ccaaagagtt agtagctaac gtacgtcagc tgcgcgaaag ctacccggat   2640
ttgatcgaac cgctgatgac ctctattggc aaaatctctc gtatcggcga acaactggtt   2700
ctgtctggcg actacgcatc catcggccgc ctgatgaacg tcaaccaggg tctcctggac   2760
gccctgggcg ttaacatctt agaactgagc cagctgatct attccgctcg tgcggcaggt   2820
gcgtttggcg ctaaaatcac gggcgctggc ggcggtggct gtatggttgc gctgaccgct   2880
ccggaaaaat gcaaccaagt ggcagaagcg gtagcaggcg ctggcggtaa agtgactatc   2940
actaaaccga ccgagcaagg tctgaaagta gattaaagtc tagttaaagt ttaaacggtc   3000
tccagcttgg ctgttttggc ggatgagaga agattttcag cctgatacag attaaatcag   3060
aacgcagaag cggtctgata aaacagaatt tgcctggcgg cagtagcgcg gtggtcccac   3120
ctgaccccat gccgaactca gaagtgaaac gccgtagcgc cgatggtagt gtggggtctc   3180
cccatgcgag agtagggaac tgccaggcat caaataaaac gaaaggctca gtcgaaagac   3240
tgggcctttc gttttatctg ttgtttgtcg gtgaacgctc tcctgagtag gacaaatccg   3300
ccgggagcgg atttgaacgt tgcgaagcaa cggcccggag ggtggcgggc aggacgcccg   3360
ccataaactg ccaggcatca aattaagcag aaggccatcc tgacggatgg cctttttgcg   3420
tttctacaaa ctctttttgt ttatttttct aaatacattc aaatatgtat ccgctcatga   3480
gacaataacc ctgataaatg cttcaataat attgaaaaag gaagagtatg agtattcaac   3540
atttccgtgt cgcccttatt cccttttttg cggcattttg ccttcctgtt tttgctcacc   3600
cagaaacgct ggtgaaagta aaagatgctg aagatcagtt gggtgcacga gtgggttaca   3660
tcgaactgga tctcaacagc ggtaagatcc ttgagagttt tcgccccgaa gaacgttttc   3720
caatgatgag cacttttaaa gttctgctat gtggcgcggt attatcccgt gttgacgccg   3780
ggcaagagca actcggtcgc cgcatacact attctcagaa tgacttggtt gagtactcac   3840
cagtcacaga aaagcatctt acggatggca tgacagtaag agaattatgc agtgctgcca   3900
taaccatgag tgataacact gcggccaact tacttctgac aacgatcgga ggaccgaagg   3960
agctaaccgc ttttttgcac aacatggggg atcatgtaac tcgccttgat cgttgggaac   4020
cggagctgaa tgaagccata ccaaacgacg agcgtgacac cacgatgcct gtagcaatgg   4080
caacaacgtt gcgcaaacta ttaactggcg aactacttac tctagcttcc cggcaacaat   4140
taatagactg gatggaggcg gataaagttg caggaccact tctgcgctcg gcccttccgg   4200
ctggctggtt tattgctgat aaatctggag ccggtgagcg tgggtctcgc ggtatcattg   4260
cagcactggg gccagatggt aagccctccc gtatcgtagt tatctacacg acggggagtc   4320
aggcaactat ggatgaacga aatagacaga tcgctgagat aggtgcctca ctgattaagc   4380
attggtaact gtcagaccaa gtttactcat atatacttta gattgattta aaacttcatt   4440
tttaatttaa aaggatctag gtgaagatcc tttttgataa tctcatgacc aaaatccctt   4500
aacgtgagtt ttcgttccac tgagcgtcag accccgtaga aaagatcaaa ggatcttctt   4560
gagatccttt ttttctgcgc gtaatctgct gcttgcaaac aaaaaaacca ccgctaccag   4620
cggtggtttg tttgccggat caagagctac caactctttt tccgaaggta actggcttca   4680
```

```
gcagagcgca gataccaaat actgtccttc tagtgtagcc gtagttaggc caccacttca   4740

agaactctgt agcaccgcct acatacctcg ctctgctaat cctgttacca gtggctgctg   4800

ccagtggcga taagtcgtgt cttaccgggt tggactcaag acgatagtta ccggataagg   4860

cgcagcggtc gggctgaacg gggggttcgt gcacacagcc cagcttggag cgaacgacct   4920

acaccgaact gagataccta cagcgtgagc tatgagaaag cgccacgctt cccgaaggga   4980

gaaaggcgga caggtatccg gtaagcggca gggtcggaac aggagagcgc acgagggagc   5040

ttccaggggg aaacgcctgg tatctttata gtcctgtcgg gtttcgccac ctctgacttg   5100

agcgtcgatt tttgtgatgc tcgtcagggg ggcggagcct atggaaaaac gccagcaacg   5160

cggccttttt acggttcctg gccttttgct ggccttttgc tcacatgttc tttcctgcgt   5220

tatcccctga ttctgtggat aaccgtatta ccgcctttga gtgagctgat accgctcgcc   5280

gcagccgaac gaccgagcgc agcgagtcag tgagcgagga agcggaagag cgcctgatgc   5340

ggtattttct ccttacgcat ctgtgcggta tttcacaccg catatggtgc actctcagta   5400

caatctgctc tgatgccgca tagttaagcc agtatacact ccgctatcgc tacgtgactg   5460

ggtcatggct gcgccccgac acccgccaac acccgctgac gcgccctgac gggcttgtct   5520

gctcccggca tccgcttaca gacaagctgt gaccgtctcc gggagctgca tgtgtcagag   5580

gttttcaccg tcatcaccga aacgcgcgag gcagcagatc aattcgcgcg cgaaggcgaa   5640

gcggcatgca tttacgttga caccatcgaa tggtgcaaaa cctttcgcgg tatggcatga   5700

tagcgcccgg aagagagtca attcagggtg gtgaatgtga aaccagtaac gttatacgat   5760

gtcgcagagt atgccggtgt ctcttatcag accgtttccc gcgtggtgaa ccaggccagc   5820

cacgtttctg cgaaaacgcg ggaaaaagtg gaagcggcga tggcggagct gaattacatt   5880

cccaaccgcg tggcacaaca actggcgggc aaacagtcgt tgctgattgg cgttgccacc   5940

tccagtctgg ccctgcacgc gccgtcgcaa attgtcgcgg cgattaaatc tcgcgccgat   6000

caactgggtg ccagcgtggt ggtgtcgatg gtagaacgaa gcggcgtcga agcctgtaaa   6060

gcggcggtgc acaatcttct cgcgcaacgc gtcagtgggc tgatcattaa ctatccgctg   6120

gatgaccagg atgccattgc tgtggaagct gcctgcacta atgttccggc gttatttctt   6180

gatgtctctg accagacacc catcaacagt attattttct cccatgaaga cggtacgcga   6240

ctgggcgtgg agcatctggt cgcattgggt caccagcaaa tcgcgctgtt agcgggccca   6300

ttaagttctg tctcggcgcg tctgcgtctg gctggctggc ataaatatct cactcgcaat   6360

caaattcagc cgatagcgga acgggaaggc gactggagtg ccatgtccgg ttttcaacaa   6420

accatgcaaa tgctgaatga gggcatcgtt cccactgcga tgctggttgc caacgatcag   6480

atggcgctgg gcgcaatgcg cgccattacc gagtccgggc tgcgcgttgg tgcggatatc   6540

tcggtagtgg gatacgacga taccgaagac agctcatgtt atatcccgcc gtcaaccacc   6600

atcaaacagg attttcgcct gctggggcaa accagcgtgg accgcttgct gcaactctct   6660

cagggccagg cggtgaaggg caatcagctg ttgcccgtct cactggtgaa aagaaaaacc   6720

accctggcgc ccaatacgca aaccgcctct ccccgcgcgt tggccgattc attaatgcag   6780

ctggcacgac aggtttcccg actggaaagc gggcagtgag cgcaacgcaa ttaatgtgag   6840

ttagcgcgaa ttgatctg                                                 6858
```

<210> SEQ ID NO 8
<211> LENGTH: 21
<212> TYPE: DNA

<213> ORGANISM: Artificial Sequence
<220> FEATURE:
<223> OTHER INFORMATION: Synthetic Construct

<400> SEQUENCE: 8
gtcaggctgg aatactcttc g 21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
gacgctttcg ccaagtcagg 20

<210> SEQ ID NO 10
<211> LENGTH: 8911
<212> TYPE: DNA
<213> ORGANISM: Artificial Sequence
<220> FEATURE:
<223> OTHER INFORMATION: Synthetic Construct

<400> SEQUENCE: 10
accttcggga gcgcctgaag cccgttctgg acgccctggg gccgttgaat cgggatatgc 60
aggccaaggc cgccgcgatc atcaaggccg tgggcgaaaa gctgctgacg gaacagcggg 120
aagtccagcg ccagaaacag gcccagcgcc agcaggaacg cgggcgcgca catttccccg 180
aaaagtgcca cctggcggcg ttgtgacaat ttaccgaaca actccgcggc cgggaagccg 240
atctcggctt gaacgaattg ttaggtggcg gtacttgggt cgatatcaaa gtgcatcact 300
tcttcccgta tgcccaactt tgtatagaga gccactgcgg gatcgtcacc gtaatctgct 360
tgcacgtaga tcacataagc accaagcgcg ttggcctcat gcttgaggag attgatgagc 420
gcggtggcaa tgccctgcct ccggtgctcg ccggagactg cgagatcata gatatagatc 480
tcactacgcg gctgctcaaa cctgggcaga acgtaagccg cgagagcgcc aacaaccgct 540
tcttggtcga aggcagcaag cgcgatgaat gtcttactac ggagcaagtt cccgaggtaa 600
tcggagtccg gctgatgttg ggagtaggtg gctacgtctc cgaactcacg accgaaaaga 660
tcaagagcag cccgcatgga tttgacttgg tcagggccga gcctacatgt gcgaatgatg 720
cccatacttg agccacctaa ctttgtttta gggcgactgc cctgctgcgt aacatcgttg 780
ctgctgcgta acatcgttgc tgctccataa catcaaacat cgacccacgg cgtaacgcgc 840
ttgctgcttg gatgcccgag gcatagactg tacaaaaaaa cagtcataac aagccatgaa 900
aaccgccact gcgccgttac caccgctgcg ttcggtcaag gttctggacc agttgcgtga 960
gcgcatacgc tacttgcatt acagtttacg aaccgaacag gcttatgtca actgggttcg 1020
tgccttcatc cgtttccacg gtgtgcgtcc atgggcaaat attatacgca aggcgacaag 1080
gtgctgatgc cgctggcgat tcaggttcat catgccgttt gtgatggctt ccatgtcggc 1140
agaatgctta atgaattaca acagttttta tgcatgcgcc caatacgcaa accgcctctc 1200
cccgcgcgtt ggccgattca ttaatgcagc tggcacgaca ggtttcccga ctggaaagcg 1260
ggcagtgagc gcaacgcaat taatgtgagt tagctcactc attaggcacc ccaggcttta 1320
cactttatgc ttccggctcg tatgttgtgt ggaattgtga gcggataaca atttcacaca 1380
ggaaacagct atgaccatga ttacgccaag cgcgcaatta accctcacta aagggaacaa 1440
aagctgggta ccgggccccc cctcgagctg ttgacaatta atcatccggc tcgtataatg 1500
tgtggaattg tgagcggata acaatttcac acaggaaaca gcgccgctga gaaaaagcga 1560
agcggcactg ctctttaaca atttatcaga caatctgtgt gggcactcga ccggaattat 1620
cgattaactt tattattaaa aattaaagag gtatatatta atgtatcgat taaataagga 1680
ggaataaacc atggatccga gctcaggagg taaaaaaaca tgaaaacagt agttattatt 1740
gatgcattac gaacaccaat tggaaaatat aaaggcagct taagtcaagt aagtgccgta 1800
gacttaggaa cacatgttac aacacaactt ttaaaaagac attccactat ttctgaagaa 1860
attgatcaag taatctttgg aaatgtttta caagctggaa atggccaaaa tcccgcacga 1920
caaatagcaa taaacagcgg tttgtctcat gaaattcccg caatgacggt taatgaggtc 1980
tgcggatcag gaatgaaggc cgttattttg gcgaaacaat tgattcaatt aggagaagcg 2040
gaagttttaa ttgctggcgg gattgagaat atgtcccaag cacctaaatt acaacgtttt 2100
aattacgaaa cagaaagcta cgatgcgcct ttttctagta tgatgtatga tggattaacg 2160
gatgccttta gtggtcaggc aatgggctta actgctgaaa atgtggccga aaagtatcat 2220
gtaactagag aagagcaaga tcaattttct gtacattcac aattaaaagc agctcaagca 2280
caagcagaag ggatattcgc tgacgaaata gccccattag aagtatcagg aacgcttgtg 2340
gagaaagatg aagggattcg ccctaattcg agcgttgaga agctaggaac gcttaaaaca 2400
gtttttaaag aagacggtac tgtaacagca gggaatgcat caaccattaa tgatggggct 2460
tctgctttga ttattgcttc acaagaatat gccgaagcac acggtcttcc ttatttagct 2520
attattcgag acagtgtgga agtcggtatt gatccagcct atatgggaat ttcgccgatt 2580
aaagccattc aaaaactgtt agcgcgcaat caacttacta cggaagaaat tgatctgtat 2640
gaaatcaacg aagcatttgc agcaacttca atcgtggtcc aaagagaact ggctttacca 2700
gaggaaaagg tcaacattta tggtggcggt atttcattag gtcatgcgat tggtgccaca 2760
ggtgctcgtt tattaacgag tttaagttat caattaaatc aaaaagaaaa gaaatatgga 2820
gtggcttctt tatgtatcgg cggtggctta ggactcgcta tgctactaga gagacctcag 2880
caaaaaaaaa acagccgatt ttatcaaatg agtcctgagg aacgcctggc ttctcttctt 2940
aatgaaggcc agatttctgc tgatacaaaa aaagaatttg aaaatacggc tttatcttcg 3000
cagattgcca atcatatgat tgaaaatcaa atcagtgaaa cagaagtgcc gatgggcgtt 3060
ggcttacatt taacagtgga cgaaactgat tatttggtac caatggcgac agaagagccc 3120
tcagttattg cggctttgag taatggtgca aaaatagcac aaggatttaa aacagtgaat 3180
caacaacgct taatgcgtgg acaaatcgtt ttttacgatg ttgcagatcc cgagtcattg 3240
attgataaac tacaagtaag agaagcggaa gtttttcaac aagcagagtt aagttatcca 3300
tctatcgtta aacggggcgg cggcttaaga gatttgcaat atcgtacttt tgatgaatca 3360
tttgtatctg tcgacttttt agtagatgtt aaggatgcaa tgggggcaaa tatcgttaac 3420
gctatgttgg aaggtgtggc cgagttgttc cgtgaatggt ttgcggagca aaagatttta 3480
ttcagtattt taagtaatta tgccacggag tcggttgtta cgatgaaaac ggctattcca 3540
gtttcacgtt taagtaaggg gagcaatggc cgggaaattg ctgaaaaaat tgttttagct 3600
tcacgctatg cttcattaga tccttatcgg gcagtcacgc ataacaaagg aatcatgaat 3660
ggcattgaag ctgtagtttt agctacagga aatgatacac gcgctgttag cgcttcttgt 3720
catgcttttg cggtgaagga aggtcgctac caaggcttga ctagttggac gctggatggc 3780
gaacaactaa ttggtgaaat ttcagttccg cttgctttag ccacggttgg cggtgccaca 3840

-continued

```
aaagtcttac ctaaatctca agcagctgct gatttgttag cagtgacgga tgcaaaagaa   3900
ctaagtcgag tagtagcggc tgttggtttg gcacaaaatt tagcggcgtt acgggcctta   3960
gtctctgaag gaattcaaaa aggacacatg gctctacaag cacgttcttt agcgatgacg   4020
gtcggagcta ctggtaaaga agttgaggca gtcgctcaac aattaaaacg tcaaaaaacg   4080
atgaaccaag accgagccat ggctatttta aatgatttaa gaaaacaata aaggaggtaa   4140
aaaaacatga caattgggat tgataaaatt agtttttttg tgcccccctta ttatattgat   4200
atgacggcac tggctgaagc cagaaatgta gaccctggaa aatttcatat tggtattggg   4260
caagaccaaa tggcggtgaa cccaatcagc caagatattg tgacatttgc agccaatgcc   4320
gcagaagcga tcttgaccaa agaagataaa gaggccattg atatggtgat tgtcgggact   4380
gagtccagta tcgatgagtc aaaagcggcc gcagttgtct tacatcgttt aatggggatt   4440
caaccttttcg ctcgctcttt cgaaatcaag gaagcttgtt acggagcaac agcaggctta   4500
cagttagcta agaatcacgt agccttacat ccagataaaa aagtcttggt cgtagcggca   4560
gatattgcaa aatatggctt aaattctggc ggtgagccta cacaaggagc tggggcggtt   4620
gcaatgttag ttgctagtga accgcgcatt ttggctttaa aagaggataa tgtgatgctg   4680
acgcaagata tctatgactt ttggcgtcca acaggccacc cgtatcctat ggtcgatggt   4740
cctttgtcaa acgaaaccta catccaatct tttgcccaag tctgggatga acataaaaaa   4800
cgaaccggtc ttgattttgc agattatgat gctttagcgt tccatattcc ttacacaaaa   4860
atgggcaaaa aagccttatt agcaaaaatc tccgaccaaa ctgaagcaga acaggaacga   4920
attttagccc gttatgaaga aagtatcgtc tatagtcgtc gcgtaggaaa cttgtatacg   4980
ggttcacttt atctgggact catttccctt ttagaaaatg caacgacttt aaccgcaggc   5040
aatcaaattg gtttattcag ttatggttct ggtgctgtcg ctgaattttt cactggtgaa   5100
ttagtagctg gttatcaaaa tcatttacaa aaagaaactc atttagcact gctggataat   5160
cggacagaac tttctatcgc tgaatatgaa gccatgtttg cagaaacttt agacacagac   5220
attgatcaaa cgttagaaga tgaattaaaa tatagtattt ctgctattaa taataccgtt   5280
cgttcttatc gaaactaaag atctgcagct ggtaccatat gggaattcga agcttgggcc   5340
cgaacaaaaa ctcatctcag aagaggatct gaatagcgcc gtcgaccatc atcatcatca   5400
tcattgagtt taaacggtct ccagcttggc tgttttggcg gatgagagaa gattttcagc   5460
ctgatacaga ttaaatcaga acgcagaagc ggtctgataa aacagaattt gcctggcggc   5520
agtagcgcgg tggtcccacc tgaccccatg ccgaactcag aagtgaaacg ccgtagcgcc   5580
gatggtagtg tggggtctcc ccatgcgaga gtagggaact gccaggcatc aaataaaacg   5640
aaaggctcag tcgaaagact gggcctttct agagcggccg ccaccgcggt ggagctccaa   5700
ttcgccctat agtgagtcgt attacgcgcg ctcactggcc gtcgttttac aacgtcgtga   5760
ctgggaaaac cctggcgtta cccaacttaa tcgccttgca gcacatcccc ctttcgccag   5820
ctggcgtaat agcgaagagg cccgcaccga tcgcccttcc caacagttgc gcagcctgaa   5880
tggcgaatgg aaattgtaag cgttaatatt ttgttaaaat tcgcgttaaa tttttgttaa   5940
atcagctcat tttttaacca ataggccgac tgcgatgagt ggcagggcgg ggcgtaattt   6000
ttttaaggca gttattggtg cccttaaacg cctggtgcta cgcctgaata agtgataata   6060
agcggatgaa tggcagaaat tcgaaagcaa attcgacccg gtcgtcggtt cagggcaggg   6120
tcgttaaata gccgcttatg tctattgctg gtttaccggt ttattgacta ccggaagcag   6180
tgtgaccgtg tgcttctcaa atgcctgagg ccagtttgct caggctctcc ccgtggaggt   6240
```

```
aataattgac gatatgatca tttattctgc ctcccagagc ctgataaaaa cggtgaatcc   6300
gttagcgagg tgccgccggc ttccattcag gtcgaggtgg cccggctcca tgcaccgcga   6360
cgcaacgcgg ggaggcagac aaggtatagg gcggcgaggc ggctacagcc gatagtctgg   6420
aacagcgcac ttacgggttg ctgcgcaacc caagtgctac cggcgcggca gcgtgacccg   6480
tgtcggcggc tccaacggct cgccatcgtc cagaaaacac ggctcatcgg gcatcggcag   6540
gcgctgctgc ccgcgccgtt cccattcctc cgtttcggtc aaggctggca ggtctggttc   6600
catgcccgga atgccgggct ggctgggcgg ctcctcgccg gggccggtcg gtagttgctg   6660
ctcgcccgga tacagggtcg ggatgcggcg caggtcgcca tgccccaaca gcgattcgtc   6720
ctggtcgtcg tgatcaacca ccacggcggc actgaacacc gacaggcgca actggtcgcg   6780
gggctggccc cacgccacgc ggtcattgac cacgtaggcc gacacggtgc cggggccgtt   6840
gagcttcacg acggagatcc agcgctcggc caccaagtcc ttgactgcgt attggaccgt   6900
ccgcaaagaa cgtccgatga gcttggaaag tgtcttctgg ctgaccacca cggcgttctg   6960
gtggcccatc tgcgccacga ggtgatgcag cagcattgcc gccgtgggtt tcctcgcaat   7020
aagcccggcc cacgcctcat gcgctttgcg ttccgtttgc acccagtgac cgggcttgtt   7080
cttggcttga atgccgattt ctctggactg cgtggccatg cttatctcca tgcggtaggg   7140
tgccgcacgg ttgcggcacc atgcgcaatc agctgcaact tttcggcagc gcgacaacaa   7200
ttatgcgttg cgtaaaagtg gcagtcaatt acagattttc tttaacctac gcaatgagct   7260
attgcggggg gtgccgcaat gagctgttgc gtaccccccct tttttaagtt gttgattttt   7320
aagtctttcg catttcgccc tatatctagt tctttggtgc ccaaagaagg gcacccctgc   7380
ggggttcccc cacgccttcg gcgcggctcc ccctccggca aaaagtggcc cctccggggc   7440
ttgttgatcg actgcgcggc cttcggcctt gcccaaggtg gcgctgcccc cttggaaccc   7500
ccgcactcgc cgccgtgagg ctcggggggc aggcgggcgg gcttcgcctt cgactgcccc   7560
cactcgcata ggcttgggtc gttccaggcg cgtcaaggcc aagccgctgc gcggtcgctg   7620
cgcgagcctt gacccgcctt ccacttggtg tccaaccggc aagcgaagcg cgcaggccgc   7680
aggccggagg cttttcccca gagaaaatta aaaaaattga tggggcaagg ccgcaggccg   7740
cgcagttgga gccggtgggt atgtggtcga aggctgggta gccggtgggc aatccctgtg   7800
gtcaagctcg tgggcaggcg cagcctgtcc atcagcttgt ccagcagggt tgtccacggg   7860
ccgagcgaag cgagccagcc ggtggccgct cgcggccatc gtccacatat ccacgggctg   7920
gcaagggagc gcagcgaccg cgcagggcga agcccggaga gcaagcccgt agggcgccgc   7980
agccgccgta ggcggtcacg actttgcgaa gcaaagtcta gtgagtatac tcaagcattg   8040
agtggcccgc cggaggcacc gccttgcgct gcccccgtcg agccggttgg acaccaaaag   8100
ggaggggcag gcatggcggc atacgcgatc atgcgatgca agaagctggc gaaaatgggc   8160
aacgtggcgg ccagtctcaa gcacgcctac cgcgagcgcg agacgcccaa cgctgacgcc   8220
agcaggacgc cagagaacga gcactgggcg gccagcagca ccgatgaagc gatgggccga   8280
ctgcgcgagt tgctgccaga gaagcggcgc aaggacgctg tgttggcggt cgagtacgtc   8340
atgacggcca gcccggaatg gtggaagtcg gccagccaag aacagcaggc ggcgttcttc   8400
gagaaggcgc acaagtggct ggcggacaag tacggggcgg atcgcatcgt gacggccagc   8460
atccaccgtg acgaaaccag cccgcacatg accgcgttcg tggtgccgct gacgcaggac   8520
ggcaggctgt cggccaagga gttcatcggc aacaaagcgc agatgacccg cgaccagacc   8580
```

-continued acgtttgcgg ccgctgtggc cgatctaggg ctgcaacggg gcatcgaggg cagcaaggca 8640
cgtcacacgc gcattcaggc gttctacgag gccctggagc ggccaccagt gggccacgtc 8700
accatcagcc cgcaagcggt cgagccacgc gcctatgcac cgcagggatt ggccgaaaag 8760
ctgggaatct caaagcgcgt tgagacgccg gaagccgtgg ccgaccggct gacaaaagcg 8820
gttcggcagg ggtatgagcc tgccctacag gccgccgcag gagcgcgtga gatgcgcaag 8880
aaggccgatc aagcccaaga gacggcccga g 8911

<210> SEQ ID NO 11
<211> LENGTH: 331
<212> TYPE: PRT
<213> ORGANISM: E. Coli

<400> SEQUENCE: 11

Met Lys Gln Thr Val Tyr Ile Ala Ser Pro Glu Ser Gln Gln Ile His
1 5 10 15

Val Trp Asn Leu Asn His Glu Gly Ala Leu Thr Leu Thr Gln Val Val
20 25 30

Asp Val Pro Gly Gln Val Gln Pro Met Val Val Ser Pro Asp Lys Arg
35 40 45

Tyr Leu Tyr Val Gly Val Arg Pro Glu Phe Arg Val Leu Ala Tyr Arg
50 55 60

Ile Ala Pro Asp Asp Gly Ala Leu Thr Phe Ala Ala Glu Ser Ala Leu
65 70 75 80

Pro Gly Ser Pro Thr His Ile Ser Thr Asp His Gln Gly Gln Phe Val
85 90 95

Phe Val Gly Ser Tyr Asn Ala Gly Asn Val Ser Val Thr Arg Leu Glu
100 105 110

Asp Gly Leu Pro Val Gly Val Val Asp Val Val Glu Gly Leu Asp Gly
115 120 125

Cys His Ser Ala Asn Ile Ser Pro Asp Asn Arg Thr Leu Trp Val Pro
130 135 140

Ala Leu Lys Gln Asp Arg Ile Cys Leu Phe Thr Val Ser Asp Asp Gly
145 150 155 160

His Leu Val Ala Gln Asp Pro Ala Glu Val Thr Thr Val Glu Gly Ala
165 170 175

Gly Pro Arg His Met Val Phe His Pro Asn Glu Gln Tyr Ala Tyr Cys
180 185 190

Val Asn Glu Leu Asn Ser Ser Val Asp Val Trp Glu Leu Lys Asp Pro
195 200 205

His Gly Asn Ile Glu Cys Val Gln Thr Leu Asp Met Met Pro Glu Asn
210 215 220

Phe Ser Asp Thr Arg Trp Ala Ala Asp Ile His Ile Thr Pro Asp Gly
225 230 235 240

Arg His Leu Tyr Ala Cys Asp Arg Thr Ala Ser Leu Ile Thr Val Phe
245 250 255

Ser Val Ser Glu Asp Gly Ser Val Leu Ser Lys Glu Gly Phe Gln Pro
260 265 270

Thr Glu Thr Gln Pro Arg Gly Phe Asn Val Asp His Ser Gly Lys Tyr
275 280 285

Leu Ile Ala Ala Gly Gln Lys Ser His His Ile Ser Val Tyr Glu Ile
290 295 300

Val Gly Glu Gln Gly Leu Leu His Glu Lys Gly Arg Tyr Ala Val Gly
305 310 315 320

Gln Gly Pro Met Trp Val Val Val Asn Ala His
325 330

<210> SEQ ID NO 12
<211> LENGTH: 238
<212> TYPE: PRT
<213> ORGANISM: P. aeruginosa

<400> SEQUENCE: 12

Met Ala Ile Ser Glu Leu Lys Leu Pro Ala Gly Val Gly Leu Gln Val
1 5 10 15

Trp Gly Ser Ala Ala Glu Gln Ala Arg Gly Leu Ala Ala Glu Val Ala
20 25 30

Gly Arg Leu Arg Ser Ala Leu Ala Glu Gln Gly Gln Ala Leu Leu Val
35 40 45

Val Ser Gly Gly Arg Ser Pro Val Ala Phe Leu Glu Ala Leu Ser Glu
50 55 60

Glu Pro Leu Asp Trp Ser Arg Ile Thr Val Ser Leu Ala Asp Glu Arg
65 70 75 80

Trp Val Pro Glu Ser His Ala Asp Ser Asn Ala Gly Leu Val Arg Arg
85 90 95

His Leu Leu Arg Gly Glu Ala Ala Lys Ala Arg Phe Ile Gly Leu Tyr
100 105 110

Gln Pro Ala Ala Ser Leu Glu Glu Ala Ala Glu Leu Ala Asp His His
115 120 125

Leu His Glu Leu Pro Leu Pro Ile Asp Val Leu Val Leu Gly Met Gly
130 135 140

Asp Asp Gly His Thr Ala Ser Leu Phe Pro Asn Ser Pro Gly Leu Asp
145 150 155 160

Leu Ala Met Asp Pro Gln Gly Thr Arg Arg Cys Leu Pro Met Trp Ala
165 170 175

Pro Ser Val Pro His Gln Arg Leu Thr Leu Pro Arg Ala Val Leu Ala
180 185 190

Ala Ala Lys Val Gln Leu Leu Ala Ile Gln Gly Gln Ser Lys Leu Ala
195 200 205

Thr Leu Asn Ala Ala Leu Ala Val Glu Asp Glu Arg Arg Met Pro Val
210 215 220

Arg Ala Phe Leu Arg Ala Pro Leu Thr Ile His Trp Tyr Pro
225 230 235

<210> SEQ ID NO 13
<211> LENGTH: 249
<212> TYPE: PRT
<213> ORGANISM: S. cerevisiae

<400> SEQUENCE: 13

Met Val Thr Val Gly Val Phe Ser Glu Arg Ala Ser Leu Thr His Gln
1 5 10 15

Leu Gly Glu Phe Ile Val Lys Lys Gln Asp Glu Ala Leu Gln Lys Lys
20 25 30

Ser Asp Phe Lys Val Ser Val Ser Gly Gly Ser Leu Ile Asp Ala Leu
35 40 45

Tyr Glu Ser Leu Val Ala Asp Glu Ser Leu Ser Ser Arg Val Gln Trp
50 55 60

Ser Lys Trp Gln Ile Tyr Phe Ser Asp Glu Arg Ile Val Pro Leu Thr
65 70 75 80

-continued

```
Asp Ala Asp Ser Asn Tyr Gly Ala Phe Lys Arg Ala Val Leu Asp Lys
                85                  90                  95

Leu Pro Ser Thr Ser Gln Pro Asn Val Tyr Pro Met Asp Glu Ser Leu
            100                 105                 110

Ile Gly Ser Asp Ala Glu Ser Asn Asn Lys Ile Ala Ala Glu Tyr Glu
        115                 120                 125

Arg Ile Val Pro Gln Val Leu Asp Leu Val Leu Leu Gly Cys Gly Pro
    130                 135                 140

Asp Gly His Thr Cys Ser Leu Phe Pro Gly Glu Thr His Arg Tyr Leu
145                 150                 155                 160

Leu Asn Glu Thr Thr Lys Arg Val Ala Trp Cys His Asp Ser Pro Lys
                165                 170                 175

Pro Pro Ser Asp Arg Ile Thr Phe Thr Leu Pro Val Leu Lys Asp Ala
            180                 185                 190

Lys Ala Leu Cys Phe Val Ala Glu Gly Ser Ser Lys Gln Asn Ile Met
        195                 200                 205

His Glu Ile Phe Asp Leu Lys Asn Asp Gln Leu Pro Thr Ala Leu Val
    210                 215                 220

Asn Lys Leu Phe Gly Glu Lys Thr Ser Trp Phe Val Asn Glu Glu Ala
225                 230                 235                 240

Phe Gly Lys Val Gln Thr Lys Thr Phe
                245
```

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct

<400> SEQUENCE: 14
accaattgca cccggcaga 19

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
gctaaagcgc atgctccaga c 21

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
gactggcctc agatgaaagc 20

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
caaacatgtg gcatggaaag 20

<210> SEQ ID NO 18
<211> LENGTH: 52
<212> TYPE: DNA
<213> ORGANISM: Artificial Sequence
<220> FEATURE:
<223> OTHER INFORMATION: Synthetic Construct

<400> SEQUENCE: 18
gggcccgttt aaactttaac tagactctgc agttagcgtt caaacggcag aa 52

<210> SEQ ID NO 19
<211> LENGTH: 38
<212> TYPE: DNA
<213> ORGANISM: Artificial Sequence
<220> FEATURE:
<223> OTHER INFORMATION: Synthetic Construct

<400> SEQUENCE: 19
cgcatgcatg tcatgagatg tagcgtgtcc accgaaaa 38

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
acaatttcac acaggaaaca gc 22

<210> SEQ ID NO 21
<211> LENGTH: 23
<212> TYPE: DNA
<213> ORGANISM: Artificial Sequence
<220> FEATURE:
<223> OTHER INFORMATION: Synthetic Construct

<400> SEQUENCE: 21
ccaggcaaat tctgttttat cag 23

<210> SEQ ID NO 22
<211> LENGTH: 22
<212> TYPE: DNA
<213> ORGANISM: Artificial Sequence
<220> FEATURE:
<223> OTHER INFORMATION: Synthetic Construct

<400> SEQUENCE: 22
gcactgtctt tccgtctgct gc 22

<210> SEQ ID NO 23
<211> LENGTH: 66
<212> TYPE: DNA
<213> ORGANISM: Artificial Sequence
<220> FEATURE:
<223> OTHER INFORMATION: Synthetic Construct

<400> SEQUENCE: 23
gcgaacgatg cataaaggag gtaaaaaaac atggtatcct gttctgcgcc gggtaagatt 60
tacctg 66

<210> SEQ ID NO 24

<211> LENGTH: 48
<212> TYPE: DNA
<213> ORGANISM: Artificial Sequence
<220> FEATURE:
<223> OTHER INFORMATION: Synthetic Construct

<400> SEQUENCE: 24
gggcccgttt aaactttaac tagactttaa tctactttca gaccttgc 48

<210> SEQ ID NO 25
<211> LENGTH: 24
<212> TYPE: DNA
<213> ORGANISM: Artificial Sequence
<220> FEATURE:
<223> OTHER INFORMATION: Synthetic Construct

<400> SEQUENCE: 25
gatagtaacg gctgcgctgc tacc 24

<210> SEQ ID NO 26
<211> LENGTH: 23
<212> TYPE: DNA
<213> ORGANISM: Artificial Sequence
<220> FEATURE:
<223> OTHER INFORMATION: Synthetic Construct

<400> SEQUENCE: 26
gacagcttat catcgactgc acg 23

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
caccatggta tcctgttctg cg 22

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
ttaatctact ttcagacctt gc 22

<210> SEQ ID NO 29
<211> LENGTH: 67
<212> TYPE: DNA
<213> ORGANISM: Artificial Sequence
<220> FEATURE:
<223> OTHER INFORMATION: Synthetic Construct

<400> SEQUENCE: 29
accgccaaaa gcgactaatt ttagctgtta cagtcagttg aattaaccct cactaaaggg 60
cggccgc 67

<210> SEQ ID NO 30
<211> LENGTH: 152
<212> TYPE: DNA
<213> ORGANISM: Artificial Sequence
<220> FEATURE:
<223> OTHER INFORMATION: Synthetic Construct -continued

<400> SEQUENCE: 30
gctggcgata taaactgttt gcttcatgaa tgctcctttg ggttacctcc gggaaacgcg 60
gttgatttgt ttagtggttg aattatttgc tcaggatgtg gcatagtcaa gggcgtgacg 120
gctcgctaat acgactcact atagggctcg ag 152

<210> SEQ ID NO 31
<211> LENGTH: 30
<212> TYPE: DNA
<213> ORGANISM: Artificial Sequence
<220> FEATURE:
<223> OTHER INFORMATION: Synthetic Construct

<400> SEQUENCE: 31
cttgatatct tagtgtgcgt taaccaccac 30

<210> SEQ ID NO 32
<211> LENGTH: 21
<212> TYPE: DNA
<213> ORGANISM: Artificial Sequence
<220> FEATURE:
<223> OTHER INFORMATION: Synthetic Construct

<400> SEQUENCE: 32
cgtgaatttg ctggctctca g 21

<210> SEQ ID NO 33
<211> LENGTH: 21
<212> TYPE: DNA
<213> ORGANISM: Artificial Sequence
<220> FEATURE:
<223> OTHER INFORMATION: Synthetic Construct

<400> SEQUENCE: 33
ggtttagttc ctcaccttgt c 21

<210> SEQ ID NO 34
<211> LENGTH: 21
<212> TYPE: DNA
<213> ORGANISM: Artificial Sequence
<220> FEATURE:
<223> OTHER INFORMATION: Synthetic Construct

<400> SEQUENCE: 34
actgaaacgt tttcatcgct c 21

<210> SEQ ID NO 35
<211> LENGTH: 26
<212> TYPE: DNA
<213> ORGANISM: Artificial Sequence
<220> FEATURE:
<223> OTHER INFORMATION: Synthetic Construct

<400> SEQUENCE: 35
accgccaaaa gcgactaatt ttagct 26

<210> SEQ ID NO 36
<211> LENGTH: 81
<212> TYPE: DNA
<213> ORGANISM: Artificial Sequence
<220> FEATURE:
<223> OTHER INFORMATION: Synthetic Construct

<400> SEQUENCE: 36

-continued

```
aaagtagccg aagatgacgg tttgtcacat ggagttggca ggatgtttga ttaaaagcaa     60

ttaaccctca ctaaagggcg g                                                81


<210> SEQ ID NO 37
<211> LENGTH: 199
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 112
<223> OTHER INFORMATION: n = A,T,C or G

<400> SEQUENCE: 37

taaatcttac ccggcgcaga acaggatacc atgttttttt acctcctttg caccttcatg     60

gtggtcagtg cgtcctgctg atgtgctcag tatcaccgcc agtggtattt angtcaacac    120

cgccagagat aatttatcac cgcagatggt tatctgtatg tttttatat gaatttaata     180

cgactcacta tagggctcg                                                  199


<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38

aaagaccgac caagcgacgt ctga                                             24


<210> SEQ ID NO 39
<211> LENGTH: 22
<212> TYPE: DNA
<213> ORGANISM: Artificial Sequence
<220> FEATURE:
<223> OTHER INFORMATION: Synthetic Construct

<400> SEQUENCE: 39

gctctgaata gtgatagagt ca                                               22


<210> SEQ ID NO 40
<211> LENGTH: 445
<212> TYPE: DNA
<213> ORGANISM: Artificial Sequence
<220> FEATURE:
<223> OTHER INFORMATION: Synthetic Construct

<400> SEQUENCE: 40

aaagaccgac caagcgacgt ctgagagctc cctggcgaat tcggtaccaa taaaagagct     60

ttattttcat gatctgtgtg ttggtttttg tgtgcggcgc ggaagttcct attctctaga    120

aagtatagga acttcctcga gccctatagt gagtcgtatt aaattcatat aaaaaacata    180

cagataacca tctgcggtga taaattatct ctggcggtgt tgacataaat accactggcg    240

gtgatactga gcacatcagc aggacgcact gaccaccatg aaggtgcaaa ggaggtaaaa    300

aaacatggta tcctgttctg cgccgggtaa gatttacctg ttcggtgaac acgccgtagt    360

ttatggcgaa actgcaattg cgtgtgcggt ggaactgcgt acccgtgttc gcgcggaact    420

caatgactct atcactattc agagc                                           445


<210> SEQ ID NO 41
<211> LENGTH: 445
```

<212> TYPE: DNA
<213> ORGANISM: Artificial Sequence
<220> FEATURE:
<223> OTHER INFORMATION: Synthetic Construct

<400> SEQUENCE: 41
aaagaccgac caagcgacgt ctgagagctc cctggcgaat tcggtaccaa taaaagagct 60
ttattttcat gatctgtgtg ttggtttttg tgtgcggcgc ggaagttcct attctctaga 120
aagtatagga acttcctcga gccctatagt gagtcgtatt aaattcatat aaaaaacata 180
cagataacca tctgcggtga taaattatct ctggcggtgt tgacctaaat accactggcg 240
gtgatactga gcacatcagc aggacgcact gaccaccatg aaggtgcaaa ggaggtaaaa 300
aaacatggta tcctgttctg cgccgggtaa gatttacctg ttcggtgaac acgccgtagt 360
ttatggcgaa actgcaattg cgtgtgcggt ggaactgcgt acccgtgttc gcgcggaact 420
caatgactct atcactattc agagc 445

<210> SEQ ID NO 42
<211> LENGTH: 442
<212> TYPE: DNA
<213> ORGANISM: Artificial Sequence
<220> FEATURE:
<223> OTHER INFORMATION: Synthetic Construct

<400> SEQUENCE: 42
aaagaccgac caagcgacgt ctgagagctc cctggcgaat tcggtaccaa taaaagagct 60
ttattttcat gatctgtgtg ttggtttttg tgtgcggcgc ggaagttcct attctctaga 120
aagtatagga acttcctcga gccctatagt gagtcgtatt aaattcatat aaaaaacata 180
cagataacca tctgcggtga taaattatct ctggcggtgt tgacctaaat accactggcg 240
gtgatactga gcacatcagc aggacgcact gaccaccatg aaggtgcaaa ggtaaaaaaa 300
catggtatcc tgttctgcgc cgggtaagat ttacctgttc ggtgaacacg ccgtagttta 360
tggcgaaact gcaattgcgt gtgcggtgga actgcgtacc cgtgttcgcg cggaactcaa 420
tgactctatc actattcaga gc 442

<210> SEQ ID NO 43
<211> LENGTH: 445
<212> TYPE: DNA
<213> ORGANISM: Artificial Sequence
<220> FEATURE:
<223> OTHER INFORMATION: Synthetic Construct

<400> SEQUENCE: 43
aaagaccgac caagcgacgt ctgagagctc cctggcgaat tcggtaccaa taaaagagct 60
ttattttcat gatctgtgtg ttggtttttg tgtgcggcgc ggaagttcct attctctaga 120
aagtatagga acttcctcga gccctatagt gagtcgtatt aaattcatat aaaaaacata 180
cagataacca tctgcggtga taaattatct ctggcggtgt tgacgtaaat accactggcg 240
gtgatactga gcacatcagc aggacgcact gaccaccatg aaggtgcaaa ggaggtaaaa 300
aaacatggta tcctgttctg cgccgggtaa gatttacctg ttcggtgaac acgccgtagt 360
ttatggcgaa actgcaattg cgtgtgcggt ggaactgcgt acccgtgttc gcgcggaact 420
caatgactct atcactattc agagc 445

<210> SEQ ID NO 44
<211> LENGTH: 30
<212> TYPE: DNA

-continued

<213> ORGANISM: Artificial Sequence
<220> FEATURE:
<223> OTHER INFORMATION: Synthetic Construct

<400> SEQUENCE: 44
gaggaataaa ccatggaagc tcgtcgttct 30

<210> SEQ ID NO 45
<211> LENGTH: 30
<212> TYPE: DNA
<213> ORGANISM: Artificial Sequence
<220> FEATURE:
<223> OTHER INFORMATION: Synthetic Construct

<400> SEQUENCE: 45
agaacgacga gcttccatgg tttattcctc 30

<210> SEQ ID NO 46

<400> SEQUENCE: 46

000

<210> SEQ ID NO 47

<400> SEQUENCE: 47

000

<210> SEQ ID NO 48
<211> LENGTH: 20
<212> TYPE: DNA
<213> ORGANISM: Artificial Sequence
<220> FEATURE:
<223> OTHER INFORMATION: Synthetic Construct

<400> SEQUENCE: 48
ctcgtacagg ctcaggatag 20

<210> SEQ ID NO 49
<211> LENGTH: 20
<212> TYPE: DNA
<213> ORGANISM: Artificial Sequence
<220> FEATURE:
<223> OTHER INFORMATION: Synthetic Construct

<400> SEQUENCE: 49
ttacgtccca acgctcaact 20

<210> SEQ ID NO 50
<211> LENGTH: 20
<212> TYPE: DNA
<213> ORGANISM: Artificial Sequence
<220> FEATURE:
<223> OTHER INFORMATION: Synthetic Construct

<400> SEQUENCE: 50
cttcggcaac gcatggaaat 20

<210> SEQ ID NO 51

<400> SEQUENCE: 51

000

<210> SEQ ID NO 52

<211> LENGTH: 23
<212> TYPE: DNA
<213> ORGANISM: Artificial Sequence
<220> FEATURE:
<223> OTHER INFORMATION: Synthetic Construct

<400> SEQUENCE: 52
cctggaatta gcaagaaaaa cgc 23

<210> SEQ ID NO 53
<211> LENGTH: 23
<212> TYPE: DNA
<213> ORGANISM: Artificial Sequence
<220> FEATURE:
<223> OTHER INFORMATION: Synthetic Construct

<400> SEQUENCE: 53
gtgaaaattg cacggcgagt agg 23

<210> SEQ ID NO 54
<211> LENGTH: 24
<212> TYPE: DNA
<213> ORGANISM: Artificial Sequence
<220> FEATURE:
<223> OTHER INFORMATION: Synthetic Construct

<400> SEQUENCE: 54
cagcaaatag caggtgtatc cagc 24

<210> SEQ ID NO 55
<211> LENGTH: 24
<212> TYPE: DNA
<213> ORGANISM: Artificial Sequence
<220> FEATURE:
<223> OTHER INFORMATION: Synthetic Construct

<400> SEQUENCE: 55
gcaaccgact gttgatagaa caac 24

<210> SEQ ID NO 56
<211> LENGTH: 24
<212> TYPE: DNA
<213> ORGANISM: Artificial Sequence
<220> FEATURE:
<223> OTHER INFORMATION: Synthetic Construct

<400> SEQUENCE: 56
ggttacaaaa tgattggcgt acgc 24

<210> SEQ ID NO 57
<211> LENGTH: 34
<212> TYPE: DNA
<213> ORGANISM: Artificial Sequence
<220> FEATURE:
<223> OTHER INFORMATION: Synthetic Construct

<400> SEQUENCE: 57
atgctcgagc tgttgacaat taatcatccg gctc 34

<210> SEQ ID NO 58
<211> LENGTH: 33
<212> TYPE: DNA
<213> ORGANISM: Artificial Sequence
<220> FEATURE:
<223> OTHER INFORMATION: Synthetic Construct

<400> SEQUENCE: 58
cgatctagaa aggcccagtc tttcgactga gcc 33

<210> SEQ ID NO 59
<211> LENGTH: 22
<212> TYPE: DNA
<213> ORGANISM: Artificial Sequence
<220> FEATURE:
<223> OTHER INFORMATION: Synthetic Construct

<400> SEQUENCE: 59
ggattttggc catttccagc tt 22

<210> SEQ ID NO 60
<211> LENGTH: 26
<212> TYPE: DNA
<213> ORGANISM: Artificial Sequence
<220> FEATURE:
<223> OTHER INFORMATION: Synthetic Construct

<400> SEQUENCE: 60
atgaaaacag tagttattat tgatgc 26

<210> SEQ ID NO 61
<211> LENGTH: 20
<212> TYPE: DNA
<213> ORGANISM: Artificial Sequence
<220> FEATURE:
<223> OTHER INFORMATION: Synthetic Construct

<400> SEQUENCE: 61
cttaaatcat ttaaaatagc 20

<210> SEQ ID NO 62
<211> LENGTH: 26
<212> TYPE: DNA
<213> ORGANISM: Artificial Sequence
<220> FEATURE:
<223> OTHER INFORMATION: Synthetic Construct

<400> SEQUENCE: 62
atgacaattg ggattgataa aattag 26

<210> SEQ ID NO 63
<211> LENGTH: 23
<212> TYPE: DNA
<213> ORGANISM: Artificial Sequence
<220> FEATURE:
<223> OTHER INFORMATION: Synthetic Construct

<400> SEQUENCE: 63
gaaatagccc cattagaagt atc 23

<210> SEQ ID NO 64
<211> LENGTH: 24
<212> TYPE: DNA
<213> ORGANISM: Artificial Sequence
<220> FEATURE:
<223> OTHER INFORMATION: Synthetic Construct

<400> SEQUENCE: 64
ttgccaatca tatgattgaa aatc 24

<210> SEQ ID NO 65
<211> LENGTH: 25
<212> TYPE: DNA

-continued

```
<213> ORGANISM: Artificial Sequence
<220> FEATURE:
<223> OTHER INFORMATION: Synthetic Construct

<400> SEQUENCE: 65

gctatgcttc attagatcct tatcg                                       25


<210> SEQ ID NO 66
<211> LENGTH: 25
<212> TYPE: DNA
<213> ORGANISM: Artificial Sequence
<220> FEATURE:
<223> OTHER INFORMATION: Synthetic Construct

<400> SEQUENCE: 66

gaaacctaca tccaatcttt tgccc                                       25
```

USE OF RECOMBINANT PGL FOR INCREASED PRODUCTION OF ISOPRENE

CROSS-REFERENCE TO RELATED APPLICATIONS

This application is a divisional patent application of U.S. patent application Ser. No. 12/978,324, filed Dec. 23, 2010, which claims priority to U.S. Provisional Patent Application No. 61/289,959, filed Dec. 23, 2009, the disclosures of which are herein incorporated by reference in their entirety.

FIELD OF THE INVENTION

This disclosure relates to improved compositions and methods for the increased production of biochemicals in *E. coli*, as well as improved compositions and methods for the increased production of isoprene in *E. coli.*

BACKGROUND

Isoprene (2-methyl-1,3-butadiene) is an important organic compound used in a wide array of applications. For instance, isoprene is employed as an intermediate or a starting material in the synthesis of numerous chemical compositions and polymers. Isoprene is also an important biological material that is synthesized naturally by many plants and animals.

Isoprene became an important monomer for utilization in the synthesis of cis-1,4-polybutadiene when its stereo-regulated polymerization became commercially possible in the early 1960s. cis-1,4-Polyisoprene made by such stereo-regulated polymerizations is similar in structure and properties to natural rubber. Even though it is not identical to natural rubber it can be used as a substitute for natural rubber in many applications. For instance, synthetic cis-1,4-polyisoprene rubber is widely used in manufacturing vehicle tires and other rubber products. This demand for synthetic cis-1,4-polyisoprene rubber consumes a majority of the isoprene available in the worldwide market. The remaining isoprene is used in making other synthetic rubbers, block copolymers, and other chemical products. For instance, isoprene is used in making butadiene-isoprene rubbers, styrene-isoprene copolymer rubbers, styrene-isoprene-butadiene rubbers, styrene-isoprene-styrene block copolymers, and styrene-isoprene block copolymers.

The isoprene used in industrial applications is typically produced as a by-product of the thermal cracking of petroleum or naphtha or is otherwise extracted from petrochemical streams. This is a relatively expensive, energy-intensive process. With the worldwide demand for petrochemical based products constantly increasing, the cost of isoprene is expected to rise to much higher levels in the long-term and its availability is limited in any case. There is concern that future supplies of isoprene from petrochemical-based sources will be inadequate to meet projected needs and that prices will rise to unprecedented levels. Accordingly, there is a need to procure a source of isoprene from a low cost, renewable source which is environmentally friendly. The improved methods and compositions described herein provide such a source of isoprene, capable of being derived at low cost and from renewable sources.

Several recent advancements have been made in the production of isoprene from renewable sources (see, for example, International Patent Application Publication No. WO 2009/076676 A2). Such methods produce isoprene at rates, titers, and purity that may be sufficient to meet the demands of a robust commercial process, however process improvements to reduce the operational costs associated with the production of isoprene derived from biological sources and to increase yields of isoprene are needed, such as the improved compositions and methods for the increased production of isoprene and other heterologous polypeptides capable of biological activity provided herein.

All patents, patent applications, documents, nucleotide and protein sequence database accession numbers and articles cited herein are incorporated herein by reference in their entirety.

SUMMARY

Disclosed herein are improved compositions and methods for the increased production of isoprene. Also provided herein are improved compositions and methods for the increased production of heterologous polypeptides capable of biological activity. The invention is based in part on the observation that chromosomal integration of 6-phosphogluconolactonase (PGL) into *E. coli* strains which lack nucleic acids encoding for PGL polypeptide improves the production of different types of products, for example, isoprene or mevalonate.

Accordingly, in one aspect, the invention provides for recombinant cell(s) of an *Escherichia coli* (*E. coli*) strain, or progeny thereof, capable of producing isoprene, the cell comprising: (a) one or more copies of a heterologous nucleic acid(s) encoding a PGL polypeptide wherein the nucleic acid is integrated in the *E. coli* chromosome; and (b) one or more heterologous nucleic acid(s) encoding isoprene synthase; wherein prior to the integration, the *E. coli* cell does not contain nucleic acid(s) encoding a PGL polypeptide, and wherein the resulting recombinant cell produces isoprene at a greater titer than that of the same cells that do not comprise (a) and (b).

In any of the aspects herein, one or more copies of a heterologous nucleic acid encoding a molybdenum uptake polypeptide is additionally integrated in the *E. coli* chromosome. In any of the aspects herein, the molybdenum uptake polypeptide is selected from the group consisting of modF, modE, modA, modB and modC. In any of the aspects herein, one or more copies of a heterologous nucleic acid encoding a galactose metabolism polypeptide is additionally integrated in the *E. coli* chromosome. In any of the aspects herein, the galactose metabolism polypeptide is selected from the group consisting of galM, galK, galT and galE. In any of the aspects herein, one or more copies of a heterologous nucleic acid encoding a galactose metabolism polypeptide and one or more copies of a heterologous nucleic acid encoding a molybdenum uptake polypeptide are additionally integrated in the *E. coli* chromosome. In any of the aspects herein, (a) the PGL polypeptide is an *E. coli* PGL polypeptide; (b) the molybdenum uptake polypeptide is selected from the group consisting of modF, modE, modA, modB and modC; and (c) the galactose metabolism polypeptide is selected from the group consisting of galM, galK, galT and galE. In any of the aspects herein, nucleic acids encoding the PGL polypeptide, galactose metabolism polypeptide, and molybdenum uptake polypeptide are part a 17,257 base pair piece as shown in FIG. 20. In any of the aspects herein, the recombinant cell produces isoprene at a higher specific productivity than that of the same cells that do not contain (a) and (b).

In any of the aspects herein, the recombinant cell has a specific productivity of at least 15 mg/OD/hr. In any of the aspects herein, the nucleic acids encoding PGL polypeptide, molybdenum uptake polypeptide, and/or galactose metabolism polypeptide are from *E. coli* strain K12 MG1655 or a derivative of *E. coli* strain K12 MG1655. In any of the aspects herein, the cell is of *E. coli* strain B. In any of the aspects herein, the cell is of *E. coli* strain BL21. In any of the aspects herein, the cell is of *E. coli* strain BL21(DE3).

In any of the aspects herein, the recombinant *E. coli* cell further comprises (c) a heterologous nucleic acid encoding an upper mevalonate (MVA) pathway polypeptide and/or a lower MVA pathway polypeptide.

In any of the aspects herein, the recombinant *E. coli* cell further comprises (d) a heterologous nucleic acid encoding an upper mevalonate (MVA) pathway polypeptide and/or a lower MVA pathway polypeptide. In any of the aspects herein, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In any of the aspects herein, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In any of the aspects herein, (a) the PGL polypeptide is an *E. coli* PGL polypeptide; (b) the molybdenum uptake polypeptide is selected from the group consisting of modF, modE, modA, modB and modC; and (c) the galactose metabolism polypeptide is selected from the group consisting of galM, galK, galT and galE. In any of the aspects herein, the isoprene synthase polypeptide is from *Populus alba.*

The invention also provides for methods of producing isoprene, the method comprising: (a) culturing a composition comprising any of the recombinant cell described herein under suitable culture conditions for the production of isoprene and (b) producing isoprene. In some aspects, the method comprises further recovering the isoprene. In other aspects, the recombinant cell has a specific productivity greater than about 15 mg/OD/hr of isoprene.

The invention also provides for methods of producing mevalonate, the method comprising: (a) culturing a composition comprising the recombinant cell of claim 15 under suitable culture conditions for the production of mevalonate and (b) producing mevalonate. In some aspects, the method comprises further recovering the mevalonate.

The invention also provides for methods of making any of the recombinant cell described herein comprising: (a) tranducing a heterologous nucleic acid encoding a PGL polypeptide into an *E. coli* cell, wherein prior to the integration, the *E. coli* cell does not contain nucleic acid(s) encoding a PGL polypeptide; (b) allowing the nucleic acid encoding a PGL polypeptide to integrate in the *E. coli* chromosome; and (c) introducing one or more heterologous nucleic acid(s) encoding isoprene synthase into *E. coli* cell.

The invention also provides for compositions comprising any of the recombinant cell described herein.

In other aspects, provided herein are cells of an *Escherichia coli* strain that does not encode a PGL polypeptide, wherein the *E. coli* cells comprise one or more copies of a heterologous gene encoding a PGL polypeptide with one or more associated expression control sequences and a nucleic acid encoding a heterologous polypeptide capable of biological activity, and wherein the cells produce the heterologous polypeptide capable of biological activity at a specific productivity greater than that of the same cells lacking one or more copies of a heterologous gene encoding a PGL polypeptide with one or more associated expression control sequences, when the cells are cultured in minimal medium. In some aspects, the one or more copies of the heterologous gene encoding a PGL polypeptide with one or more associated expression control sequences is/are chromosomal copies (e.g., integrated into the *E. coli* chromosome). In some aspects, the *E. coli* cells are in culture. In some aspects, the cells are of *E. coli* strain B. In some aspects, the cells are of *E. coli* strain BL21. In some aspects, the cells are of *E. coli* strain BL21(DE3). In some aspects, the minimal medium is supplemented with 0.1% (w/v) yeast extract or less. In some aspects, the minimal medium is supplemented with 1% (w/v) glucose or less. In some aspects, the minimal medium is supplemented with 0.1% (w/v) yeast extract or less and 1% (w/v) glucose or less. In some aspects, the heterologous gene encoding a PGL polypeptide is from *E. coli* strain K12 MG1655 or a derivative of *E. coli* strain K12 MG1655. In some aspects, the heterologous gene encoding a PGL polypeptide is from the genus *Pseudomonas*. In some aspects, the *Pseudomonas* is *Pseudomonas aeruginosa.*

In some aspects, the heterologous polypeptide capable of biological activity comprises one or more polypeptides involved in the biosynthesis of terpenoid (isoprenoid) or carotenoid compounds, and the cells produce a terpenoid or carotenoid at a higher specific productivity than that of the same cells lacking one or more copies of a heterologous gene encoding a PGL polypeptide with one or more associated expression control sequences, when the cells are cultured in minimal medium. In some aspects, the terpenoid is selected from the group consisting of hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid is geranyl pyrophosphate, eucalyptol, limonene, or pinene. In some aspects, the sesquiterpenoid is farnesyl pyrophosphate, artemisinin, or bisabolol. In some aspects, the diterpenoid is geranylgeranyl pyrophosphate, retinol, retinal, phytol, taxol, forskolin, or aphidicolin. In some aspects, the triterpenoid is squalene or lanosterol. In some aspects, the tetraterpenoid is lycopene or carotene. In some aspects, the carotenoid is selected from the group consisting of xanthophylls and carotenes. In some aspects, the xanthophyll is lutein or zeaxanthin. In some aspects, the carotene is α-carotene, β-carotene, γ-carotene, β-cryptoxanthin or lycopene.

In another aspect, provided herein are cells of an *Escherichia coli* strain that does not encode a PGL polypeptide, wherein the *E. coli* cells comprise one or more copies of a heterologous gene encoding a PGL polypeptide with one or more associated expression control sequences and a heterologous nucleic acid encoding an isoprene synthase polypeptide, and wherein the cells have a specific productivity of isoprene greater than that of the same cells lacking one or more copies of a heterologous gene encoding a PGL polypeptide with one or more associated expression control sequences, when the cells are cultured in minimal medium. In some aspects, the one or more copies of the heterologous gene encoding a PGL polypeptide with one or more associated expression control sequences is/are chromosomal copies (e.g., integrated into the *E. coli* chromosome). In some aspects, the *E. coli* cells are in culture. In some aspects, the cells further comprise a heterologous nucleic acid encoding an MVA pathway polypeptide. In some aspects, the MVA pathway polypeptide is an upper MVA pathway polypeptide. In some aspects, the MVA pathway polypeptide is a lower MVA pathway polypeptide.

In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is from the genus *Enterococcus*. In some aspects, the upper MVA pathway polypeptide is from *Enterococcus faecalis*. In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some aspects, the lower MVA pathway polypeptide is an MVK polypeptide. In some aspects, the MVK polypeptide is from the genus *Methanosarcina*. In some aspects, the MVK polypeptide is from *Methanosarcina mazei*.

In some aspects, the cells are of *E. coli* strain B. In some aspects, the cells are of *E. coli* strain BL21. In some aspects, the cells are of *E. coli* strain BL21(DE3). In some aspects, the minimal medium is supplemented with 0.1% (w/v) yeast extract or less. In some aspects, the minimal medium is supplemented with 1% (w/v) glucose or less. In some aspects, the minimal medium is supplemented with 0.1% (w/v) yeast extract or less and 1% (w/v) glucose or less. In some aspects, the heterologous gene encoding a PGL polypeptide is from *E. coli* strain K12 MG1655 or a derivative of *E. coli* strain K12 MG1655. In some aspects, the heterologous gene encoding a PGL polypeptide is from the genus *Pseudomonas*. In some aspects, the *Pseudomonas* is *Pseudomonas aeruginosa*.

In some aspects, the cells have a specific productivity greater than about 20 mg/OD/hr of isoprene. In some aspects, the cells have a specific productivity greater than about 25 mg/OD/hr of isoprene. In some aspects, the heterologous nucleic acid encoding an isoprene synthase polypeptide is operably linked to a promoter and the cells have a specific productivity greater than about 20 mg/OD/hr of isoprene. In some aspects, the heterologous nucleic acid encoding an isoprene synthase polypeptide is operably linked to a promoter and the cells have a specific productivity greater than about 25 mg/OD/hr of isoprene.

In some aspects, the isoprene synthase polypeptide is a plant isoprene synthase polypeptide. In some aspects, the cells further comprise a heterologous nucleic acid encoding an IDI polypeptide. In some aspects, the cells further comprise a chromosomal copy of an endogenous nucleic acid encoding an IDI polypeptide. In some aspects, the cells further comprise a heterologous nucleic acid encoding a DXS polypeptide. In some aspects, the cells further comprise a chromosomal copy of an endogenous nucleic acid encoding a DXS polypeptide. In some aspects, the cells further comprise one or more nucleic acids encoding an IDI polypeptide and a DXS polypeptide. In some aspects, one nucleic acid encodes the isoprene synthase polypeptide, IDI polypeptide, and DXS polypeptide. In some aspects, one plasmid encodes the isoprene synthase polypeptide, IDI polypeptide, and DXS polypeptide.

In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*.

In some aspects, the cells comprise (i) an integrated nucleic acid encoding the lower MVA pathway from *S. cerevisiae* comprising a glucose isomerase promoter and a nucleic acid encoding mevalonate kinase (MVK); a nucleic acid encoding phosphomevalonate kinase (PMK); a nucleic acid encoding diphosphomevalonate decarboxylase (MVD); and a nucleic acid encoding isopentenyl diphosphate isomerase (IDI); (ii) a nucleic acid encoding *P. alba* isoprene synthase; (iii) a nucleic acid encoding *M. mazei* mevalonate kinase; and (iv) a nucleic acid encoding the upper MVA pathway from *Enterococcus faecalis*, comprising a nucleic acid encoding an acetoacetyl-Coenzyme A synthase (thiolase) polypeptide; a nucleic acid encoding a 3-hydroxy-3-methylglutaryl-Coenzyme A synthase polypeptide; and a nucleic acid encoding a 3-hydroxy-3-methylglutaryl-Coenzyme A reductase polypeptide.

In another aspect, provided herein are improved methods of producing a heterologous polypeptide capable of biological activity, the method comprising: (a) culturing cells of an *E. coli* strain that does not encode a PGL polypeptide, wherein the *E. coli* cells comprise one or more copies of a heterologous gene encoding a PGL polypeptide with one or more associated expression control sequences and a nucleic acid encoding a heterologous polypeptide capable of biological activity; and (b) producing the heterologous polypeptide capable of biological activity, wherein the cells produce the heterologous polypeptide at a specific productivity greater than that of the same cells lacking one or more copies of a heterologous gene encoding a PGL polypeptide with one or more associated expression control sequences, when the cells are cultured in minimal medium. In some aspects, the one or more copies of the heterologous gene encoding a PGL polypeptide with one or more associated expression control sequences are chromosomal copies (e.g., integrated into the *E. coli* chromosome). In some aspects, the method further comprises the step of recovering the heterologous polypeptide capable of biological activity.

In some aspects, the cells are of *E. coli* strain B. In some aspects, the cells are of *E. coli* strain BL21. In some aspects, the cells are of *E. coli* strain BL21(DE3). In some aspects, the minimal medium is supplemented with 0.1% (w/v) yeast extract or less. In some aspects, the minimal medium is supplemented with 1% (w/v) glucose or less. In some aspects, the minimal medium is supplemented with 0.1% (w/v) yeast extract or less and 1% (w/v) glucose or less. In some aspects, the heterologous polypeptide having PGL activity is from *E. coli* strain K12 MG1655 or a derivative of *E. coli* strain K12 MG1655. In some aspects, the heterologous polypeptide having PGL activity is from the genus *Pseudomonas*. In some aspects, the *Pseudomonas* is *Pseudomonas aeruginosa*.

In some aspects, the heterologous polypeptide capable of biological activity comprises one or more polypeptides involved in the biosynthesis of terpenoid (isoprenoid) or carotenoid compounds, and the cells produce a terpenoid or carotenoid at a higher specific productivity than that of the same cells lacking one or more copies of a heterologous gene encoding a PGL polypeptide with one or more associated expression control sequences, when the cells are cultured in minimal medium. In some aspects, the terpenoid is selected from the group consisting of hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid is geranyl pyrophosphate, eucalyptol, limonene, or pinene. In some aspects, the sesquiterpenoid is farnesyl pyrophosphate, artemisinin, or bisabolol. In some aspects, the diterpenoid is geranylgeranyl pyrophosphate, retinol, retinal, phytol, taxol, forskolin, or aphidicolin. In some aspects, the triterpenoid is squalene or lanosterol. In some aspects, the tetraterpenoid is lycopene or carotene. In some aspects, the carotenoid is selected from the group consisting of xanthophylls and carotenes. In some aspects, the xanthophyll is lutein or zeaxanthin.

In another aspect, provided herein are improved methods of producing isoprene, the method comprising: (a) culturing cells of an *E. coli* strain that does not encode a PGL polypeptide, wherein the *E. coli* cells comprise one or more copies of a heterologous gene encoding a PGL polypeptide with one or more associated expression control sequences and a heterologous nucleic acid encoding an isoprene synthase polypeptide; and (b) producing isoprene, wherein the cells have a specific productivity of isoprene greater than that of the same cells lacking one or more copies of a heterologous gene encoding a PGL polypeptide with one or more associated expression control sequences, when the cells are cultured in minimal medium. In some aspects, the one or more copies of the heterologous gene encoding a PGL polypeptide with one or more associated expression control sequences are chromosomal copies (e.g., integrated into the *E. coli* chromosome). In some aspects, the improved method further comprises a step of recovering the isoprene. In some aspects, the cells further comprise a heterologous nucleic acid encoding an MVA pathway polypeptide. In some aspects, the MVA pathway polypeptide is an upper MVA pathway polypeptide. In some aspects, the MVA pathway polypeptide is a lower MVA pathway polypeptide.

In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is from the genus *Enterococcus*. In some aspects, the upper MVA pathway polypeptide is from *Enterococcus faecalis*. In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some aspects, the lower MVA pathway polypeptide is an MVK polypeptide. In some aspects, the MVK polypeptide is from the genus *Methanosarcina*. In some aspects, the MVK polypeptide is from *Methanosarcina mazei*. In some aspects, the cells are of *E. coli* strain B. In some aspects, the cells are of *E. coli* strain BL21. In some aspects, the cells are of *E. coli* strain BL21 (DE3). In some aspects, the minimal medium is supplemented with 0.1% (w/v) yeast extract or less. In some aspects, the minimal medium is supplemented with 1% (w/v) glucose or less. In some aspects, the minimal medium is supplemented with 0.1% (w/v) yeast extract or less and 1% (w/v) glucose or less. In some aspects, the heterologous gene encoding a PGL polypeptide is from *E. coli* strain K12 MG1655 or a derivative of *E. coli* strain K12 MG1655. In some aspects, the heterologous gene encoding a PGL polypeptide is from the genus *Pseudomonas*. In some aspects, the *Pseudomonas* is *Pseudomonas aeruginosa*.

In some aspects, the cells have a specific productivity greater than about 20 mg/OD/hr of isoprene. In some aspects, the cells have a specific productivity greater than about 25 mg/OD/hr of isoprene. In some aspects, the heterologous nucleic acid encoding an isoprene synthase polypeptide is operably linked to a promoter, and wherein the cells have a specific productivity greater than about 20 mg/OD/hr of isoprene. In some aspects, the heterologous nucleic acid encoding an isoprene synthase polypeptide is operably linked to a promoter, and wherein the cells have a specific productivity greater than about 25 mg/$L_{broth}$/hr of isoprene.

In some aspects, the isoprene synthase polypeptide is a plant isoprene synthase polypeptide. In some aspects, the cells further comprise a heterologous nucleic acid encoding an IDI polypeptide. In some aspects, the cells further comprise a chromosomal copy of an endogenous nucleic acid encoding an IDI polypeptide. In some aspects, the cells further comprise a heterologous nucleic acid encoding a DXS polypeptide. In some aspects, the cells further comprise a chromosomal copy of an endogenous nucleic acid encoding a DXS polypeptide. In some aspects, the cells further comprise one or more nucleic acids encoding an IDI polypeptide and a DXS polypeptide. In some aspects, one nucleic acid encodes the isoprene synthase polypeptide, IDI polypeptide, and DXS polypeptide. In some aspects, one plasmid encodes the isoprene synthase polypeptide, IDI polypeptide, and DXS polypeptide. In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*.

In some aspects, the cells comprise (i) an integrated nucleic acid encoding the lower MVA pathway from *S. cerevisiae* comprising a glucose isomerase promoter and a nucleic acid encoding mevalonate kinase (MVK); a nucleic acid encoding phosphomevalonate kinase (PMK); a nucleic acid encoding diphosphomevalonate decarboxylase (MVD); and a nucleic acid encoding isopentenyl diphosphate isomerase (IDI); (ii) a nucleic acid encoding *P. alba* isoprene synthase; (iii) a nucleic acid encoding *M. mazei* mevalonate kinase; and (iv) a nucleic acid encoding the upper MVA pathway from *Enterococcus faecalis*, comprising a nucleic acid encoding an acetoacetyl-Coenzyme A synthase (thiolase) polypeptide; a nucleic acid encoding a 3-hydroxy-3-methylglutaryl-Coenzyme A synthase polypeptide; and a nucleic acid encoding a 3-hydroxy-3-methylglutaryl-Coenzyme A reductase polypeptide.

BRIEF DESCRIPTION OF THE DRAWINGS

FIG. 3A-B are the nucleotide sequence of plasmid pET24 *P. alba* HGS (SEQ ID NO:1).

FIGS. 6A-B are the nucleotide sequence of plasmid EWL230 (SEQ ID NO:2).

FIGS. 9A-B are the nucleotide sequence of plasmid EWL244 (SEQ ID NO:3).

FIGS. 10B-C are the nucleotide sequence of the *M. mazei* archaeal Lower Pathway operon (SEQ ID NO:4).

FIGS. 11B-C are the nucleotide sequence of MCM376-MVK from *M. mazei* archaeal Lower in pET200D (SEQ ID NO:5).

FIGS. 13A-B are the nucleotide sequence of plasmid pBBRCMPGI1.5-pgl (SEQ ID NO:6).

FIG. 14A shows the time course of optical density within the 15-L bioreactor fed with glucose. FIG. 14B shows the time course of isoprene titer within the 15-L bioreactor fed with glucose. The titer is defined as the amount of isoprene produced per liter of fermentation broth. Method for calculating isoprene: cumulative isoprene produced in 59 hrs, g/Fermentor volume at 59 hrs, L [=] g/L broth. FIG. 14C also shows the time course of isoprene titer within the 15-L bioreactor fed with glucose. Method for calculating isoprene: ∫(Instantaneous isoprene production rate, g/L/hr)dt from t=0 to 59 hours [=] g/L broth. FIG. 14D shows the time course of total isoprene produced from the 15-L bioreactor fed with glucose. FIG. 14E shows volumetric productivity within the 15-L bioreactor fed with glucose. FIG. 14F shows carbon dioxide evolution rate (CER), or metabolic activity profile, within the 15-L bioreactor fed with glucose.

FIG. 19A shows a map of plasmid pDW34, encoding a truncated version of *P. alba* isoprene synthase (MEA variant) under the control of the PTrc promoter and *M. mazei* MVK. FIG. 19B-D shows the complete nucleotide sequence of plasmid pDW34 (SEQ ID NO:7).

FIG. 20 shows the chromosomal organization of *E. coli* K12 strain MG1655 around the pgl locus (Graph imported from www.ecocyc.com). The region deleted in *E. coli* BL21 (DE3) compared to *E. coli* K12 MG655 and restored in strains CMP215 and CMP258 is shown in brackets. The predicted ORF of the ybgS gene is circled. A forward arrow (→) indicates the annealing site of the galMF primer (SEQ ID NO:8). A reverse arrow (←) indicates the annealing site of the galMR primer (SEQ ID NO:9).

FIG. 40A shows the amino acid sequence of 6-phosphogluconolactonase (PGL) from *E. coli* K12 MG1655 (SEQ ID NO:11). FIG. 40B shows the amino acid sequence of PGL from *P. aeruginosa* (SEQ ID NO:12). FIG. 40C shows the amino acid sequence of PGL from *S. cerevisiae* (SEQ ID NO:13).

FIG. 41A shows the growth of BL21 and strain CMP258 (labeled as BL21 pgl). FIG. 41B shows specific growth rate (μ) of BL21 with and without pgl. Restoring the 17,257 bp deletion comprising pgl in BL21 results in a strain with around 15% increase in specific growth rate.

DETAILED DESCRIPTION

Figure 1A:
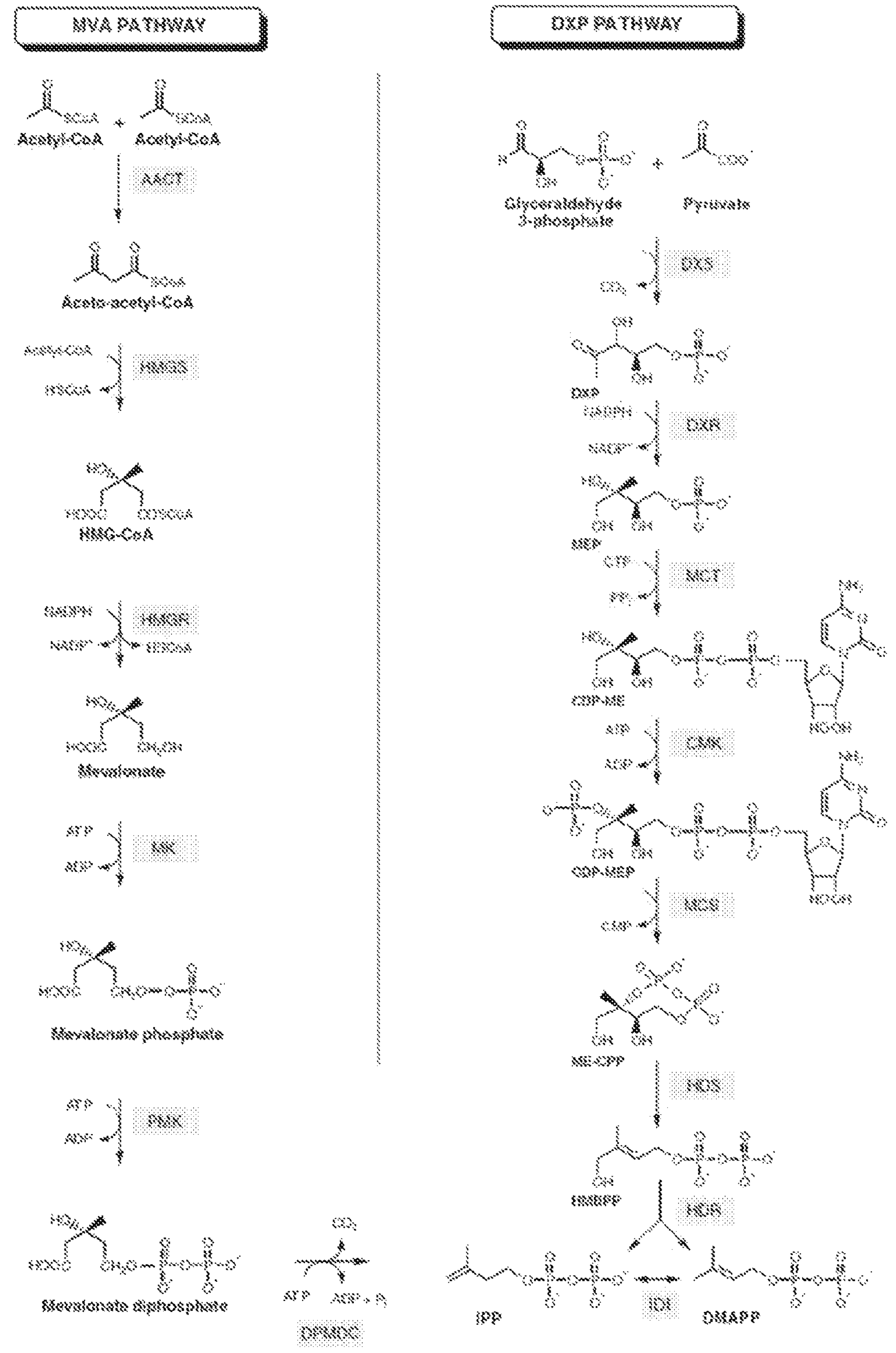
FIG. 1A shows the MVA and DXP metabolic pathways for isoprene (based on F. Bouvier et al., Progress in Lipid Res. 44: 357-429, 2005). The following description includes alternative names for each polypeptide in the pathways and a reference that discloses an assay for measuring the activity of the indicated polypeptide. Mevalonate Pathway: AACT; Acetyl-CoA acetyltransferase, MvaE, EC 2.3.1.9. Assay: J. Bacteriol. 184:2116-2122, 2002; HMGS; Hydroxymethylglutaryl-CoA synthase, MvaS, EC 2.3.3.10. Assay: J. Bacteriol. 184: 4065-4070, 2002; HMGR; 3-Hydroxy-3-methylglutaryl-CoA reductase, MvaE, EC 1.1.1.34. Assay: J. Bacteriol. 184: 2116-2122, 2002; MVK; Mevalonate kinase, ERG12, EC 2.7.1.36. Assay: Curr Genet 19:9-14, 1991. PMK; Phosphomevalonate kinase, ERGS, EC 2.7.4.2, Assay: Mol Cell Biol. 11:620-631, 1991; DPMDC; Diphosphomevalonate decarboxylase, MVD1, EC 4.1.1.33. Assay: Biochemistry 33:13355-13362, 1994; IDI; Isopentenyl-diphosphate delta-isomerase, IDI1, EC 5.3.3.2. Assay: J. Biol. Chem. 264: 19169-19175, 1989. DXP Pathway: DXS; 1-Deoxyxylulose-5-phosphate synthase, dxs, EC 2.2.1.7. Assay:PNAS 94:12857-62, 1997; DXR; 1-Deoxy-D-xylulose 5-phosphate reductoisomerase, dxr, EC 2.2.1.7. Assay: Eur. J. Biochem. 269:4446-4457, 2002; MCT; 4-Diphosphocytidyl-2C-methyl-D-erythritol synthase, IspD, EC 2.7.7.60. Assay:PNAS 97:6451-6456, 2000; CMK; 4-Diphosphocytidyl-2-C-methyl-D-erythritol kinase, IspE, EC 2.7.1.148. Assay:PNAS 97:1062-1067, 2000; MCS; 2C-Methyl-D-erythritol 2,4-cyclodiphosphate synthase, IspF, EC 4.6.1.12. Assay:PNAS 96:11758-11763, 1999; HDS; 1-Hydroxy-2-methyl-2-(E)-butenyl 4-diphosphate synthase, ispG, EC 1.17.4.3. Assay: J. Org. Chem. 70:9168-9174, 2005; HDR; 1-Hydroxy-2-methyl-2-(E)-butenyl 4-diphosphate reductase, IspH, EC 1.17.1.2. Assay: JACS, 126:12847-12855, 2004.

*E. coli* BL21 and BL21(DE3) are widely used hosts for the production of recombinant proteins. They can also be used to produce other products, such as isoprene. Yields of recombinant proteins, biochemicals, and other products in such *E. coli* strains can be improved by increasing activity of the pentose phosphate pathway, a metabolic pathway important for cell growth. Comparison of the genomic sequence of *E. coli* BL21 prepared by Codon Genomics (St. Louis, Mo.) using an Illumina Genome Analyzer II (GA II) Sequencing System to that of *E. coli* MG1655 (GenBank Accession No. U00096) revealed that the *E. coli* BL21 genome carried a deletion of 17,257 bp in the region encoding genes involved in the utilitization of galactose as well as other genes that are described in greater detail herein. Unexpectedly, that deletion also encompassed the ybhE gene (Thomason, L., Court, D., Datta, A., Khanna, R. and Rosner, J., "Identification of the *Escherichia coli* K-12 ybhE gene as pgl, encoding 6-phosphogluconolactonase," *J. Bact.* 186:8248-8253 (2004)), which encodes the enzyme 6-phosphogluconolactonase (PGL), the second enzyme in the pentose phosphate pathway. The deletion was made by UV irradiation of a parent strain of *E. coli* BL21 and passed via P1 transduction (Studier F., Daegelen, P., Lenski, R., Maslov, S., Kim, J. F., "Understanding the differences between genome sequences of *Escherichia coli* B strains REL606 and BL21(DE3) and comparison of the *E. coli* B and K-12 genomes," *J. Mol. Biol.* published ahead of print Sep. 15, 2009). Consequently, *E. coli* BL21 and BL21 (DE3) lack both PGL activity and the ability to utilize galactose as a carbon source. (Aon et al., "Suppressing posttranslational gluconoylation of heterologous proteins by metabolic engineering of *Escherichia coli*," *Appl. Environ. Microbiol.* 74:950-958 (2008)).

Additionally, the deletion also included genes required for high affinity transport of molybdate. While required in only trace amounts, molybdenum plays an important role in several metabolic pathways in all organisms. Molybdate is used as an enzymatic cofactor by bacteria in a number of oxidation/reduction reactions, plays a critical role in nitrogen metabolism, and, particularly in the case of anaerobic respiration, contributes to energy production. (See, e.g., Self et al., *Res Microbiol.* 152:311-321 (2001); Grunden & Shanmugam, *Arch Microbiol.* 168:345-354 (1997)).

The pentose phosphate pathway (PPP) is used during growth to provide NADPH and pentoses (5-carbon sugars)

(Neidhart, F., Ingraham, J., and Schaechter, M., 1990, Physiology of the bacterial cell: a molecular approach (Sinauer Associates, Inc. Sunderland, Mass.)). The PPP has two distinct phases: (1) the oxidative phase, in which NADPH is generated; and (2) the non-oxidative synthesis of 5-carbon sugars. The PPP is an alternative to glycolysis, and while it does involve oxidation of glucose, its primary role is anabolic rather than catabolic. The primary results of the pathway are: (1) the generation of reducing equivalents in the form of NADPH, for use in reductive biosynthesis reactions within cells, such as fatty acid synthesis; (2) production of ribose-5-phosphate (R5P), used in the synthesis of nucleotides and nucleic acids; and (3) production of erythrose-4-phosphate (E4P), used in the synthesis of aromatic amino acids. Aromatic amino acids, in turn, are precursors for many biosynthetic pathways. Dietary pentose sugars derived from the digestion of nucleic acids may be metabolized through the pentose phosphate pathway, and the carbon skeletons of dietary carbohydrates may be converted into glycolytic or gluconeogenic intermediates. In mammals, the PPP occurs exclusively in the cytoplasm, and is one of the three main ways the body creates molecules with reducing power, accounting for approximately 60% of NADPH production in humans.

Restoring the PGL gene and its associated expression control sequences in *E. coli* BL21 and BL21(DE3) strains conveys a substantial growth benefit, as the pentose phosphate pathway provides reducing equivalents for use in reductive biosynthesis reactions within cells, such as fatty acid synthesis, ribose-5-phosphate (R5P) for use in the synthesis of nucleotides and nucleic acids, and (3) erythrose-4-phosphate (E4P) for use in the synthesis of aromatic amino acids. In addition, it will be useful for industrial purposes to have a homologous strain (e.g., an *E. coli* BL21 or BL21(DE3) strain) able to utilize galactose, in order to extend the range of available carbon sources.

Furthermore, restoring genes that encode high affinity molybdate transport proteins will provide an additional growth benefit, as the cell will be able to utilize molybdate more efficiently in those metabolic reactions that require molybdenum as a cofactor. The invention encompasses improved methods and compositions for recombinant bacterial cells expressing a heterologous nucleic acid encoding a PGL polypeptide integrated into the bacterial chromosome. The PGL integration alone or in combination with one or more other heterologous nucleic acids encoding polypeptides for galactose metabolism and/or molybdenum transport can improve a recombinant bacterial cell's ability for the production of isoprene.

Accordingly in one aspect, the invention encompasses recombinant cell(s) of an *Escherichia coli* (*E. coli*) strain capable of producing isoprene, wherein the cell(s) comprise: (a) one or more copies of a heterologous nucleic acid(s) encoding a PGL polypeptide wherein the nucleic acid(s) is/are integrated in the *E. coli* chromosome; and (b) one or more heterologous nucleic acid(s) encoding isoprene synthase; wherein prior to the integration, the *E. coli* cell does not contain (a) nucleic acid(s) that encodes a encoding a PGL polypeptide, and wherein the resulting recombinant cell produces isoprene at a greater titer than that of the same cell(s) that do not comprise (a) and (b). In some cases, the recombinant *E. coli* cell can use its own endogenous promoter(s) and/or its other regulatory systems to regulate the transcription and subsequent expression of the integrated PGL nucleic acid. In such cases, the expression of the heterologous nucleic acids (e.g., PGL or isoprene) is not constitutive expression driven by a plasmid or elements on a plasmid. In other cases, the recombinant *E. coli* cell can use promoter(s) and/or other regulatory systems that have been introduced to the *E. coli* cell to regulate the transcription and subsequent expression of the integrated PGL nucleic acid.

The invention also encompasses cells of an *Escherichia coli* strain that does not encode a 6-phosphogluconolactonase (PGL) polypeptide, wherein the *E. coli* cells comprise one or more copies of a heterologous gene encoding a PGL polypeptide with one or more associated expression control sequences and a nucleic acid encoding a heterologous polypeptide capable of biological activity. In one aspect, the PGL polypeptide is not encoded by nucleic acids on a plasmid. In some aspects, the *E. coli* cells produce the polypeptide capable of biological activity at a specific productivity greater than that of the same cells lacking one or more copies of a heterologous gene encoding a PGL polypeptide with one or more associated expression control sequences, when the cells are cultured in minimal medium. Also provided herein are improved methods of producing heterologous polypeptides capable of biological activity, comprising the steps of culturing the *E. coli* cells that do not encode a PGL polypeptide in minimal medium, wherein the cells comprise one or more copies of a heterologous gene encoding a PGL polypeptide with one or more associated expression control sequences and a nucleic acid encoding a heterologous polypeptide capable of biological activity, and producing the heterologous polypeptide. In some aspects, the cells produce the heterologous polypeptide at a specific productivity greater than that of the same cells lacking one or more copies of a heterologous gene encoding a PGL polypeptide with one or more associated expression control sequences, when the cells are cultured in minimal medium.

In another aspect, provided herein are cells of an *Escherichia coli* strain that does not encode a PGL polypeptide, wherein the *E. coli* cells comprise one or more copies of a heterologous gene encoding a PGL polypeptide with one or more associated expression control sequences and a heterologous nucleic acid encoding an upper mevalonate (MVA) pathway polypeptide, a lower MVA pathway polypeptide, and/or an isoprene synthase polypeptide. In some aspects, the *E. coli* cells have a specific productivity of isoprene greater than that of the same cells lacking one or more copies of a heterologous gene encoding a PGL polypeptide with one or more associated expression control sequences, when the cells are cultured in minimal medium. Also provided herein are improved methods of producing isoprene, comprising the steps of culturing the *E. coli* cells that do not encode a PGL polypeptide in minimal medium, wherein the cells comprise one or more copies of a heterologous gene encoding a PGL polypeptide with one or more associated expression control sequences and a heterologous nucleic acid encoding an upper mevalonate (MVA) pathway polypeptide, a lower MVA pathway polypeptide, or an isoprene synthase polypeptide, and producing isoprene. In some aspects, the cells have a specific productivity of isoprene greater than that of the same cells lacking one or more copies of a heterologous gene encoding a PGL polypeptide with one or more associated expression control sequences, when the cells are cultured in minimal medium.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Definitions

The term "isoprene" refers to 2-methyl-1,3-butadiene (CAS#78-79-5). It can be the direct and final volatile C5 hydrocarbon product from the elimination of pyrophosphate from 3,3-dimethylallyl pyrophosphate (DMAPP). It may not involve the linking or polymerization of IPP molecules to DMAPP molecules. The term "isoprene" is not generally intended to be limited to its method of production unless indicated otherwise herein.

As used herein, the term "6-phosphogluconolactone" refers to 6-phospho-D-glucono-1,5-lactone (CAS#2641-81-8). As used herein, the term "6-phosphogluconate" refers to 6-phospho-D-gluconate (CAS#921-62-0).

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide. An isolated polypeptide can be a non-naturally occurring polypeptide.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. In some aspects, a recombinant nucleic acid is a nucleic acid that encodes a non-naturally occurring polypeptide.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature. For example, a nucleic acid encoding a PGL polypeptide isolated from *E. coli* K12 strain MG1655 or a derivative thereof, integrated into the chromosome of *E. coli* BL21(DE3) by P1 transduction and expressed in the cell is a heterologous nucleic acid. In one aspect, a "heterologous nucleic acid" can mean the introduction of a nucleic acid into a host cell that does not have that nucleic acid. In some cases, a heterologous nucleic acid can be a heterologous gene. One of skill in the art would appreciate the differences and also be able to use the context of the teaching accordingly.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation. The expression control sequence is operably linked to the nucleic acid segment to be transcribed.

As used herein, the terms "minimal medium" or "minimal media" refer to growth medium containing the minimum nutrients possible for cell growth, generally without the presence of amino acids. Minimal medium typically contains: (1) a carbon source for bacterial growth; (2) various salts, which may vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "terpenoid" or "isoprenoid" refers to a large and diverse class of naturally-occurring organic chemicals similar to terpenes. Terpenoids are derived from five-carbon isoprene units assembled and modified in a variety of ways, and are classified in groups based on the number of isoprene units used in group members. Hemiterpenoids have one isoprene unit. Monoterpenoids have two isoprene units. Sesquiterpenoids have three isoprene units. Diterpenoids have four isoprene units. Sesterterpenoids have five isoprene units. Triterpenoids have six isoprene units. Tetraterpenoids have eight isoprene units. Polyterpenoids have more than eight isoprene units.

As used herein, the term "carotenoid" refers to a group of naturally occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Genes Encoding Polypeptides Restored to *E. coli* Bl21 or BL21(DE3)

The 17,257 bp deletion in the *E. coli* BL21 and BL21(DE3) genomes includes the yghE gene (PGL), genes encoding proteins involved in the utilization of galactose as a carbon source, genes encoding proteins involved in molybdenum transport, as well as several other genes of unknown functionality. See, for example, FIG. 20. The genes involved in the utilization of galactose are galM which encodes galactose-1-epimerase, galK, which encodes galactokinase, galT, which encodes galactose-1-phosphate uridylyltransferase, and galE, which encodes UDP-glucose 4-epimerase. The genes encoding proteins involved in molybdenum transport are modF, which encodes the fused molybdate transporter subunits of the ABC superfamily, modE, which encodes the repressor of the modABC operon for molybdenum transport, and modA, modB, and modC, which each encode a molybdate transporter subunit protein.

Accordingly, bacterial (e.g., *E. coli*) cells can be engineered to integrate nucleic acids encoding a PGL polypeptide in the *E. coli* chromosome. Introduction of heterologous nucleic acids encoding for isoprene synthase (e.g., *P. alba* isoprene synthase) can increase the total titer and/or specific activity for isoprene production. Furthermore, in addition to the PGL integration, one or more genes encoding proteins involved in the utilization of galactose as a carbon source or proteins involved in molybdenum transport can also be introduced into the *E. coli* cell to increase the overall fitness of the recombinant cell, which, in turn, can lead to increased production of isoprene.

Various options of integrated PGL alone or integrated PGL in combination with one or more genes encoding proteins involved in the utilization of galactose as a carbon source or proteins involved in molybdenum transport are contemplated within the scope of the invention. Thus, in some aspects, the gene restored to the BL21 or BL21(DE3) genome is PGL. In some aspects, the genes restored to the BL21 or BL21(DE3) genome are PGL and galM. In some aspects, genes restored to the BL21 or BL21(DE3) genome are PGL and galK. In some aspects, the genes restored to the BL21 or BL21(DE3) genome are PGL and galT. In some aspects, the genes restored to the BL21 or BL21(DE3) genome are PGL and galE. In some aspects, the genes restored to the BL21 or BL21(DE3) genome are PGL, galM, and galK. In some aspects, the genes restored to the BL21 or BL21(DE3) genome are PGL, galM, and galT. In some aspects, the genes restored to the BL21 or BL21(DE3) genome are PGL, galM, and galE. In some aspects, the genes restored to the BL21 or BL21(DE3) genome are PGL, galK, and galT. In some aspects, the genes restored to the BL21 or BL21(DE3) genome are PGL, galK, and galE. In some aspects, the genes restored to the BL21 or BL21(DE3) genome are PGL, galT, and galE. In some aspects, the genes restored to the BL21 or BL21(DE3) genome are PGL, galM, galK, and galT. In some aspects, genes restored to the BL21 or BL21(DE3) genome are PGL, galM, galK, and galE. In some aspects, genes restored to the BL21 or BL21(DE3) genome are PGL, galK, galT, and galE.

In some aspects, genes restored to the BL21 or BL21(DE3) genome are PGL and modF. In some aspects, the genes restored to the BL21 or BL21(DE3) genome are PGL and modE. In some aspects, the genes restored to the BL21 or BL21(DE3) genome are PGL and modA, modB, and modC. In some aspects, the genes restored to the BL21 or BL21 (DE3) genome are PGL, modF, and modE. In some aspects, the genes restored to the BL21 or BL21(DE3) genome are PGL, modF, modA, modB, and modC. In some aspects, the genes restored to the BL21 or BL21(DE3) genome are PGL, modE, modA, modB, and modC. In some aspects, the genes restored to the BL21 or BL21(DE3) genome are PGL, modF, modE, modA, modB, and modC.

In some aspects, the genes restored to the BL21 or BL21 (DE3) genome are PGL, galM, and modF. In some aspects, the genes restored to the BL21 or BL21(DE3) genome are PGL, galM, and modE. In some aspects, genes restored to the BL21 or BL21(DE3) genome are PGL, galM, and modA, modB, and modC. In some aspects, the genes restored to the BL21 or BL21(DE3) genome are PGL, galK, and modF. In some aspects, the genes restored to the BL21 or BL21(DE3) genome are PGL, galK, and modE. In some aspects, the genes restored to the BL21 or BL21(DE3) genome are PGL, galK, modA, modB, and modC. In some aspects, the genes restored to the BL21 or BL21(DE3) genome are PGL, galT, and modF. In some aspects, the genes restored to the BL21 or BL21 (DE3) genome are PGL, galT, and modE. In some aspects, the genes restored to the BL21 or BL21(DE3) genome are PGL, galT, modA, modB, and modC. In some aspects, the genes restored to the BL21 or BL21(DE3) genome are PGL, galK, and modF. In some aspects, the genes restored to the BL21 or BL21(DE3) genome are PGL, galE, and modE. In some aspects, the genes restored to the BL21 or BL21(DE3) genome are PGL, galE, modA, modB, and modC.

In some aspects, the genes restored to the BL21 or BL21 (DE3) genome are PGL, galM, galK, and modF. In some aspects, the genes restored to the BL21 or BL21(DE3) genome are PGL, galM, galK, and modE. In some aspects, the genes restored to the BL21 or BL21(DE3) genome are PGL, galM, galK, and modA, modB, and modC. In some aspects, the genes restored to the BL21 or BL21(DE3) genome are PGL, galM, galT, and modF. In some aspects, the genes restored to the BL21 or BL21(DE3) genome are PGL, galM, galT, and modE. In some aspects, the genes restored to the BL21 or BL21(DE3) genome are PGL, galM, galT, and modA, modB, and modC. In some aspects, the genes restored to the BL21 or BL21(DE3) genome are PGL, galM, galE, and modF. In some aspects, the genes restored to the BL21 or BL21(DE3) genome are PGL, galM, galE, and modE. In some aspects, the genes restored to the BL21 or BL21(DE3) genome are PGL, galM, galE, and modA, modB, and modC. In some aspects, the genes restored to the BL21 or BL21 (DE3) genome are PGL, galK, galT, and modF. In some aspects, the genes restored to the BL21 or BL21(DE3) genome are PGL, galK, galT, and modE. In some aspects, the genes restored to the BL21 or BL21(DE3) genome are PGL, galK, galT, and modA, modB, and modC. In some aspects, the genes restored to the BL21 or BL21(DE3) genome are PGL, galK, galE, and modF. In some aspects, the genes restored to the BL21 or BL21(DE3) genome are PGL, galK, galE, and modE. In some aspects, the genes restored to the BL21 or BL21(DE3) genome are PGL, galK, galE, and modA, modB, and modC. In some aspects, the genes restored to the BL21 or BL21(DE3) genome are PGL, galE, galT, and modF. In some aspects, the genes restored to the BL21 or BL21(DE3) genome are PGL, galE, galT, and modE. In some aspects, the genes restored to the BL21 or BL21(DE3) genome are PGL, galE, galT, and modA, modB, and modC.

In some aspects, the genes restored to the BL21 or BL21 (DE3) genome are PGL, galM, galK, galT and modF. In some aspects, the genes restored to the BL21 or BL21(DE3) genome are PGL, galM, galK, galT, and modE. In some aspects, the genes restored to the BL21 or BL21(DE3) genome are PGL, galM, galK, galT, and modA, modB, and modC. In some aspects, the genes restored to the BL21 or BL21(DE3) genome are PGL, galM, galK, galE and modF. In some aspects, the genes restored to the BL21 or BL21(DE3) genome are PGL, galM, galK, galE, and modE. In some aspects, the genes restored to the BL21 or BL21(DE3) genome are PGL, galM, galK, galE, and modA, modB, and modC. In some aspects, the genes restored to the BL21 or BL21(DE3) genome are PGL, galE, galK, galT and modF. In some aspects, the genes restored to the BL21 or BL21(DE3) genome are PGL, galE, galK, galT, and modE. In some aspects, the genes restored to the BL21 or BL21(DE3) genome are PGL, galE, galK, galT, and modA, modB, and modC.

In some aspects, the one or more copies of one or more genes encoded on the 17,257 bp genomic piece (except for PGL) are restored to *E. coli* BL21 or BL21(DE3) on a plasmid. In some aspects, the one or more copies of one or more genes encoded on the 17,257 bp genomic piece are restored to *E. coli* BL21 or BL21(DE3) on a constitutively expressing plasmid. In some aspects one or more copies of one or more genes encoded on the 17,257 bp genomic piece are restored to *E. coli* BL21 or BL21(DE3) on an inducible plasmid. In some aspects, the entire 17,257 bp genomic piece is a plasmid which is transfected into *E. coli* BL21 or BL21(DE3) cells. In some aspects, the one or more copies of one or more genes encoded on the 17,257 bp genomic piece are restored (e.g., as depicted in FIG. 20) to *E. coli* BL21 or BL21(DE3) by chromosomal integration. In some aspects, the entire 17,257 bp genomic piece is restored to *E. coli* BL21 or BL21(DE3) by chromosomal integration.

Exemplary PGL Polypeptides and Nucleic Acids 6-phosphogluconolactonase (PGL) converts 6-phosphogluconolactone to 6-phosphogluconate. Exemplary PGL polypeptides include polypeptides, fragments of polypeptides, peptides, and fusion polypeptides that have at least one activity of a PGL polypeptide. Exemplary PGL polypeptides and nucleic acids include naturally-occurring polypeptides and nucleic acids from any of the source organisms described herein as well as mutant polypeptides and nucleic acids derived from any of the source organisms described herein that have at least one activity of a PGL polypeptide.

Mutant PGL polypeptides include those in which one or more amino acid residues have undergone an amino acid substitution while retaining PGL activity (i.e., the ability to convert 6-phosphogluconolactone to 6-phosphogluconate). The amino acid substitutions may be conservative or non-conservative and such substituted amino acid residues may or may not be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the PGL polypeptide can be introduced to improve the functionality of the molecule. For example, amino acid substitutions that increase the binding affinity of the PGL polypeptide for its substrate, or that improve its ability to convert 6-phosphogluconolactone to 6-phosphogluconate can be introduced into the PGL polypeptide. In some aspects, the mutant PGL polypeptides contain one or more conservative amino acid substitutions. In some aspects, the mutant PGL polypeptides contain one or more non-conservative amino acid substitutions.

Standard methods, such as those described by A. Sinha and P. K. Maitra, "Induction of specific enzymes of the oxidative pentose phosphate pathway by glucono-delta-lactone in *Saccharomyces cerevisiae*," *J. Gen. Microbiol.* 138:1865-1873 (1992), can be used to determine whether a polypeptide has PGL activity, by measuring the ability of a polypeptide to reduce NADP+ to NADPH. In an exemplary assay, PGL activity is assayed by pre-incubating a reaction mixture containing 50 μM glucose-6-phosphate 0.5 mM NADP+, and 0.5 units glucose-6-phosphate dehydrogenase in 50 mM MES Buffer, pH=6.5, 25 mM KCl, 10 mM $MgCl_2$, until the reaction was complete. This was followed by addition of 1 unit of 6-phosphogluconate dehydrogenase which resulted in a slow increase in fluorescence due to spontaneous hydrolysis of the lactone formed during the earlier reaction. Next, cell-free extracts are added, leading to an increased rate of NADP+ reduction to NADPH via the lactonase reaction catalyzed by PGL. The actual lactonase rate is calculated by subtracting the previous blank rate from this final rate.

Alternatively, conversion of 6-phosphogluconolactone to 6-phosphogluconate can be monitored by nuclear magnetic resonance (NMR) spectroscopy. See, e.g., E. Miclet et al., "NMR Spectroscopic Analysis of the First Two Steps of the Pentose-Phosphate Pathway Elucidates the Role of 6-Phosphogluconolactonase," *J. Biol. Chem.* 276(37):34840-34846 (2001).

Figure 40D:
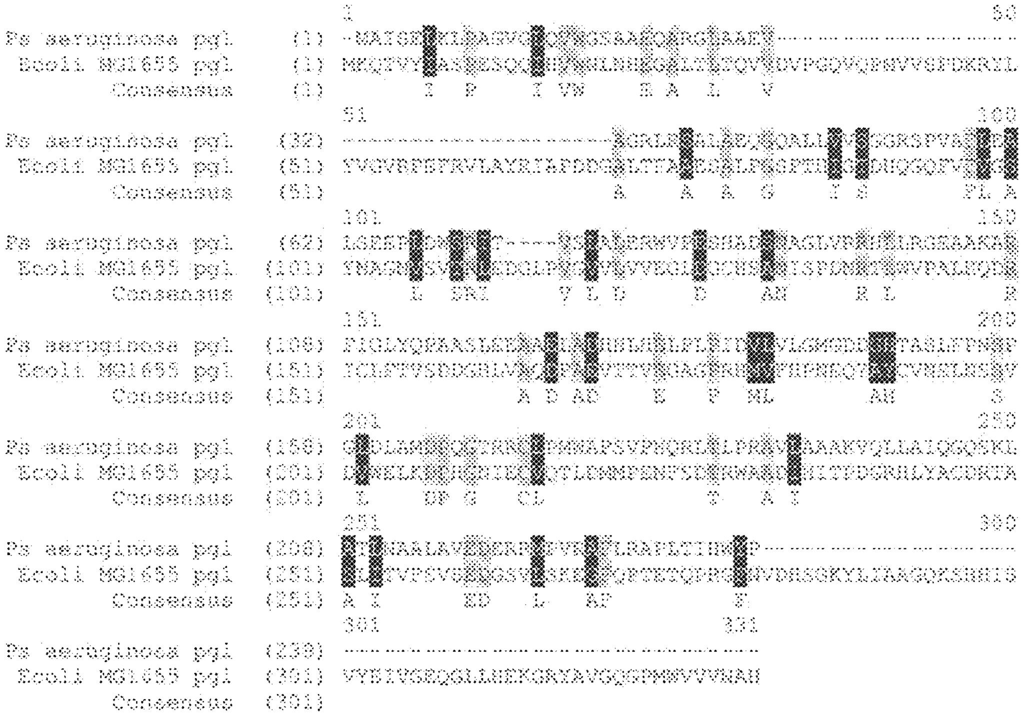
FIG. 40D shows an alignment of the amino acid sequences of *E. coli* PGL and *P. aeruginosa* PGL. Identical amino acids are shown highlighted in grey. Conservative amino acid substitutions are shown highlighted in black.
Figure 41A:
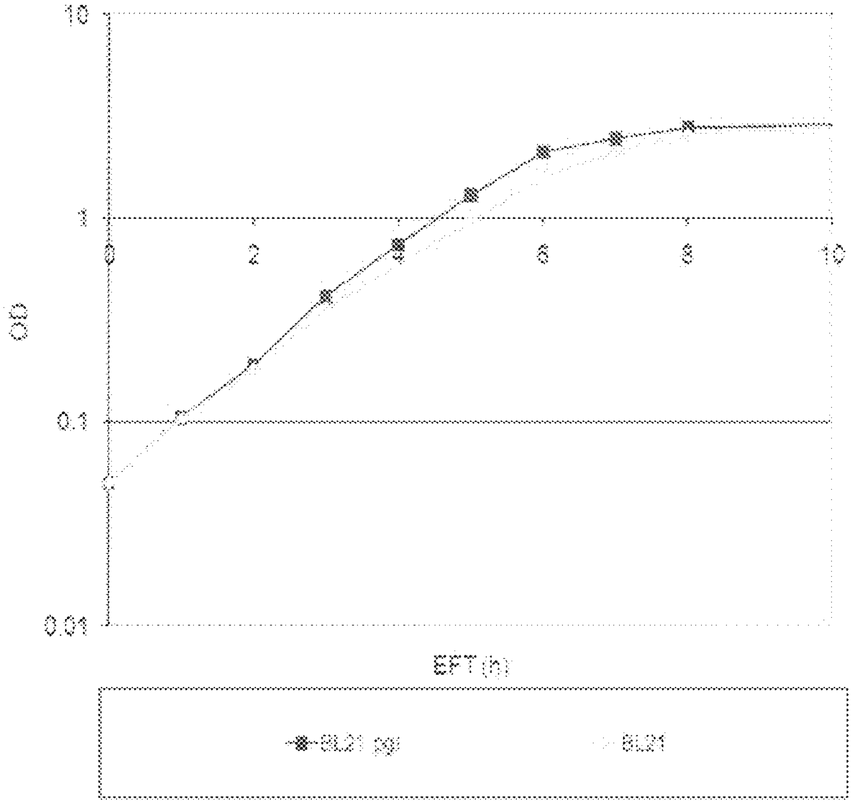
FIG. 41A-B shows the growth rate of BL21 (Novagen) and strain CMP258 (example 6), labeled as BL21 pgl. Growth was assessed in M9 minimal medium (6 g/L $Na_2HPO_4$, 3 g/L $KH_2PO_4$, 0.5 g/L NaCl, 0.5 g/L $NH_4Cl$, 0.1 mM $CaCl_2$, 2 mM $MgSO_4$) containing 0.4% (w/v) glucose. Growth was measured at $OD_{600}$.
Figure 41B:
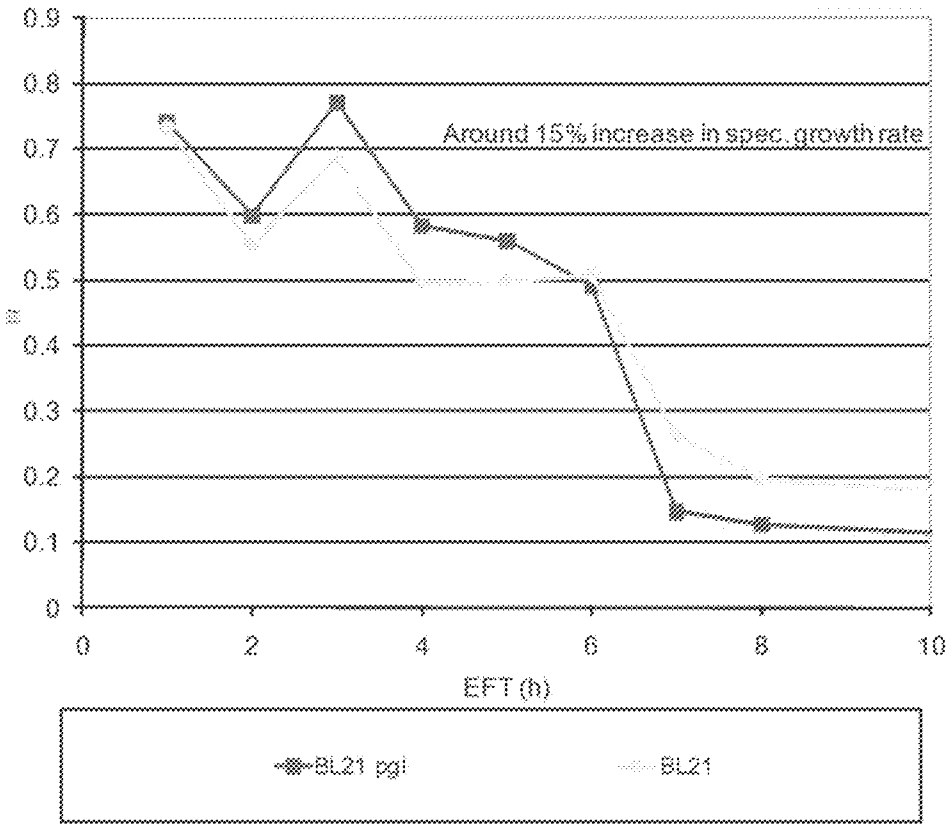

Exemplary PGL nucleic acids include nucleic acids that encode a polypeptide, fragment of a polypeptide, peptide, or fusion polypeptide that has at least one activity of a PGL polypeptide. Exemplary isoprene synthase polypeptides and nucleic acids include naturally-occurring polypeptides and nucleic acids from any of the source organisms described herein as well as mutant polypeptides and nucleic acids derived from any of the source organisms described herein. Exemplary PGL nucleic acids include, for example, PGL isolated from *E. coli* K12 MG1655 or derivatives thereof (EcoGene Accession No. EG13231; part of *E. coli* K12 MG1655 genomic sequence referenced by GenBank Accession No. U0096; see also UniProtKB/Swiss-Prot Accession No. P52697 (PGL polypeptide))(see FIG. 40A and SEQ ID NO:11); PGL isolated from *Pseudomonas aeruginosa* strain PA01 (Locus Tag PA3182 of GenBank Accession No. AE004091); see also GenBank Accession No. AAG06570.1 (PGL polypeptide))(see FIG. 40B and SEQ ID NO:12); and PGL isolated from *Saccharomyces cerevisiae* (Locus Tag YHR163W of GenBank Accession No. NC_001140; see also UNIProtKB/Swiss-Prot Accession No. P38858 (PGL polypeptide))(see FIG. 40C and SEQ ID NO:13). Other exemplary PGL nucleic acids can be isolated from any genus in the family Enterobacteriaceae including, for example,

*Alishewanella, Alterococcus, Aquamonas, Citrobacter, Cronobacter, Edwardsiella, Enterobacter, Klebsiella* (e.g., *Klebsiella pneumoniae*), *Pantoea* (e.g., *Pantoea citroea*), *Proteus* (e.g., *Proteus vulgaris*), *Salmonella, Serratia* (e.g., *Serratia marcescens*), *Shigella*, and *Yersinia* (e.g., *Yersinia pestis*).

Exemplary Galactose Metabolism Polypeptides and Nucleic Acids

Galactose-1-epimerase (galM) catalyzes the conversion of 13-D-galactose to α-D-galactose. Exemplary galactose-1-epimerase polypeptides include polypeptides, fragments of polypeptides, peptides, and fusion polypeptides that have at least one activity of a galactose-1-epimerase polypeptide. Exemplary galactose-1-epimerase polypeptides and nucleic acids include naturally-occurring polypeptides and nucleic acids from any of the source organisms described herein as well as mutant polypeptides and nucleic acids derived from any of the source organisms described herein that have at least one activity of a galactose-1-epimerase polypeptide.

Galactokinase (galK) catalyzes the phosphorylation of D-galactose to D-galactose-1-phosphate. Exemplary galactokinase polypeptides include polypeptides, fragments of polypeptides, peptides, and fusion polypeptides that have at least one activity of a galactokinase polypeptide. Exemplary galactokinase polypeptides and nucleic acids include naturally-occurring polypeptides and nucleic acids from any of the source organisms described herein as well as mutant polypeptides and nucleic acids derived from any of the source organisms described herein that have at least one activity of a galactokinase polypeptide.

Galactose-1-phosphate uridylyltransferase (galT) catalyzes the second step of the Leloir pathway of galactose metabolism by converting UDP-glucose and galactose 1-phosphate to glucose 1-phosphate and UDP-galactose. Exemplary galactose-1-phosphate uridylyltransferase polypeptides include polypeptides, fragments of polypeptides, peptides, and fusion polypeptides that have at least one activity of a galactose-1-phosphate uridylyltransferase polypeptide. Exemplary galactose-1-phosphate uridylyltransferase polypeptides and nucleic acids include naturally-occurring polypeptides and nucleic acids from any of the source organisms described herein as well as mutant polypeptides and nucleic acids derived from any of the source organisms described herein that have at least one activity of a galactose-1-phosphate uridylyltransferase polypeptide.

UDP-galactose-4-epimerase (galE) catalyzes the reversible conversion of UDP-galactose to UDP-glucose. Exemplary UDP-galactose-4-epimerase polypeptides include polypeptides, fragments of polypeptides, peptides, and fusion polypeptides that have at least one activity of a UDP-galactose-4-epimerase polypeptide. Exemplary UDP-galactose-4-epimerase polypeptides and nucleic acids include naturally-occurring polypeptides and nucleic acids from any of the source organisms described herein as well as mutant polypeptides and nucleic acids derived from any of the source organisms described herein that have at least one activity of a UDP-galactose-4-epimerase polypeptide.

Exemplary galactose metabolic nucleic acids include nucleic acids that encode a polypeptide, fragment of a polypeptide, peptide, or fusion polypeptide that has at least one activity of a galactose metabolic polypeptide. Exemplary galactose metabolic nucleic acids include, for example, galactose metabolic genes isolated from *E. coli* K12 MG1655 or derivatives thereof; galactose metabolic genes isolated from *Pseudomonas aeruginosa* strain PAO1; and galactose metabolic genes isolated from *Saccharomyces cerevisie*. Other exemplary galactose metabolic nucleic acids can be isolated from any genus in the family Enterobacteriaceae including, for example, *Alishewanella, Alterococcus, Aquamonas, Citrobacter, Cronobacter, Edwardsiella, Enterobacter, Klebsiella* (e.g., *Klebsiella pneumoniae*), *Pantoea* (e.g., *Pantoea citroea*), *Proteus* (e.g., *Proteus vulgaris*), *Salmonella, Serratia* (e.g., *Serratia marcescens*), *Shigella*, and *Yersinia* (e.g., *Yersinia pestis*).

Exemplary Molybdenum Transporter Polypeptides and Nucleic Acids

The polypeptide encoded by the modF gene is an uncharacterized member of the fused molybdate transporter subunits of ABC superfamily. Exemplary modF encoded polypeptides include polypeptides, fragments of polypeptides, peptides, and fusion polypeptides that have at least one activity of a modF encoded polypeptide. Exemplary modF encoded polypeptides and nucleic acids include naturally-occurring polypeptides and nucleic acids from any of the source organisms described herein as well as mutant polypeptides and nucleic acids derived from any of the source organisms described herein that have at least one activity of a modF encoded polypeptide.

Repressor of the modABC operon for molybdenum transport (modE) polypeptide is a regulatory protein that is believed to feedback inhibit the transcription of the modABC operon in the presence of molybdate. Exemplary modE encoded polypeptides include polypeptides, fragments of polypeptides, peptides, and fusion polypeptides that have at least one activity of a modE encoded polypeptide. Exemplary modE encoded polypeptides and nucleic acids include naturally-occurring polypeptides and nucleic acids from any of the source organisms described herein as well as mutant polypeptides and nucleic acids derived from any of the source organisms described herein that have at least one activity of a modE encoded polypeptide.

The high affinity trimeric molybdenum transporter protein encoded by modA, modB, and modC is a membrane-associated ABC-type transporter system for the uptake of molybdenum into the cell. When any one of the modABC genes are mutated or absent, molybdate transport is accomplished by the ABC-type sulfate transport system or by a non-specific anion transporter, but with about 100 times less efficiency. (Self et al., 2001, *Res. Microbiol.* 152:311-321). Exemplary modABC encoded polypeptides include polypeptides, fragments of polypeptides, peptides, and fusion polypeptides that have at least one activity of a modABC encoded polypeptide. Exemplary modABC encoded polypeptides and nucleic acids include naturally-occurring polypeptides and nucleic acids from any of the source organisms described herein as well as mutant polypeptides and nucleic acids derived from any of the source organisms described herein that have at least one activity of one of the modABC encoded polypeptides.

Exemplary molybdenum transport nucleic acids include nucleic acids that encode a polypeptide, fragment of a polypeptide, peptide, or fusion polypeptide that has at least one activity of a molybdenum transport polypeptide. Exemplary molybdenum transport nucleic acids include, for example, molybdenum transport genes isolated from *E. coli* K12 MG1655 or derivatives thereof; molybdenum transport genes isolated from *Pseudomonas aeruginosa* strain PAO1; and galactose metabolic genes isolated from *Saccharomyces cerevisie*. Other exemplary molybdenum transport nucleic acids can be isolated from any genus in the family Enterobacteriaceae including, for example, *Alishewanella, Alterococcus, Aquamonas, Citrobacter, Cronobacter, Edwardsiella, Enterobacter, Klebsiella* (e.g., *Klebsiella pneumoniae*), *Pantoea* (e.g., *Pantoea citroea*), *Proteus* (e.g., *Proteus vulgaris*),

*Salmonella, Serratia* (e.g., *Serratia marcescens*), *Shigella*, and *Yersinia* (e.g., *Yersinia pestis*).

Exemplary Host Cells

*E. coli* host cells can be used to express isoprene synthase, PGL polypeptide, DXP pathway polypeptides, IDI, and MVA pathway polypeptides in the methods described herein. In one aspect, the host cell is a recombinant cell of an *Escherichia coli* (*E. coli*) strain, or progeny thereof, capable of producing isoprene, the cell comprising: (a) one or more copies of a heterologous nucleic acid(s) encoding a PGL polypeptide wherein the nucleic acid is integrated in the *E. coli* chromosome; and (b) one or more heterologous nucleic acid(s) encoding isoprene synthase; wherein prior to the integration, the *E. coli* cell does not contain nucleic acid(s) encoding a PGL polypeptide, and wherein the resulting recombinant cell produces isoprene at a greater titer than that of the same cells that do not comprise (a) and (b). In some aspects, the host cells are bacterial cells of an *Escherichia coli* strain that does not encode a 6-phosphogluconolactonase (PGL) polypeptide, further comprising one or more copies of a heterologous gene encoding a PGL polypeptide with one or more associated expression control sequences and a nucleic acid encoding a heterologous polypeptide capable of biological activity. In some aspects, the bacterial cells produce the heterologous polypeptide at a specific productivity greater than that of the same cells lacking one or more copies of a heterologous gene encoding a PGL polypeptide with one or more associated expression control sequences when the cells are cultured in minimal medium. In some aspects, the one or more copies of a heterologous gene encoding a PGL polypeptide with one or more associated expression control sequences are chromosomal copies (e.g., integrated into the *E. coli* chromosome). In some aspects, the *E. coli* cells are in culture.

In some aspects, the heterologous polypeptide capable of biological activity comprises one or more polypeptides involved in the biosynthesis of terpenoid (isoprenoid) or carotenoid compounds, and the cells produce a terpenoid or carotenoid at a higher specific productivity than that of the same cells lacking one or more copies of a heterologous gene encoding a PGL polypeptide with one or more associated expression control sequences when cultured in minimal medium. In some aspects, the method further comprises a step of recovering the terpenoid or carotenoid.

In some aspects, the host cells are bacterial cells of an *Escherichia coli* strain that does not encode a 6-phosphogluconolactonase (PGL) polypeptide, further comprising one or more copies of a heterologous gene encoding a PGL polypeptide with one or more associated expression control sequences and a heterologous nucleic acid encoding an isoprene synthase polypeptide. In some aspects, the bacterial cells produce isoprene at a specific productivity greater than that of the same cells lacking one or more copies of a heterologous gene encoding a PGL polypeptide with one or more associated expression control sequences, when the cells are cultured in minimal medium.

In some aspects, the cells further comprise an MVA pathway polypeptide. In some aspects, the MVA pathway polypeptide is an upper MVA pathway polypeptide. In some aspects, the MVA pathway polypeptide is a lower MVA pathway polypeptide. In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is from the genus *Enterococcus*. In some aspects, the upper MVA pathway polypeptide is from *Enterococcus faecalis*. In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some aspects, the lower MVA pathway polypeptide is an MVK polypeptide. In some aspects, the MVK polypeptide is from the genus *Methanosarcina*. In some aspects, the MVK polypeptide is from *Methanosarcina mazei*.

In some aspects, the one or more copies of a heterologous gene encoding a PGL polypeptide with one or more associated expression control sequences are chromosomal copies (e.g., integrated into the *E. coli* chromosome). In some aspects, the *E. coli* cells are in culture. In some aspects, the bacterial cells are of *E. coli* strain B. In some aspects, the bacterial strains are of *E. coli* strain BL21. In some aspects, the bacterial cells are of *E. coli* strain BL21(DE3).

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which may vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 μl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$*$7H_2O$; (4) 1 g $CoCl_2$*$6H_2O$; (5) 1 g $ZnSO_4$*$7H_2O$; (6) 100 mg $CuSO_4$*$5H_2O$; (7) 100 mg $H_3BO_3$; and (8) 100 mg $NaMoO_4$*$2H_2O$; pH is adjusted to ~3.0.

Any carbon source can be used to cultivate the host cells. The term "carbon source" refers to one or more carbon-containing compounds capable of being metabolized by a host cell or organism. For example, the cell medium used to cultivate the host cells may include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques may be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more isoprene synthase, DXS, IDI, DXP pathway polypeptides or MVA pathway polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Reactions may be performed under aerobic, anoxic, or anaerobic conditions based on the requirements of the host cells.

Standard culture conditions and modEs of fermentation, such as batch, fed-batch, or continuous fermentation, that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples may be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions may allow more favorable regulation of the cells.

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

In some aspects, the *E. coli* cells are grown in batch culture. In some aspects, the *E. coli* cells are grown in fed-batch culture. In some aspects, the *E. coli* cells are grown in continuous culture. In some aspects, the *E. coli* cells are cultured in minimal medium. In some aspects, the minimal medium is M9 medium or TM3 medium. In some aspects, the minimal medium is M9 medium. In some aspects, the minimal medium is TM3 medium. In some aspects, the minimal medium is supplemented with 1.0% (w/v) glucose or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In certain aspects, the minimal medium is supplemented 0.1% (w/v) or less yeast extract. In some aspects, the minimal medium is supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is supplemented with 1% (w/v) glucose or less and 0.1% (w/v) or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the heterologous gene encoding a PGL polypeptide is from *E. coli* strain K12 MG1655. In some aspects, the heterologous gene encoding a PGL polypeptide is from a derivative of *E. coli* strain K12 MG1655. In some aspects, the heterologous gene encoding a PGL polypeptide is from the genus *Pseudomonas*. In some aspects, the *Pseudomonas* is *Pseudomonas aeruginosa*.

The invention encompasses recombinant cell(s) of an *Escherichia coli* (*E. coli*) strain capable of producing isoprene, the cell(s) comprising: (a) one or more copies of a heterologous nucleic acid(s) encoding a PGL polypeptide wherein the nucleic acid(s) is/are integrated in the *E. coli* chromosome; and (b) one or more heterologous nucleic acid(s) encoding isoprene synthase; wherein prior to the integration, the *E. coli* cell does not contain nucleic acid(s) that encode(s) a encoding a PGL polypeptide, and wherein the resulting recombinant cell(s) produce(s) isoprene at a greater titer than that of the same cell(s) that does/do not comprise (a) and (b).

In some aspects, the host cells are bacterial cells of an *Escherichia coli* strain that do not encode a 6-phosphogluconolactonase (PGL) polypeptide, further comprising one or more copies of a heterologous gene encoding a PGL polypeptide with one or more associated expression control sequences and a heterologous nucleic acid encoding an isoprene synthase polypeptide. In some aspects, the host cells are bacterial cells of an *Escherichia coli* strain that does not encode a 6-phosphogluconolactonase (PGL) polypeptide, polypeptides transcribed from genes for galactose metabolism (for example, galM, galK, galT, and galE), or polypeptides transcribed from genes for molybdate transport (for example, modF, modE, modA, modB, and modC) further comprising one or more copies of a heterologous gene encoding a PGL polypeptide with one or more associated expression control sequences, a heterologous nucleic acid encoding an isoprene synthase polypeptide, a heterologous nucleic acid encoding one or more copies of one or more galactose metabolism polypeptides, and a heterologous nucleic acid encoding one or more copies of one or more molybdate transporter polypeptides. In some aspects, the one or more copies of the heterologous gene encoding a PGL polypeptide with one or more associated expression control sequences are chromosomal copies (e.g., integrated into the *E. coli* chromosome). In some aspects, the one or more copies of the heterologous gene encoding a PGL polypeptide, the one or more copies of the heterologous gene encoding one or more galactose metabolism polypeptides, and/or the one or more copies of the heterologous gene encoding one or more molybdate transport polypeptides are chromosomal copies (e.g., integrated into the *E. coli* chromosome).

In some aspects, the bacterial cells are of *E. coli* strain B. In some aspects, the bacterial strains are of *E. coli* strain BL21. In some aspects, the bacterial cells are of *E. coli* strain BL21 (DE3). In some aspects, the minimal medium is supplemented with 0.1% (w/v) yeast extract or less. In some aspects, the minimal medium is supplemented with 1.0% (w/v) glucose or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In certain aspects, the minimal medium is supplemented 0.1% (w/v) or less yeast extract. In some aspects, the minimal medium is supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is supplemented with 1% (w/v) glucose or less and 0.1% (w/v) or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is M9 medium or TM3 medium. In some aspects, the minimal medium is M9 medium. In some aspects, the minimal medium is TM3 medium. In some aspects, the minimal medium is M9 medium. In some aspects, the minimal medium is TM3 medium. In some aspects, the heterologous gene encoding a PGL polypeptide is from *E. coli* strain K12 MG1655. In some aspects, the heterologous gene encoding a PGL polypeptide is from a derivative of *E. coli* strain K12 MG1655. In some aspects, the heterologous gene encoding a PGL polypeptide is from the genus *Pseudomonas*. In some aspects, the *Pseudomonas* is *Pseudomonas aeruginosa.*

In some aspects, the cells further comprise an MVA pathway polypeptide. In some aspects, the MVA pathway polypeptide is an upper MVA pathway polypeptide. In some aspects, the MVA pathway polypeptide is a lower MVA pathway polypeptide. In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is from the genus *Enterococcus*. In some aspects, the upper MVA pathway polypeptide is from *Enterococcus faecalis*. In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some aspects, the lower MVA pathway polypeptide is an MVK polypeptide. In some aspects, the MVK polypeptide is from the genus *Methanosarcina*. In some aspects, the MVK polypeptide is from *Methanosarcina mazei.*

The recombinant bacterial cells described herein have the ability to produce isoprene at a specific productivity greater than that of the same cells lacking one or more copies of a heterologous gene encoding a PGL polypeptide with one or more associated expression control sequences when cultured in minimal medium. In some cases, the heterologous gene encoding a PGL polypeptide is a heterologous nucleic acid encoding a PGL polypeptide that is integrated into the host cell's chromosome. In some aspects, the bacterial cells produce isoprene at a specific productivity greater than that of the same cells lacking one or more copies of a heterologous gene encoding a PGL polypeptide with one or more associated expression control sequences, one or more copies of a heterologous gene encoding one or more galactose metabolism polypeptides, and/or one or more copies of a heterologous gene encoding one or more molybdate transport polypeptides when cultured in minimal medium.

In some aspects, the *E. coli* cells have a specific productivity greater than about 5, 6, 7, 8, 9, 10, 11, 12, 13, or 14 mg/OD/hr of isoprene. In some aspects, the *E. coli* cells have a specific productivity greater than about 15 mg/OD/hr of isoprene. In some aspects, the *E. coli* cells have a specific productivity greater than about 16 mg/OD/hr of isoprene. In some aspects, the *E. coli* cells have a specific productivity greater than about 17 m mg/OD/hr of isoprene. In some aspects, the *E. coli* cells have a specific productivity greater than about 18 mg/OD/hr of isoprene. In some aspects, the *E. coli* cells have a specific productivity greater than about 19 mg/OD/hr of isoprene. In some aspects, the *E. coli* cells have a specific productivity greater than about 20 mg/$L_{broth}$/hr of isoprene. In some aspects, the *E. coli* cells have a specific productivity greater than about 21 mg/OD/hr of isoprene. In some aspects, the *E. coli* cells have a specific productivity greater than about 22 mg/OD/hr of isoprene. In some aspects, the *E. coli* cells have a specific productivity greater than about 23 mg/OD/hr of isoprene. In some aspects, the *E. coli* cells have a specific productivity greater than about 24 mg/OD/hr of isoprene. In some aspects, the *E. coli* cells have a specific productivity greater than about 25 mg/OD/hr of isoprene.

In other aspects, the *E. coli* cells have an upper limit of specific productivity of about 25, 24, 23, 22, 21, 20, 19, 18, 17, 16, 15, 14, 13, 12, 11, 10, 9, 8, 7, 6, or 5 mg/OD/hr of isoprene. In other aspects, the *E. coli* cells have a lower limit of specific productivity of about 5, 6, 7, 8, 9, 10, 11, 12, 13, 14, 15, 16, 17, 18, 19, 20, 21, 22, 23, 24, or 25 mg/OD/hr of isoprene.

In some aspects, the heterologous nucleic acid encoding an isoprene synthase polypeptide is operably linked to a promoter, and the cells have a specific productivity greater than about 15 mg/OD/hr of isoprene. In some aspects, the heterologous nucleic acid encoding an isoprene synthase polypeptide is operably linked to a promoter, and the cells have a specific productivity greater than about 16 mg/OD/hr of isoprene. In some aspects, the heterologous nucleic acid encoding an isoprene synthase polypeptide is operably linked to a promoter, and the cells have a specific productivity greater than about 17 mg/OD/hr of isoprene. In some aspects, the heterologous nucleic acid encoding an isoprene synthase polypeptide is operably linked to a promoter, and the cells have a specific productivity greater than about 18 mg/OD/hr of isoprene. In some aspects, the heterologous nucleic acid encoding an isoprene synthase polypeptide is operably linked to a promoter, and the cells have a specific productivity greater than about 19 mg/OD/hr of isoprene. In some aspects, the heterologous nucleic acid encoding an isoprene synthase polypeptide is operably linked to a promoter, and the cells have a specific productivity greater than about 20 mg/OD/hr of isoprene. In some aspects, the heterologous nucleic acid encoding an isoprene synthase polypeptide is operably linked to a promoter, and the cells have a specific productivity greater than about 21 mg/OD/hr of isoprene. In some aspects, the heterologous nucleic acid encoding an isoprene synthase polypeptide is operably linked to a promoter, and the cells have a specific productivity greater than about 22 mg/OD/hr of isoprene. In some aspects, the heterologous nucleic acid encoding an isoprene synthase polypeptide is operably linked to a promoter, and the cells have a specific productivity greater than about 23 mg/OD/hr of isoprene. In some aspects, the heterologous nucleic acid encoding an isoprene synthase polypeptide is operably linked to a promoter, and the cells have a specific productivity greater than about 24 mg/OD/hr of isoprene. In some aspects, the heterologous nucleic acid encoding an isoprene synthase polypeptide is operably linked to a promoter, and the cells have a specific productivity greater than about 25 mg/OD/hr of isoprene.

In some aspects, the *E. coli* cells further comprise a heterologous nucleic acid encoding an IDI polypeptide. In some aspects, the *E. coli* cells further comprise a chromosomal copy of an endogenous nucleic acid encoding an IDI polypeptide. In some aspects, the *E. coli* cells further comprise a heterologous nucleic acid encoding a DXS polypeptide or other DXP pathway polypeptides. In some aspects, the *E. coli* cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

In some aspects, the *E. coli* cells further comprise a heterologous nucleic acid encoding an isoprene synthase polypeptide. In some cases, the isoprene synthase polypeptide can be one or more copies of an endogenous isoprene synthase. In some aspects, the isoprene synthase polypeptide is a plant isoprene synthase polypeptide. In some aspects, the isoprene synthase polypeptide is a naturally-occurring polypeptide from the genus *Pueraria*. In some aspects, the isoprene synthase polypeptide is a naturally-occurring polypeptide from *Pueraria montana*. In some aspects, the isoprene synthase polypeptide is a naturally-occurring polypeptide from the genus *Populus*. In some aspects, the isoprene synthase polypeptide is a naturally-occurring polypeptide from *Populus alba*. Other isoprene synthase polypeptides or isoprene synthase variants that can be used to practice the invention include, but is not limited to, the isoprene synthases, variants thereof and/or isoprene synthase mutants as described in WO 2009/132220 or WO 2010/124146 (the contents of which are incorporated by reference in their entirety, especially with respect to isoprene synthases, variants thereof and/or isoprene synthase mutants).

Methods for the Increased Production of Isoprene

Genetically engineered cell cultures in bioreactors have produced isoprene more efficiently, in larger quantities, in higher purities and/or with unique impurity profiles, and methods of producing commercially useful quantities of isoprene from renewable resources are described and exemplified, for example, in International Patent Application Publication No. WO2009/076676 A2, U.S. Patent Application Publication Nos. US2009/0203102 A1, US2010/0003716 A1, US2010/0048964 A1, US2010/0086978 A1, US2010/0167370 A1, US2010/0113846 A1, US2010/0184178 A1, US2010/0167371 A1, US2010/0196977 A1, US2010/0196977 A1; U.S. Provisional Patent Application Nos. 61/187,930, 61/187,941 and 61/187,959.

Also provided herein are improved methods for the production of isoprene. In some aspects, the improved method for producing isoprene comprises: (a) culturing a composition comprising recombinant cell(s) of an *Escherichia coli* (*E. coli*) strain, or progeny thereof, capable of producing isoprene, the cell comprising: (i) one or more copies of a heterologous nucleic acid(s) encoding a PGL polypeptide wherein the nucleic acid is integrated in the *E. coli* chromosome; and (ii) one or more heterologous nucleic acid(s) encoding isoprene synthase; wherein prior to the integration, the *E. coli* cell does not contain nucleic acid(s) encoding a PGL polypeptide, and wherein the resulting recombinant cell produces isoprene at a greater titer than that of the same cells that do not comprise (i) and (ii) and (b) producing the isoprene. In some aspects, the improved method of producing isoprene comprises the steps of: (a) culturing bacterial cells of an *Escherichia coli* strain that does not encode a 6-phosphogluconolactonase (PGL) polypeptide in minimal medium, wherein the *E. coli* cells comprise one or more copies of a heterologous gene encoding a PGL polypeptide with one or more associated expression control sequences and a heterologous nucleic acid encoding an isoprene synthase polypeptide; and (b) producing isoprene, wherein the *E. coli* cells have a specific productivity of isoprene greater than that of the same cells lacking one or more copies of a heterologous gene encoding a PGL polypeptide with one or more associated expression control sequences, when the cells are cultured in minimal medium. In some aspects, the one or more copies of a heterologous gene encoding a PGL polypeptide with one or more associated expression control sequences are chromosomal copies (e.g., integrated into the *E. coli* chromosome). In some aspects, the improved method of producing isoprene further comprises a step of recovering the isoprene.

In some aspects, the improved method of producing isoprene comprises the steps of culturing the recombinant cells described herein under conditions suitable for the production of isoprene and allowing the recombinant cells to produce isoprene. In some aspects, the improved method of producing isoprene further comprises a step of recovering the isoprene.

Without being bound by theory, recombinant cells having chromosomally integrated heterologous nucleic acids encoding PGL polypeptide produce isoprene at a higher titer and a higher specific productivity than cells where a heterologous PGL nucleic acid is on a plasmid. Surprisingly, recombinant cells comprising one or more copies of chromosomally integrated PGL polypeptide, and optionally with one or more copies of one or more polypeptides encoded by chromosomally integrated galactose metabolism genes (for example, galM, galK, galT and galE), and/or one or more copies of one or more polypeptides encoded by chromosomally integrated molybdenum transport genes (for example, modF, modE, modA, modB, and modC) convey a substantial growth benefit to the cells, a higher titer of isoprene production, and/or a higher specific production of isoprene versus cells comprising a heterologous PGL nucleic acid on a plasmid.

Therefore, in one aspect the improved method of producing isoprene comprises the steps of: (a) culturing bacterial cells of an *Escherichia coli* strain that does not encode a 6-phosphogluconolactonase (PGL) polypeptide, one or more polypeptides encoded by genes for galactose metabolism (for example, galM, galK, galT and galE), and/or one or more polypeptides encoded by genes for molybdenum transport (for example, modF, modE, modA, modB, and modC), wherein the *E. coli* cells comprise one or more copies of a chromosomally integrated heterologous gene encoding a PGL polypeptide with one or more associated expression control sequences, a heterologous nucleic acid encoding an isoprene synthase polypeptide, one or more copies of a chromosomally integrated heterologous nucleic acid encoding one or more galactose metabolism polypeptides and/or one or more molybdenum transport polypeptides; and (b) producing isoprene, wherein the *E. coli* cells have a higher specific growth rate, specific productivity of isoprene and/or titer production of isoprene than that of the same cells wherein the heterologous gene encoding PGL is located on a plasmid.

In some aspects, the cells further comprise an MVA pathway polypeptide. In such cases, the invention contemplates compositions and methods for producing mevalonate as well. The methods for producing mevalonate using a chromosomally integrated PGL host cell system can optionally include recovery of the mevalonate. In some aspects, the MVA pathway polypeptide is an upper MVA pathway polypeptide. In some aspects, the MVA pathway polypeptide is a lower MVA pathway polypeptide.

In some aspects, the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide. In some aspects, the upper MVA pathway polypeptide is acetoacetyl-Coenzyme A synthase (thiolase). In some aspects, the upper MVA pathway polypeptide is 3-hydroxy-3-methylglutaryl-Coenzyme A synthase polypeptide. In some aspects, the upper MVA pathway polypeptide is 3-hydroxy-3-methylglutaryl-Coenzyme A reductase. In some aspects, the upper MVA pathway polypeptide is from a bacterium. In some aspects, the bacterium is from the genus *Enterococcus*. In some aspects, bacterium is from *Enterococcus faecalis*.

In some aspects, the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI). In some aspects, the lower MVA pathway polypeptide is MVK. In some aspects, the MVK is from the genus *Methanosarcina*. In some aspects, the *Methanosarcina* is *Methanosarcina mazei*. In some aspects, the lower MVA pathway polypeptide is PMK, MVD, or IDI. In some aspects, the PMK, MVD, or IDI is from the genus *Saccharomyces*. In some aspects, the *Saccharomyces* is *Saccharomyces cerevisiae*. In some aspects, the lower MVA pathway polypeptide is PMK. In some aspects, the PMK is from the genus *Saccharomyces*. In some aspects, the *Saccharomyces* is *Saccharomyces cerevisiae*. In some aspects, the lower MVA pathway polypeptide is MVD.

In some aspects, the MVD is from the genus *Saccharomyces*. In some aspects, the *Saccharomyces* is *Saccharomyces cerevisiae*. In some aspects, the lower MVA pathway polypeptide is IDI. In some aspects, the lower MVA pathway polypeptide is from the genus *Saccharomyces*. In some aspects, the *Saccharomyces* is *Saccharomyces cerevisiae*.

In some aspects, the isoprene synthase polypeptide is from a plant. In some aspects, the plant is kudzu. In some aspects, the plant is poplar (*Populus alba×tremula* CAC35696). In some aspects, the plant is aspen (*Populus tremuloides*). In some aspects, the plant is English oak (*Quercus robur*). In one aspect, the plant is *Populus alba*. Other isoprene synthase polypeptides or isoprene synthase variants that can be used to practice the invention include, but is not limited to, the isoprene synthases, variants thereof and/or isoprene synthase mutants as described in WO 2009/132220 or WO 2010/124146 (the contents of which are incorporated by reference in their entirety, especially with respect to isoprene synthases, variants thereof and/or isoprene synthase mutants).

In some aspects, the *E. coli* cells further comprise a heterologous nucleic acid encoding an IDI polypeptide. In some aspects, the *E. coli* cells further comprise one or more copies of an endogenous nucleic acid encoding an IDI polypeptide. In some aspects, the *E. coli* cells further comprise a chromosomal copy of an endogenous nucleic acid encoding an IDI polypeptide. In some aspects, the *E. coli* cells further comprise a heterologous nucleic acid encoding a DXS polypeptide or other DXP pathway polypeptides. In some aspects, the *E. coli* cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

In some aspects, the heterologous gene encoding a PGL polypeptide is from *E. coli* strain K12 MG1655. In some aspects, the heterologous gene encoding a PGL polypeptide is from a derivative of *E. coli* strain K12 MG1655. In some aspects, the *E. coli* K12 strain MG1655 polypeptide having PGL activity is SEQ ID NO:11. In some aspects, the *E. coli* K12 strain MG1655 polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:11. In some aspects, the amino acid substitutions are conservative. In some aspects, the amino acid substitutions are non-conservative. In some aspects, the *E. coli* K12 strain MG1655 polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:11.

In some aspects, the heterologous gene encoding a PGL polypeptide is from the genus *Pseudomonas*. In some aspects, the *Pseudomonas* is *Pseudomonas aeruginosa*. In some aspects, the *P. aeruginosa* polypeptide having PGL activity is SEQ ID NO:12. In some aspects, the *P. aeruginosa* polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:12. In some aspects, the amino acid substitutions are conservative. In some aspects, the amino acid substitutions are non-conservative. In some aspects, the *E. coli* K12 strain MG1655 polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:12.

In some aspects, the heterologous gene encoding a PGL polypeptide is from the genus *Saccharomyces*. In some aspects, the *Saccharomyces* is *Saccharomyces cerevisiae*. In some aspects, the *S. cerevisiae* polypeptide having PGL activity is SEQ ID NO:13. In some aspects, the *S. cerevisiae* polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:13. In some aspects, the amino acid substitutions are conservative. In some aspects, the amino acid substitutions are non-conservative. In some aspects, the *E. coli* K12 strain MG1655 polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:13.

In some aspects, the bacterial cells of an *Escherichia coli* strain that does not encode a PGL polypeptide are of *E. coli* strain B. In some aspects, the bacterial cells are of *E. coli* strain BL21. In some aspects, the bacterial cells are of *E. coli* strain BL21(DE3).

In some aspects, the *E. coli* cells are cultured in minimal medium. In some aspects, the *E. coli* cells of *E. coli* strain B are cultured in minimal medium. In some aspects, the *E. coli* cells of *E. coli* strain BL21 are cultured in minimal medium. In some aspects, the *E. coli* cells of *E. coli* strain BL21(DE3) are cultured in minimal medium. In some aspects, the minimal medium is supplemented with 1% (w/v) or less glucose. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In certain aspects, the minimal medium is supplemented 0.1% (w/v) or less yeast extract. In some aspects, the minimal medium is supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is supplemented with 1% (w/v) glucose or less and 0.1% (w/v) or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is M9 medium or TM3 medium. In some aspects, the minimal medium is M9 medium. In some aspects, the minimal medium is TM3 medium.

In some aspects, the *E. coli* cells have a specific productivity greater than about 15 mg/$L_{broth}$/hr of isoprene. In some aspects, the *E. coli* cells have a specific productivity greater than about 16 mg/OD/hr of isoprene. In some aspects, the *E. coli* cells have a specific productivity greater than about 17 mg/OD/hr of isoprene. In some aspects, the *E. coli* cells have a specific productivity greater than about 18 mg/OD/hr of isoprene. In some aspects, the *E. coli* cells have a specific productivity greater than about 19 mg/OD/hr of isoprene. In some aspects, the *E. coli* cells have a specific productivity greater than about 20 mg/OD/hr of isoprene. In some aspects, the *E. coli* cells have a specific productivity greater than about 21 mg/OD/hr of isoprene. In some aspects, the *E. coli* cells have a specific productivity greater than about 22 mg/OD/hr of isoprene. In some aspects, the *E. coli* cells have a specific productivity greater than about 23 mg/OD/hr of isoprene. In some aspects, the *E. coli* cells have a specific productivity greater than about 24 mg/OD/hr of isoprene. In some aspects, the *E. coli* cells have a specific productivity greater than about 25 mg/OD/hr of isoprene.

In some aspects, the heterologous nucleic acid encoding an isoprene synthase polypeptide is operably linked to a promoter and the *E. coli* cells have a specific productivity greater than about 15 mg/OD/hr of isoprene. In some aspects, the heterologous nucleic acid encoding an isoprene synthase polypeptide is operably linked to a promoter and the *E. coli* cells have a specific productivity greater than about 16 mg/OD/hr of isoprene. In some aspects, the heterologous nucleic acid encoding an isoprene synthase polypeptide is operably linked to a promoter and the *E. coli* cells have a specific productivity greater than about 17 mg/OD/hr of isoprene. In some aspects, the heterologous nucleic acid encoding an isoprene synthase polypeptide is operably linked to a promoter and the *E. coli* cells have a specific productivity greater than about 18 mg/OD/hr of isoprene. In some aspects, the heterologous nucleic acid encoding an isoprene synthase polypeptide is operably linked to a promoter and the *E. coli* cells have a specific productivity greater than about 19 mg/OD/hr of isoprene. In some aspects, the heterologous nucleic acid encoding an isoprene synthase polypeptide is operably linked to a promoter and the *E. coli* cells have a specific productivity greater than about 20 mg/OD/hr of isoprene. In some aspects, the heterologous nucleic acid encoding an isoprene synthase polypeptide is operably linked to a promoter and the *E. coli* cells have a specific productivity greater than about 21 mg/OD/hr of isoprene. In some aspects, the heterologous nucleic acid encoding an isoprene synthase polypeptide is operably linked to a promoter and the *E. coli* cells have a specific productivity greater than about 22 mg/OD/hr of isoprene. In some aspects, the heterologous nucleic acid encoding an isoprene synthase polypeptide is operably linked to a promoter and the *E. coli* cells have a specific productivity greater than about 23 mg/OD/hr of isoprene. In some aspects, the heterologous nucleic acid encoding an isoprene synthase polypeptide is operably linked to a promoter and the *E. coli* cells have a specific productivity greater than about 24 mg/OD/hr of isoprene. In some aspects, the heterologous nucleic acid encoding an isoprene synthase polypeptide is operably linked to a promoter and the *E. coli* cells have a specific productivity greater than about 25 mg/OD/hr of isoprene. In some aspects, the heterologous nucleic acid encoding an isoprene synthase polypeptide is operably linked to a promoter and the *E. coli* cells have a specific productivity greater than about 25 mg/OD/hr of isoprene to about 100 mg/OD/hr of isoprene. In some aspects, the heterologous nucleic acid encoding an isoprene synthase polypeptide is operably linked to a promoter and the *E. coli* cells have a specific productivity greater than about 15 mg/OD/hr of isoprene to about 100 mg/OD/hr of isoprene.

The invention also provides for recombinant *E. coli* cells with PGL integration that have been engineered to produce isoprene that also have better growth due to their increased overall fitness. One of skill in the art can appreciate that increased growth rate can lead to enhanced production of isoprene, such as higher specific activity, more isoprene produced over a period of time, or higher isoprene titers. In one aspect, the recombinant *E. coli* cells with PGL integration that have been engineered to produce isoprene has at least 10% increased growth as compared to those cells without PGL integration and/or the restoration of the 17,257 base pair piece as described herein (see, for example, FIG. 20). In other aspects, the recombinant *E. coli* cells with PGL integration that have been engineered to produce isoprene has at least about 11%, 12%, 13%, 14%, 15%, 16%, 17%, 18%, 19%, 20%, 21%, 22%, 23%, 24%, or 25% growth as compared to those cells without PGL integration and/or the restoration of the 17,257 base pair piece as described herein.

Methods for the Increased Production of Other Heterologous Polypeptides Capable of Biological Activity Also provided herein are improved methods for the production of other heterologous polypeptides capable of biological activity or other products. One non-limiting example of a product is mevalonate. One of skill in the art can produce mevalonate by: (a) culturing a composition comprising the recombinant cell of an *Escherichia coli* (*E. coli*) strain, or progeny thereof, capable of producing isoprene, the cell comprising: (i) one or more copies of a heterologous nucleic acid(s) encoding a PGL polypeptide wherein the nucleic acid is integrated in the *E. coli* chromosome; (ii) one or more heterologous nucleic acid(s) encoding isoprene synthase; and (iii) (c) a heterologous nucleic acid encoding an upper mevalonate (MVA) pathway polypeptide and/or a lower MVA pathway polypeptide; wherein prior to the integration, the *E. coli* cell does not contain nucleic acid(s) encoding a PGL polypeptide, and wherein the resulting recombinant cell produces isoprene at a greater titer than that of the same cells that do not comprise (i) and (ii) under suitable culture conditions for the production of mevalonate and (b) producing mevalonate.

In some aspects, the improved method of producing heterologous polypeptides capable of biological activity comprises the steps of: (a) culturing cells of an *Escherichia coli* strain that does not encode a 6-phosphogluconolactonase (PGL) polypeptide, further comprising one or more copies of a heterologous gene encoding a PGL polypeptide with one or more associated expression control sequences and a nucleic acid encoding a heterologous polypeptide capable of biological activity; and (b) producing the heterologous polypeptide, wherein the *E. coli* cells have a specific productivity of the heterologous polypeptide greater than that of the same cells lacking one or more copies of a heterologous gene encoding a PGL polypeptide with one or more associated expression control sequences, when the cells are cultured in minimal medium. In some aspects, the one or more copies of a heterologous gene encoding a PGL polypeptide with one or more associated expression control sequences are chromosomal copies (e.g., integrated into the *E. coli* chromosome). In some aspects, the *E. coli* cells are in culture. In some aspects, the improved method of producing heterologous polypeptides capable of biological activity further comprises a step of recovering the polypeptide.

In some aspects, the bacterial cells of an *Escherichia coli* strain that does not encode a PGL polypeptide are of *E. coli* strain B. In some aspects, the bacterial cells are of *E. coli* strain BL21. In some aspects, the bacterial cells are of *E. coli* strain BL21(DE3).

In some aspects, the heterologous gene encoding a PGL polypeptide is from *E. coli* strain K12 MG1655. In some aspects, the heterologous gene encoding a PGL polypeptide is from a derivative of *E. coli* strain K12 MG1655. In some aspects, the *E. coli* K12 strain MG1655 polypeptide having PGL activity is SEQ ID NO:11. In some aspects, the *E. coli* K12 strain MG1655 polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:11. In some aspects, the amino acid substitutions are conservative. In some aspects, the amino acid substitutions are non-conservative. In some aspects, the *E. coli* K12 strain MG1655 polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:11.

In some aspects, the heterologous gene encoding a PGL polypeptide is from the genus *Pseudomonas*. In some aspects, the *Pseudomonas* is *Pseudomonas aeruginosa*. In some aspects, the *P. aeruginosa* polypeptide having PGL activity is SEQ ID NO:12. In some aspects, the *P. aeruginosa* polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:12. In some aspects, the amino acid substitutions are conservative. In some aspects, the amino acid substitutions are non-conservative. In some aspects, the *P. aeruginosa* polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:12.

In some aspects, the heterologous gene encoding a PGL polypeptide is from the genus *Saccharomyces*. In some aspects, the *Saccharomyces* is *Saccharomyces cerevisiae*. In some aspects, the *S. cerevisiae* polypeptide having PGL activity is SEQ ID NO:13. In some aspects, the *S. cerevisiae* polypeptide having PGL activity comprises 1, 2, 3, 4, 5, 6, 7, 8, 9, 10, 11, 12, 13, 14, 15, 16, 17, 18, 19, 20, or more amino acid substitutions compared to SEQ ID NO:13. In some aspects, the amino acid substitutions are conservative. In some aspects, the amino acid substitutions are non-conservative. In some aspects, the *E. coli* K12 strain MG1655 polypeptide having PGL activity has 99%, 98%, 97%, 96%, 95%, 95%, 93%, 92%, 91%, 90%, 89%, 88%, 87%, 86%, or 85% amino acid sequence identity to SEQ ID NO:13.

In some aspects, the bacterial cells of an *Escherichia coli* strain that does not encode a 6-phosphogluconolactonase (PGL) polypeptide are cultured in minimal medium. In some aspects, the bacterial cells of *E. coli* strain B are cultured in minimal medium. In some aspects, the bacterial cells of *E. coli* strain BL21 are cultured in minimal medium. In some aspects, the bacterial cells of *E. coli* strain BL21(DE3) are cultured in minimal medium. In some aspects, the minimal medium is supplemented with 1% (w/v) or less glucose. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In certain aspects, the minimal medium is supplemented 0.1% (w/v) or less yeast extract. In some aspects, the minimal medium is supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is supplemented with 1% (w/v) glucose or less and 0.1% (w/v) or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is M9 medium or TM3 medium. In some aspects, the minimal medium is M9 medium. In some aspects, the minimal medium is TM3 medium.

Also provided herein are improved methods for the production of other heterologous polypeptides capable of biological activity. In some aspects, the improved method of producing heterologous polypeptides capable of biological activity comprises the steps of: (a) culturing cells of an *Escherichia coli* strain that does not encode a 6-phosphogluconolactonase (PGL) polypeptide, a gene that encodes one or more galactose metabolism polypeptides (for example, galM, galK, galT, and galE), and/or a gene that encodes one or more molybdenum transporter polypeptides (for example, modF, modE, modA, modB, and modC) further comprising one or more copies of a heterologous gene encoding a PGL polypeptide with one or more associated expression control sequences and a nucleic acid encoding a heterologous polypeptide capable of biological activity, one or more copies of a heterologous gene encoding one or more galactose metabolism polypeptides, and/or one or more copies of a heterologous gene encoding one or more molybdenum transport polypeptides; and (b) producing the heterologous polypeptide, wherein the *E. coli* cells have a specific productivity of the heterologous polypeptide greater than that of the same cells lacking one or more copies of a heterologous gene encoding a PGL polypeptide with one or more associated expression control sequences, one or more copies of a heterologous gene encoding one or more galactose metabolism polypeptides, and/or one or more copies of a heterologous gene encoding one or more molybdenum transport polypeptides when the cells are cultured in minimal medium. In some aspects, the one or more copies of a heterologous gene encoding a PGL polypeptide with one or more associated expression control sequences, the one or more copies of a heterologous gene encoding one or more galactose metabolism polypeptides, and/or the one or more copies of a heterologous gene encoding one or more molybdenum transporter polypeptides are chromosomal copies (e.g., integrated into the *E. coli* chromosome). In some aspects, the *E. coli* cells are in culture. In some aspects, the improved method of producing heterologous polypeptides capable of biological activity further comprises a step of recovering the polypeptide.

In some aspects, the bacterial cells of an *Escherichia coli* strain that does not encode a PGL polypeptide, one or more galactose metabolic genes, and/or one or more molybdenum transport genes are of *E. coli* strain B. In some aspects, the bacterial cells are of *E. coli* strain BL21. In some aspects, the bacterial cells are of *E. coli* strain BL21(DE3).

In some aspects, the heterologous gene encoding a PGL polypeptide, one or more galactose metabolic genes, and/or one or more molybdenum transport genes is from *E. coli* strain K12 MG1655. In some aspects, the heterologous gene encoding a PGL polypeptide, one or more galactose metabolic genes, and/or one or more molybdenum transport genes is from a derivative of *E. coli* strain K12 MG1655. In some aspects, the *E. coli* K12 strain MG1655 polypeptide having PGL activity, galactose metabolic activity, and/or molybdenum transport activity comprises 1, 2, 3, 4, 5, 6, 7, 8, 9, 10, 11, 12, 13, 14, 15, 16, 17, 18, 19, 20, or more amino acid substitutions compared to the native *E. coli* K12 strain MG1655 polypeptide. In some aspects, the amino acid substitutions are conservative. In some aspects, the amino acid substitutions are non-conservative. In some aspects, the *E. coli* K12 strain MG1655 polypeptide having PGL activity, galactose metabolic activity, and/or molybdenum transport activity has 99%, 98%, 97%, 96%, 95%, 95%, 93%, 92%, 91%, 90%, 89%, 88%, 87%, 86%, or 85% amino acid sequence identity to the native *E. coli* K12 strain MG1655 polypeptide.

In some aspects, the heterologous gene encoding a PGL polypeptide, one or more galactose metabolism polypeptides, and/or one or more molybdenum transport polypeptides is from the genus *Pseudomonas*. In some aspects, the *Pseudomonas* is *Pseudomonas aeruginosa*. In some aspects, the *P. aeruginosa* polypeptide having PGL activity, galactose metabolic activity, and/or molybdenum transport activity comprises 1, 2, 3, 4, 5, 6, 7, 8, 9, 10, 11, 12, 13, 14, 15, 16, 17, 18, 19, 20, or more amino acid substitutions compared to the native *P. aeruginosa* polypeptide. In some aspects, the amino acid substitutions are conservative. In some aspects, the amino acid substitutions are non-conservative. In some aspects, the *P. aeruginosa* polypeptide having PGL activity, galactose metabolic activity, and/or molybdenum transport activity has 99%, 98%, 97%, 96%, 95%, 95%, 93%, 92%, 91%, 90%, 89%, 88%, 87%, 86%, or 85% amino acid sequence identity to the native *P. aeruginosa* polypeptide.

In some aspects, the heterologous gene encoding a PGL polypeptide, one or more galactose metabolism polypeptides, and/or one or more molybdenum transport polypeptides is from the genus *Saccharomyces*. In some aspects, the *Saccharomyces* is *Saccharomyces cerevisiae*. In some aspects, the *S. cerevisiae* polypeptide having PGL activity, galactose metabolic activity, and/or molybdenum transport activity comprises 1, 2, 3, 4, 5, 6, 7, 8, 9, 10, 11, 12, 13, 14, 15, 16, 17, 18, 19, 20, or more amino acid substitutions compared to the native *Saccharomyces cerevisiae*. In some aspects, the amino acid substitutions are conservative. In some aspects, the amino acid substitutions are non-conservative. In some aspects, the *Saccharomyces cerevisiae* polypeptide having PGL activity has 99%, 98%, 97%, 96%, 95%, 95%, 93%, 92%, 91%, 90%, 89%, 88%, 87%, 86%, or 85% amino acid sequence identity to the native *Saccharomyces cerevisiae* polypeptide.

In some aspects, the bacterial cells of an *Escherichia coli* strain that does not encode a 6-phosphogluconolactonase (PGL) polypeptide, one or more galactose metabolism polypeptides, and/or one or more molybdenum transport polypeptides are cultured in minimal medium. In some aspects, the bacterial cells of *E. coli* strain B are cultured in minimal medium. In some aspects, the bacterial cells of *E. coli* strain BL21 are cultured in minimal medium. In some aspects, the bacterial cells of *E. coli* strain BL21(DE3) are cultured in minimal medium. In some aspects, the minimal medium is supplemented with 1% (w/v) or less glucose. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. In certain aspects, the minimal medium is supplemented 0.1% (w/v) or less yeast extract. In some aspects, the minimal medium is supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is supplemented with 1% (w/v) glucose or less and 0.1% (w/v) or less. In some aspects, the minimal medium is supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the minimal medium is M9 medium or TM3 medium. In some aspects, the minimal medium is M9 medium. In some aspects, the minimal medium is TM3 medium.

In some aspects, the heterologous polypeptide capable of biological activity comprises one or more polypeptides involved in the biosynthesis of terpenoid (isoprenoid) or carotenoid compound(s), and the cells produce a terpenoid or carotenoid at a higher specific productivity than that of the same cells lacking one or more copies of a heterologous gene encoding a PGL polypeptide with one or more associated expression control sequences when cultured in minimal medium. In some aspects, the method further comprises a step of recovering the terpenoid or carotenoid.

As used herein, the term "terpenoid" or "isoprenoid" refers to a large and diverse class of naturally-occurring organic chemicals similar to terpenes. Terpenoids are derived from five-carbon isoprene units assembled and modified in a variety of ways, and are classified in groups based on the number of isoprene units used in group members. Hemiterpenoids have one isoprene unit. Monoterpenoids have two isoprene units. Sesquiterpenoids have three isoprene units. Diterpenoids have four isoprene units. Sesterterpenoids have five isoprene units. Triterpenoids have six isoprene units. Tetraterpenoids have eight isoprene units. Polyterpenoids have more than eight isoprene units. One of ordinary skill in the art would be able to identify heterologous polypeptides capable of biological activity, e.g., capable of making terpenoids of various classes by assembling the appropriate number of isoprene units and modifying them as appropriate.

As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes.

In some aspects, the terpenoids are selected from the group consisting of hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid is geranyl pyrophosphate, eucalyptol, limonene, or pinene. In some aspects, the sesquiterpenoid is farnesyl pyrophosphate, artemisinin, or bisabolol. In some aspects, the diterpenoid is geranylgeranyl pyrophosphate, retinol, retinal, phytol, taxol, forskolin, or aphidicolin. In some aspects, the triterpenoid is squalene or lanosterol. In some aspects, the tetraterpenoid is lycopene or carotene. In some aspects, the carotenoids are selected from the group consisting of xanthophylls and carotenes. In some aspects, the xanthophyll is lutein or zeaxanthin. In some aspects, the carotene is α-carotene, β-carotene, γ-carotene, β-cryptoxanthin or lycopene.

In some aspects, the source organism for the heterologous polypeptide capable of biological activity is a fungus. In some aspects, the fungus is a species of *Aspergillus* such as *A. oryzae* and *A. niger*, a species of *Saccharomyces* such as *S. cerevisiae*, a species of *Schizosaccharomyces* such as *S. pombe*, or a species of *Trichoderma* such as *T. reesei*. In some aspects, the source organism for the heterologous polypeptide capable of biological activity is a filamentous fungal cell. In some aspects, the filamentous fungal cell is from *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In some aspects, the source organism is a yeast, such as *Saccharomyces* sp., *Schizosaccharomyces* sp., *Pichia* sp., or *Candida* sp. In some aspects, the *Saccharomyces* sp. is *Saccharomyces cerevisiae*.

In some aspects, the source organism for the heterologous polypeptide capable of biological activity is a bacterium. In some aspects, the bacterium is of the genus *Bacillus*, such as *B. lichenformis* or *B. subtilis*, the genus *Pantoea*, such as *P. citrea*, the genus *Pseudomonas*, such as *P. alcaligenes, P. putida*, or *P. fluorescens*, the genus *Streptomyces*, such as *S. lividans, S. coelicolor, S. griseus*, or *S. rubiginosus*, the genus *Corynebacterium*, such as *Corynebacterium glutamicum*, the genus *Rhodopseudomonas*, such as *Rhodopseudomonas palustris*, or the genus *Escherichia*, such as *E. coli*. In some aspects, the bacterium is selected from group consisting of *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*.

In some aspects, the source organism is a plant, such as a plant from the family Fabaceae, such as the Faboideae subfamily. In some aspects, the source organism is kudzu, poplar (such as *Populus alba* or *Populus alba×tremula* CAC35696), aspen (such as *Populus tremuloides*), or *Quercus robur*. In some aspects, the source organism is an algae, such as a green algae, red algae, glaucophytes, chlorarachniophytes, euglenids, chromista, or dinoflagellates. In some aspects, the source organism is a cyanobacterium, such as cyanobacterium classified into any of the following groups based on morphology: Chlorococcales, Pleurocapsales, Oscillatoriales, Nostocales, or Stigonematales.

Isoprene Compositions Produced from Renewable Resources

Isoprene compositions produced from renewable resources are distinguished from petro-isoprene compositions in that isoprene produced from renewable resources is produced with other biological byproducts (compounds derived from the biological sources and/or associated the biological processes that are obtained together with isoprene) that are not present or present in much lower levels in petro-isoprene compositions, such as alcohols, aldehydes, ketone and the like. The biological byproducts may include, but are not limited to, ethanol, acetone, methanol, acetaldehyde, methacrolein, methyl vinyl ketone, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), 2-heptanone, 6-methyl-5-hepten-2-one, 2,4,5-trimethylpyridine, 2,3,5-trimethylpyrazine, citronellal, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3,7-dimethyl-1,3,6-octatriene, (Z)-3,7-dimethyl-1,3,6-octatriene, or a linear isoprene polymer (such as a linear isoprene dimer or a linear isoprene trimer derived from the polymerization of multiple isoprene units). Products derived from isoprene produced from renewable resources contain one or more of the biological byproducts or compounds derived from any of the by-products. In addition, products derived from isoprene produced from renewable resources may contain compounds formed from these by-products during subsequent chemical conversion. Examples of such compounds include those derived from Diels-Alder cycloaddition of dienophiles to isoprene, or the oxidation of isoprene.

Isoprene compositions produced from renewable resources, including particular byproducts or impurities, are described in more detail in U.S. Provisional Patent Application No. 61/187,959 and WO 2010/14825.

The amount of isoprene produced by cells can be greatly increased by introducing a heterologous nucleic acid encoding an isoprene synthase polypeptide (e.g., a plant isoprene synthase polypeptide), a DXS polypeptide, other DXP pathway polypeptide, and/or an MVA pathway polypeptide into the cells, e.g., as described in International Patent Application Publication No. WO2009/076676 A2, U.S. patent application Ser. No. 12/335,071, U.S. patent application Ser. Nos. 12/429,143, 12/496,573, 12/560,390, 12/560,317, 12/560,370, 12/560,305, and 12/560,366; U.S. Provisional Patent Application Nos. 61/187,930; 61/187,941; 61/187,959; U.S. Publ. No. 2010/0196977 and WO 2010/078457.

Exemplary isoprene synthase polypeptide (e.g., a plant isoprene synthase polypeptide), a DXS, a DXP pathway, or an MVA pathway polypeptides and nucleic acids include naturally-occurring polypeptides and nucleic acids from any of the source organisms described herein as well as mutant polypeptides and nucleic acids derived from any of the source organisms described herein.

Exemplary Isoprene Synthase Polypeptides and Nucleic Acids

In some aspects, the *E. coli* cells comprise a heterologous nucleic acid encoding an isoprene synthase polypeptide. In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., Plant Physiology 137:700-712, 2005), *Pueraria lobata*, poplar (such as *Populus alba, Populus nigra, Populus trichocarpa*, or *Populus alba×tremula* (CAC35696) Miller et al., Planta 213:483-487, 2001) aspen (such as *Populus tremuloides*) Silver et al., JBC 270(22):13010-1316, 1995), or English Oak (*Quercus robur*) (Zimmer et al., WO 98/02550). In some aspects, the isoprene synthase polypeptide or nucleic acid is a naturally-occurring isoprene synthase polypeptide or nucleic acid. In some aspects, the isoprene synthase polypeptide or nucleic acid is not a naturally-occurring isoprene synthase polypeptide or nucleic acid. Exemplary isoprene synthase polypeptides and nucleic acids and methods of measuring isoprene synthase activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXS Polypeptides and Nucleic Acids

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP Pathway Polypeptides and Nucleic Acids

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, IDI polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

IDI polypeptides convert isopentenyl diphosphate into dimethylallyl diphosphate. Standard methods can be used to determine whether a polypeptide has IDI polypeptides activity by measuring the ability of the polypeptide to convert isopentenyl diphosphate in vitro, in a cell extract, or in vivo.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethyl allyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI polypeptides and nucleic acids and methods of measuring IDI activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary MVA Pathway Polypeptides and Nucleic Acids

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway polypeptides and nucleic acids and methods of measuring IDI activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In some aspects, the cells contain the upper MVA pathway, which includes AA-CoA thiolase, HMG-CoA synthase, and HMG-CoA reductase nucleic acids. In some aspects, the cells contain the lower MVA pathway, which includes MVK, PMK, MVD, and IDI nucleic acids. In some aspects, the cells contain an entire MVA pathway that includes AA-CoA thiolase, HMG-CoA synthase, HMG-CoA reductase, MVK, PMK, MVD, and IDI nucleic acids. In some aspects, the cells contain an entire MVA pathway that includes AA-CoA thiolase, HMG-CoA synthase, HMG-CoA reductase, MVK, PMDC, IPK, and IDI nucleic acids.

The *E. coli* cells described herein can also be used for improved methods of producing isoprene and a co-product, such as hydrogen, ethanol, or propanediol (e.g., 1,2-propanediol or 1,3-propanediol). Exemplary hydrogenase polypeptides and nucleic acids, polypeptides and nucleic acids for genes related to production of fermentation side products, and polypeptides and nucleic acids for genes relating to hydrogen reuptake can also be used with the compositions and methods described in. Such polypeptides and nucleic acids are described in U.S. Publ. No. 2010/0196977 and WO 2010/078457.

Exemplary Methods for Isolating Nucleic Acids

Isoprene synthase, DXS, IDI, DXP pathway, MVA pathway, PGL, hydrogenase, hydrogenase maturation and/or transcription factor nucleic acids can be isolated using standard methods. Methods of obtaining desired nucleic acids from a source organism of interest (such as a bacterial genome) are common and well known in the art of molecular biology (see, for example, WO 2004/033646 and references cited therein). Standard methods of isolating nucleic acids, including PCR amplification of known sequences, synthesis of nucleic acids, screening of genomic libraries, screening of cosmid libraries are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Promoters and Vectors

Any of the isoprene synthase, DXS, DXP pathway, IDI, MVA pathway, PGL, hydrogenase, hydrogenase maturation, transcription factor, galactose metabolic, and/or molybdenum transport nucleic acids described herein can be included in one or more vectors. Accordingly, also described herein are vectors with one more nucleic acids encoding any of the isoprene synthase, DXS, IDI, DXP pathway, MVA pathway, PGL, hydrogenase, hydrogenase maturation, transcription factor polypeptides, galactose metabolic polypeptides, and/or molybdenum transport polypeptides that are described herein. In some aspects, the vector contains a nucleic acid under the control of an expression control sequence. In some aspects, the expression control sequence is a native expression control sequence. In some aspects, the expression control sequence is a non-native expression control sequence. In some aspects, the vector contains a selective marker or selectable marker. In some aspects, an isoprene synthase, DXS, IDI, MVA pathway, PGL, hydrogenase, hydrogenase maturation, transcription regulatory, galactose metabolic, and/or molybdenum transport nucleic acid integrates into a chromosome of the cells without a selectable marker. In some aspects, an isoprene synthase, DXS, IDI, DXP pathway, MVA pathway, PGL, hydrogenase, hydrogenase maturation, transcription regulatory, galactose metabolic, and/or molybdenum transport nucleic acid integrates into a chromosome of the cells with a selectable marker.

Suitable vectors are those which are compatible with the host cell employed. Suitable vectors can be derived, for example, from a bacterium, a virus (such as bacteriophage T7 or a M-13 derived phage), a cosmid, a yeast, or a plant. Suitable vectors can be maintained in low, medium, or high copy number in the host cell. Protocols for obtaining and using such vectors are known to those in the art (see, for example, Sambrook et al., Molecular Cloning: A Laboratory Manual, 2$^{nd}$ ed., Cold Spring Harbor, 1989). Suitable vectors compatible with the cells and methods described herein are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Promoters are well known in the art. Any promoter that functions in the host cell can be used for expression of an isoprene synthase, DXS, IDI, DXP pathway, MVA pathway, PGL, hydrogenase, hydrogenase maturation, transcription factor, galactose metabolic and/or molybdenum transport nucleic acid in the host cell. Initiation control regions or promoters, which are useful to drive expression of isoprene synthase, DXS, IDI, DXP pathway, MVA pathway, PGL, hydrogenase, hydrogenase maturation, transcription factor, galactose metabolic and/or molybdenum transport nucleic acids in various host cells are numerous and familiar to those skilled in the art (see, for example, WO 2004/033646 and references cited therein). Virtually any promoter capable of driving these nucleic acids can be used including a glucose isomerase promoter (see, for example, U.S. Pat. No. 7,132, 527 and references cited therein). Suitable promoters compatible with the cells and methods described herein are described in International Publication No. WO 2009/076676 A2 and U.S. Patent Application Publication No. US2009/0203102 A1.

In some aspects, the expression vector also includes a termination sequence. Termination control regions may also be derived from various genes native to the host cell. In some aspects, the termination sequence and the promoter sequence are derived from the same source. Suitable termination sequences compatible with the cells and methods described herein are described in International Publication No. WO 2009/076676 A2 and U.S. Patent Application Publication No. US2009/0203102 A1

An isoprene synthase, DXS, IDI, DXP pathway, MVA pathway, PGL, hydrogenase, hydrogenase maturation, transcription factor, galactose metabolic and/or molybdenum nucleic acid can be incorporated into a vector, such as an expression vector, using standard techniques (Sambrook et al., Molecular Cloning: A Laboratory Manual, Cold Spring Harbor, 1982). Suitable techniques compatible with the cells and methods described herein are described in International Publication No. WO 2009/076676 A2 and U.S. Patent Application Publication No. US2009/0203102 A1.

In some aspects, it may be desirable to over-express isoprene synthase, DXP pathway, IDI, MVA pathway, PGL, hydrogenase, hydrogenase maturation, transcription factor, galactose metabolic and/or molybdenum transport nucleic acids at levels far higher than currently found in naturally-occurring cells. In some aspects, it may be desirable to under-express (e.g., mutate, inactivate, or delete) isoprene synthase, DXP pathway, IDI, MVA pathway, PGL, hydrogenase, hydrogenase maturation, transcription factor polypeptide, galactose metabolic polypeptide and/or molybdenum transport polypeptide-encoding nucleic acids at levels far below that those currently found in naturally-occurring cells. Suitable methods for over- or under-expressing the isoprene synthase, DXP pathway, IDI, MVA pathway, PGL, hydrogenase, hydrogenase maturation, transcription factor, galactose metabolic and/or molybdenum transport nucleic acids compatible with cells and methods described herein are described in International Publication No. WO 2009/076676 A2 and U.S. Patent Application Publication No. US2009/0203102 A1.

Exemplary Source Organisms

Figure 1B:
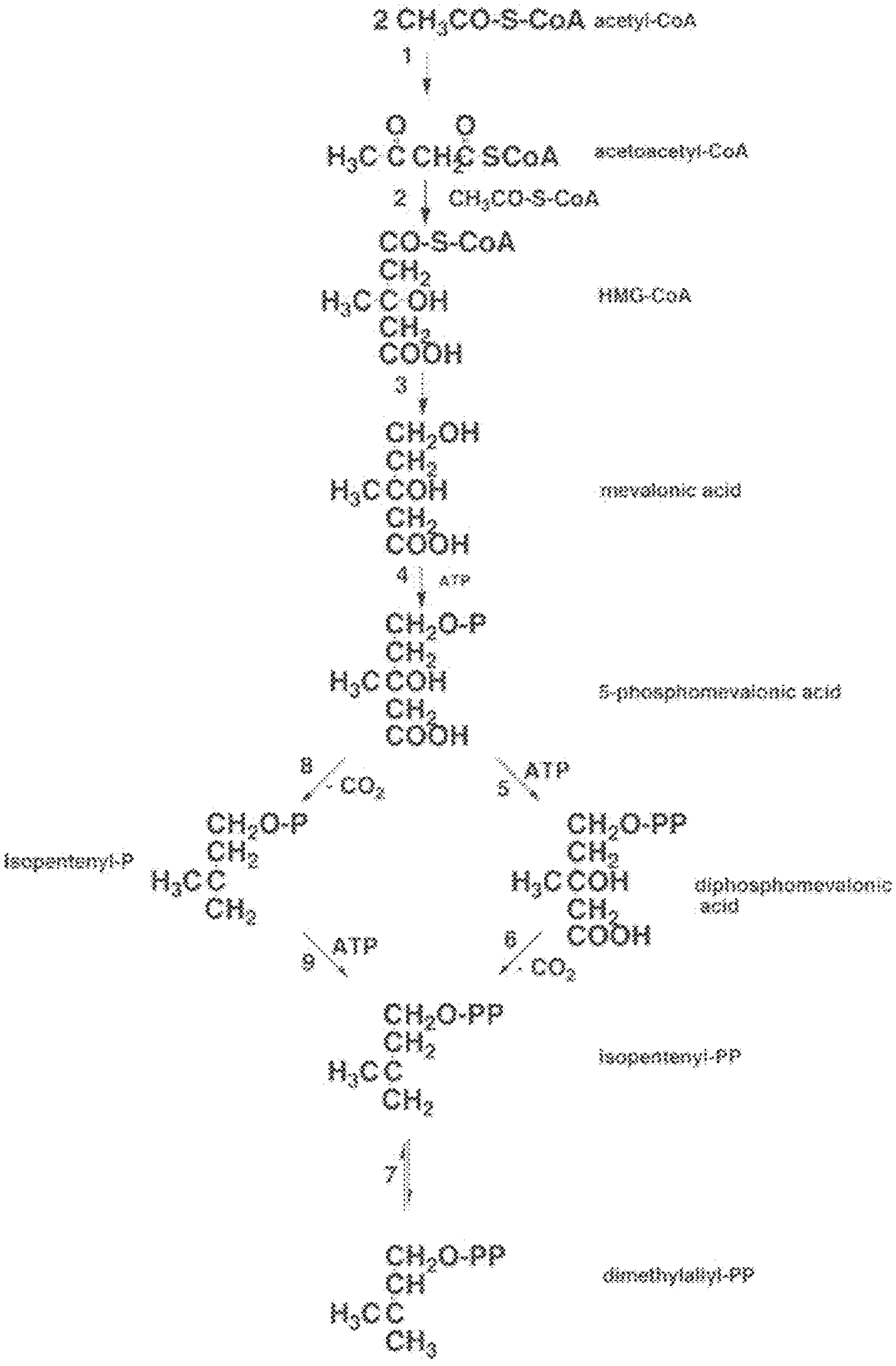
FIG. 1B illustrates the classical and modified MVA pathways. 1, acetyl-CoA acetyltransferase (AACT); 2, HMG-CoA synthase (HMGS); 3, HMG-CoA reductase (HMGR); 4, mevalonate kinase (MVK); 5, phosphomevalonate kinase (PMK); 6, diphosphomevalonate decarboxylase (MVD or DPMDC); 7, isopentenyl diphosphate isomerase (IDI); 8, phosphomevalonate decarboxylase (PMDC); 9, isopentenyl phosphate kinase (IPK). The classical MVA pathway proceeds from reaction 1 through reaction 7 via reactions 5 and 6, while a modified MVA pathway goes through reactions 8 and 9. P and PP in the structural formula are phosphate and pyrophosphate, respectively. This figure was taken from Koga and Morii, *Microbiology and Mol. Biology Reviews* 71:97-120, 2007. The modified MVA pathway is present, for example, in some archaeal organisms, such as *Methanosarcina mazei.*

Isoprene synthase, DXP pathway, IDI, MVA pathway, PGL, hydrogenase, hydrogenase maturation, transcription factor, galactose metabolic and/or molybdenum transport nucleic acids (and their encoded polypeptides) can be obtained from any organism that naturally contains isoprene synthase, DXP pathway, IDI, MVA pathway, PGL, hydrogenase, hydrogenase maturation, transcription factor, galactose metabolic and/or molybdenum transport nucleic acids. As noted above, isoprene is formed naturally by a variety of organisms, such as bacteria, yeast, plants, and animals. Organisms contain the MVA pathway, DXP pathway, or both the MVA and DXP pathways for producing isoprene (FIGS. 1A and 1B). Thus, DXP pathway nucleic acids can be obtained, e.g., from any organism that contains the DXP pathway or contains both the MVA and DXP pathways. IDI and isoprene synthase nucleic acids can be obtained, e.g., from any organism that contains the MVA pathway, DXP pathway, or both the MVA and DXP pathways. MVA pathway nucleic acids can be obtained, e.g., from any organism that contains the MVA pathway or contains both the MVA and DXP pathways. Hydrogenase nucleic acids can be obtained, e.g., from any organism that oxidizes hydrogen or reduces hydrogen ions. Fermentation side product genes can be obtained or identified, e.g., from any organism that undergoes oxygen-limited or anaerobic respiration, such as glycolysis.

The nucleic acid sequence of the isoprene synthase, DXP pathway, IDI, MVA pathway, PGL, hydrogenase, hydrogenase maturation, transcription factor, galactose metabolic and/or molybdenum transport nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba*× *tremula* CAC35696) or aspen (e.g., *Populus tremuloides*). Exemplary host organisms are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Transformation Methods

Isoprene synthase, DXP pathway, IDI, MVA pathway, PGL, hydrogenase, hydrogenase maturation, transcription factor, galactose metabolic and/or molybdenum transport nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., *Curr. Genet.* 16:53-56, 1989). The introduced nucleic acids may be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (see, e.g., U.S. Prov. 61/288,142 or U.S. application Ser. No. 12/969,440). In some aspects, any of the methods described herein further include a step of recovering the heterologous polypeptide. In some aspects, any of the methods described herein further include a step of recovering the terpenoid or carotenoid.

Suitable purification methods are described in more detail in U.S. Patent Application Publication US2010/0196977 A1; and U.S. Provisional Patent Application No. 61/187,959.

Other Techniques

Additional examples of efficient methods for the production and recovery of isoprene and a coproduct, such as hydrogen, are described in U.S. Patent Application Publication No. US2010/0196977.

Examples of other techniques (e.g., decoupling isoprene production from cell growth, methods of producing isoprene within safe operating ranges, cell viability at high isoprene titers, efficient methods for the production and recovery of isoprene and a co-product (e.g., hydrogen, ethanol, or 1,3-propanediol)) that can be used with the cells and methods described herein are described in International Patent Publication No. WO 2009/076676 A2; U.S. Patent Application Publication Nos. US2010/0048964 A1, US2010/0086978 A1, US2010/0113846 A1, US2010/0184178 A1 and US2010/0167371 A1, US2010/0196977 A1; U.S. Provisional Patent Application Nos. 61/187,930, 61/187,959, and 61/187,941; and International Patent Application Publication Nos. WO 2004/033646 A2 and WO 1996/035796 A2.

The invention can be further understood by reference to the following examples, which are provided by way of illustration and are not meant to be limiting.

EXAMPLES

Example 1

Construction of *E. coli* Strains Expressing the *S. cerevisiae* gi1.2KKDyI Operon, *P. alba* Isoprene Synthase, *M. mazei* Mevalonate Kinase, pCL Upper MVA (*E. faecalis* mvaE and mvaS) and ybhE (pgl)

(i) Construction of Strain EWL201 (BL21, Cm-GI1.2-KKDyI)

*E. coli* BL21 (Novagen brand, EMD Biosciences, Inc.) was a recipient strain, transduced with MCM331 P1 lysate (lysate prepared according to the method described in Ausubel, et al., *Current Protocols in Molecular Biology*. John Wiley and Sons, Inc.). MCM331 cells contain chromosomal construct gi1.2KKDyI encoding *S. cerevisiae* mevalonate kinase, mevalonate phosphate kinase, mevalonate pyrophosphate decarboxylase, and IPP isomerase (i.e., the gi1.2-KKDyI operon from *S. cerevisiae*; construction of which is described in Example 10 of International Publication No. WO 2009/076676 A2 and U.S. patent application Ser. No. 12/335,071 (US Publ. No. 2009/0203102)). Transductants were selected for by spreading cells onto L Agar and 20 chloramphenicol. The plates were incubated overnight at 30° C. Analysis of transductants showed no colonies on control plates (water+cells control plate for reversion and water and P1 lysate control plate for lysate contamination.

Four transductants were picked and used to inoculate 5 mL L Broth and 20 chloramphenicol. The cultures were grown overnight at 30° C. with shaking at 200 rpm. To make genomic DNA preparations of each transductant for PCR analysis, 1.5 mL of overnight cell culture were centrifuged. The cell pellet was resuspended with 400 μl Resuspension Buffer (20 mM Tris, 1 mM EDTA, 50 mM NaCl, pH 7.5) and 4 μl RNase, DNase-free (Roche) was added. The tubes were incubated at 37° C. for 30 minutes followed by the addition of 4 μl 10% SDS and 4 μl of 10 mg/ml Proteinase K stock solution (Sigma-Aldrich). The tubes were incubated at 37° C. for 1 hour. The cell lysate was transferred into 2 ml Phase Lock Light Gel tubes (Eppendorf) and 200 μl each of saturated phenol pH7.9 (Ambion Inc.) and chloroform were added. The tubes were mixed well and microcentrifuged for 5 minutes. A second extraction was done with 400 μl chloroform and the aqueous layer was transferred to a new eppendorf tube. The genomic DNA was precipitated by the addition of 1 ml of 100% ethanol and centrifugation for 5 minutes. The genomic DNA pellet was washed with 1 ml 70% ethanol. The ethanol was removed and the genomic DNA pellet was allowed to air dry briefly. The genomic DNA pellet was resuspended with 200 μl TE.

Using Pfu Ultra II DNA polymerase (Stratagene) and 200 ng/μl of genomic DNA as template, 2 different sets of PCR reaction tubes were prepared according to manufacturer's protocol. For set 1, primers MCM130 and GB Cm-Rev (Table 1) were used to ensure transductants were successfully integrated into the attTn7 locus. PCR parameters for set 1 were 95° C. for 2 minutes (first cycle only), 95° C. for 25 seconds, 55° C. for 25 seconds, 72° C. for 25 seconds (repeat steps 2-4 for 28 cycles), 72° C. for 1 minute. For set 2, primers MVD For and MVD Rev (Table 1) were used to ensure that the gi1.2-KKDyI operon integrated properly. PCR parameters for set 2 were 95° C. for 2 minutes (first cycle only), 95° C. for 25 seconds, 55° C. for 25 seconds, 72° C. for 10 seconds (repeat steps 2-4 for 28 cycles), 72° C. for 1 minute. Analysis of PCR amplicons on a 1.2% E-gel (Invitrogen Corp.) showed that all 4 transductant clones were correct. One was picked and designated as strain EWL201.

(ii) Construction of Strain EWL204 (BL21, Loopout-GI1.2-KKDyI)

The chloramphenicol marker was looped out of strain EWL201 using plasmid pCP20 as described by Datsenko and Wanner (2000) (Datsenko et al., *Proc Natl. Acad. Sci USA* 97:6640-6645, 2000). EWL201 cells were grown in L Broth to midlog phase and then washed three times in ice-cold, sterile water. An aliquot of 50 μl of cell suspension was mixed with 1 μl of pCP20 and the cell suspension mixture was electroporated in a 2 mm cuvette (Invitrogen Corp.) at 2.5 Volts and 25 μFd using a Gene Pulser Electroporator (Bio-Rad Inc.). 1 ml of LB was immediately added to the cells, then transferred to a 14 ml polypropylene tube (Sarstedt) with a metal cap. Cells were allowed to recover by growing for 1 hour at 30° C. Transformants were selected on L Agar and 20 μg/μl chloramphenicol and 50 μg/μl carbenicillin and incubated at 30° C. overnight. The next day, a single clone was grown in 10 ml L Broth and 50 μg/μl carbenicillin at 30° C. until early log phase. The temperature of the growing culture was then shifted to 42° C. for 2 hours. Serial dilutions were made, the cells were then spread onto LA plates (no antibiotic selection), and incubated overnight at 30° C. The next day, 20 colonies were picked and patched onto L Agar (no antibiotics) and LA and 20 μg/μl chloramphenicol plates. Plates were then incubated overnight at 30° C. Cells able to grow on LA plates, but not LA and 20 μg/μl chloramphenicol plates, were deemed to have the chloramphenicol marker looped out (picked one and designated as strain EWL204).

(iii) Construction of Plasmid pEWL230 (pTrc *P. alba*)

Figure 2:
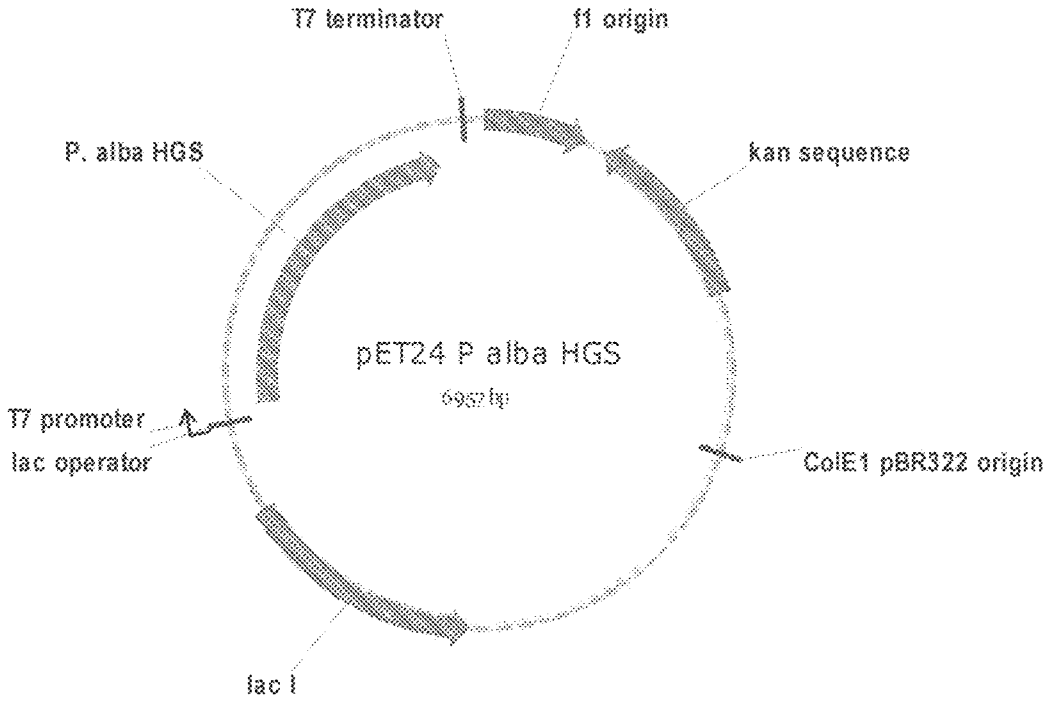
FIG. 2 is a map of plasmid pET24 *P. alba* HGS.

Generation of a synthetic gene encoding *Populus alba* isoprene synthase (*P. alba* HGS) was outsourced to DNA2.0 Inc. (Menlo Park, Calif.) based on their codon optimization method for *E. coli* expression. The synthetic gene was custom cloned into plasmid pET24a (Novagen brand, EMD Biosciences, Inc.) and delivered lyophilized (FIGS. 2, 3A-B; SEQ ID NO:1).

A PCR reaction was performed to amplify the *P. alba* isoprene synthase (*P. alba* HGS) gene using pET24 *P. alba* HGS as the template, primers MCM182 and MCM192, and Herculase II Fusion DNA polymerase (Stratagene) according to manufacturer's protocol. PCR conditions were as follows: 95° C. for 2 minutes (first cycle only), 95° C. for 25 seconds, 55° C. for 20 seconds, 72° C. for 1 minute, repeat for 25 cycles, with final extension at 72° C. for 3 minutes. The *P. alba* isoprene synthase PCR product was purified using QIAquick PCR Purification Kit (Qiagen Inc.).

Figure 4:
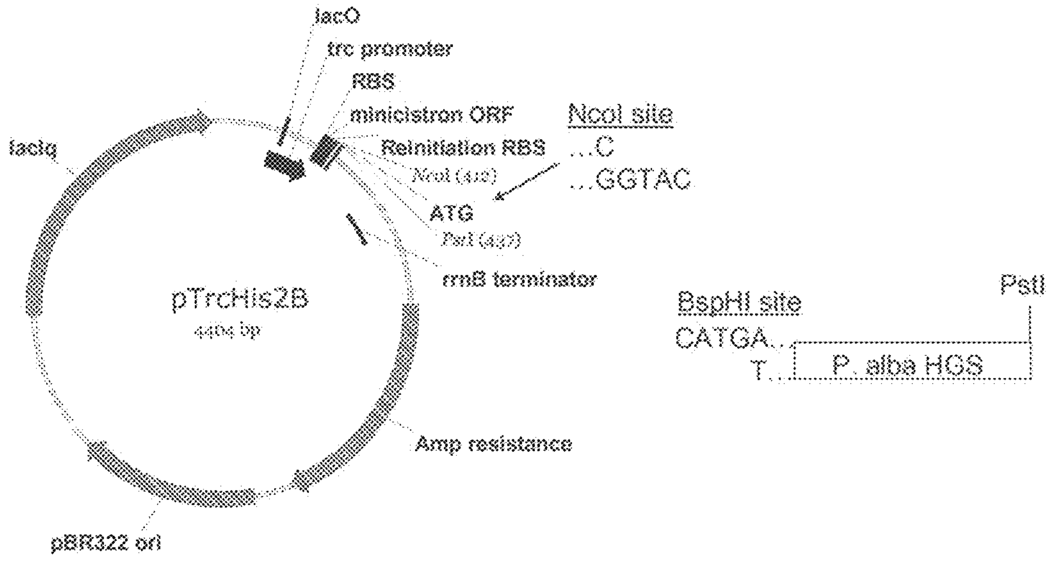
FIG. 4 is a schematic diagram showing restriction sites used for endonuclease digestion to construct plasmid EWL230 and compatible cohesive ends between BspHI and NcoI sites.
Figure 5:
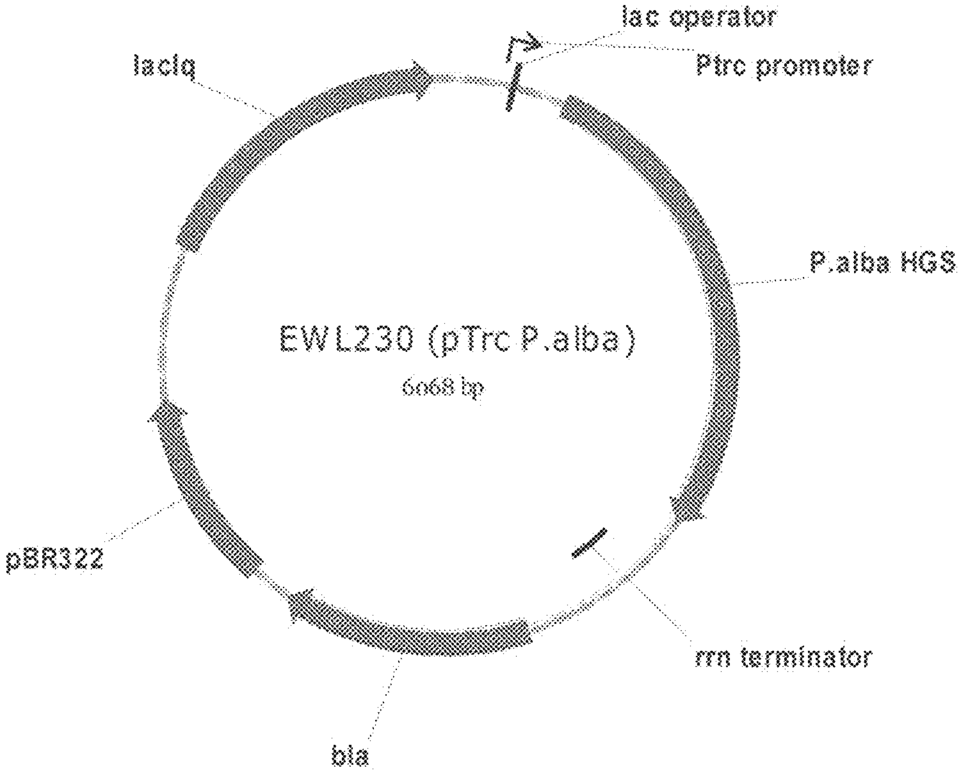
FIG. 5 is a map of plasmid EWL230.

*P. alba* isoprene synthase PCR product was then digested in a 20 μl reaction containing 1 μl BspHI endonuclease (New England Biolabs) with 2 μl 10×NEB Buffer 4. The reaction was incubated for 2 hours at 37° C. The digested PCR fragment was then purified using the QIAquick PCR Purification Kit. A secondary restriction digest was performed in a 20 μl reaction containing 1 μl PstI endonuclease (Roche) with 2 μl 10× Buffer H. The reaction was incubated for 2 hours at 37° C. The digested PCR fragment was then purified using the QIAquick PCR Purification Kit. Plasmid pTrcHis2B (Invitrogen Corp.) was digested in a 20 μl reaction containing 1 μl NcoI endonuclease (Roche), 1 μl PstI endonuclease, and 2 μl 10× Buffer H. The reaction was incubated for 2 hours at 37° C. The digested pTrcHis2B vector was gel purified using a 1.2% E-gel (Invitrogen Corp.) and extracted using the QIAquick Gel Extraction Kit (Qiagen) (FIG. 4). Using the compatible cohesive ends of BspHI and NcoI sites, a 20 μl ligation reaction was prepared containing 5 μl *P. alba* isoprene synthase insert, 2 μl pTrc vector, 1 μl T4 DNA ligase (New England Biolabs), 2 μl 10× ligase buffer, and 10 μl $ddH_2O$. The ligation mixture was incubated at room temperature for 40 minutes. The ligation mixture was desalted by floating a 0.025 μm nitrocellulose membrane filter (Millipore) in a petri dish of $ddH_2O$ and applying the ligation mixture gently on top of the nitrocellulose membrane filter for 30 minutes at room temperature. MCM446 cells were grown in LB to midlog phase and then washed three times in ice-cold, sterile water. An aliquot of 50 μl of cell suspension was mixed with 5 μl of desalted pTrc *P. alba* HGS ligation mix. The cell suspension mixture was electroporated in a 2 mm cuvette at 2.5 Volts and 25 μFd using a Gene Pulser Electroporator. 1 ml of LB was immediately added to the cells, then transferred to a 14 ml polypropylene tube (Sarstedt) with a metal cap. Cells were allowed to recover by growing for 2 hour at 30° C. Transformants were selected on L Agar and 50 μg/μl carbenicillin and 10 mM mevalonic acid and incubated at 30° C. The next day, 6 transformants were picked and grown in 5 ml L Broth and 50 μg/μl carbenicillin tubes overnight at 30° C. Plasmid preps were performed on the overnight cultures using QIAquick Spin Miniprep Kit (Qiagen). Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 μl reaction to ensure the correct sized linear fragment. All 6 plasmids were the correct size and shipped to Quintara Biosciences (Berkeley, Calif.) for sequencing with primers MCM65, MCM66, EL1000 (Table 1). DNA sequencing results showed all 6 plasmids were correct. One plasmid was picked designated as plasmid EWL230 (FIGS. 5, 6A-B; SEQ ID NO:2).

iv) Construction of Plasmid pEWL244 (pTrc *P. alba*-mMVK)

A PCR reaction was performed to amplify the *Methanosarcina mazei* (*M. mazei*) MVK gene using MCM376 as the template, primers MCM165 and MCM177 (see Table 1), and Pfu Ultra II Fusion DNA polymerase (Stratagene) according to manufacturer's protocol. PCR conditions were as follows: 95° C. for 2 minutes (first cycle only), 95° C. for 25 seconds, 55° C. for 25 seconds, 72° C. for 18 seconds, repeat for 28 cycles, with final extension at 72° C. for 1 minute. The *M. mazei* MVK PCR product was purified using QIAquick PCR Purification Kit (Qiagen Inc.).

Figure 7:
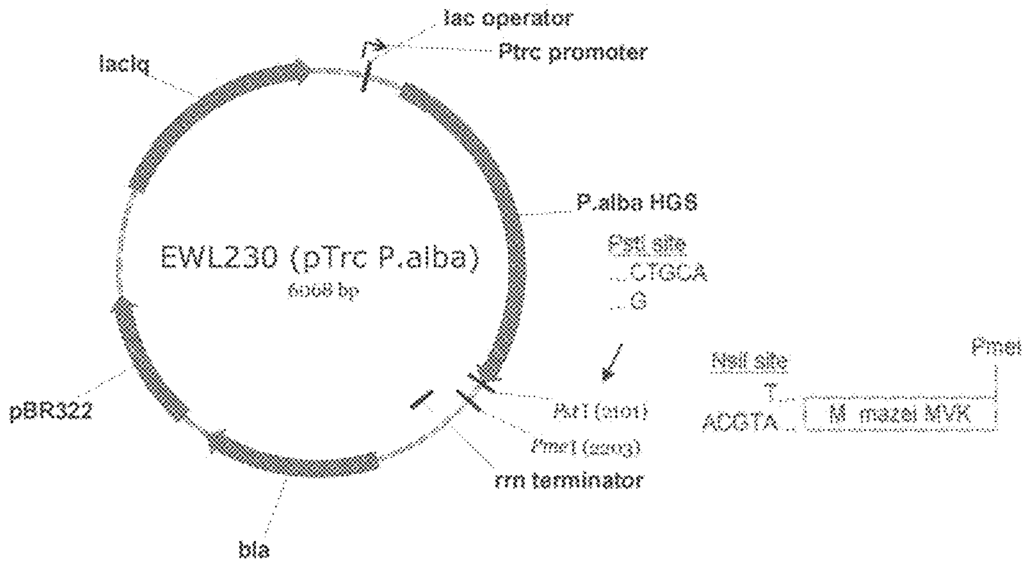
FIG. 7 is a schematic diagram showing restriction sites used for endonuclease digestion to construct plasmid EWL244 and compatible cohesive ends between NsiI and PstI sites.
Figure 8:
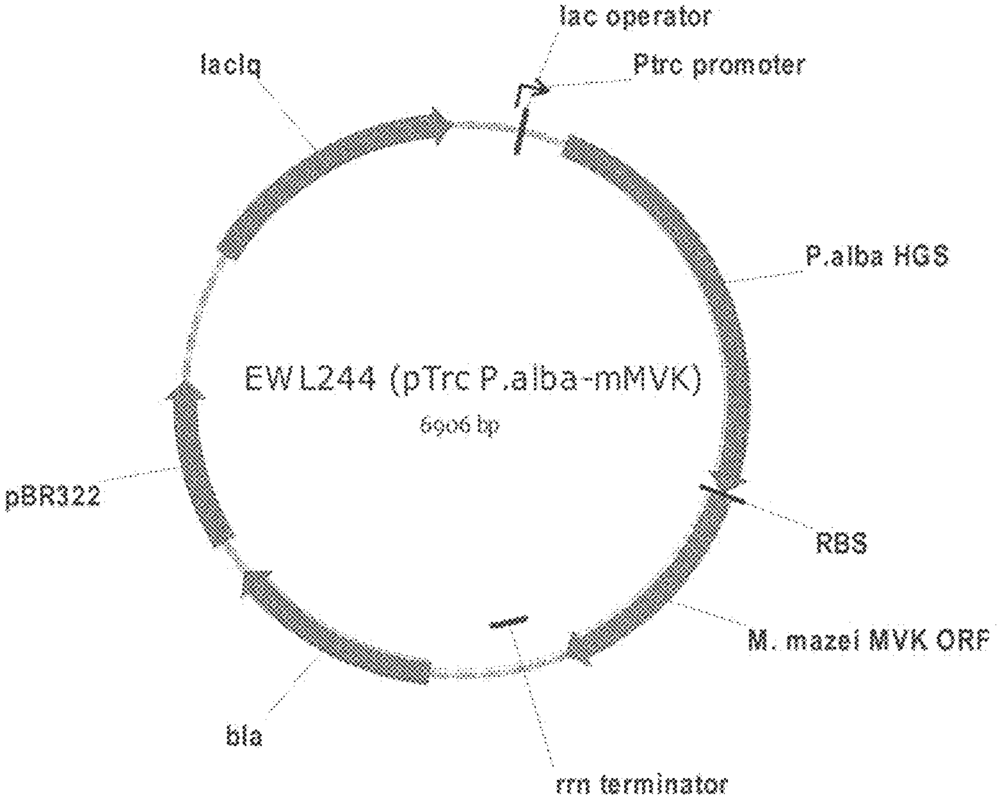
FIG. 8 is a map of plasmid EWL244.

The *M. mazei* MVK PCR product was then digested in a 40 μl reaction containing 8 μl PCR product, 2 μl PmeI endonuclease (New England Biolabs), 4 μl 10×NEB Buffer 4, 4 μl 10×NEB BSA, and 22 μl of $ddH_2O$. The reaction was incubated for 3 hours at 37° C. The digested PCR fragment was then purified using the QIAquick PCR Purification Kit. A secondary restriction digest was performed in a 47 μl reaction containing 2 μl NsiI endonuclease (Roche), 4.7 μl 10× Buffer H, and 40 μl of PmeI digested *M. mazei* MVK fragment. The reaction was incubated for 3 hours at 37° C. The digested PCR fragment was then gel purified using a 1.2% E-gel and extracted using the QIAquick Gel Extraction Kit. Plasmid EWL230 was digested in a 40 μl reaction containing 10 μl plasmid, 2 μl PmeI endonuclease, 4 μl 10×NEB Buffer 4, 4 μl 10×NEB BSA, and 20 μl of $ddH_2O$. The reaction was incubated for 3 hours at 37° C. The digested PCR fragment was then purified using the QIAquick PCR Purification Kit. A secondary restriction digest was performed in a 47 μl reaction containing 2 μl PstI endonuclease, 4.7 μl 10× Buffer H, and 40 μl of PmeI digested EWL230 linear fragment. The reaction was incubated for 3 hours at 37° C. The digested PCR fragment was then gel purified using a 1.2% E-gel and extracted using the QIAquick Gel Extraction Kit (FIG. 7). Using the compatible cohesive ends of NsiI and PstI sites, a 20 μl ligation reaction was prepared containing 8 μl *M. mazei* MVK insert, 3 μl EWL230 plasmid, 1 μl T4 DNA ligase, 2 μl 10× ligase buffer, and 6 μl $ddH_2O$. The ligation mixture was incubated overnight at 16° C. The next day, the ligation mixture was desalted by floating a 0.025 μm nitrocellulose membrane filter in a petri dish of $ddH_2O$ and applying the ligation mixture gently on top of the nitrocellulose membrane filter for 30 minutes at room temperature. MCM446 cells were grown in LB to midlog phase and then washed three times in ice-cold, sterile water. An aliquot of 50 μl of cell suspension was mixed with 5 μl of desalted pTrc *P. alba*-mMVK ligation mix. The cell suspension mixture was electroporated in a 2 mm cuvette at 2.5 Volts and 25 μFd using a Gene Pulser Electroporator. 1 ml of LB is immediately added to the cells, then the cells are transferred to a 14 ml polypropylene tube with a metal cap. Cells were allowed to recover by growing for 2 hour at 30° C. Transformants were selected on LA and 50 μg/μl carbenicillin and 5 mM mevalonic acid plates and incubated at 30° C. The next day, 6 transformants were picked and grown in 5 ml LB and 50 μg/μl carbenicillin tubes overnight at 30° C. Plasmid preps were performed on the overnight cultures using QIAquick Spin Miniprep Kit. Due to the use of BL21 cells for propagating plasmids, a modification of washing the spin columns with PB Buffer 5× and PE Buffer 3× was incorporated to the standard manufacturer's protocol for achieving high quality plasmid DNA. Plasmids were digested with PstI in a 20 μl reaction to ensure the correct sized linear fragment. Three of the 6 plasmids were the correct size and shipped to Quintara Biosciences for sequencing with primers MCM65, MCM66, EL1000, EL1003, and EL1006 (Table 1). DNA sequencing results showed all 3 plasmids were correct. One was picked and designated as plasmid EWL244 (FIGS. 8 and 9A-B; SEQ ID NO:3).

v) Construction of Plasmid MCM376—MVK from *M. mazei* Archaeal Lower in pET200D.

Figure 10A:
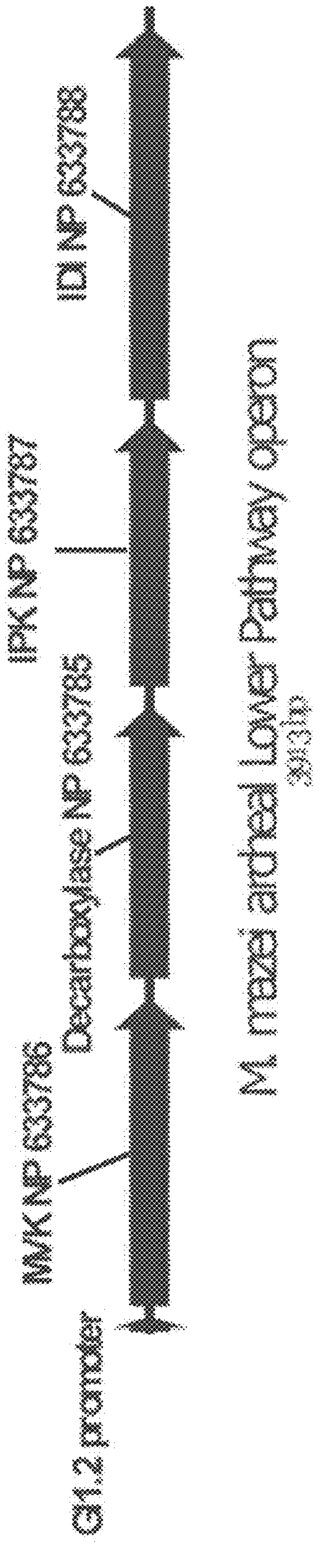
FIG. 10A is a map of the *M. mazei* archaeal Lower Pathway operon.

The MVK ORF from the *M. mazei* archaeal Lower Pathway operon (FIGS. 10A-C; SEQ ID NO:4) was PCR amplified using primers MCM161 and MCM162 (Table 1) using the Invitrogen Platinum HiFi PCR mix. 45 μL of PCR mix was combined with 1 μL template, 1 μL of each primer at 10 μM, and 2 μL water. The reaction was cycled as follows: 94°

Figure 11A:
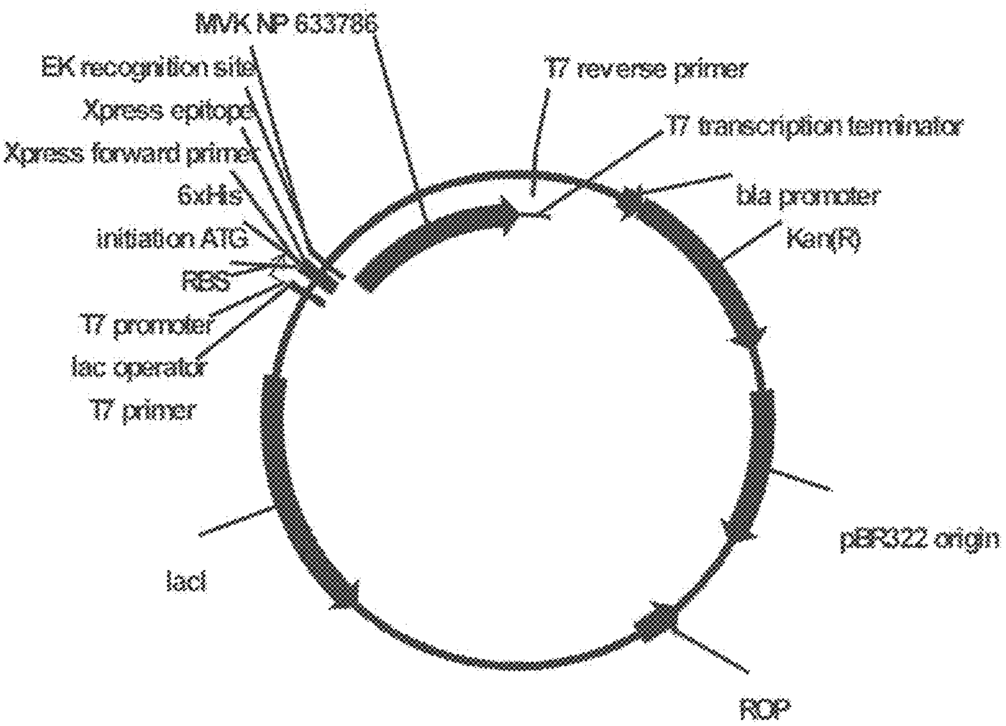
FIG. 11A is a map of MCM376-MVK from *M. mazei* archaeal Lower in pET200D.

C. for 2:00 minutes; 30 cycles of 94° C. for 0:30 minutes, 55° C. for 0:30 minutes and 68° C. for 1:15 minutes; and then 72° C. for 7:00 minutes, and 4° C. until cool. 3 μL of this PCR reaction was ligated to Invitrogen pET200D plasmid according to the manufacturer's protocol. 3 μL of this ligation was introduced into Invitrogen TOP10 cells, and transformants were selected on LA/kan50. A plasmid from a transformant was isolated and the insert sequenced, resulting in MCM376 (FIGS. 11A-C).

vi) Construction of Strain EWL251 (BL21(DE3), Cm-GI1.2-KKDyI, pTrc *P.alba*-mMVK)

MCM331 cells (which contain chromosomal construct gi1.2KKDyI encoding *S. cerevisiae* mevalonate kinase, mevalonate phosphate kinase, mevalonate pyrophosphate decarboxylase, and IPP isomerase) were grown in LB to midlog phase and then washed three times in ice-cold, sterile water. Mixed 50 μl of cell suspension with 1 μl of plasmid EWL244. The cell suspension mixture was electroporated in a 2 mm cuvette at 2.5 Volts and 25 μFd using a Gene Pulser Electroporator. 1 ml of LB is immediately added to the cells, and then the cells were transferred to a 14 ml polypropylene tube with a metal cap. Cells were allowed to recover by growing for 2 hours at 30° C. Transformants were selected on LA and 50 μg/μl carbenicillin and 5 mM mevalonic acid plates and incubated at 37° C. One colony was selected and designated as strain EWL251.

vii) Construction of Strain EWL256 (BL21(DE3), Cm-GI1.2-KKDyI, pTrc *P.alba*-mMVK, pCL Upper MVA)

EWL251 cells were grown in LB to midlog phase and then washed three times in ice-cold, sterile water. Mixed 50 μl of cell suspension with 1 μl of plasmid MCM82 (comprising pCL PtrcUpperPathway (also known as "pCL Upper MVA"), encoding *E. faecalis* mvaE and mvaS). Plasmid pCL Ptrc Upper Pathway was constructed as described in Example 8 of International Publication No. WO 2009/076676 A2 and U.S. patent application Ser. No. 12/335,071 (US Publ. No. 2009/0203102). The cell suspension mixture was electroporated in a 2 mm cuvette at 2.5 Volts and 25 μFd using a Gene Pulser Electroporator. 1 ml of LB was immediately added to the cells. Cells were then transferred to a 14 ml polypropylene tube with a metal cap. Cells were allowed to recover by growing for 2 hours at 30° C. Transformants were selected on LA and 50 μg/μl carbenicillin and 50 μg/μl spectinomycin plates and incubated at 37° C. One colony was picked and designated as strain EWL256.

TABLE 1

Primer Sequences

| Primer name | Primer sequence |
|---|---|
| MCM130 | ACCAATTGCACCCGGCAGA (SEQ ID NO: 14) |
| GB Cm Rev | GCTAAAGCGCATGCTCCAGAC (SEQ ID NO: 15) |
| MVD For | GACTGGCCTCAGATGAAAGC (SEQ ID NO: 16) |
| MVD Rev | CAAACATGTGGCATGGAAAG (SEQ ID NO: 17) |
| MCM182 | GGGCCCGTTTAAACTTTAACTAGACTCTGCAGTTAGCGTTCAAACGGCAGAA (SEQ ID NO: 18) |
| MCM192 | CGCATGCATGTCATGAGATGTAGCGTGTCCACCGAAAA (SEQ ID NO: 19) |
| MCM65 | ACAATTTCACACAGGAAACAGC (SEQ ID NO: 20) |
| MCM66 | CCAGGCAAATTCTGTTTTATCAG (SEQ ID NO: 21) |
| EL1000 | GCACTGTCTTTCCGTCTGCTGC (SEQ ID NO: 22) |
| MCM165 | GCGAACGATGCATAAAGGAGGTAAAAAAACATGGTATCCTGTTCTGCGCCGGG TAAGATTTACCTG (SEQ ID NO: 23) |
| MCM177 | GGGCCCGTTTAAACTTTAACTAGACTTTAATCTACTTTCAGACCTTGC (SEQ ID NO: 24) |
| EL1003 | GATAGTAACGGCTGCGCTGCTACC (SEQ ID NO: 25) |
| EL1006 | GACAGCTTATCATCGACTGCACG (SEQ ID NO: 26) |
| MCM161 | CACCATGGTATCCTGTTCTGCG (SEQ ID NO: 27) |
| MCM162 | TTAATCTACTTTCAGACCTTGC (SEQ ID NO: 28) |

viii) Construction of Strain RM111608-2 (Cm-GI1.2-KKDyI, pTrc *P.alba*-mMVK, pCL Upper MVA, pBBRCMPGI1.5-pgl)

The BL21 strain of *E. coli* producing isoprene (EWL256) was constructed with constitutive expression of the ybhE gene (encoding *E. coli* 6-phosphogluconolactonase) on a replicating plasmid pBBR1MCS5(Gentamycin) (obtained from Dr. K. Peterson, Louisiana State University).

FRT-based recombination cassettes, and plasmids for Red/ET-mediated integration and antibiotic marker loopout were obtained from Gene Bridges GmbH (Germany). Procedures using these materials were carried out according to Gene Bridges protocols. Primers Pgl-F (SEQ ID NO:29) and PglGI1.5-R (SEQ ID NO:30) were used to amplify the resistance cassette from the FRT-gb2-Cm-FRT template using Stratagene Herculase II Fusion kit according to the manufacturer's protocol. The PCR reaction (50 μL final volume) contained: 5 μL buffer, 1 μL template DNA (FRT-gb2-Cm-F from Gene Bridges), 10 pmols of each primer, and 1.5 μL 25 mM dNTP mix, made to 50 μL with $dH_2O$. The reaction was cycled as follows: 1×2 minutes, 95° C. then 30 cycles of (30 seconds at 95° C.; 30 seconds at 63° C.; 3 minutes at 72° C.).

The resulting PCR product was purified using the QIAquick® PCR Purification Kit (Qiagen) and electroporated into electrocompetent MG1655 cells harboring the pRed-ET recombinase-containing plasmid as follows. Cells were prepared by growing in 5 mLs of L broth to and OD600~0.6 at 30° C. The cells were induced for recombinase expression by the addition of 4% arabinose and allowed to grow for 30 minutes at 30° C. followed by 30 minutes of growth at 37° C. An aliquot of 1.5 mLs of the cells was washed 3-4 times in ice cold $dH_2O$. The final cell pellet was resuspended in 40 μL of ice cold $dH_2O$ and 2-5 μL of the PCR product was added. The electroporation was carried out in 1-mm gap cuvettes, at 1.3 kV in a Gene Pulser Electroporator (Bio-Rad Inc.). Cells were recovered for 1-2 hours at 30° C. and plated on L agar containing chloramphenicol (5 μg/mL). Five transformants were analyzed by PCR and sequencing using primers flanking the integration site (2 primer sets: pgl and 49 rev and 3' EcoRV-pglstop; Bottom Pgb2 and Top GB's CMP (946)). A correct transformant was selected and this strain was designated MG1655 GI1.5-pgl::CMP.

Figure 12:
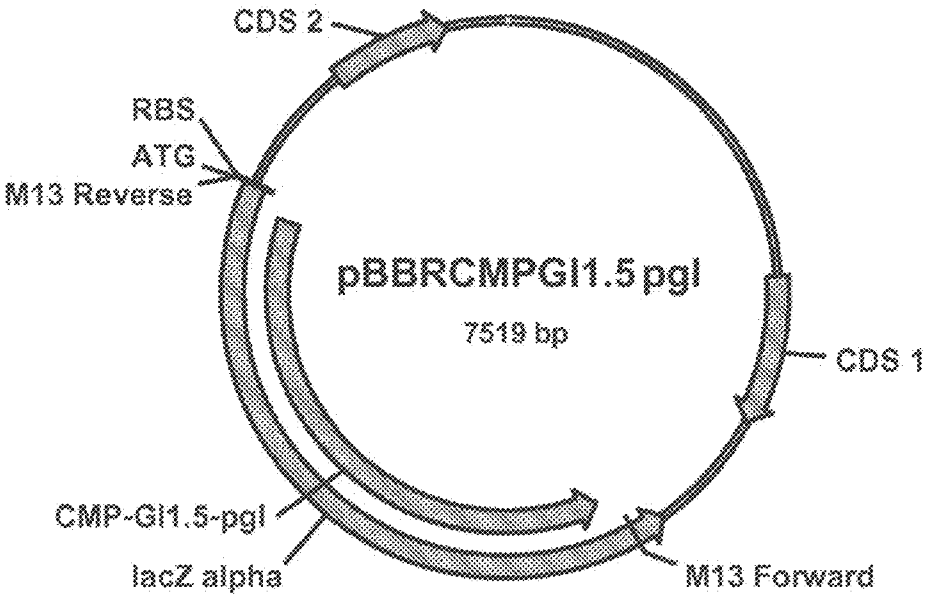
FIG. 12 is a map of plasmid pBBRCMPGI1.5-pgl.

The chromosomal DNA of MG1655 GI1.5-pgl::CMP was used as template to generate a PCR fragment containing the FRT-CMP-FRT-GI1.5-ybhE construct. This construct was cloned into pBBR1MCS5(Gentamycin) as follows. The fragment, here on referred to as CMP-GI1.5-pgl, was amplified using the 5' primer Pglconfirm-F (SEQ ID NO:31) and 3' primer 3' EcoRV-pglstop (SEQ ID NO:32). The resulting fragment was cloned using the Invitrogen TOPO-Blunt cloning kit into the plasmid vector pCR-Blunt II-TOPO as suggested from the manufacturer. The NsiI fragment harboring the CMP-GI1.5-pgl fragment was cloned into the PstI site of pBBR1MCS5 (Gentamycin). A 20 μl ligation reaction was prepared containing 5 μl CMP-GI1.5-pgl insert, 2 μl pBBR1MCS5 (Gentamycin) vector, 1 μl T4 DNA ligase (New England Biolabs), 2 μl 10× ligase buffer, and 10 μl $ddH_2O$. The ligation mixture was incubated at room temperature for 40 minutes then 2-4 μL were electroporated into electrocompetent Top 10 cells (Invitrogen) using the parameters disclosed above. Transformants were selected on L agar containing 10 μg/ml chloramphenicol and 5 μg/ml Gentamycin. The sequence of the selected clone was determined using a number of the primers described above as well as with the in-house T3 and Reverse primers provided by Sequetech, Calif. This plasmid was designated pBBRCMPGI1.5-pgl (FIGS. 12, 13A-B and SEQ ID NO:6).

Plasmid pBBRCMPGI1.5-pgl was electroporated into EWL256, as described herein and transformants were plated on L agar containing Chloramphenicol (10 μg/mL), Gentamycin (5 μg/mL), spectinomycin (50 μg/mL), and carbenicillin (50 μg/mL). One transformant was selected and designated strain RM111608-2.

Primers:

```
Pgl-F
                                    (SEQ ID NO: 29)
5'-
ACCGCCAAAAGCGACTAATTTTAGCTGTTACAGTCAGTTGAATTAACCCT
CACTAAAGGGCGGCCGC-3'
```

-continued

```
PglGI1.5-R
                                    (SEQ ID NO: 30)
5'-
GCTGGCGATATAAACTGTTTGCTTCATGAATGCTCCTTTGGGTTACCTCC
GGGAAACGCGGTTGATTTGTTTAGTGGTTGAATTATTTGCTCAGGATGTG
GCATAGTCAAGGGCGTGACGGCTCGCTAATACGACTCACTATAGGGCTCG
AG-3'

3' EcoRV-pglstop:
                                    (SEQ ID NO: 31)
5'-CTT GAT ATC TTA GTG TGC GTT AAC CAC CAC

pgl +49 rev:
                                    (SEQ ID NO: 32)
CGTGAATTTGCTGGCTCTCAG

Bottom Pgb2:
                                    (SEQ ID NO: 33)
GGTTTAGTTCCTCACCTTGTC

Top GB's CMP (946):
                                     (SEQ ID NO:34)
ACTGAAACGTTTTCATCGCTC

Pglconfirm-F
                                    (SEQ ID NO: 35)
5'-ACCGCCAAAAGCGACTAATTTTAGCT-3'
```

Example 2

Improvement of Isoprene Production by Constitutive Expression of vbhE (Pgl) from a Plasmid in *E. coli*

This example shows production of isoprene in a strain constitutively expressing *E. coli* ybhE (pgl) compared to a control strain expressing ybhE at wild-type levels (i.e., EWL256). The gene ybhE (pgl) encodes *E. coli* 6-phosphogluconolactonase that suppresses posttranslational gluconylation of heterologously expressed proteins and improves product solubility and yield while also improving biomass yield and flux through the pentose phosphate pathway (Aon et al., *Applied and Environmental Microbiology* 74(4): 950-958, 2008).

i) Small Scale Analysis

Media Recipe (per liter fermentation media): $K_2HPO_4$ 13.6 g, $KH_2PO_4$ 13.6 g, $MgSO_4$*$7H_2O$ 2 g, citric acid monohydrate 2 g, ferric ammonium citrate 0.3 g, $(NH_4)_2SO_4$ 3.2 g, yeast extract 1 g, 1000× Trace Metals Solution 1 ml. All of the components were added together and dissolved in $diH_2O$. The pH was adjusted to 6.8 with ammonium hydroxide (30%) and brought to volume. Media was filter-sterilized with a 0.22 micron filter. Glucose 5.0 g and antibiotics were added after sterilization and pH adjustment.

1000× Trace Metal Solution (per liter fermentation media): Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in $diH_2O$. The pH was adjusted to 3.0 with HCl/NaOH, and then the solution was brought to volume and filter-sterilized with a 0.22 micron filter.

(a) Experimental Procedure

Isoprene production was analyzed by growing the strains in a Cellerator™ from MicroReactor Technologies, Inc. The working volume in each of the 24 wells was 4.5 mL. The temperature was maintained at 30° C., the pH setpoint was 7.0, the oxygen flow setpoint was 20 sccm and the agitation rate was 800 rpm. An inoculum of *E. coli* strain taken from a frozen vial was streaked onto an LB broth agar plate (with antibiotics) and incubated at 30° C. A single colony was inoculated into media with antibiotics and grown overnight. The bacteria were diluted into 4.5 mL of media with antibiotics to reach an optical density of 0.05 measured at 550 nm.

Off-gas analysis of isoprene was performed using a gas chromatograph-mass spectrometer (GC-MS) (Agilent) headspace assay. Sample preparation was as follows: 100 μL of whole broth was placed in a sealed GC vial and incubated at 30° C. for a fixed time of 30 minutes. Following a heat kill step, consisting of incubation at 70° C. for 5 minutes, the sample was loaded on the GC.

Optical density (OD) at a wavelength of 550 nm was obtained using a microplate reader (Spectramax) during the course of the run. Specific productivity was obtained by dividing the isoprene concentration (μg/L) by the OD reading and the time (hour).

The two strains EWL256 and RM11608-2 were assessed at 200 and 400 μM IPTG induction levels. Samples were analyzed for isoprene production and cell growth (OD550) at 1, 2.5, 4.75, and 8 hours post-induction. Samples were done in duplicate.

(b) Results

The experiment demonstrated that at 2 different concentrations of IPTG the strain expressing the ybhE (pgl) had a dramatic 2-3 fold increase in specific productivity of isoprene compared to the control strain.

ii) Isoprene Fermentation from *E. coli* Expressing Cm-GI1.2-KKDyI, *M. mazei* Mevalonate Kinase, *P. alba* Isoprene Synthase, and ybhE (Pgl) (RM111608-2) and Grown in Fed-Batch Culture at the 15-L Scale Medium Recipe (per liter fermentation medium): $K_2HPO_4$ 7.5 g, $MgSO_4*7H_2O$ 2 g, citric acid monohydrate 2 g, ferric ammonium citrate 0.3 g, yeast extract 0.5 g, 1000× Modified Trace Metal Solution 1 ml. All of the components were added together and dissolved in $diH_2O$. This solution was autoclaved. The pH was adjusted to 7.0 with ammonium hydroxide (30%) and q.s. to volume. Glucose 10 g, thiamine*HCl 0.1 g, and antibiotics were added after sterilization and pH adjustment.

1000× Modified trace Metal Solution: Citric Acids*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component was dissolved one at a time in Di $H_2O$, pH to 3.0 with HCl/NaOH, then q.s. to volume and filter sterilized with a 0.22 micron filter Fermentation was performed in a 15-L bioreactor with BL21 (DE3) *E. coli* cells containing the upper mevalonic acid (MVA) pathway (pCL Upper), the integrated lower MVA pathway (gi1.2KKDyI), high expression of mevalonate kinase from *M. mazei* and isoprene synthase from *P. alba* (pTrcAlba-mMVK), and high expression of *E. coli* pgl (pBBR-pgl). This experiment was carried out to monitor isoprene formation from glucose at the desired fermentation pH 7.0 and temperature 34° C. A frozen vial of the *E. coli* strain was thawed and inoculated into tryptone-yeast extract medium. After the inoculum grew to OD 1.0, measured at 550 nm, 500 mL was used to inoculate a 15-L bioreactor bringing the initial volume to 5-L.

Figure 14A:
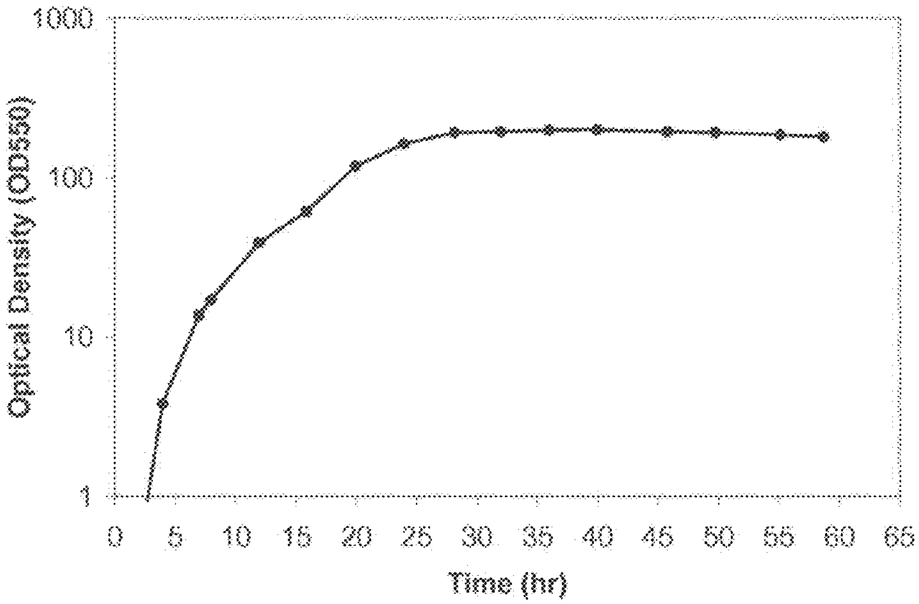
FIGS. 14A-F are graphs of isoprene production by *E. coli* strain expressing *M. mazei* mevalonate kinase, *P. alba* isoprene synthase, and pgl (RHM111608-2), and grown in fed-batch culture at the 15-L scale.
Figure 14B:
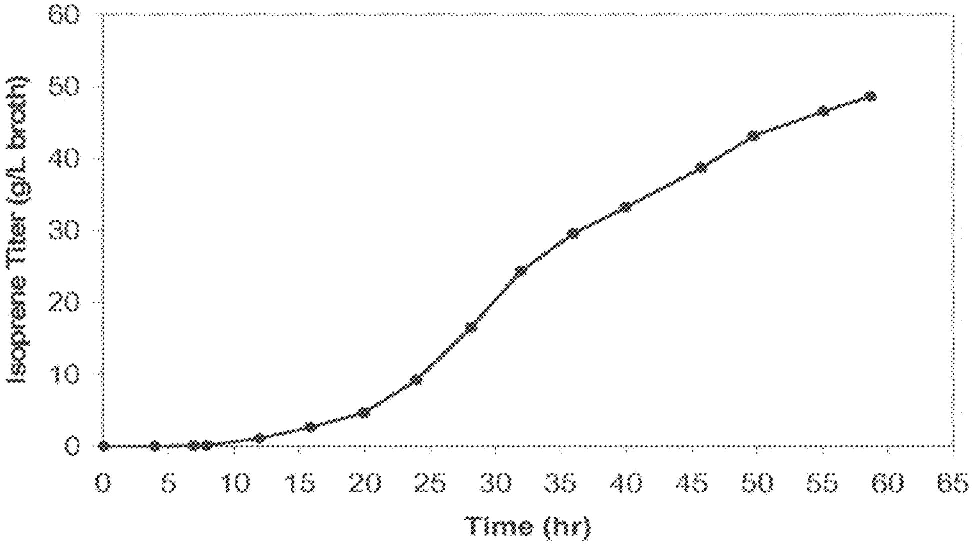
Figure 14C:
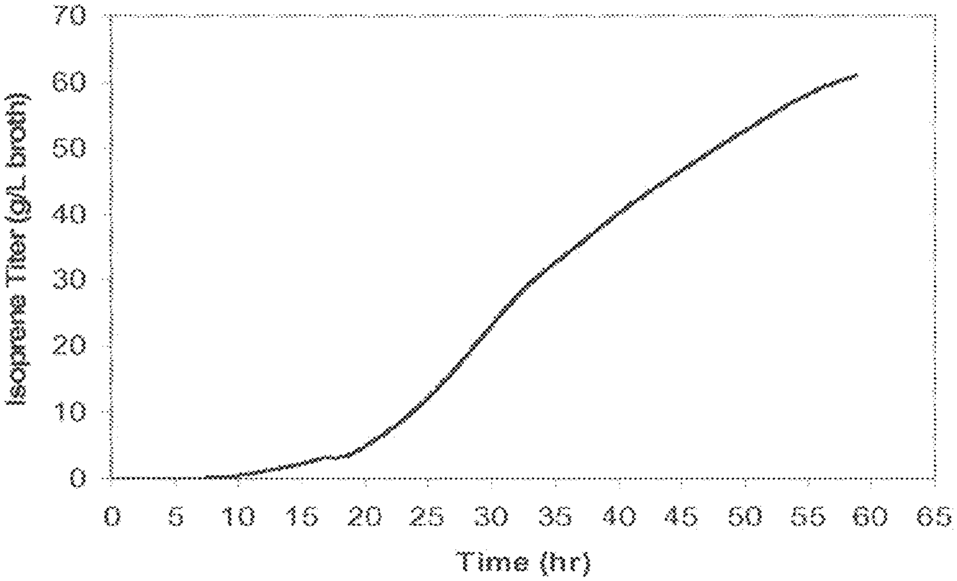
Figure 14D:
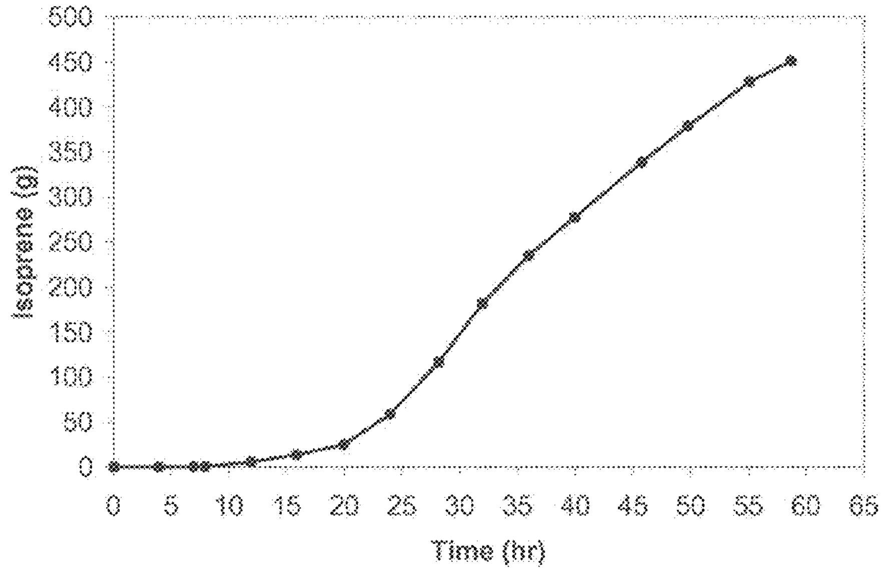
Figure 14E:
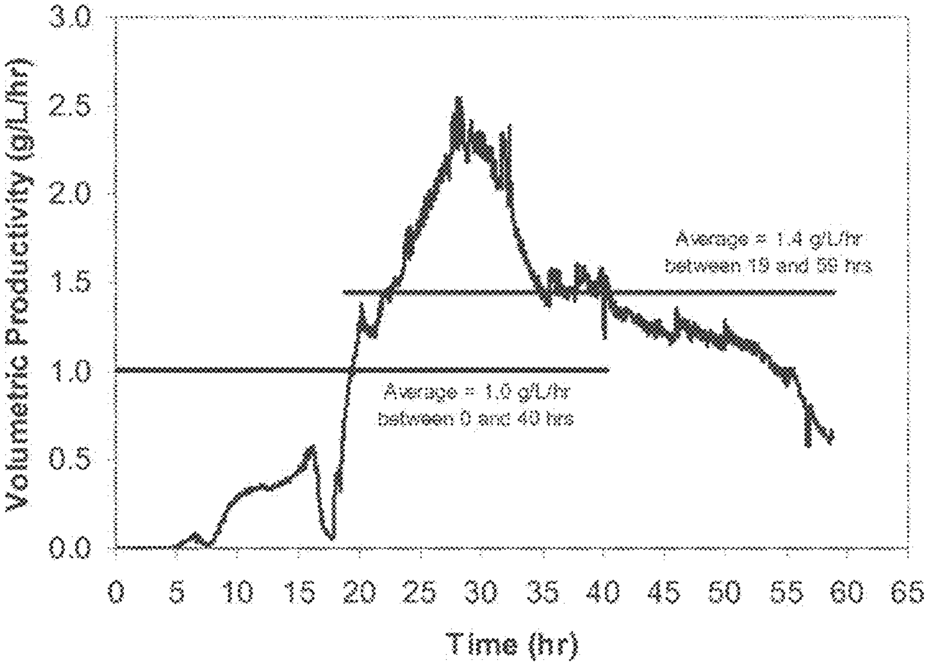
Figure 14F:
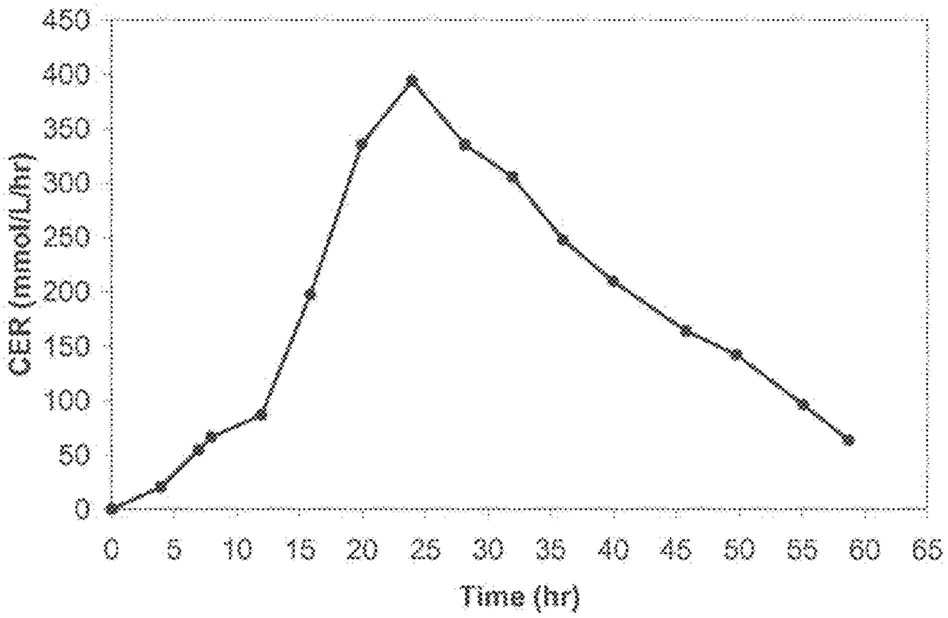
Figure 15:
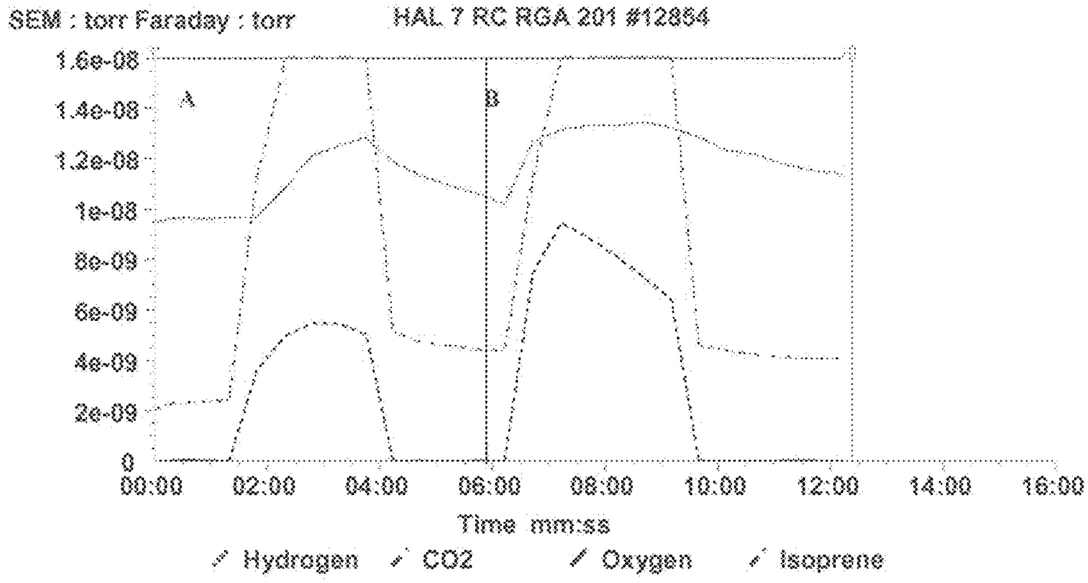
FIGS. 15A-B are graphs showing analysis of off-gas from fermentation in 15 L bioreactors. Sample A is strain RM111608-2 sampled at 64.8 hours. Sample B is strain EWL256 was *E. coli* BL21 (DE3), pCL upper, cmR-gi1.2-yKKDyI, pTrcAlba-mMVK sampled at 34.5 hours. Hydrogen is detected above the baseline ($0.95\times10^{-8}$ torr) for both samples.

Glucose was fed at an exponential rate until cells reached the stationary phase. After this time the glucose feed was decreased to meet metabolic demands. The total amount of glucose delivered to the bioreactor during the 40 hour (59 hour) fermentation was 3.1 kg (4.2 kg at 59 hour). Induction was achieved by adding IPTG. The IPTG concentration was brought to 110 kM when the optical density at 550 nm ($OD_{550}$) reached a value of 4. The IPTG concentration was raised to 192 kM when $OD_{550}$ reached 150. The $OD_{550}$ profile within the bioreactor over time is shown in FIG. 14A. The isoprene level in the off gas from the bioreactor was determined using a Hiden mass spectrometer. The isoprene titer increased over the course of the fermentation to a maximum value of 33.2 g/L at 40 hours (48.6 g/L at 59 hours) (FIG. 14B). The isoprene titer increased over the course of the fermentation to a maximum value of 40.0 g/L at 40 hours (60.5 g/L at 59 hours) (FIG. 14C). The total amount of isoprene produced during the 40-hour (59-hour) fermentation was 281.3 g (451.0 g at 59 hours) and the time course of production is shown in FIG. 14D. The time course of volumetric productivity is shown in FIG. 14E and shows that an average rate of 1.0 g/L/hr was maintained between 0 and 40 hours (1.4 g/L/hour between 19 and 59 hour). The metabolic activity profile, as measured by CER, is shown in FIG. 14F. The molar yield of utilized carbon that went into producing isoprene during fermentation was 19.6% at 40 hours (23.6% at 59 hours). The weight percent yield of isoprene from glucose was 8.9% at 40 hours (10.7% at 59 hours).

Example 3

Recovery of Isoprene Produced from Renewable Resources

Figure 16A:
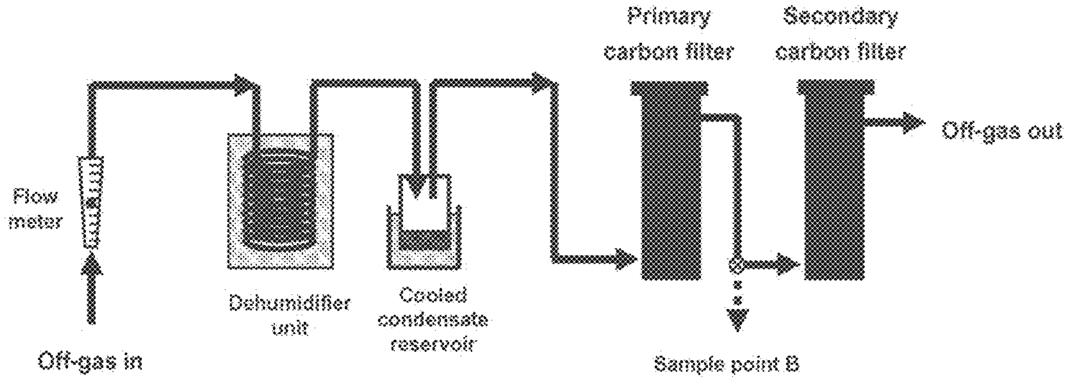
FIG. 16A shows an exemplary isoprene recovery unit.
Figure 16B:
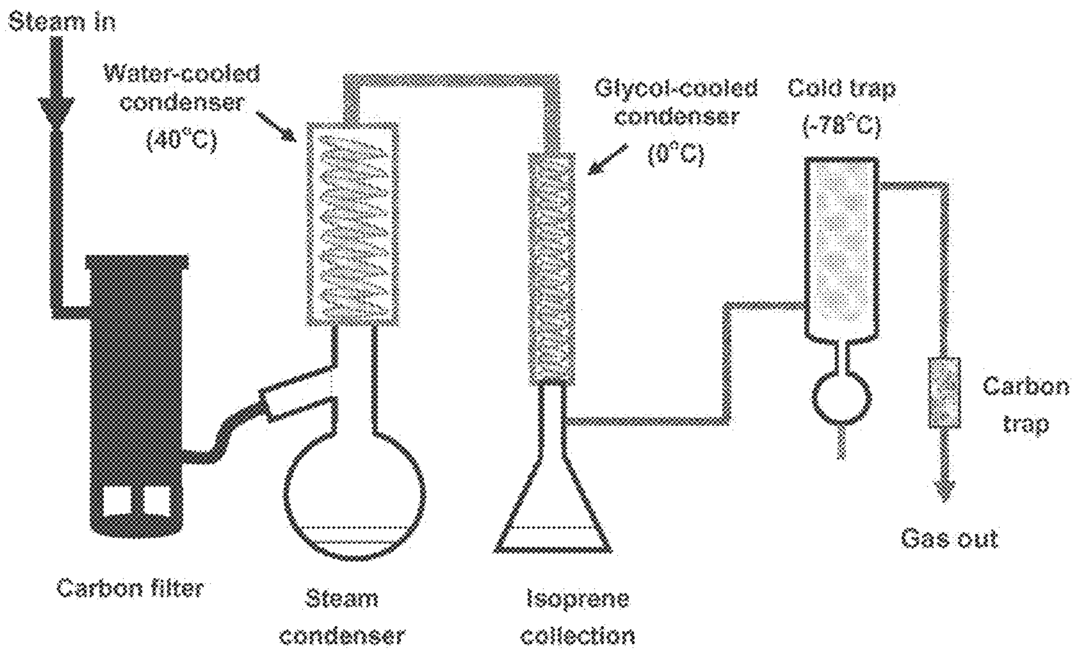
FIG. 16B shows an exemplary isoprene desorption/condensation setup.

Isoprene was recovered from a set of four 14-L scale fermentations in a two-step operation involving stripping of isoprene from the fermentation off-gas stream by adsorption to activated carbon, followed by off-line steam desorption and condensation to give liquid isoprene (FIGS. 16A and 16B). The total amount of isoprene produced by the four fermentors was 1150 g (16.9 mol), of which 953 g (14 mol, 83%) was adsorbed by the carbon filters. Following the steam desorption/condensation step, the amount of liquid isoprene recovered was 810 g, corresponding to an overall recovery yield of 70%. The recovered isoprene was analyzed for the presence of impurities.

Analysis and Impurity Profile of Isoprene Liquid

Figure 17:
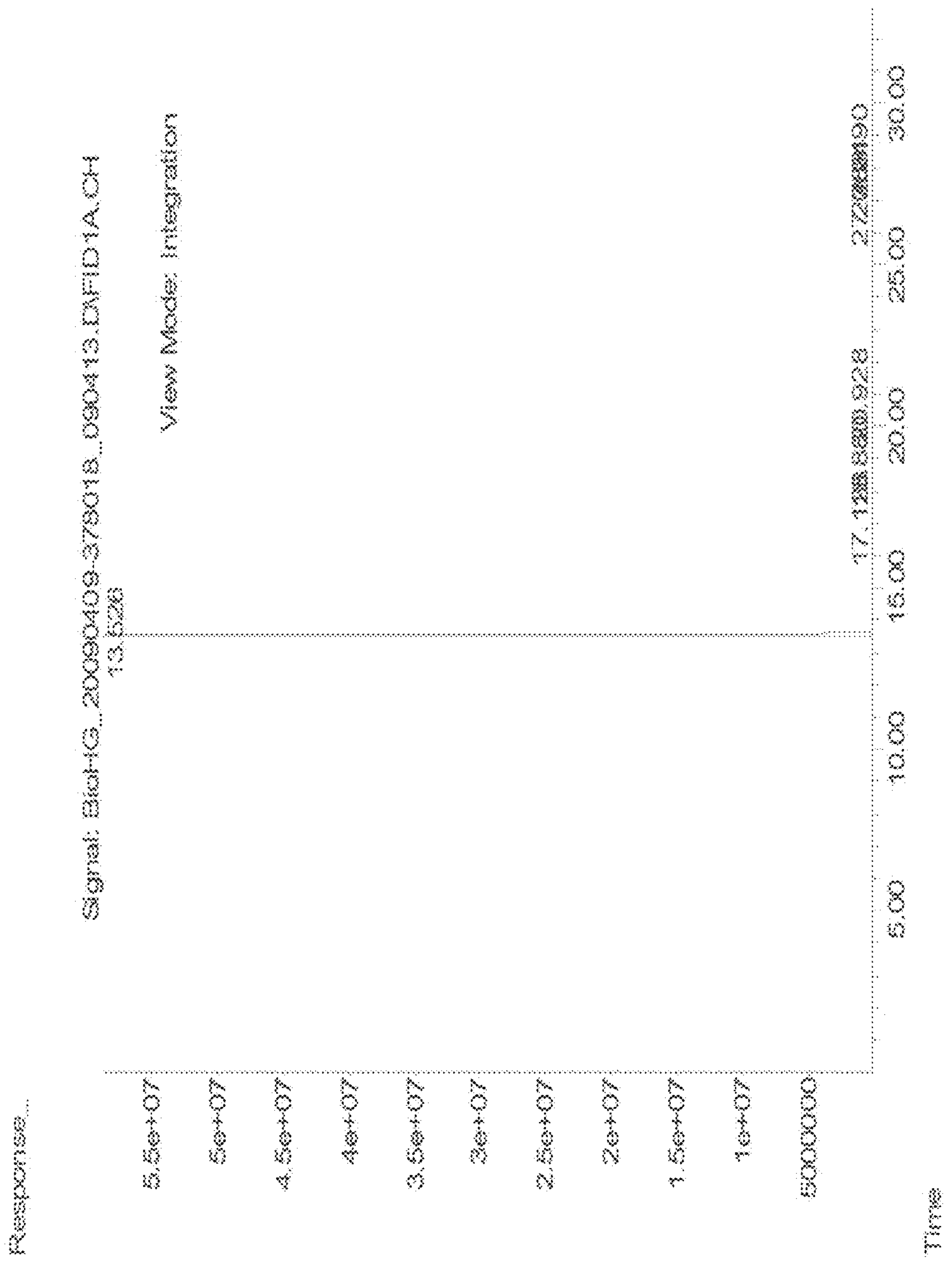
FIG. 17 shows a GC/FID chromatogram of an isoprene product. The material was determined to be 99.7% pure.

Recovered isoprene liquid was analyzed by GC/MS and gas chromatography/flame ionization detection (GC/FID) to determine the nature and levels of impurities. The product was determined to be >99.5% pure and contained several dominant impurities in addition to many minor components. The GC/FID chromatogram is depicted in FIG. 17, and the typical levels of impurities are shown in Table 19. The impurity profile was similar to other isoprene batches produced on this scale.

TABLE 2

Summary of the nature and levels of impurities seen in several batches of isoprene produced from renewable resources

| Compound | Retention Time (min) GC/MS | GC/FID | Conc. Range |
|---|---|---|---|
| Ethanol | 1.59 | 11.89 | <50 ppm |
| Acetone | 1.624 | 12.673 | <100 ppm |
| Methacrolein | 1.851 | 15.369 | <200 ppm |
| Methyl vinyl ketone | 1.923 | 16.333 | <20 ppm |
| Ethyl acetate | 2.037 | 17.145 | 100 to 800 ppm |
| 3-Methyl-1,3-pentadiene | 2.27 | 18.875 | 50 to 530 ppm |

TABLE 2-continued

Summary of the nature and levels of impurities seen in several batches of isoprene produced from renewable resources

| Compound | Retention Time (min) GC/MS | GC/FID | Conc. Range |
|---|---|---|---|
| Methyl vinyl oxirane | 2.548 | 19.931 | <100 ppm |
| Isoprenol | 2.962 | 21.583 | <500 ppm |
| 3-methyl-1-butanol | 2.99 | 21.783 | <50 ppm |
| 3-hexen-1-ol | 4.019 | 24.819 | <100 ppm |
| Isopentenyl acetate | 4.466 | 25.733 | 200 to 1000 ppm |
| 3-hexen-1-yl acetate | 5.339 | 27.223 | <400 ppm |
| limonene | 5.715 | 27.971 | <500 ppm |
| Other cyclics | 5.50-6.50 | 27.5-28.0 | <200 ppm |

Figures 18A, 18B, 18C:
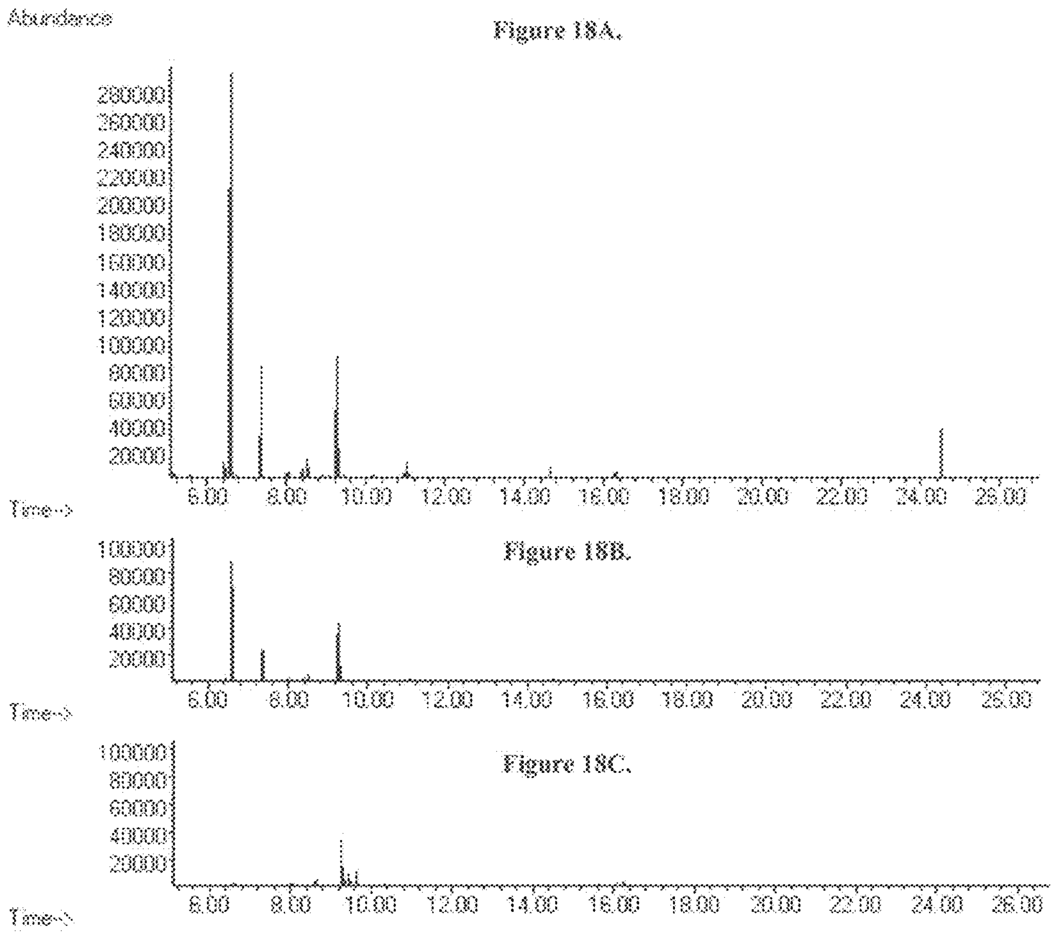
FIGS. 18A-C show the GC/FID chromatograms of an isoprene sample before (A) and after treatment with alumina (B) or silica (C). The isoprene peak is not shown in these chromatograms.

Purification of Isoprene Produced from Renewable Resources by Treatment with Adsorbents Adsorbents are widely used by industry for the removal of trace impurities from hydrocarbon feedstocks. Suitable adsorbents include zeolite, alumina and silica-based materials. Isoprene produced from renewable resources can be substantially purified by passage over silica gel, and to a lesser extent with alumina. FIG. 18 shows the GC/FID chromatograms of an isoprene sample before (A) and after treatment with alumina (B) or silica (C). The Selexsorb™ adsorbent products from BASF is one of the adsorbents of choice for the removal of polar impurities from isoprene produced from renewable resources. Specifically, the Selexsorb™ CD and CDX products are preferred given their proven utility for removal of polar impurities from isoprene and butadiene feedstocks.

Example 4

Construction of Strains MCM518-521 and 528-531: Lambda Promoters Driving Integrated mKKDyI P1 transduction enables movement of up to 100 kb of DNA between bacterial strains (Thomason et al. 2007). A 17,257 bp deletion in *E. coli* BL21(DE3) (see FIG. 20) was replaced by moving a piece of the bacterial chromosome from *E. coli* K12 MG1655 to *E. coli* BL21(DE3) using P1 transduction.

Two strategies were used employing different selectable markers to identify colonies containing the recombined bacterial chromosome. First, an antibiotic marker in a gene close to the 17,257 bp sequence to be transferred, whose deletion was not likely to be detrimental to the strain, was inserted. A strain containing that antibiotic marker would likely have the 17,257 bp piece of bacterial chromosome transduced at the same time as the marker. In this case, a gene encoding kanamycin resistance ("kan$^R$") was inserted into the ybgS gene, encoding a 126 amino acid protein of unknown function. Second, since it is known that a number of genes involved in utilization of galactose are close to pgl in the 17,257 bp piece to be transduced into *E. coli* BL21(DE3), colonies transduced with a P1 lysate obtained from *E. coli* K12 MG1655 (which contains the 17,257 bp sequence deleted in *E. coli* BL21 (DE3)) and isolated in M9 medium (6 g/L $Na_2HPO_4$, 3 g/L $KH_2PO_4$, 0.5 g/L NaCl, 0.5 g/L $NH_4Cl$, 0.1 mM $CaCl_2$, 2 mM $MgSO_4$) containing 0.4% (w/v) galactose would likely contain the 17,257 bp piece of bacterial chromosome.

Primers MCM120 (SEQ ID NO:36) and MCM224 (SEQ ID NO:37) were used to amplify the chloramphenicol resistance ("Cm$^R$") cassette from the GeneBridges FRT-gb2-Cm-FRT template using the Stratagene Herculase™ II Fusion kit (Agilent Technologies, Stratagene Products Division, La Jolla, Calif.) according to the manufacturer's protocol. Four 50 μL PCR reactions were cycled as follows: 95° C./2 minutes; 30 cycles of 95° C./20 seconds, 55° C./20 seconds, 72° C./1 minute; and 72° C./3 minutes. Reactions were then cooled to 4° C. The four reactions were pooled, loaded onto a Qiagen PCR column according to the manufacturer's protocol and eluted with 60 μL elution buffer ("EB") at 55° C.

Plasmid pRedET-carbenicillin$^R$ (GeneBridges, Heidelberg, Germany) was electroporated into *E. coli* BL21(DE3) strain MCM446 (Cm$^R$, gi1.6mKKDyI A1-3) using standard procedures. Transformants were recovered by shaking for one hour in SOC medium at 30° C. and then selected on LB+50 μg/mL carbenicillin ("LB/carb50") plates at 30° C. overnight. A carbenicillin-resistant colony was frozen as strain MCM508.

Strain MCM508 was grown from a fresh streak in 5 mL LB/carb50 at 30° C. to an $OD_{600}$ of ~0.5. At that point, 40 mM L-arabinose was added, and the culture was incubated at 37° C. for 1.5 hours. Cells were then harvested by centrifugation, electroporated with 3 μL of purified amplicons as described above, and then recovered in 500 μL SOC medium at 37° C. for 1.5-3 hours. Transformants were selected on LB+ 10 μg/mL kanamycin (LB/kan10) plates at 37° C.

Recombination of the amplicon at the target locus was confirmed by PCR with primers GB-DW (SEQ ID NO:38) and MCM208 (SEQ ID NO:39). The resulting amplicons were sequenced to identify four clones having the sequences listed below. Four carbenicillin-sensitive clones were frozen as strains MCM518-MCM521.

Strains MCM518-MCM521 were re-streaked onto LB/kan10 and grown overnight at 37° C. Colonies of strains MCM518-MCM521 were picked, cultured in LB/kan10 at 37° C. and electrotransformed with plasmid pCP20, which encodes the yeast Flp recombinase, chloramphenicol and ampicillin resistance genes and confers temperature sensitive replication on host cells (Cherepanov, P. P. et al., *Gene* 158 (1):9-14 (1995)). Cells were recovered in 500 μL SOC medium by shaking at 30° C. for 1 hour. Transformants were selected on LB/carb50 plates at 30° C. overnight. The following morning a colony from each plate was grown at 30° C. in LB/carb50 medium until visibly turbid. The culture was then shifted to 37° C. for at least 3 hours. Cells were streaked from that culture onto LB plates and grown overnight at 37° C.

The following day colonies were patched to LB, LB/carb50 and LB/kan10. Clones that were sensitive to both carbenicillin and kanamycin (i.e., which could not grow on carb50 and kan10) were cultured in liquid LB and frozen as strains MCM528-MCM531.

TABLE 3

*E. coli* strains

| Strain | Description | Parent |
|---|---|---|
| MCM508 | BL21 gi1.6-mKKDyI + predet.-carb | MCM446 |
| MCM518 | BL21 neo-PL.6-mKKDyI, clone 10 | MCM508 |
| MCM519 | BL21 neo-PL.0-mKKDyI, clone 11 | MCM508 |
| MCM520 | BL21 neo-PL.0-mKKDyI (bad RBS in front of mMVK), clone 13 | MCM508 |
| MCM521 | BL21 neo-PL.2-mKKDyI, clone 15 | MCM508 |
| MCM528 | BL21 PL.6-mKKDyI, neo$^R$ looped out | MCM518 |
| MCM529 | BL21 PL.0-mKKDyI, neo$^R$ looped out | MCM519 |
| MCM530 | BL21 PL.0-mKKDyI (bad RBS in front of mMVK), neo$^R$ looped out | MCM520 |
| MCM531 | BL21 PL.2-mKKDyI, neo$^R$ looped out | MCM521 |

TABLE 4

| Primer sequences | |
|---|---|
| Primer name | Sequence (5' → 3') |
| MCM120 | aaagtagccgaagatgacggtttgtcacatggagttggcaggatgtttgattaaaagcaattaaccctcactaaagggcgg (SEQ ID NO: 36) |
| MCM224 | taaatcttacccggcgcagaacaggataccatgtttttttacctcctttgcaccttcatggtggtcagtgcgtcctgctgatgtgctcagtatcaccgccagtggtatttaNgtcaacaccgccagagataatttatcaccgcagatggttatctgtatgtttttatatgaatttaatacgactcactatagggctcg (SEQ ID NO: 37)(where N can be a, t, c, or g) |
| GB-DW | aaagaccgaccaagcgacgtctga (SEQ ID NO: 38) |
| MCM208 | gctctgaatagtgatagagtca (SEQ ID NO: 39) |

The assemblies integrated into the chromosomes of strains MCM518-MCM521 include new $P_L$ promoters derived from bacteriophage lambda (λ) and the very beginning of the mMVK ORF, with sequences from the Gene Bridges FRT-gb2-Cm-FRT cassette integrated upstream of the promoter/mMVK assembly, as well as the remainder of the mMVK ORF followed by the rest of the lower MVA pathway integron from strain MCM508.

Example 5

Construction of Strains DW199 and DW202

This example describes the construction of an isoprene-producing *E. coli* strain harboring the truncated version of *P. alba* isoprene synthase (the MEA variant) under control of the PTrc promoter.

Promoter/mMVK sequence integrated into MCM518 (SEQ ID NO: 40):
aaagaccgaccaagcgacgtctgagagctccctggcgaattcggtaccaataaaagagctttattttcatgatctgtgtgttggtttttgtgtgc ggcgcggaagttcctattctctagaaagtataggaacttcctcgagccctatagtgagtcgtattaaattcatataaaaaacatacagataacca tctgcggtgataaattatctctggcggtgttgacataaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc Promoter/mMVK sequence integrated into MCM519 (SEQ ID NO: 41):
aaagaccgaccaagcgacgtctgagagctccctggcgaattcggtaccaataaaagagctttattttcatgatctgtgtgttggtttttgtgtgc ggcgcggaagttcctattctctagaaagtataggaacttcctcgagccctatagtgagtcgtattaaattcatataaaaaacatacagataacca tctgcggtgataaattatctctggcggtgttgacctaaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc Promoter/mMVK sequence integrated into MCM520 (SEQ ID NO: 42):
aaagaccgaccaagcgacgtctgagagctccctggcgaattcggtaccaataaaagagctttattttcatgatctgtgtgttggtttttgtgtgc ggcgcggaagttcctattctctagaaagtataggaacttcctcgagccctatagtgagtcgtattaaattcatataaaaaacatacagataacca tctgcggtgataaattatctctggcggtgttgacctaaataccactggcggtgatactgagcacatcagcaggacgcactgaccaccatgaa ggtgcaaaggtaaaaaaacatggtatcctgttctgcgccgggtaagatttacctgttcggtgaacacgccgtagtttatggcgaaactgcaatt gcgtgtgcggtggaactgcgtacccgtgttcgcgcggaactcaatgactctatcactattcagagc Promoter/mMVK sequence integrated into MCM521 (SEQ ID NO: 43):
aaagaccgaccaagcgacgtctgagagctccctggcgaattcggtaccaataaaagagctttattttcatgatctgtgtgttggtttttgtgtgc ggcgcggaagttcctattctctagaaagtataggaacttcctcgagccctatagtgagtcgtattaaattcatataaaaaacatacagataacca tctgcggtgataaattatctctggcggtgttgacgtaaataccactggcggtgatactgagcacatcagcaggacgcactgaccaccatgaa ggtgcaaaggaggtaaaaaaacatggtatcctgttctgcgccgggtaagatttacctgttcggtgaacacgccgtagtttatggcgaaactgc aattgcgtgtgcggtggaactgcgtacccgtgttcgcgcggaactcaatgactctatcactattcagagc The plasmid harboring truncated *P. alba* isoprene synthase (IspS) was constructed by Quikchange™ (Agilent Technologies, Stratagene Products Division, La Jolla, Calif.) PCR mutagenesis from the template pEWL244 (also referred to as pTrc-*P.alba*(MEA)-mMVK (described in Example 10 of U.S. patent application Ser. No. 12/335,071). The PCR reaction contained the following components: 1 μl pEWL244 (encoding pTrc *P.alba*-mMVK), 5 μl 10× PfuUltra High Fidelity buffer, 1 μl 100 mM dNTPs, 1 μl 50 μM QC EWL244 MEA F primer (SEQ ID NO:44), 1 μl 150 μM QC EWL244 MEA R primer (SEQ ID NO:45), 2 μl DMSO, 1 μl PfuUltra High Fidelity polymerase (Agilent Technologies, Stratagene Products Division, La Jolla, Calif.), and 39 μl di$H_2O$. The PCR reaction was cycled as follows: 95° C./1 minute; and 18 cycles of 95° C./30 seconds, 55° C./1 minute, 68° C./7.3 minutes. The reaction was then cooled to 4° C.

The PCR product was visualized by gel electrophoresis using an E-gel (Invitrogen, Carlsbad, Calif.), and then treated with 1 μl DpnI restriction endonuclease (Roche, South San Francisco, Calif.) for three hours at 37° C. Ten μl of the PCR product were then de-salted using a microdialysis membrane (MilliPore, Billerica, Mass.) and transformed into electrocompetent *E. coli* strain MCM531 (prepared as described above) using standard molecular biology techniques. Cells were recovered in one ml of LB medium for 1.5 hours at 30° C., plated onto LB-agar plates containing 50 μg/ml carbenicillin and 5 mM mevalonic acid, and then incubated overnight at 37° C. The next day, positive colonies (of strain DW195, see below) were selected for growth, plasmid purification (Qiagen, Valencia, Calif.), confirmed by DNA sequencing (Quintara Biosciences, Berkeley, Calif.) with the primers listed below. The final plasmid, pDW34 (FIG. 19A; SEQ ID NO:7), was confirmed to carry the open reading frame that encodes the truncated version of *P. alba* IspS.

Strain DW199 was generated by transformation of pDW34 and pMCM82 (described in Example 10 of U.S. patent application Ser. No. 12/335,071) into electrocompetent MCM531 (prepared as described above). Cells were recovered in 1 ml of LB medium for 1 hour at 37° C., plated on LB agar plates containing 50 μg/ml spectinomycin and 50 μg/ml carbenicillin, and then incubated overnight at 37° C. The next day, antibiotic resistant colonies of strain DW199 were chosen for further study.

Strain DW202 was generated by transformation of pBBRCMPGI1.5-pgl (described in example 1) into electrocompetent DW199 (prepared as described above). Cells were recovered in 1 ml of LB medium for 1 hour at 37° C., plated on LB agar plates containing 50 μg/ml spectinomycin, 50 μg/ml carbenicillin and 5 μg/ml gentamycin, and then incubated overnight at 37° C. The next day, antibiotic resistant colonies of strain DW202 were chosen for further study.

TABLE 5

| Primers | |
|---|---|
| Primer Name | Sequence (5' → 3') |
| QC EWL244 MEA F | gaggaataaaccatggaagctcgtcgttct (SEQ ID NO: 44) |
| QC EWL244 MEA R | agaacgacgagcttccatggtttattcctc (SEQ ID NO: 45) |
| EL-1006 | gacagcttatcatcgactgcacg (SEQ ID NO: 26) |
| EL-1000 | gcactgtctttccgtctgctgc (SEQ ID NO: 22) |
| A-rev | ctcgtacaggctcaggatag (SEQ ID NO: 48) |
| A-rev-2 | ttacgtcccaacgctcaact (SEQ ID NO: 49) |
| QB1493 | cttcggcaacgcatggaaat (SEQ ID NO: 50) |
| MCM208 | gctctgaatagtgatagagtca (SEQ ID NO: 39) |
| MCM66 (aka pTrc Reverse) | ccaggcaaattctgttttatcag (SEQ ID NO: 21) |

TABLE 6

| Strains | | | | |
|---|---|---|---|---|
| Strain | Background | Plasmid | Resistance | Genotype |
| DW195 | MCM531 | pDW34 | Carb | BL21 (Novagen) PL.2mKKDyI, pTrc-P. alba(MEA)-mMVK |
| DW199 | MCM531 | pDW34 MCM82 | Carb/Spec | BL21 (Novagen) PL.2mKKDyI, pTrc-P. alba(MEA)-mMVK, pCL pTrc-Upper |
| DW02 | MCM531 | pDW34 MCM82 pBBRCM PGI1.5-pgl | Carb/Spec/Gm | BL21 (Novagen) PL.2mKKDyI, pTrc-P. alba(MEA)-mMVK, pCL pTrc-Upper, pBBRCMPGI1.5-pgl |

Example 6

Construction of *E. coli* BL21 strains CMP215, CMP258 and CMP234

This example describes the construction of *E. coli* strains derived from BL21 transduced with P1 phage containing *E. coli* MG1655 genomic DNA and selected for recombination of a 17,257 bp piece present in MG1655 but absent in BL21 and BL21(DE3).

A P1 lysate was made of strain JW0736, in which the ybgS gene was replaced with a kanamycin resistance gene ("Kan$^R$") (i.e., ybgS::Kan$^R$ mutation) from the Keio collection (Baba et al. 2006). That lysate was used to infect strain MCM531 (described above), producing strain CMP215. The genotype of CMP215 was confirmed by PCR using primers galM R (5'-GTC AGG CTG GAA TAC TCT TCG-3'; SEQ ID NO:8) and galM F (5'-GAC GCT TTC GCC AAG TCA GG-3'; SEQ ID NO:9). Those primers anneal to the galM gene, as shown on FIG. 20, but only produce a PCR product from *E. coli* BL21(DE3) chromosomal DNA having the 17,257 bp deletion.

Integration of the 17,257 bp fragment following P1 transduction was verified by PCR with the following protocol. One bacterial colony was stirred in 30 μl $H_2O$ and heated to 95° C. for 5 minutes. The resulting solution was spun down and 2 μl of the supernatant used as template in the following PCR reaction: 2 μl colony in $H_2O$, 5 μl Herculase® Buffer, 1 μl 100 mM dNTPs, 1 μl 10 μM Forward primer, 1 μl 10 μM Reverse primer, 0.5 μl of Herculase® Enhanced DNA Polymerase (Agilent Technologies, Stratagene Products Division, La Jolla, Calif.), and 39.5 μl di$H_2O$. The PCR reaction was cycled in a PCR Express Thermal Cycler (Thermo Hybaid, Franklin, Mass.) as follows: 95° C./2 minutes; 30 cycles of 95° C./30 seconds, 52° C./30 seconds, 72° C./60 seconds; and 72° C./7 minutes. The reaction was then cooled to 4° C. The annealing temperature of 52° C. was 3° C. lower than the lower $T^m$ of the primer pair. The size of the resulting PCR fragment was determined on a pre-cast 0.8% E-Gel® (Invitrogen, Carlsbad, Calif.), using DNA Molecular Weight Marker X (75-12,216 bp) (Roche Diagnostics, Mannheim, Germany) as size marker. Successful transduction was also confirmed by the ability of strain CMP215 to grow on galactose.

Alternatively, a lysate of *E. coli* MG1655 was used to transduce strain BL21 (as described in Example 1 above). A colony selected on M9 medium supplemented with 0.4% (w/v) galactose was named CMP258. Presence of the 17,257 bp region containing pgl was confirmed by PCR using primers galM R (SEQ ID NO:9) and galM F (SEQ ID NO:8), essentially as described above.

Strain CMP215 was cotransformed by electroporation with plasmids pCLPtrcUpperPathway expressing mvaE and mvaS (described in Example 8 of U.S. patent application Ser. No. 12/335,071) and pDW34 (containing a truncated *P. alba* isoprene synthase and *M. mazei* mevalonate kinase, as described above). Transformants were selected on LB agar plates including 50 μg/ml carbenicillin+50 μg/ml spectinomycin. One colony was picked and named CMP234.

Example 7

Construction of *E. coli* BL21 strains CMP269 and CMP312

This example describes the construction of *E. coli* strains derived from BL21 transduced with P1 phage containing *E. coli* MG1655 genomic DNA and selected for recombination of a 17,257 bp piece present in MG1655 but absent in BL21 and BL21(DE3). The marker used for selection has been looped out.

Strain CMP215 (described above) was transformed with pCP20 (Cherepanov, P. P. et al., 1995, *Gene* 158(1):9-14; Datsenko and Wanner, 2000, *Proc. Nat'l Acad. Sci. USA,* 97(12):6645) and the $kan^R$ marker contained in the ybgS gene was looped out according to a previously described procedure (Datsenko and Wanner, *Proc. Nat'l Acad. Sci. USA,* 97(12): 6645 (2000)). Marker loopout was verified by PCR as described above, but using ybgSAmp F primer (5'-CCT GGA ATT AGC AAG AAA AAC GC-3'; SEQ ID NO:52) and ybgSAmp R primer (5'-GTG AAA ATT GCA CGG CGA GTA GG-3'; SEQ ID NO:53). That strain was designated CMP269. Strain CMP269 was cotransformed by electroporation with plasmids pCLPtrcUpperPathway (expressing mvaE and mvaS) and pDW34 (see FIG. 19A) containing a truncated *P. alba* IspS and *M. mazei* MVK to produce strain CMP312.

Example 8

Construction of *E. Coli* BL21 Strains CMP296, CMP315 and CMP323

This example describes the construction of strains derived from *E. coli* BL21 transduced with P1 phage containing *E. coli* MG1655 genomic DNA and selected for recombination of a 17,257 bp piece present in MG1655 but deleted in BL21 and BL21(DE3), thereby restoring a functional copy of pgl to the *E. coli* BL21 and BL21(DE3) derived strains. A strain in which the restored pgl gene has been precisely knocked out by inserting a kanamycin cassette which was subsequently looped out was also constructed.

A PCR product containing a copy of pgl/ybhE in which a $kan^R$ gene has been inserted (pgl/ybhE::$kan^R$) was amplified from *E. coli* strain JW0750 from the Keio collection using the primer pair pglAmpF (5'-Cagcaaatagcaggtgtatccagc-3'; SEQ ID NO:54) and pglAmpR (5'-GCA ACC GAC TGT TGA TAG AAC AAC-3'; SEQ ID NO:55). That primer pair produces a fragment containing pgl/ybhE::$kan^R$ plus ~350 bp of flanking sequence from each side of the mutation. PCR template was prepared as follows: one colony of *E. coli* JW0750 carrying pgl/ybhE::$kan^R$ was stirred in 30 μl $H_2O$ and heated to 95° C. for 5 minutes. The resulting solution was spun down and 2 μl of the supernatant was used as the template in a PCR reaction performed as follows: 2 μl colony in $H_2O$, 5 μl Pfu Ultra II Buffer, 1 μl 100 mM dNTPs, 1 μl 10 μM Forward primer, 1 μl 10 μM Reverse primer, 11 of Pfu Ultra II polymerase (Agilent Technologies, Stratagene Products Division, La Jolla, Calif.), and 39 μl $H_2O$. The PCR reaction was cycled in a PCR Express Thermal Cycler (Thermo Hybaid, Franklin, Mass.) as follows: 95° C./2 minutes; 30 cycles of 95° C./20 seconds, 53.4° C./20 seconds, 72° C./40 seconds; 72° C./3 minutes. The reactions were then cooled to 4° C.

The size of the resulting PCR fragments was determined on a pre-cast 0.8% E-Gel® (Invitrogen, Carlsbad, Calif.), using DNA Molecular Weight Marker X (75-12,216 bp)(Roche Diagnostics, Mannheim, Germany) as size marker. The PCR reaction was purified using the QIAquick® PCR Purification Kit (Qiagen, La Jolla, Calif.).

Plasmid pRedETAmp (GeneBridges Gmbh, Heidelberg, Germany) was electroporated into CMP269 to form CMP296. CMP296 was grown and induced with L-arabinose according to the manufacturer's instructions (GeneBridges) and transformed with the pgl/ybhE::$kan^R$ PCR product described in this example. Transformants were selected on LB agar including 20 ppm kanamycin. One colony was picked, its genotype checked by PCR with Herculase® polymerase using pglAmpF (5'-cagcaaatagcaggtgtatccagc-3'; SEQ ID NO:54) and pglRecCheck (5'-GGT TAC AAA ATG ATT GGC GTA CGC-3'; SEQ ID NO:56) and named CMP298. The marker was removed as described above in Example 2 to form strain CMP315. Plasmids pCLPtrcUpperPathway and pDW34 (see Example 1) were introduced in CMP315 as described above in Examples 4-5 to form strain CMP323.

TABLE 7

| Description of strains | | |
|---|---|---|
| Strain | Description | Parent |
| MCM531 | BL21 PL2-mKKDyI | |
| CMP215 | BL21 PL2-mKKDyI t ybgS::Kan | MCM531 |
| CMP258 | BL21 t pgl | BL21 (Novagen) |
| CMP234 | BL21 PL2-mKKDyI t ybgS::Kan, pCLPtrcUpperPathway, pDW34 | CMP215 |
| CMP269 | BL21 PL2-mKKDyI t ybgS ML | CMP215 |
| CMP296 | BL21 PL.2-mKKDyI t ybgS ML, pRedETAmp | CMP269 |
| CMP312 | BL21 PL2-mKKDyI t ybgS ML, pCLPtrcUpperPathway, pDW34 | CMP269 |
| CMP315 | BL21 PL2-mKKDyI t ybgS ML r pgl ML | CMP296 |
| CMP323 | BL21 PL2-mKKDyI t ybgS ML r pgl ML, pCLPtrcUpperPathway, pDW34 | CMP315 |

References cited: Aon et al., 2008, "Suppressing posttranslational gluconoylation of heterologous proteins by metabolic engineering of *Escherichia coli*," *Appl. Environ. Microbiol.* 74:950-958; Baba et al., 2006, "Construction of *Escherichia coli* K-12 in-frame, single-gene knockout mutants: the Keio collection," *Mol. Syst. Biol.* 2: 2006.0008; Cherepanov, P. P. et al., 1995, "Gene disruption in *Escherichia coli*: TcR and KmR cassettes with the option of Flp-catalyzed excision of the antibiotic-resistance determinant," *Gene* 158(1):9-14; Datsenko, K., and Wanner, B., 2000, "One-step inactivation of chromosomal genes in *Escherichia coli* K-12 using PCR products, *Proc. Nat. Acad. Sci. USA* 97:6640-6645; Neidhart, F., Ingraham, J., and Schaechter, M., 1990, Physiology of the bacterial cell: a molecular approach (Sinauer Associates, Inc. Sunderland, Mass.); Thomason, L., Court, D., Datta, A., Khanna, R. and Rosner, J., 2004, "Identification of the *Escherichia coli* K-12 ybhE gene as pgl, encoding 6-phosphogluconolactonase," *J. Bact.* 186: 8248-8253; Thomason, L., Costantino, N., Court, D., 2007, "*E. coli* genome manipulation by P1 transduction," *Curr. Protocols Mol. Biol. Chapter* 1, Unit 1.17; Studier F., Daegelen, P., Lenski, R., Maslov, S., Kim, J. F., 2009, "Understanding the differences between genome sequences of *Escherichia coli* B strains REL606 and BL21(DE3) and comparison of the *E. coli* B and K-12 genomes," *J. Mol. Biol.* 394(4):653-80, 2009).

Example 9

Isoprene Production in a BL21 Strain Transduced with the 17,257 bp Chromosomal Fragment Encoding Pgl This example demonstrates that high specific productivity of isoprene in 4.5-mL batch mini-fermentations by *E. coli* harboring the mevalonic acid pathway requires the restoration of pgl to the bacterial chromosome.

Medium Recipe (Per Liter Fermentation Medium):

13.6 g $K_2HPO_4$, 13.6 g $KH_2PO_4$, 2 g citric acid monohydrate, 0.3 g ferric ammonium citrate, 3.2 g $(NH_4)_2SO_4$, 1 ml 1000× Trace Metals Solution were added together and dissolved in $diH_2O$. The pH was adjusted to 6.8 with 28% (w/v) ammonium hydroxide and brought up to final volume. The medium was filter-sterilized with a 0.22 micron filter. Glucose (10 g for overnight culture and 5.0 g for main culture) and appropriate antibiotics were added after sterilization and pH adjustment, followed by 1 g of yeast extract from a 100 g/L stock solution and 1 g of $MgSO_4$ from a 1 M $MgSO_4$ solution.

Trace Metal Solution (Per Liter Fermentation Medium):

40 g Citric Acid*$H_2O$, 30 g $MnSO_4$*$H_2O$, 10 g NaCl, 1 g $FeSO_4$*$7H_2O$, 1 g $CoCl_2$*$6H_2O$, 1 g $ZnSO_4$*$7H_2O$, 100 mg $CuSO_4$*$5H_2O$, 100 mg $H_3BO_3$, and 100 mg $NaMoO_4$*$2H_2O$ were dissolved one at a time in $diH_2O$. The pH was then adjusted to 3.0 with HCl/NaOH, the solution was brought up to final volume and filter-sterilized with a 0.22 micron filter.

*E. coli* Strains:

(1) CMP312: *E. coli* BL21 cells engineered to contain the upper mevalonic acid (MVA) pathway (pCL Upper), the integrated lower MVA pathway (PL.2KKDyI), and a plasmid with a truncated *P. alba* IspS (MEA isolate) and mevalonate kinase from *M. mazei* (pTrcAlba(MEA)+mMVK). This strain also includes an integrated copy of the 17,257 bp segment containing genes for galactose utilization and encoding pgl that was found to be deleted in *E. coli* BL21(DE3). That segment was derived from *E. coli* K-12 chromosomal DNA.

(2) CMP323: This strain is identical to strain CMP312 described above, except that pgl has been precisely excised from the transduced piece of K-12 DNA and replaced with a gene conferring kanamycin resistance (pgl/ybhE::$kan^R$).

Experimental Procedures:

Isoprene production was analyzed by growing the strains in a Cellerator™ from MicroReactor Technologies, Inc. (Mountain View, Calif.). The working volume in each of the 24 wells was 4.5 mL. The temperature was maintained at 30° C., the pH was not controlled, the oxygen flow setpoint was 10 sccm ("standard cubic centimeters per minute") and the agitation rate was 550 rpm. The *E. coli* inoculum was obtained from a frozen vial and streaked onto an LB agar plate containing the appropriate antibiotic and incubated at 30° C. A single colony was inoculated into growth medium with antibiotics and grown overnight. The bacteria were diluted into 4.5 mL of medium with the appropriate antibiotics to reach an optical density ("OD") of 0.05 measured at 550 nm ("$OD_{550}$"). Production of isoprene was induced by the addition of isopropyl-beta-D-1-thiogalactopyranoside (IPTG) to a final concentration of 200 μM at the start of the run.

Off-gas analysis of isoprene was performed using an online Hiden mass spectrometer (Hiden Analytical, Warrington, UK) with a customized low-flow *Proteus* valve. The valve sampled one well at a time as it cycled through the 24-well plate. A custom headplate was built to attach capillaries from each of the 24 wells to corresponding ports on the *Proteus* valve, because offgas flows continuously through the capillaries to the mass spectrometer, but only one port is sampled at a time. The headplate also facilitated external sampling while the plate was rotating.

$OD_{550}$ measurements were obtained offline using a microplate reader (Spectramax, MDS Analytical Technologies, Sunnyvale, Calif.) during the course of the run. Microplate ODs were converted to OD (1 cm path length) using an established calibration curve. Specific productivity was obtained by multiplying the isoprene concentration (μg/L) measured by the mass spectrometer by the flow rate of oxygen and dividing that number by the OD reading and the volume remaining in the well. OD samples for the wells of interest were taken at four time points over the course of the mini-fermentations. OD values in between these time points were calculated using linear interpolation between the measured values.

Results.

Figure 21:
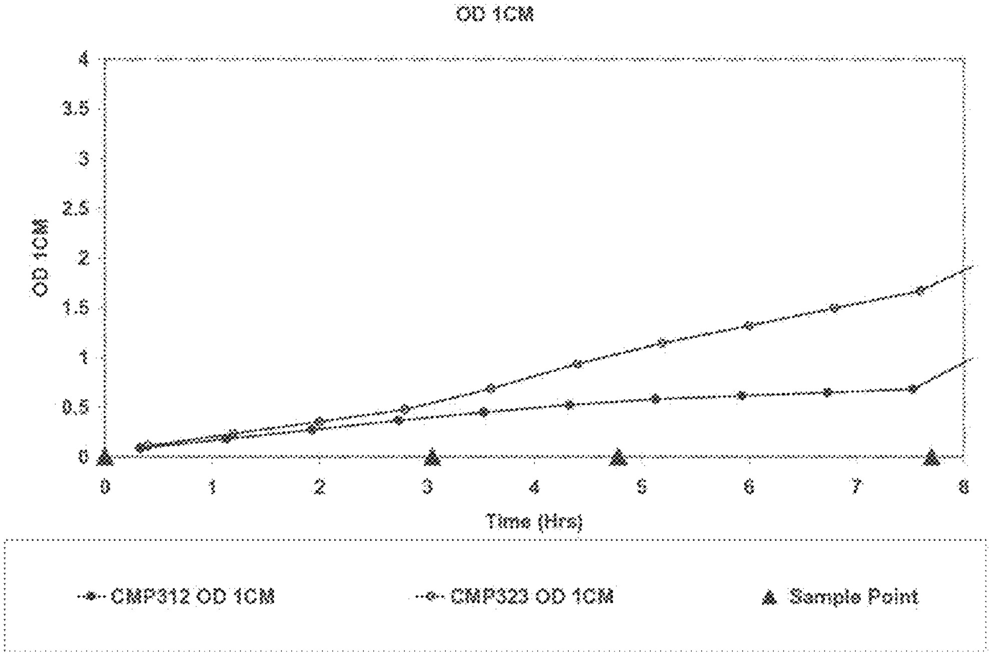
FIG. 21 shows optical density (OD) plots from microfermentation experiments conducted with PGL+ (CMP312) and PGL− (CMP323) cultures. Black triangles along the X-axis indicate when offline samples were taken. Other OD values are interpolated.
Figure 22:
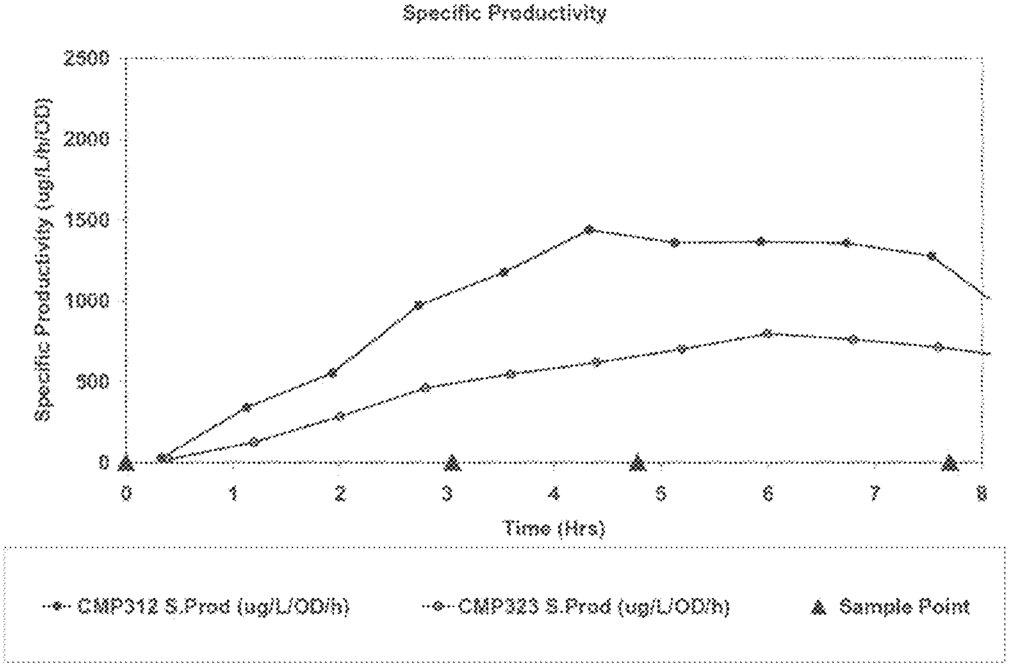
FIG. 22 shows isoprene specific productivity plots from microfermentation experiments conducted with PGL+ (CMP312) and PGL− (CMP323) cultures. Black triangles along the X-axis indicate when offline samples were taken. Other OD values are interpolated.

A representative plot of OD (FIG. 21) and specific productivity (FIG. 22) is shown for both strains. Specific productivity of isoprene from the pgl+ strain (with the pgl gene integrated into the bacterial chromosome) was compared to a $pgl^-$ strain. The bacteria were grown under identical conditions in defined medium with glucose as a carbon source in mini-fermentations. Online isoprene measurements over time revealed that the pgl+ strain (CMP312) had higher specific productivity of isoprene (FIG. 22) compared to the pgl$^-$ strain (CMP323), even with fewer cells in the culture (FIG. 21).

Example 10

*M. mazei* Mevalonate Kinase and *P. alba* Isoprene Synthase Overexpression, with and without Pgl Expression This example shows isoprene production from *E. coli* BL21 expressing genes from the mevalonic acid pathway and isoprene synthase, grown in fed-batch culture at the 15-L scale.

Medium Recipe (Per Liter of Fermentation Medium):

7.5 g $K_2HPO_4$, 2 g $MgSO_4$*7$H_2O$, 2 g citric acid monohydrate, 0.3 g ferric ammonium citrate, 0.5 g yeast extract, and 1 ml 1000× Modified Trace Metal Solution were added together and dissolved in di$H_2O$. The solution was heat sterilized at 123° C. for 20 minutes, then adjusted to pH=7.0 with 28% (w/v) ammonium hydroxide and brought up to final volume. Ten grams of glucose, 8 mL Mercury Vitamin Solution, and the appropriate antibiotics were added after sterilization and pH adjustment.

1000× Modified Trace Metal Solution (Per Liter):

40 g citric acid*$H_2O$, 30 g $MnSO_4$*$H_2O$, 10 g NaCl, 1 g $FeSO_4$*7$H_2O$, 1 g $CoCl_2$*6$H_2O$, 1 g $ZnSO_4$*7$H_2O$, 100 mg $CuSO_4$*5$H_2O$, 100 mg $H_3BO_3$, and 100 mg $NaMoO_4$*2$H_2O$ were dissolved one at a time in di$H_2O$, the pH was adjusted to 3.0 with HCl/NaOH, the solution was brought up to final volume and filter sterilized with a 0.22 micron filter.

Mercury Vitamin Solution (Per Liter):

1 g thiamine hydrochloride, 1 g D-(+)-biotin, 1 g nicotinic acid, 4.8 g D-pantothenic acid, and 4 g pyridoxine hydrochloride were dissolved one at a time in di$H_2O$, the pH was adjusted to 3.0 with HCl/NaOH, the solution was brought up to final volume and filter sterilized with a 0.22 micron filter.

Feed Solution (Per Kilogram):

0.57 kg glucose, 0.38 kg di$H_2O$, 7.5 g $K_2HPO_4$, and 10 g 100% Foamblast were mixed together and autoclaved. After cooling the sterile solution to 25° C., 3.4 mL Macro Salt Solution, 0.8 ml 1000× Modified Trace Metal Solution, and 6.7 mL Mercury Vitamin Solution were added.

Macro Salt Solution (Per Liter):

296 g $MgSO_4$*7$H_2O$, 296 g citric acid monohydrate, and 49.6 g ferric ammonium citrate were dissolved in di$H_2O$, brought up to final volume and filter sterilized with a 0.22 micron filter.

Fermentation was performed in 15-L bioreactors with three different *E. coli* BL21 cell strains: (1) DW199 expresses the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba(MEA)+mMVK (pDW34)) but lacks the pgl gene; (2) CMP312 expresses the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba (MEA)+mMVK (pDW34)), and contains a restored chromosomal 17,257 bp segment encoding the pgl gene (the ybgS::kan$^R$ marker used during strain construction was looped out); and (3) CMP323 is identical to CMP312 except the pgl gene was precisely excised from the restored piece of DNA and replaced with a gene conferring kanamycin resistance (pgl/ybhE::kan$^R$).

This experiment was carried out to monitor isoprene production from glucose at the desired fermentation pH and temperature (pH=7.0 and 34° C.). A frozen vial of each *E. coli* strain was thawed and inoculated into tryptone-yeast extract medium for each bioreactor. After the inoculum grew to $OD_{550}$=1.0, 500 mL of the culture was used to inoculate a 15-L bioreactor before bringing the initial tank volume to 5 L.

Figure 23:
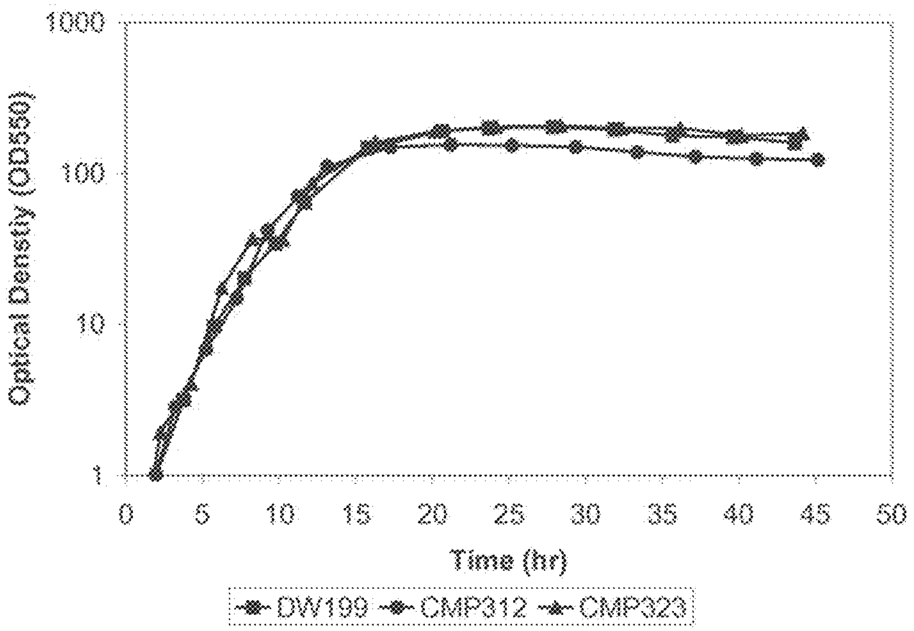
FIG. 23 shows a time course of optical density in a 15-L bioreactor fed with glucose.
Figure 24:
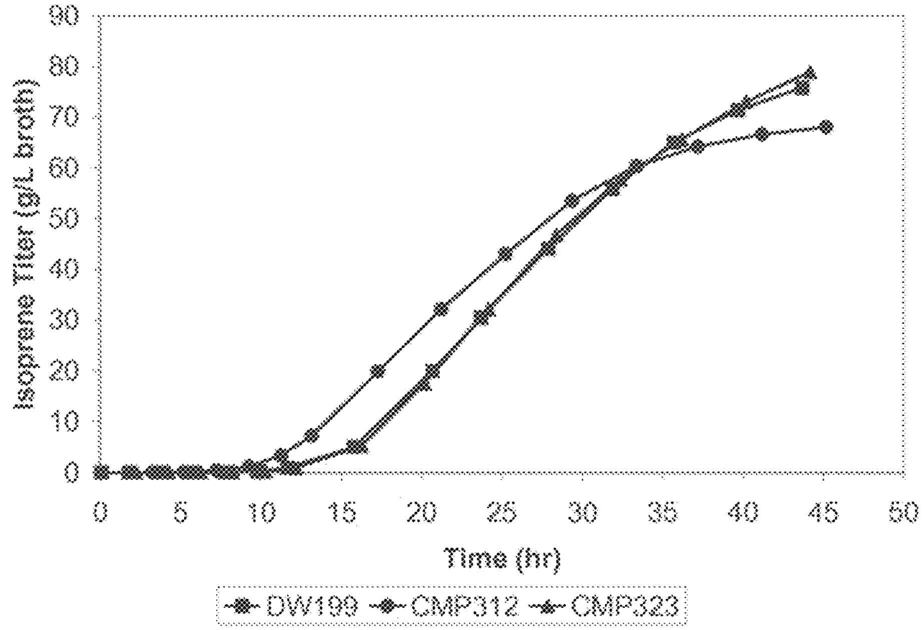
FIG. 24 shows a time course of isoprene titer in a 15-L bioreactor fed with glucose. Isoprene titer is defined as the amount of isoprene produced per liter of fermentation broth. The equation for calculating isoprene titer is: ∫(Instantaneous isoprene production rate, g/L/hr)dt from t=0 to t hrs [=] g/L broth.
Figure 25:
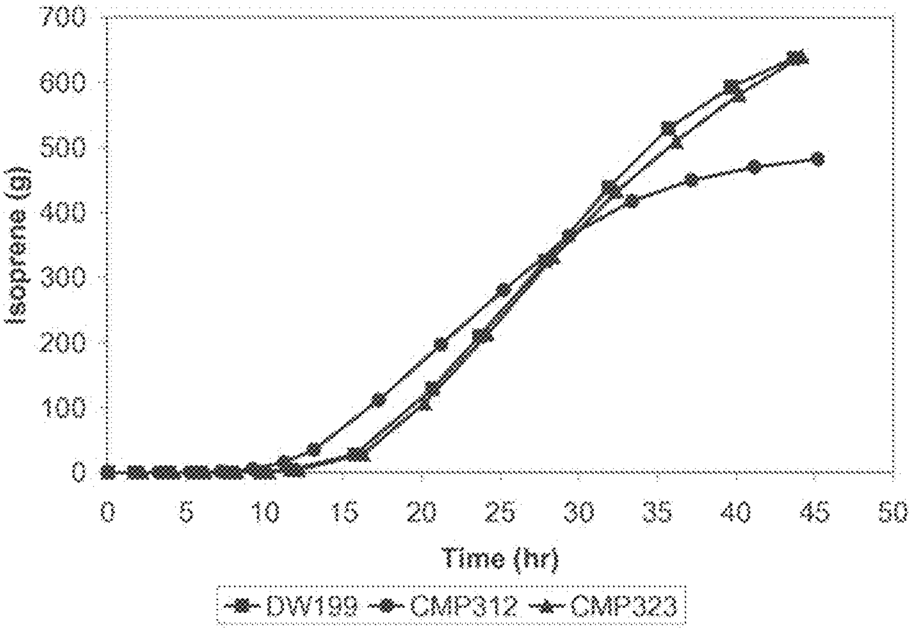
FIG. 25 shows the time course of total isoprene produced from the 15-L bioreactors fed with glucose.
Figure 26:
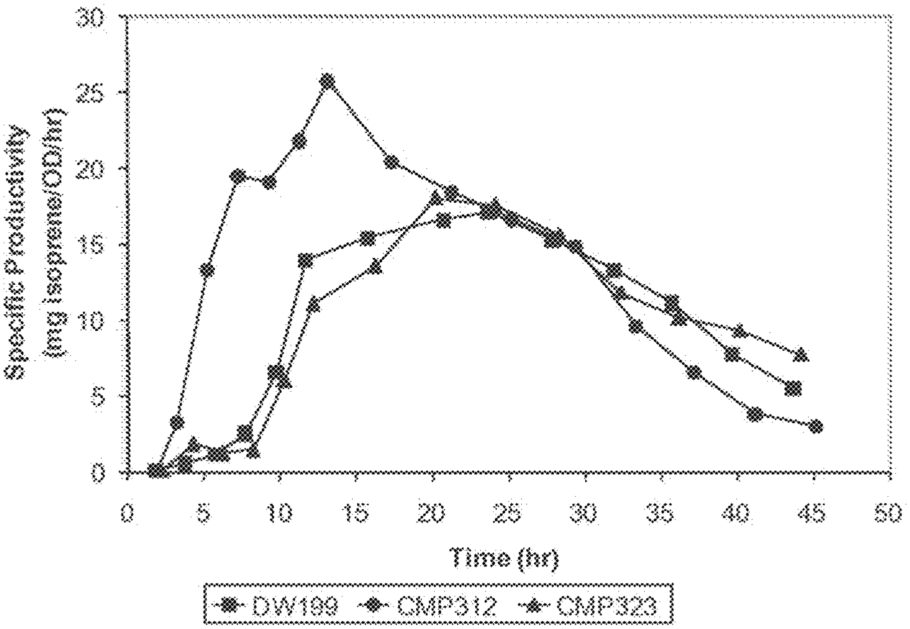
FIG. 26 shows isoprene specific productivity within the 15-L bioreactors fed with glucose. Equation for calculating Specific Productivity levels: (mg $\text{isoprene}_t$−mg $\text{isoprene}_{to}$)/[($\text{OD550}_t$*L $\text{broth}_t$−$\text{OD550}_{to}$*L $\text{broth}_{to}$)/(2.7 OD*L/g cell)]/($t-t_0$) [=] mg isoprene/g cell/hr.

The feed solution was fed at an exponential rate until a top feed rate of 5.8 g/minute was reached. After this time the glucose feed was added to meet metabolic demands at rates less than or equal to 5.8 g/minute. The total amount of glucose delivered to the bioreactors was 5.8 kg to strain DW199 over 44 hours of fermentation, 3.4 kg to strain CMP312 over 45 hours of fermentation, and 6.3 kg to strain CMP323 over 44 hours of fermentation. Induction of isoprene production was achieved by adding isopropyl-beta-D-1-thiogalactopyranoside ("IPTG") at the levels shown in Table 25. The $OD_{550}$ profiles within the bioreactors over time are shown in FIG. 23. The isoprene levels in the offgas from the bioreactors were determined using a Hiden mass spectrometer (Hiden Analytical, Warrington, UK). The isoprene titer increased over the course of the fermentation to a maximum value of 76 g/L at 44 hours for strain DW199, 68 g/L at 45 hours for strain CMP312, and 79 g/L at 44 hours for strain CMP323 (see FIG. 24). The total amount of isoprene produced during fermentation was 637 g over 44 hours for strain DW199, 482 g over 45 hours for strain CMP312, and 640 g over 44 hours for strain CMP323 (FIG. 25). The time course of specific productivity is shown in FIG. 26. The molar and mass yields of isoprene from glucose are shown in Table 9.

TABLE 8

IPTG addition during the fermentations of strains DW199, CMP312 and CMP323

| Strain | Induction | $OD_{550}$ | IPTG concentration, μM |
|---|---|---|---|
| DW199 | 1$^{st}$ | 5 | 105 |
| | 2$^{nd}$ | 105 | 195 |
| CMP312 | 1$^{st}$ | 5 | 115 |
| | 2$^{nd}$ | 80 | 225 |
| CMP323 | 1$^{st}$ | 5 | 115 |
| | 2$^{nd}$ | 115 | 215 |

TABLE 9

Molar and mass yield of isoprene from glucose for strains DW199, CMP312 and CMP323

| Strain | Time, hr | Molar yield, % | Mass yield, % |
|---|---|---|---|
| DW199 | 44 | 23.9 | 11.0 |
| CMP312 | 45 | 30.3 | 14.5 |
| CMP323 | 44 | 22.0 | 10.2 |

Example 11

*M. mazei* Mevalonate Kinase and *P. alba* Isoprene Synthase Overexpression, and Restored K12 DNA Including pgl (CMP312) Compared to the Same Strain with pgl Precisely Excised (CMP323)

This example compares isoprene production from *E. coli* strains expressing genes from the mevalonic acid pathway and isoprene synthase with the pgl gene restored and with the restored pgl gene precisely deleted, grown in fed-batch culture at the 15-L scale.

Medium Recipe (Per Liter Fermentation Medium):

7.5 g $K_2HPO_4$, 2 g $MgSO_4*7H_2O$, 2 g citric acid monohydrate, 0.3 g ferric ammonium citrate, 0.5 g yeast extract, 1 ml 1000× Modified Trace Metal Solution were added together and dissolved in $diH_2O$. This solution was heat sterilized at 123° C. for 20 minutes, the pH was then adjusted to 7.0 with 28% (w/v) ammonium hydroxide and brought up to final volume. 10 g glucose, 0.05 g thiamine hydrochloride, and appropriate antibiotics were added after sterilization and pH adjustment.

1000× Modified Trace Metal Solution (Per Liter):

40 g citric acid*$H_2O$, 30 g $MnSO_4*H_2O$, 10 g NaCl, 1 g $FeSO_4*7H_2O$, 1 g $CoCl_2*6H_2O$, 1 g $ZnSO_4*7H_2O$, 100 mg $CuSO_4*5H_2O$, 100 mg $H_3BO_3$, and 100 mg $NaMoO_4*2H_2O$ were dissolved one at a time in $diH_2O$, pH was adjusted to 3.0 with HCl/NaOH, and then the solution was brought up to final volume and filter sterilized with a 0.22 micron filter.

Feed Solution (Per Kilogram):

0.57 kg glucose, 0.38 kg $diH_2O$, and 10 g 100% Foamblast were mixed together and autoclaved.

This experiment was performed to compare isoprene formation from glucose at the desired fermentation pH and temperature (pH=7.0 and 34° C.) in strains with pgl restored and with restored pgl precisely knocked out. Fermentations were performed in 15-L bioreactors with two *E. coli* strains: (1) CMP312, *E. coli* BL21 cells expressing the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba (MEA) mMVK (pDW34)), and containing a restored 17,259 bp segment of the bacterial chromosome including the pgl gene (with the ybgS::$Kan^R$ marker looped out); and (2) CMP323, an *E. coli* strain with pgl precisely excised from the restored piece of DNA, as described above. A frozen vial of each strain was thawed and inoculated into tryptone-yeast extract medium for each bioreactor. After the inoculum grew to $OD_{550}$=1.0, measured at 550 nm ($OD_{550}$), 500 mL was used to inoculate a 15-L bioreactor, and the initial tank volume was brought up to 5 L.

The feed solution was added at an exponential rate until a top feed rate of 5.8 g/minute was reached. After this time the glucose feed was added to meet metabolic demands at rates less than or equal to 5.8 g/minute. The total amount of glucose delivered to the bioreactors during the 20 hour fermentation was 1.6 kg for the pgl+ strain and 2.0 kg for the $pgl^-$ strain. These strains were fed to avoid glucose accumulation in the medium.

Isoprene production was induced by adding isopropyl-beta-D-1-thiogalactopyranoside ("IPTG") to 90 μM when the $OD_{550}$ reached a value of 4. The IPTG concentration was raised to 170 μM when the $OD_{550}$ reached 100.

Figure 27:
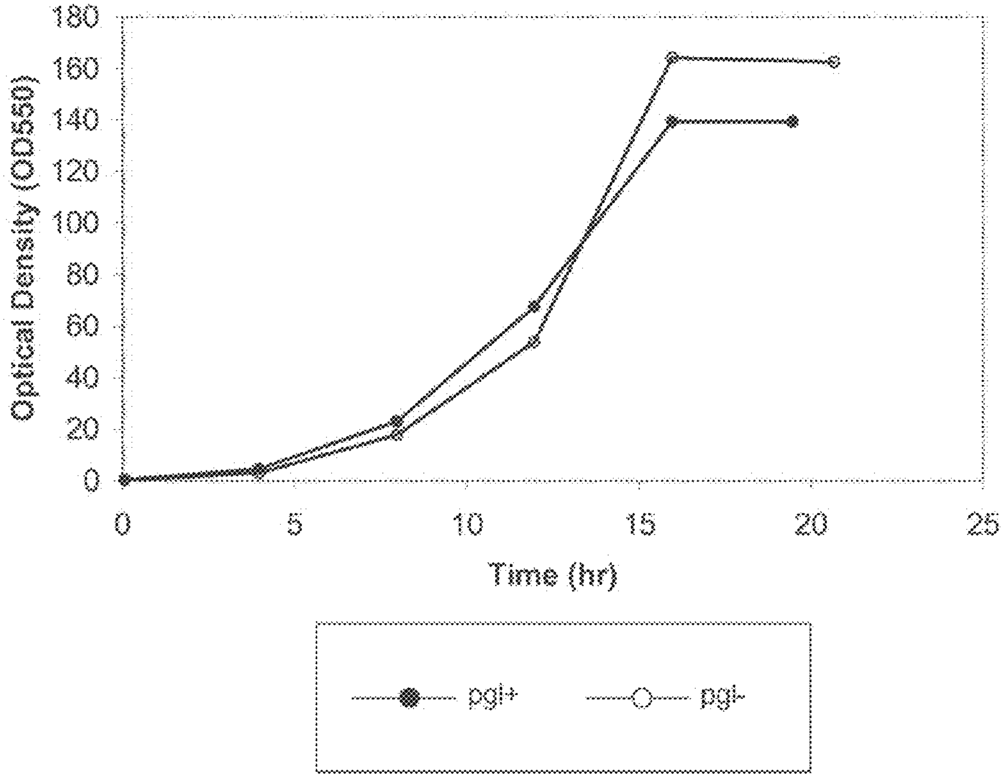
FIG. 27 shows a time course of optical density within the 15-L bioreactor fed with glucose. The pgl+ sample was a culture of strain CMP312. The pgl− sample was a culture of strain CMP323.
Figure 28:
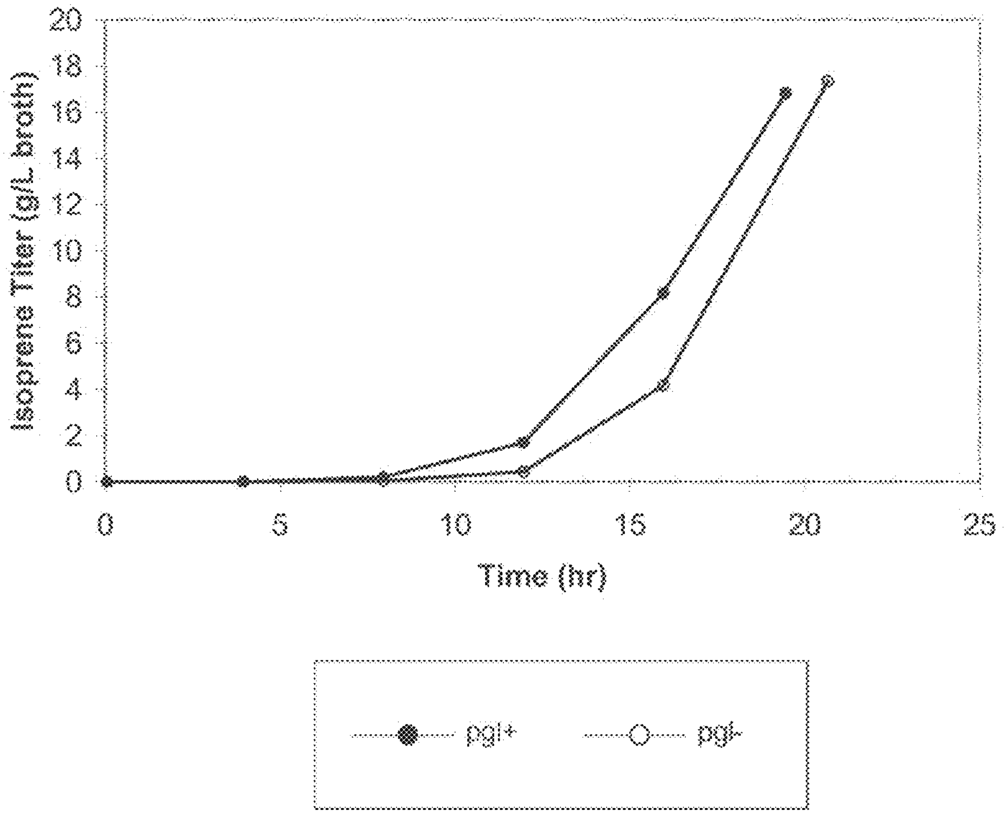
FIG. 28 shows a time course of isoprene titer within the 15-L bioreactor fed with glucose. The titer is defined as the amount of isoprene produced per liter of fermentation broth. The pgl+ sample was a culture of strain CMP312. The pgl− sample was a culture of strain CMP323. Equation for calculating Isoprene Titer: ∫(Instantaneous isoprene production rate, g/L/hr)dt from t=0 to 20 hrs [=] g/L broth.
Figure 29:
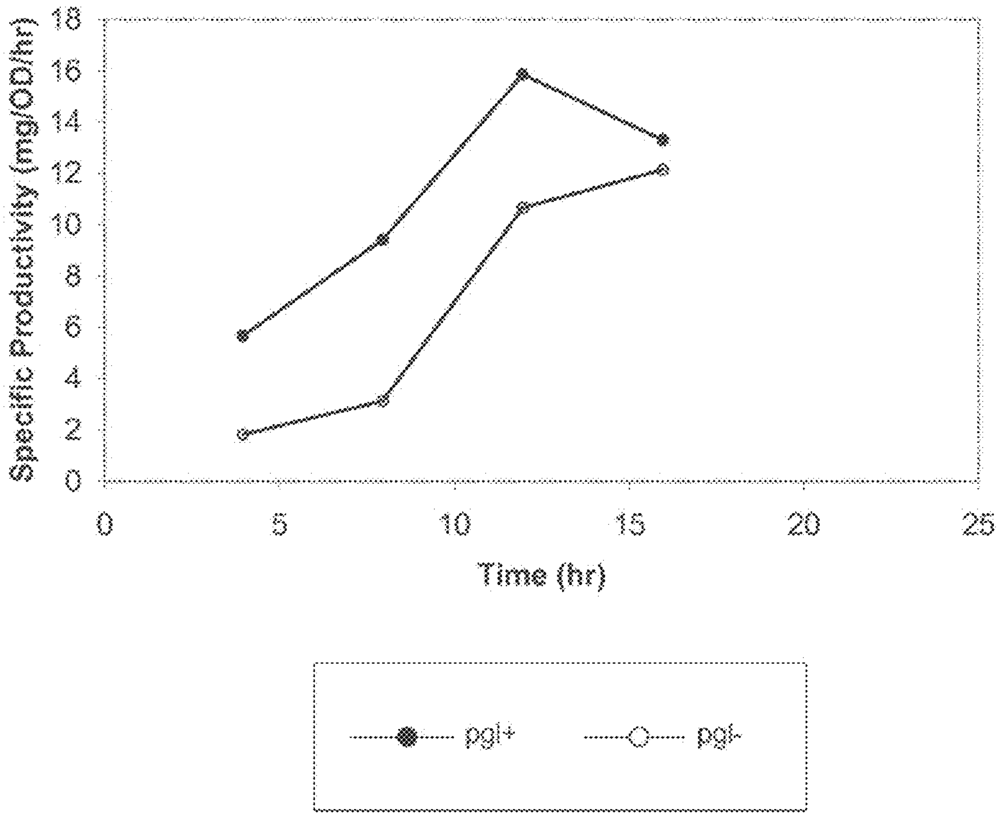
FIG. 29 shows isoprene specific productivity within the 15-L bioreactor fed with glucose. The pgl+ sample was a culture of strain CMP312. The pgl− sample was a culture of strain CMP323. Equation for calculating Specific Productivity levels: (mg $isoprene_t$−mg $isoprene_{to}$)/[($OD550_t$*L $broth_t$−$OD550_{to}$*L $broth_{to}$)/(2.7 OD*L/g cell)]/(t−$t_0$) [=] mg isoprene/g cell/hr

FIG. 27 shows the $OD_{550}$ profiles in the bioreactors over the course of the fermentation, which were similar for the two tanks. The isoprene level in the off-gas from the bioreactors was determined using a Hiden mass spectrometer (Hiden Analytical, Warrington, UK). The isoprene titer increased over the course of the fermentation to a maximum value of 17 g/L at the last time point sampled (see FIG. 28). However, the $pgl^+$ strain reached this titer faster than the $pgl^-$ strain. The time course of specific productivity is shown in FIG. 29. According to the OD and titer trends, the $pgl^+$ strain had a higher specific productivity in the run compared to the $pgl^-$ strain.

Example 12

*M. mazei* Mevalonate Kinase and *P. alba* Isoprene Synthase Overexpression

This example show the isoprene production from *E. coli* K12 MG1655 (which contains the 17,257 bp deleted from *E. coli* BL21 (DE3)) expressing genes from the mevalonic acid pathway and isoprene synthase, grown in fed-batch culture at the 15-L scale.

Medium Recipe (Per Liter Fermentation Medium):

7.5 g $K_2HPO_4$, 2 g $MgSO_4*7H_2O$, 2 g citric acid monohydrate, 0.3 g ferric ammonium citrate, 0.5 g yeast extract, and 1 ml 1000× Modified Trace Metal Solution were added together and dissolved in $diH_2O$. This solution was heat sterilized at 123° C. for 20 minutes, the pH was adjusted to 7.0 with 28% (w/v) ammonium hydroxide brought up to the final volume. 10 g glucose, 8 mL Mercury Vitamin Solution, and appropriate antibiotics were added after sterilization and pH adjustment.

1000× Modified Trace Metal Solution (per liter): 40 g citric acid*$H_2O$, 30 g $MnSO_4*H_2O$, 10 g NaCl, 1 g $FeSO_4*7H_2O$, 1 g $CoCl_2*6H_2O$, 1 g $ZnSO_4*7H_2O$, 100 mg $CuSO_4*5H_2O$, 100 mg $H_3BO_3$, and 100 mg $NaMoO_4*2H_2O$ were dissolved one at a time in $diH_2O$, the pH was adjusted to 3.0 with HCl/NaOH, and then the solution was brought up to final volume and filter sterilized with a 0.22 micron filter.

Mercury Vitamin Solution (Per Liter):

1 g thiamine hydrochloride, 1 g D-(+)-biotin, 1 g nicotinic acid, and 4.8 g D-pantothenic acid, 4 g pyridoxine hydrochloride were dissolved one at a time in $diH_2O$, the pH was adjusted to 3.0 with HCl/NaOH, and then the solution was brought up to final volume and filter sterilized with a 0.22 micron filter.

Feed Solution (Per Kilogram):

0.57 kg glucose, 0.38 kg $diH_2O$, 7.5 g $K_2HPO_4$, and 10 g 100% Foamblast were mixed together and autoclaved. 3.4 mL Macro Salt Solution, 0.8 mL 1000× Modified Trace Metal Solution, and 6.7 mL Mercury Vitamin Solution were added after the solution had cooled to 25° C.

Macro Salt Solution (Per Liter):

296 g $MgSO_4*7H_2O$, 296 g citric acid monohydrate, and 49.6 g ferric ammonium citrate were dissolved in $diH_2O$, brought up to final volume and filter sterilized with a 0.22 micron filter.

This experiment was carried out to monitor isoprene formation from glucose at the desired fermentation pH and temperature (pH=7.0 and 34° C.). Fermentation was performed in a 15-L bioreactor with strain MCM769: *E. coli* MG1655 cells expressing the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba(MEA)+mMVK (pDW34)). A frozen vial of strain MCM769 was thawed and inoculated into tryptone-yeast extract medium for each bioreactor. After the inoculum grew to $OD_{550}$=1.0, 500 mL was used to inoculate a 15-L bioreactor and the initial tank volume was brought to 5-L.

Figure 30:
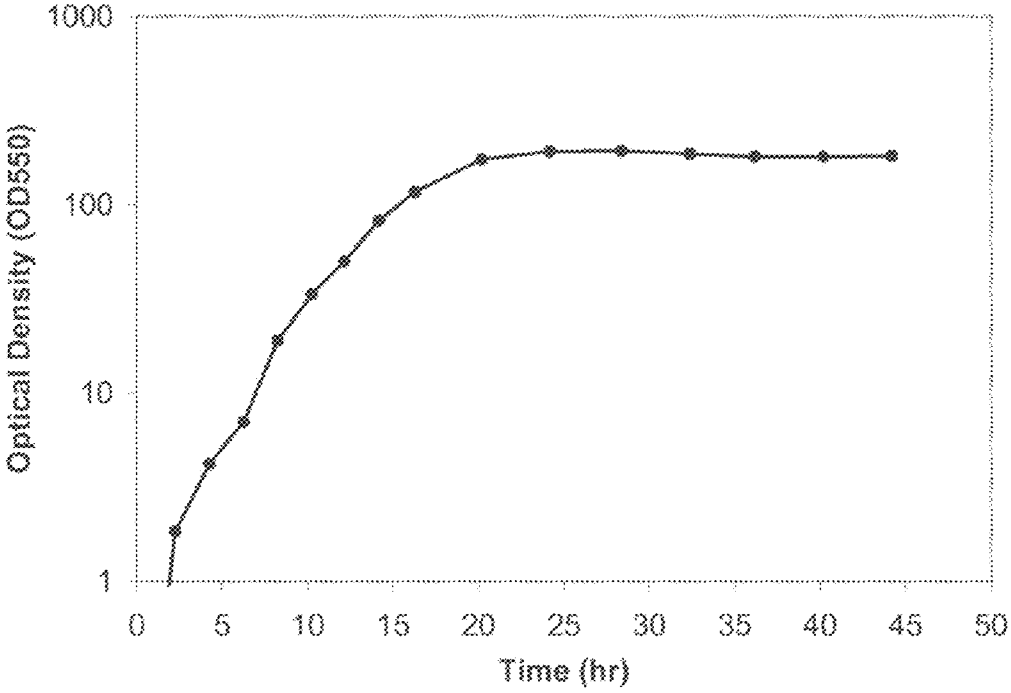
FIG. 30 shows a time course of optical density within a 15-L bioreactor containing *E. coli* K12 strain MG1655 fed with glucose.
Figure 31:
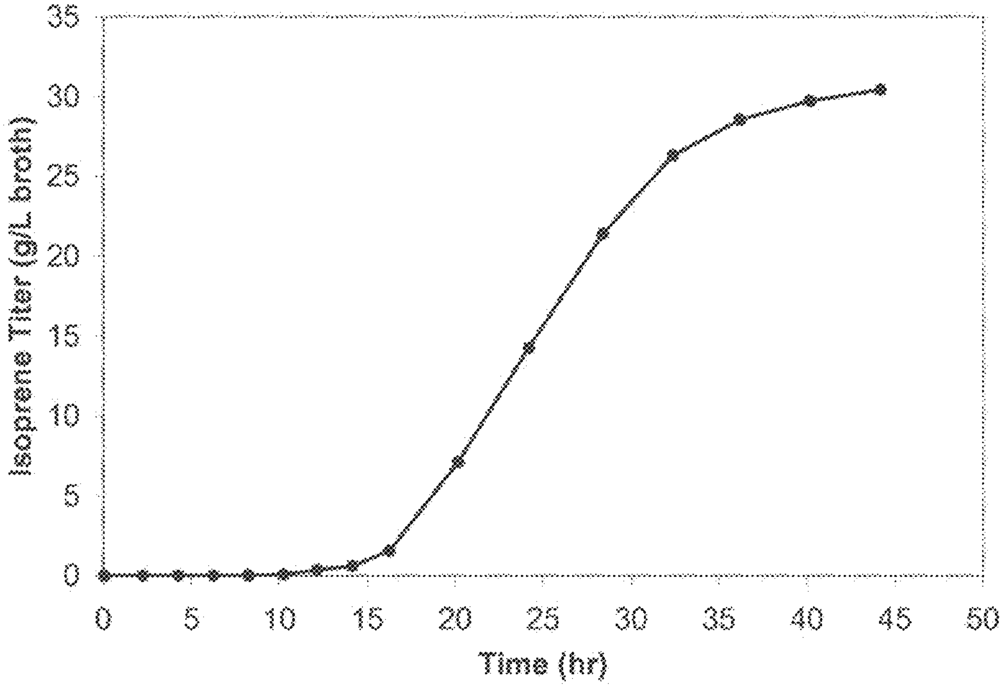
FIG. 31 shows a time course of isoprene titer within the 15-L bioreactor containing *E. coli* K-12 strain MG1655 fed with glucose. The titer is defined as the amount of isoprene produced per liter of fermentation broth. Equation for calculating Isoprene Titer: ∫(Instantaneous isoprene production rate, g/L/hr)dt from t=0 to t hrs [=] g/L broth.
Figure 32:
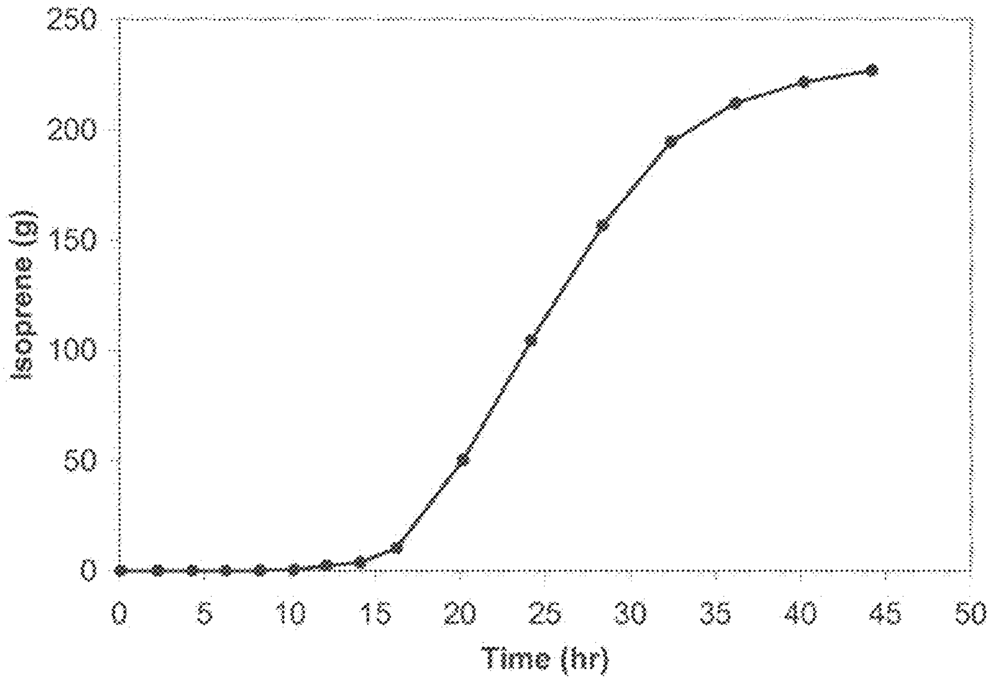
FIG. 32 shows a time course of total isoprene produced from the 15-L bioreactor containing *E. coli* K-12 strain MG1655 fed with glucose.
Figure 33:
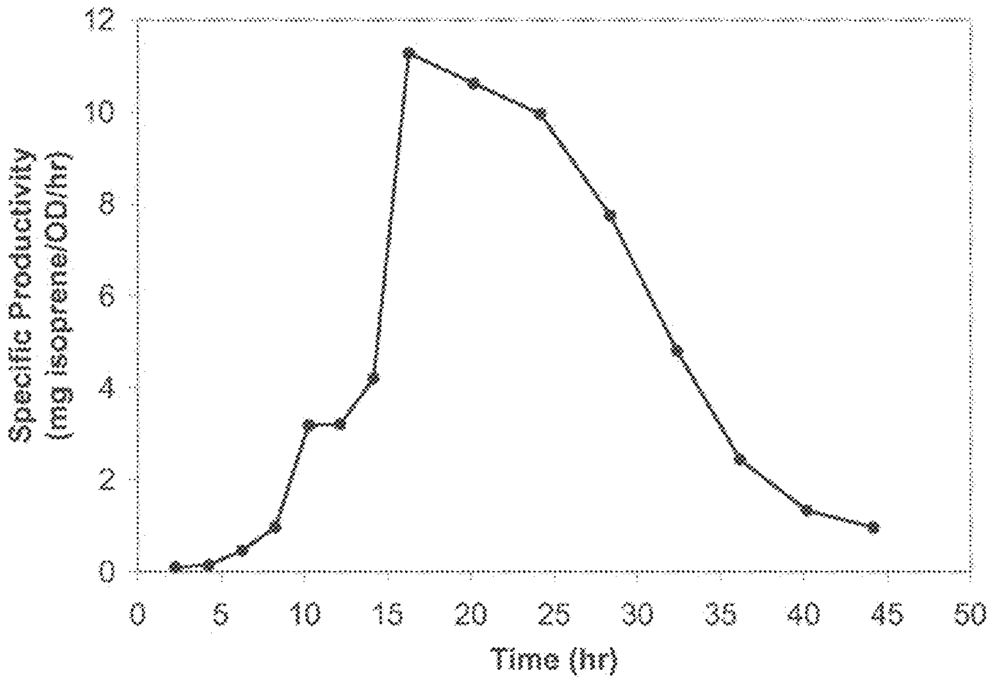
FIG. 33 shows a time course of isoprene specific productivity in a 15-L bioreactor containing *E. coli* strain K12 MG1655 fed with glucose. Equation for calculating specific productivity: (mg $isoprene_t$−mg $isoprene_{to}$)/[($OD550_t$*L $broth_t$−$OD550_{to}$*L $broth_{to}$)/(2.7 OD*L/g cell)]/(t−$t_0$) [=] mg isoprene/g cell/hr.

The feed solution was added at an exponential rate until a top feed rate of 3.9 g/minute was reached. After this time, the feed solution was added to meet metabolic demands at rates less than or equal to 3.9 g/minute. The total amount of glucose delivered to the bioreactor during the 44 hour fermentation was 2.3 kg. Isoprene production was induced by adding shots of isopropyl-beta-D-1-thiogalactopyranoside ("IPTG") to achieve the levels shown in Table 10 at the measured $OD_{550}$ values. The $OD_{550}$ profiles within the bioreactors over time are shown in FIG. 30. The isoprene level in the offgas from the bioreactors was determined using a Hiden mass spectrometer (Hiden Analytical, Warrington, UK). The isoprene titer increased over the course of the fermentation to a maximum value of 30.4 g/L at 44 hours (FIG. 31). The total amount of isoprene produced during fermentation was 226.8 g at 44 hours (FIG. 32). The time course of specific productivity is shown in FIG. 33. The molar yield of utilized carbon that went into producing isoprene during fermentation was 21.1% at 44 hours. The weight percent yield of isoprene from glucose was 9.7% at 44 hours.

TABLE 10

IPTG additions during the fermentation of strain MCM769

| $OD_{550}$ | IPTG concentration after addition, uM |
|---|---|
| 13 | 41 |
| 36 | 61 |
| 70 | 81 |
| 105 | 100 |
| 195 | 117 |
| 115 | 215 |

Example 13

The Effect of pgl on the Specific Productivity of Mevalonate in *E. coli* BL21

The mevalonate biosynthetic pathway comprises two parts: (1) the upper mevalonate pathway, containing acetoacetyl-CoA synthase (thiolase), HMG-CoA synthase (HMGS) and HMG-CoA reductase (HMGR); and (2) the lower mevalonate pathway containing mevalonate kinase (MVK), phosphomevalonate kinase (PMK), diphosphomevalonate decarboxylase (MVD) and isopentenyl diphosphate isomerase (IDI). Expression of the upper pathway proteins produces mevalonate, an intermediate in the production of isoprene.

These experiments were designed to investigate how and by which mechanism pgl affects the specific productivity of mevalonate in *E. coli* BL21. The fused thiolase/HMGR (mvaE) and the HMGS (mvaS) of *Enterococcus faecalis* were constructed on pCL, pBBR, and pTrc plasmids and transformed into both *E. coli* BL21 lacking pgl and *E. coli* BL21 containing pgl integrated in the bacterial chromosome.

Strains containing pgl had a greater specific productivity than strains lacking pgl during growth in minimal medium with high concentrations of yeast extract, growth conditions that mimic the early stages of fed batch fermentation. The presence of pgl during growth in minimal medium with low yeast extract concentration also resulted in significantly higher production of mevalonate compared to strains lacking pgl. This effect, however, was not due to increased concentration of mevalonate pathway enzymes, demonstrating that the presence of pgl under these growth conditions positively influences the flux to or through the mevalonate pathway possibly by affecting central metabolism of *E. coli*. These growth conditions mimic those found late during the exponential part of fed batch fermentation.

Construction of pDW15 (Ptrc-upper MVA pathway on pBBR1MCS-5). To insert the upper MVA pathway into the pBBR1MCS-5 vector, the entire expression cassette containing Ptrc, mvaE, mvaS, and the rrn transcription terminator was amplified by PCR using a plasmid pMCM82 template with the primers Upper5'XhoI (SEQ ID NO:57) and Upper3'XbaI (SEQ ID NO:58). PCR primer sequences are listed below in Table 28. Each reaction contained 1 μl pMCM82 (~30 ng), 10 μl 5× Herculase® Buffer (Stratagene, La Jolla, Calif.), 0.5 μl dNTPs (100 mM each), 1 μl Upper5'XhoI (20 μM), 1 μl Upper3'XbaI (20 μM), 35.5 μl $diH_2O$, and 1 μl Herculase® DNA Polymerase (Stratagene, La Jolla, Calif.). Reactions were heated to 95° C. for 4 minutes, subject to 5 cycles of 95° C. for 20 minutes/52° C. for 20 seconds/72° C. for 4 minutes, to 25 cycles of 95° C. for 20 minutes/55° C. for 20 seconds/72° C. for 4 minutes, followed by 10 minutes at 72° C., and finally, cooled to 4° C.

Figure 34:
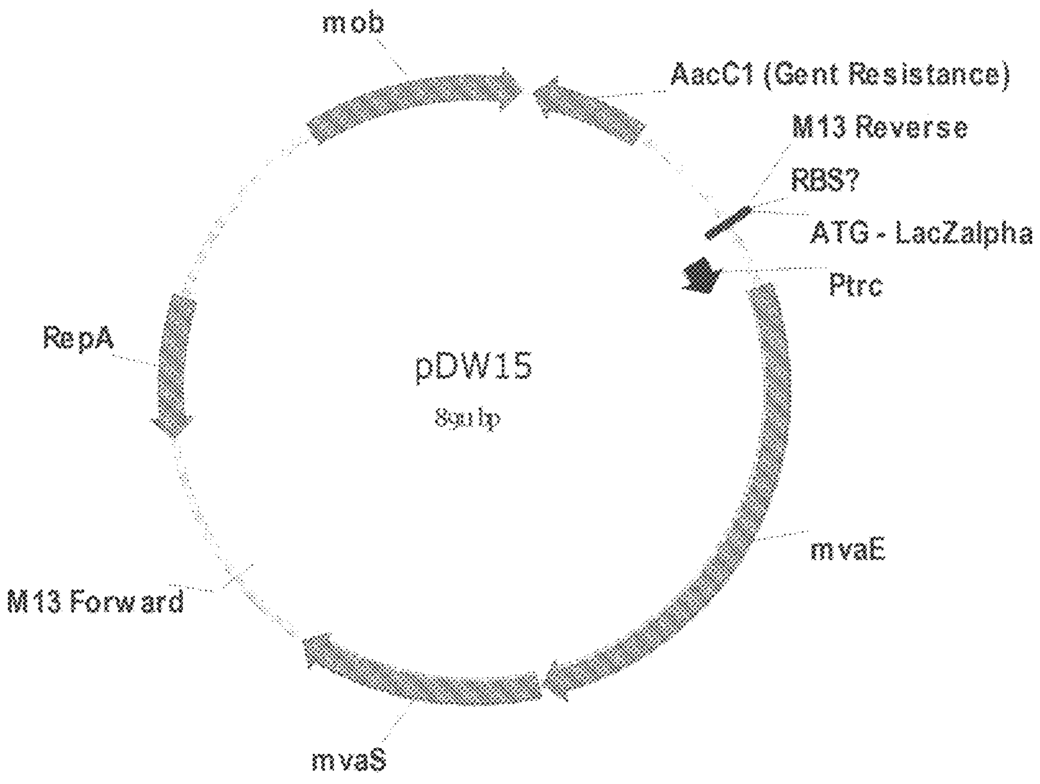
FIG. 34A shows a map of plasmid pDW15, expressing the upper MVA pathway polypeptides mvaE and mvaS from *Enterobacter faecalis*.
FIGS. 34B-D shows the complete nucleotide sequence of plasmid pDW15 (SEQ ID NO:10).

The size of the PCR product was confirmed by gel electrophoresis using a pre-cast E-Gel® (Invitrogen, Carlsbad, Calif.) and the 4.2 kb product was purified using QiaQuick® purification columns (Qiagen, Valencia, Calif.) according to the manufacturer's recommended protocol. Purified PCR product and the pBBR1MCS-5 vector were then digested with XbaI and XhoI restriction endonucleases overnight at 37° C. as follows: 6 μl diH2O, 2 μl 10× SuRE/Cut Buffer H (Roche Applied Science, Indianapolis, Ind.), 10 μl DNA (pBBR1MCS-5 or PCR insert), 1 μl XhoI (Roche Applied Science), and 1 μl XbaI (Roche Applied Science). The next day, the restriction enzymes were heat-inactivated at 65° C. for 20 minutes before ligation. Ligation reactions (see below for conditions) included 2 μl $diH_2O$, 1 μl 10× Ligase buffer (New England Biolabs, Ipswich, Mass.), 1 μl T4 DNA ligase (New England Biolabs), 2 μl vector (pBBR1MCS-5), and 4 μl insert (upper MVA expression cassette), and were carried out at 4° C. overnight. The ligation reactions were desalted by microdialysis (Millipore, Billerica, Mass.) and approximately 5 μl of each reaction was transformed into chemically competent *E. coli* TOP10 cells (Invitrogen, Carlsbad, Calif.) according to the manufacturer's recommended protocol. Electroporated cells were recovered at 37° C. in LB for 1 hour, and then plated onto LB plates containing X-gal and 10 μg/ml Gentamicin. Colonies displaying no β-galactosidase activity were selected for further analysis by PCR using primers M13 Reverse and MCM163 to confirm the presence of the insert. Plasmid from one of these colonies was purified (Qiagen), completely sequenced (Quintara Biosciences, see Table 11 for primer sequences) to verify that it contained the complete upper MVA pathway expression cassette in the correct orientation, and designated pDW15 (SEQ ID NO:69). A map of plasmid pDW15 is shown in FIG. 34A, and the complete sequence is listed in FIG. 34B-C-D.

TABLE 11

PCR and Sequencing Primers

| Primer name | Primer sequence |
|---|---|
| Upper5'XhoI | atgctcgagctgttgacaattaatcatccggctc (SEQ ID NO: 57) |
| Upper3'XbaI | cgatctagaaaggcccagtctttcgactgagcc (SEQ ID NO: 58) |
| MCM163 | ggattttggccatttccagctt (SEQ ID NO: 59) |
| CF07-58 | atgaaaacagtagttattattgatgc (SEQ ID NO: 60) |
| CF07-59 | cttaaatcatttaaaatagc (SEQ ID NO: 61) |
| CF07-82 | atgacaattgggattgataaaattag (SEQ ID NO: 62) |
| CF07-86 | gaaatagccccattagaagtatc (SEQ ID NO: 63) |
| CF07-87 | ttgccaatcatatgattgaaaatc (SEQ ID NO: 64) |

TABLE 11-continued

| PCR and Sequencing Primers | |
|---|---|
| Primer name | Primer sequence |
| CF07-88 | gctatgcttcattagatccttatcg (SEQ ID NO: 65) |
| CF07-89 | gaaacctacatccaatcttttgccc (SEQ ID NO: 66) |

Construction of MVA Producing Strains MCM870-877.

Plasmids encoding the *E. faecalis* mvaE and mvaS genes were introduced into *E. coli* hosts by electroporation. Host cells were grown in LB medium at 37° C., 250 rpm to $OD_{600}$≈1. Cultures were placed on ice until cold. For each electroporation reaction, 1.5 mL of culture was centrifuged in an Eppendorf microcentrifuge at room temperature for 2-3 minutes at 6000 rpm. After removing the supernatant, the cell pellet was resuspended in 1 mL ice cold sterile, deionized $H_2O$. The spin and wash procedure was repeated three times, and the pellet was finally resuspended in 100 μL.

A mixture of plasmids consisting of 1 μL each of pDW15 (SEQ ID NO: 10), pTrcHis2AUpperPathway#1 and pCLPtrcUpperPathway (construction of both plasmids is described in Example 8 of U.S. patent application Ser. No. 12/335,071) was added to 100 μL of cell suspension and electroporated into competent *E. coli* cells in a 2 mm cuvette at 2.5 volts, 25 μFd. Similarly, 1 μL of either pDW15, pTrcHis2AUpperPathway#1 or pCLPtrcUpperPathway was added to 100 μL of cell suspension and electroporated into competent *E. coli* cells in a 2 mm cuvette at 2.5 volts, 25 μFd. Cells were immediately allowed to recover in 500 μL LB medium for one hour at 37° C. Transformants were selected on LB with the appropriate antibiotic(s) as listed in Table 12 below. A single colony from each transformation was grown in LB medium plus the indicated antibiotic(s) at 37° C., 250 rpm to $OD_{600}$≈1 and then 0.5 mL of culture was mixed with 1 mL of 50% sterile glycerol, frozen on dry ice, and stored at −80° C.

TABLE 12

| Bacterial Strains for Measuring Specific Productivity of Mevalonate | | | |
|---|---|---|---|
| Host | Antibiotic Selection | Plasmid(s) Selected | Strain |
| BL21 (Novagen; MCM98) | Spectinomycin 50 ppm | pCLPtrcUpperPathway (pMCM82) | MCM870 |
| BL21 (Novagen; MCM98) | Gentamycin 10 ppm | Ptrc-upper MVA pathway on pBBR1MCS-5 (pDW15) | MCM871 |
| BL21 (Novagen; MCM98) | Carbenicillin 50 ppm | pTrcHis2AUpperPathway#1 (pCF449) | MCM872 |
| BL21 (Novagen; MCM98) | Spectinomycin 50 ppm, Gentamycin 10 ppm, Carbenicillin 50 ppm | pCLPtrcUpperPathway (pMCM82), Ptrc-upper MVA pathway on pBBRlMCS-5 (pDW15), pTrcHis2AUpperPathway#1 (pCF449) | MCM873 |
| BL21 t pgl+ (CMP258) | Spectinomycin 50 ppm | pCLPtrcUpperPathway (pMCM82) | MCM874 |
| BL21 t pgl+ (CMP258) | Gentamycin 10 ppm | Ptrc-upper MVA pathway on pBBRlMCS-5 (pDW15) | MCM875 |
| BL21 t pgl+ (CMP258) | Carbenicillin 50 ppm | pTrcHis2AUpperPathway#1 (pCF449) | MCM876 |
| BL21 t pgl+ (CMP258) | Spectinomycin 50 ppm, Gentamycin 10 ppm, Carbenicillin 50 ppm | pCLPtrcUpperPathway (pMCM82), Ptrc-upper MVA pathway on pBBRlMCS-5 (pDW15), pTrcHis2AUpperPathway#1 (pCF449) | MCM877 |

Construction of strains CMP215, CMP258 and CMP234 is described in Example 6, above. To assay mevalonate specific productivity, all strains were grown in triplicate overnight at 30° C. in TM3 medium containing 0.1% (w/v) yeast extract, 1% (w/v) glucose, and the appropriate antibiotic. The overnight cultures were diluted to an $OD_{600}$ of 0.05 in fresh TM3 medium containing 1% (w/v)glucose and either 0.1% (w/v) or 0.02% (w/v) yeast extract. The cultures were incubated at 34° C. until reaching $OD_{600}$ of 0.5-1.0, at which point protein expression was induced with 400 μM IPTG. Samples were collected 1 hour and 2 hours post-induction to measure OD, mevalonate concentration and concentrations of MvaS and MvaE proteins. The specific productivity of mevalonate was determined by dividing the difference in mevalonate concentration over the 1 hour time period by the average OD (calculated from the 1 hour and 2 hour ODs) over the 1 hour time period.

To measure mevalonate concentration, 300 μL of broth was centrifuged at 14,000×g for 5 minutes. Next, 250 μL of supernatant was added to 7.5 μL of 70% (w/v) perchloric acid and incubated on ice for 5 minutes. The mixture was then centrifuged for 5 minutes at 14,000×g and the supernatant collected for HPLC analysis run under the following conditions: (1) BioRad—Aminex HPX-87H Ion Exclusion Column (300 mm×7.8 mm)(Catalog #125-0140) (BioRad, Hercules, Calif.); (2) column temperature=50° C.; (3) BioRad—Microguard Cation H guard column refill (30 mm×4.6 mm)(Catalog #125-0129)(BioRad); (4) running buffer=0.01N$H_2SO_4$; (5) running buffer flow rate=0.6 ml/min; (6) approximate running pressure=~950 psi; (7) injection volume=100 microliters; (8) runtime=26 minutes.

Results.

Strains Grown in TM3 Media Containing 0.1% (w/v) Yeast Extract and 1% (w/v) Glucose.

Figure 35:
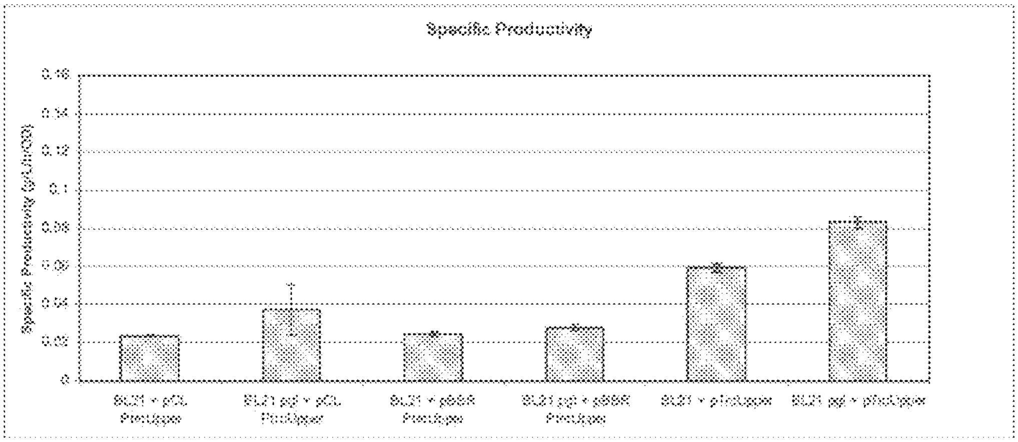
FIG. 35 shows mevalonate specific productivity of bacterial strains in TM3 minimal medium containing 0.1% yeast extract and 1% glucose. Experiments were run in triplicate from unique colonies. Strains are described in more detail in Table 29. BL21+pCL pTrcUpper=strain MCM870; BL21 pgl+pCL pTrcUpper=strain MCM874; BL21+pBBR pTrcUpper=strain MCM871; BL21 pgl+pBBR pTrcUpper=strain MCM875; BL21+pTrcUpper=MCM872; BL21 pgl+pTrcUpper=MCM876.

Six strains were constructed to test the effect of pgl expressed from the bacterial chromosome on mevalonate production (Table 13). Strains were cultured as described above. Strains expressing pgl from the bacterial chromosome had greater mevalonate specific productivities than strains that were isogenic except for the deletion of the pgl region (see FIG. 35), demonstrating that chromosomal expression of pgl improves the specific productivity of mevalonate in *E. coli* BL21. Mevalonate is the substrate for the lower mevalonate pathway. Therefore, strains that have a greater mevalonate specific productivity may also have a greater isoprene specific productivity in the presence of a complementary lower pathway and isoprene synthase.

TABLE 13

Strains used to measure specific production of mevalonate

| Strain Name | Plasmid Type | Pgl |
|---|---|---|
| BL21 pCL | pCL | no |
| BL21 + pgl pCL | pCL | yes |
| BL21 pBBR | pBBR | no |
| BL21 + pgl pBBR | pBBR | yes |
| BL21 pTrc | pTrc | no |
| BL21 + pgl pTrc | pTrc | yes |

Strains Grown in TM3 Media Containing 0.02% Yeast Extract and 1% Glucose.

Figure 36:
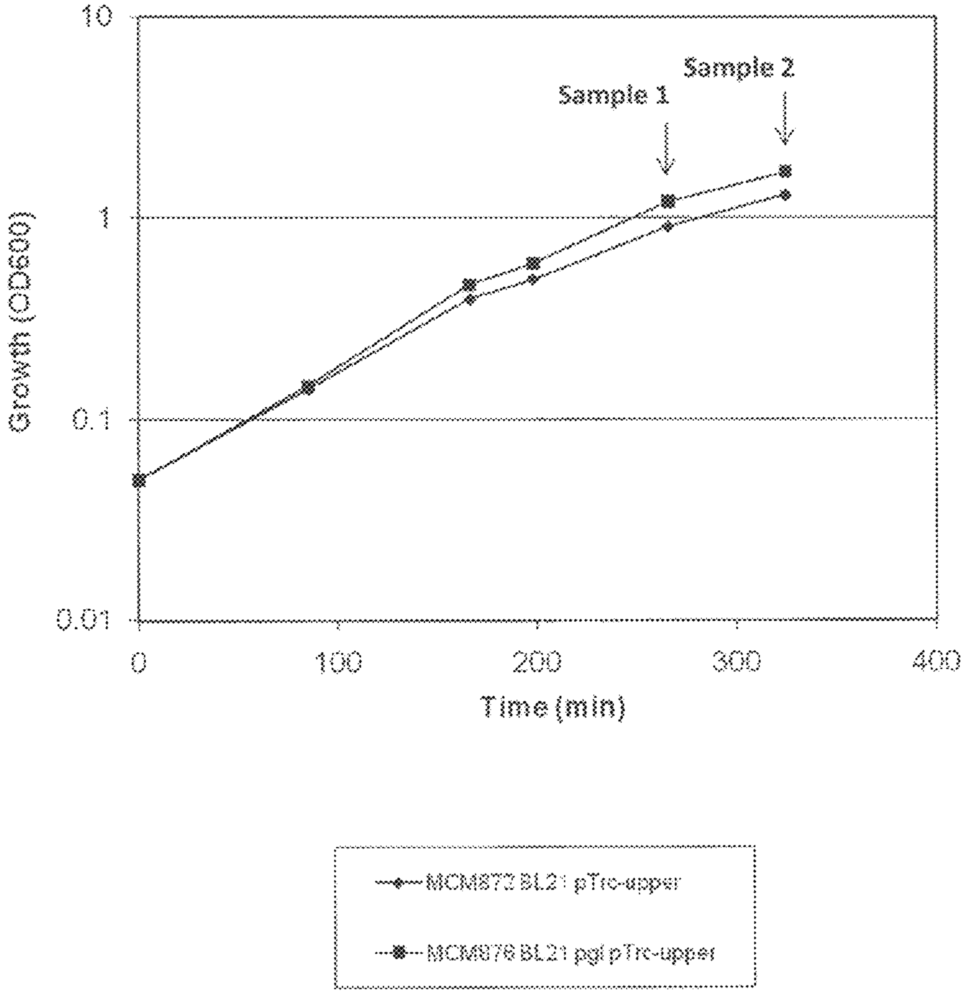
FIG. 36 shows growth of *E. coli* strains MCM872 and MCM876 in TM3 minimal medium containing 0.02% yeast extract and 1% glucose.

To further investigate the role of chromosomal expression of pgl in the production of mevalonate under conditions with low concentrations of yeast extract in minimal medium, the two strains MCM872 and MCM876 were grown in TM3 medium containing 0.02% yeast extract as described above. This growth medium mimics the conditions found late during the exponential part of fed batch fermentation. The two strains are isogenic except for the functional chromosomal copy of pgl present in MCM876. Although the strains grew similarly in the minimal medium, it was clear from the present experiment that MCM876 grew faster than MCM872 as shown in FIG. 36, indicating that chromosomal expression of pgl positively influences growth of *E. coli* in minimal medium with low concentrations of yeast extract.

Figure 37:
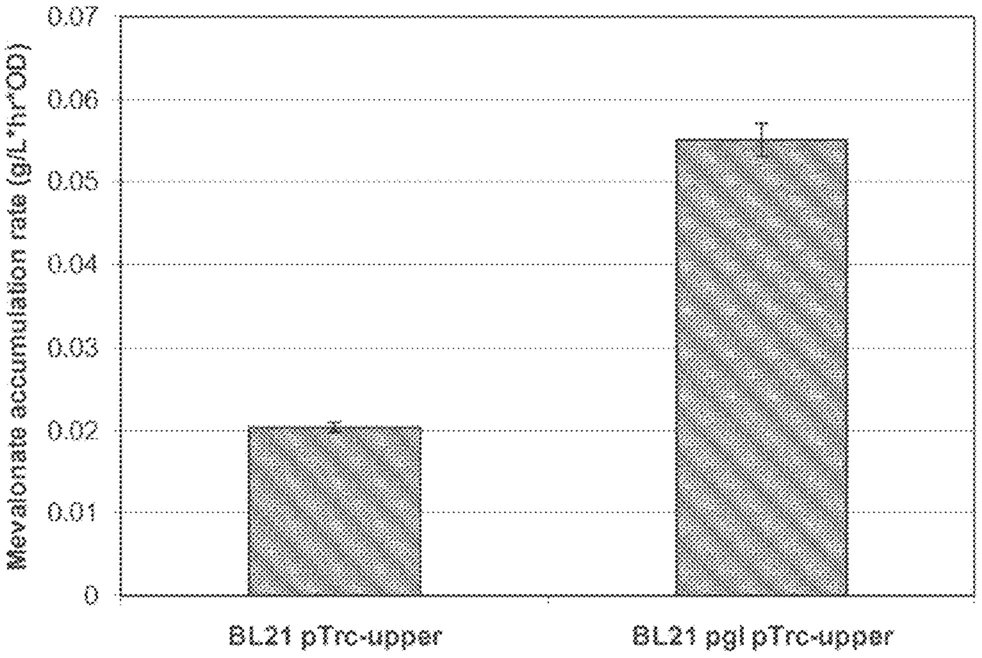
FIG. 37 shows mevalonate production rate of *E. coli* strains MCM872 (BL21 pTrc-Upper) and MCM876 (BL21 pgl pTrc-Upper) in TM3 minimal medium containing 0.02% yeast extract and 1% glucose.

The rate of mevalonate accumulation per cell was significantly higher (2.7-fold) for MCM876 compared to MCM872, as shown in FIG. 37, demonstrating that the presence of pgl on the bacterial chromosome significantly increases mevalonate production during growth in minimal medium containing limiting levels of yeast extract.

Figure 38:
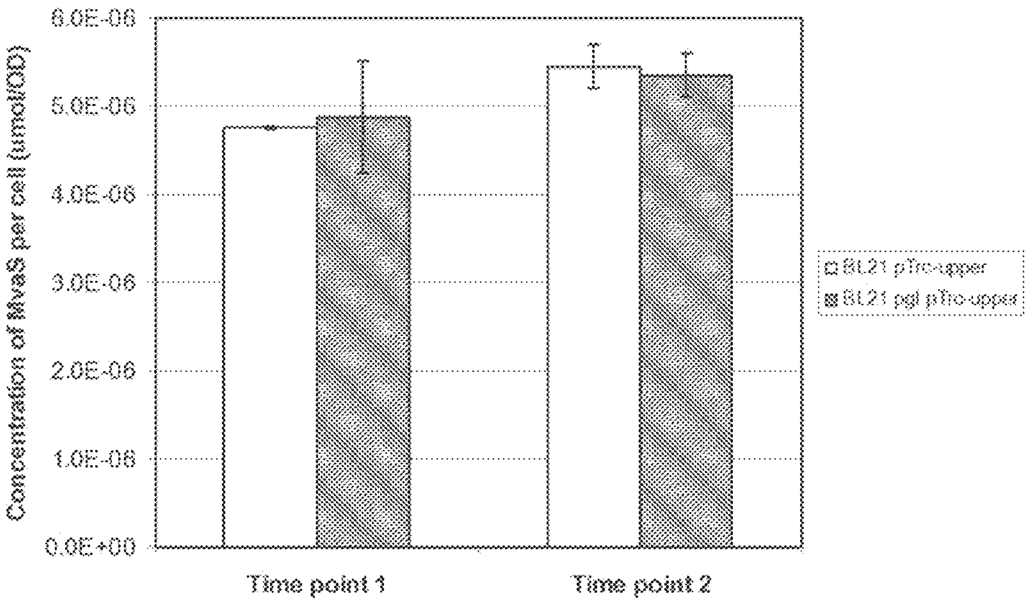
FIG. 38 shows the concentration of MvaS protein per OD in *E. coli* strains MCM872 (BL21 pTrc-Upper) and MCM876 (BL21 pgl pTrc-Upper) in TM3 minimal medium with 0.02% yeast extract, taken at two different timepoints.
Figure 39:
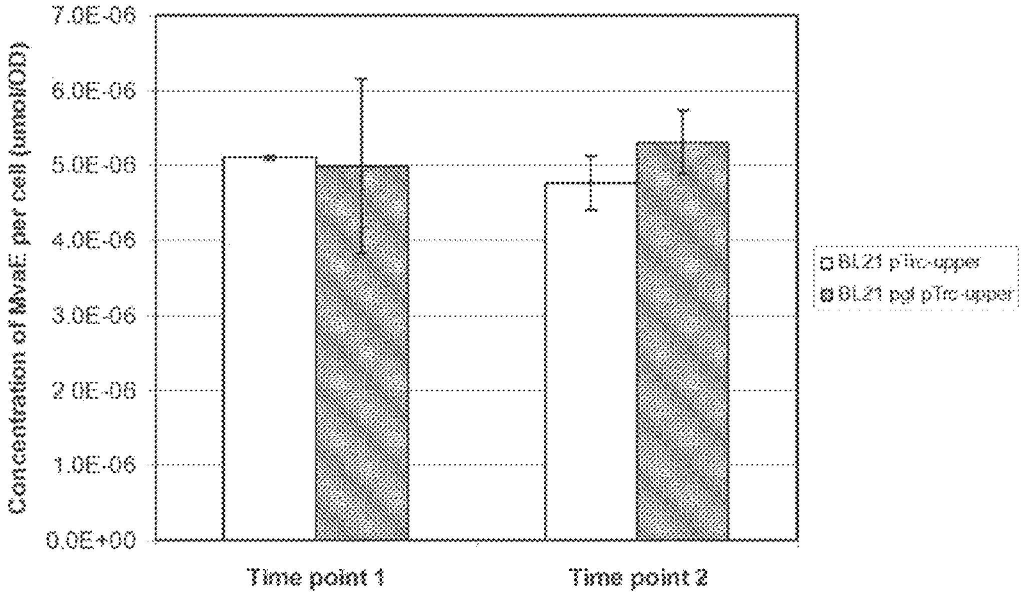
FIG. 39 shows the concentration of MvaE per OD in *E. coli* strains MCM872 (BL21 pTrc-Upper) and MCM876 (BL21 pgl pTrc-Upper) grown in TM3 minimal medium with 0.02% yeast extract.

To investigate if the increased mevalonate production rate in the MCM876 strain resulted from higher protein production in medium with low yeast extract concentration, the concentration of the upper pathway enzymes, MvaS and MvaE was measured and normalized to the optical density of the respective cultures (FIGS. 38 and 39). The presence of pgl on the bacterial chromosome did not significantly change the concentrations of mevalonate pathway enzymes under the specific growth conditions tested. However, since the mevalonate production rate increased 2.7-fold under those growth conditions, chromosomal expression of pgl must increase the mevalonate production rate by mechanism other than by increasing concentrations of mevalonate pathway enzymes. One such mechanism could be the production of reducing equivalents through the pentose phosphate pathway. This was not further tested in the present experiments.

A functional chromosomal copy of pgl in *E. coli* increases the production of mevalonate and therefore likely also the production of isoprene not only through the increased production of pathway proteins under nutrient rich growth conditions (early in the fermentation), but also through factors that control carbon flux through the MVA pathway during growth in minimal medium with low yeast extract concentrations late in the fermentation. Surprisingly, this increase is greater than that observed in strains constitutively expressing PGL from a plasmid, suggesting that the chromosomal context or the ability of the bacteria to regulate PGL expression from its natural chromosomal context plays a role in increased production of biochemicals such as isoprene.

Example 14

Comparison of PGL Enzyme Activity in Isoprene-Producing Strains

The PGL enzyme activity is measured in three strains: RHM111608-2 (production of this *E. coli* strain is described in Example 13 of International Publication No. WO 2009/076676 A2 and U.S. patent application Ser. No. 12/335,071), DW199, CMP312 and CMP323 (described in other examples). The enzyme activity can be determined by NMR methods as described (see, e.g., E. Miclet et al., *J. Biol. Chem.* 276(37):34840-34846 (2001)). RHM111608-2 contains the ybhE gene (encoding PGL) under control of a constitutive promoter, DW199 lacks any gene expressing PGL, CMP312 and CMP323 are isogenic, CMP312 has ybhE restored by transduction and is the parent of CMP323 which has ybhE deleted.

The PGL enzyme activity was measured as follows: Briefly, a mixture of 6-D-6-Phospho-glucono-1,5-lactone and γ-D-6-Phospho-glucono-1,4-lactone was prepared by incubation of 5 mM glucose-6-phosphate, 7.5 mM NADP+, and 100 mM BES pH 7.4 with glucose-6-phosphate dehydrogenase (Sigma-Aldrich, St. Louis, Mo.) for about 3 minutes. Following incubation, the solution was allowed to equilibrate at room temperature for about 15-30 minutes. Subsequently, 400 μL of lactone solution was added into the NMR cuvette and an initial spectrum was taken (Varian 500 mHz, Palo Alto, Calif.). Subsequently, 50 μL of crude cell lysate was added to the lactone solution and NMR spectra was read at 2 and 8 minute time points. Sigma and delta lactone signals were normalized to their respective starting peak intensity. Normalized peak intensities for the runs are shown in shown in Table 14.

TABLE 14

Lactonase Activity

| extract | time (min.) | 6-P-gluconate (umol product formed) | delta lactone (umol consumed) | gamma lactone (umol consumed) |
|---|---|---|---|---|
| chromosomal pgl | 2 | 0.49 | 0.41 | 0.08 |
| plasmid pgl | 2 | 0.67 | 0.50 | 0.16 |
| no pgl | 2 | 0.00 | 0.00 | 0.01 |

The strains were run in the microfermentor and in 15-L fed batch fermentation (as described in Examples 9 and 10 above). PGL activity was measured in all strains over the course of the small scale run or the fermentation. DW199 is the negative control and demonstrates little to no activity (trace activity may be observed, because the reaction can proceed by chemical catalysis at a slow rate). RHM111608-2 has similar activity over the entire run. CMP323 shows activity levels similar to those of DW199. CMP312 shows varied activity over the course of the fermentation, higher activity is seen during the early time points of the fermentation when the strain shows an increase in specific productivity, and less activity over later times in the fermentation. The ability of the cell to regulate the activity contributes to the overall improvement of isoprene production.

The expression of the ybhE gene in CMP312 can be determined by using transcription arrays (NimbleGen/Agilent Technologies). RNA samples are isolated from 15-L fermentations (as above) over the course of the entire fermentation by harvesting samples into RNAlater (Qiagen). The RNA samples are prepared using RNeasy Minikit (Qiagen) according to manufacturer's specifications. Further processing of samples and hybridization to the custom arrays are done by Agilent Technologies. Expression of the ybhE gene is analyzed using software such as GeneSpring GX (Agilent Technologies).

Example 15 pgl Expressed on the Plasmid Vs pgl Integrated on the Chromosome

This example shows isoprene production from *E. coli* BL21 expressing genes from the mevalonic acid pathway and isoprene synthase, grown in fed-batch culture at the 15-L scale.

Medium Recipe (Per Liter of Fermentation Medium):

7.5 g $K_2HPO_4$, 2 g $MgSO_4*7H_2O$, 2 g citric acid monohydrate, 0.3 g ferric ammonium citrate, 0.5 g yeast extract, and 1 ml 1000× Modified Trace Metal Solution were added together and dissolved in di$H_2O$. The solution was heat sterilized at 123° C. for 20 minutes, then adjusted to pH=7.0 with 28% (w/v) ammonium hydroxide and brought up to final volume. Ten grams of glucose, 8 mL Mercury Vitamin Solution, and the appropriate antibiotics were added after sterilization and pH adjustment.

1000× Modified Trace Metal Solution (Per Liter):

40 g citric acid*$H_2O$, 30 g $MnSO_4*H_2O$, 10 g NaCl, 1 g $FeSO_4*7H_2O$, 1 g $CoCl_2*6H_2O$, 1 g $ZnSO_4*7H_2O$, 100 mg $CuSO_4*5H_2O$, 100 mg $H_3BO_3$, and 100 mg $NaMoO_4*2H_2O$ were dissolved one at a time in di$H_2O$, the pH was adjusted to 3.0 with HCl/NaOH, the solution was brought up to final volume and filter sterilized with a 0.22 micron filter.

Mercury Vitamin Solution (Per Liter):

1 g thiamine hydrochloride, 1 g D-(+)-biotin, 1 g nicotinic acid, 4.8 g D-pantothenic acid, and 4 g pyridoxine hydrochloride were dissolved one at a time in di$H_2O$, the pH was adjusted to 3.0 with HCl/NaOH, the solution was brought up to final volume and filter sterilized with a 0.22 micron filter.

Feed Solution (Per Kilogram):

0.57 kg glucose, 0.38 kg di$H_2O$, 7.5 g $K_2HPO_4$, and 10 g 100% Foamblast were mixed together and autoclaved. After cooling the sterile solution to 25° C., 3.4 mL Macro Salt Solution, 0.8 ml 1000× Modified Trace Metal Solution, and 6.7 mL Mercury Vitamin Solution were added.

Macro Salt Solution (Per Liter):

296 g $MgSO_4*7H_2O$, 296 g citric acid monohydrate, and 49.6 g ferric ammonium citrate were dissolved in di$H_2O$, brought up to final volume and filter sterilized with a 0.22 micron filter.

Fermentation was performed in 15-L bioreactors with two different *E. coli* BL21 cell strains: (1) DW202 expresses the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba(MEA)+mMVK (pDW34)) and pgl expressed in the plasmid pBBRCMPGI1.5-pgl (see example 1); (2) CMP234 expresses the upper mevalonic acid (MVA) pathway (pCL Upper), the integrated lower MVA pathway (PL.2 mKKDyI), mevalonate kinase from *M. mazei* and truncated isoprene synthase from *P. alba* (pTrcAlba(MEA)+mMVK (pDW34)), and contains a restored chromosomal 17,257 bp segment encoding the pgl gene (the ybgS::kan$^R$ marker used during strain construction was looped out).

This experiment was carried out to monitor isoprene production from glucose at the desired fermentation pH and temperature (pH=7.0 and 34° C.). A frozen vial of each *E. coli* strain was thawed and inoculated into tryptone-yeast extract medium for each bioreactor. After the inoculum grew to $OD_{550}$=1.0, 500 mL of the culture was used to inoculate a 15-L bioreactor before bringing the initial tank volume to 5 L.

Figure 42A:
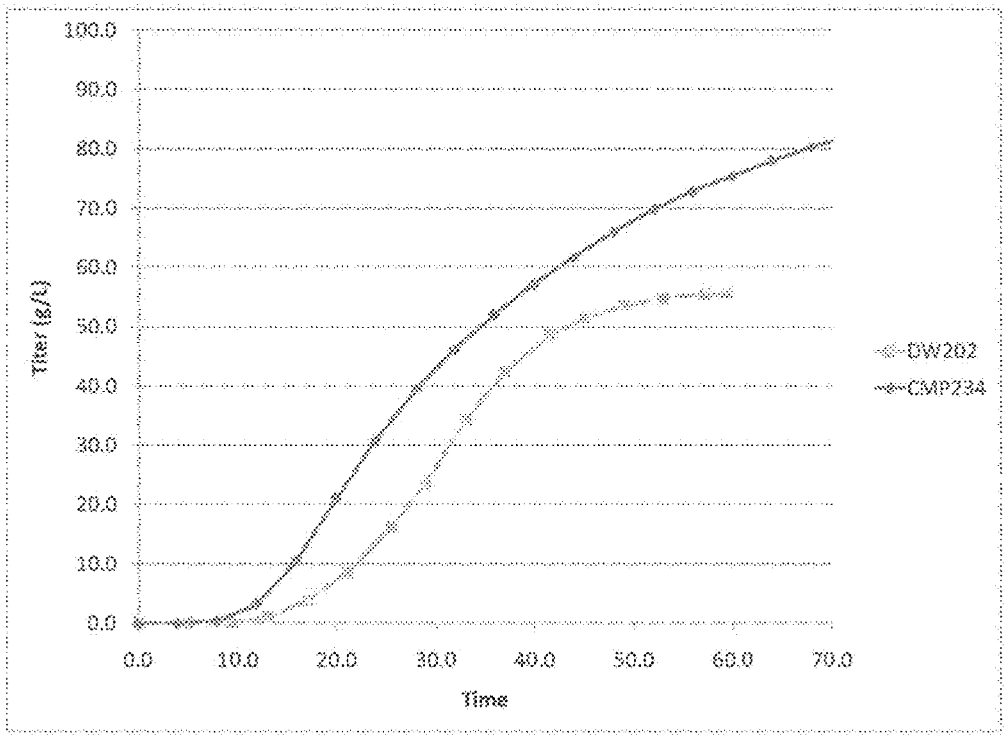
FIG. 42A shows a time course of isoprene titer in a 15-L bioreactor fed with glucose. Isoprene titer is defined as the amount of isoprene produced per liter of fermentation broth. The equation for calculating isoprene titer is: ∫(Instantaneous isoprene production rate, g/L/hr)dt from t=0 to t hrs [=] g/L broth.
Figure 42B:
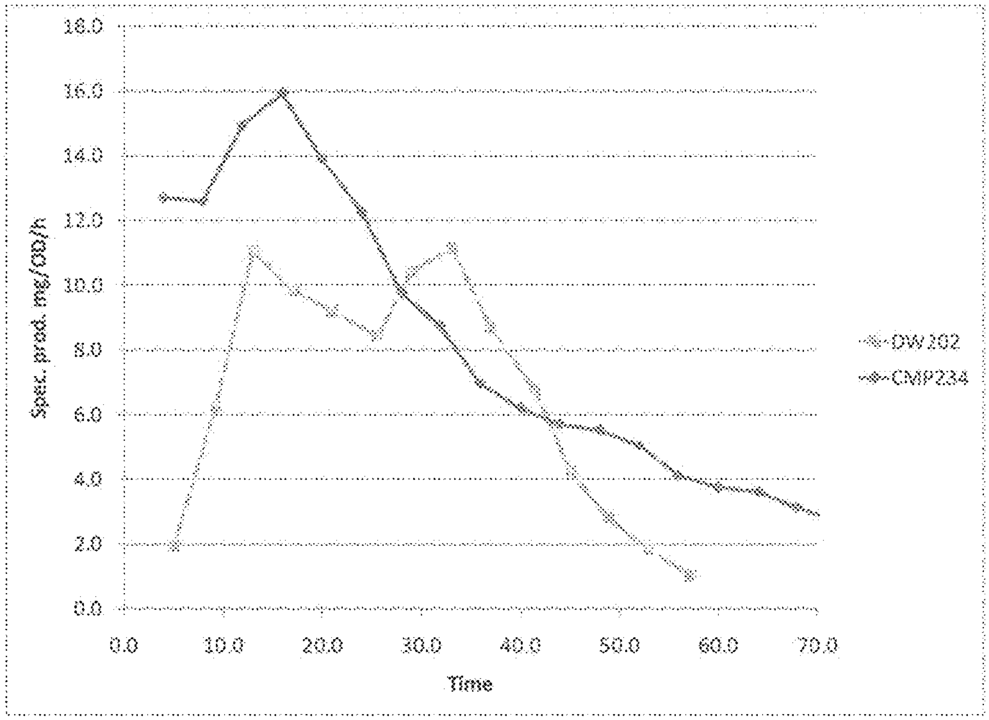
FIG. 42B shows isoprene specific productivity within the 15-L bioreactors fed with glucose. Equation for calculating Specific Productivity levels: (mg $isoprene_t$−mg $isoprene_{to}$)/[($OD550_t$*L $broth_s$−$OD550_{to}$*L $broth_{to}$)/(2.7 OD*L/g cell)]/(t−$t_0$) [=] mg isoprene/g cell/hr.

The feed solution was fed at an exponential rate until a top feed rate of 5.8 g/minute was reached. After this time the glucose feed was added to meet metabolic demands at rates less than or equal to 5.8 g/minute. The total amount of glucose delivered to the bioreactors was 5.5 kg to strain DW202 over 59 hours of fermentation, and 7.8 kg to strain CMP234 over 72 hours of fermentation. Induction of isoprene production was achieved by adding isopropyl-beta-D-1-thiogalactopyranoside ("IPTG") at the levels shown in Table 15. The isoprene levels in the offgas from the bioreactors were determined using a Hiden mass spectrometer (Hiden Analytical, Warrington, UK). The isoprene titer increased over the course of the fermentation to a maximum value of 56 g/L at 59 hours for strain DW202 and 81 g/L at 70 hours for strain CMP234 (see FIG. 42A). The time course of specific productivity is shown in FIG. 42B

TABLE 15

IPTG addition during the fermentations of strains DW202 and CMP234

| Strain | Induction | $OD_{550}$ | IPTG concentration, μM |
|---|---|---|---|
| DW202 | 1$^{st}$ | 5 | 100 |
| | 2$^{nd}$ | 140 | 184 |
| CMP234 | 1$^{st}$ | 5 | 110 |
| | 2$^{nd}$ | 110 | 197 |

The headings provided herein are not limitations of the various aspects or aspects of the invention which can be had by reference to the specification as a whole.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of producing isoprene, the method comprising: (a) culturing a composition comprising a recombinant cell of an *Escherichia coli* (*E. coli*) strain, or progeny thereof, under suitable culture conditions for the production of isoprene, wherein the cell comprises (i) one or more copies of a heterologous nucleic acid(s) encoding a 6-phosphogluconolactonase (PGL) polypeptide, wherein the nucleic acid is integrated in the *E. coli* chromosome and (ii) one or more heterologous nucleic acid(s) encoding isoprene synthase, wherein prior to the integration, the *E. coli* does not contain nucleic acids(s) encoding a PGL polypeptide, and wherein the resulting cell produces isoprene at a greater titer than that of the same cells that do not comprise (i); and (b) producing isoprene.

2. The method of claim 1 comprising further recovering the isoprene.

3. The method of claim 1, wherein the recombinant cell has a specific productivity greater than about 15 mg/OD/hr of isoprene.

4. The method of claim 1, wherein the PGL polypeptide is an *E. coli* PGL polypeptide.

5. The method of claim 4, wherein nucleic acids encoding the PGL polypeptide is part of a 17,257 base pair piece as shown in FIG. 20.

6. The method of claim 1, wherein the cell produces isoprene at a higher specific productivity than that of the same cells that do not contain (i).

7. The method of claim 1, wherein the specific productivity of isoprene by the cell is at least 15 mg/OD/hr.

8. The method of claim 4, wherein the nucleic acid encoding PGL polypeptide is from *E. coli* strain K12 MG1655 or a derivative of *E. coli* strain K12 MG1655.

9. The method of claim 1, wherein the cell is of *E. coli* strain B.

10. The method of claim 9, wherein the cell is of *E. coli* strain BL21.

11. The method of claim 9, wherein the cell is of *E. coli* strain BL21(DE3).

12. The method of claim 1, wherein the cell further comprises (iii) a heterologous nucleic acid encoding an upper mevalonate (MVA) pathway polypeptide and/or a lower MVA pathway polypeptide.

13. The method of claim 12, wherein the upper MVA pathway polypeptide is selected from the group consisting of: (i) an acetoacetyl-Coenzyme A synthase (thiolase) polypeptide; (ii) a 3-hydroxy-3-methylglutaryl-Coenzyme A synthase polypeptide; and (iii) a 3-hydroxy-3-methylglutaryl-Coenzyme A reductase polypeptide.

14. The method of claim 12, wherein the lower MVA pathway polypeptide is selected from the group consisting of: (i) mevalonate kinase (MVK); (ii) phosphomevalonate kinase (PMK); (iii) diphosphomevalonate decarboxylase (MVD); and (iv) isopentenyl diphosphate isomerase (IDI).

15. The method of claim 1, wherein the isoprene synthase polypeptide is from *Pueraria* or *Populus* or *Populus alba*× *Populus tremula*, or a variant thereof.

16. The method of claim 15, wherein the isoprene synthase polypeptide is from *Populus alba* or a variant thereof.

* * * * *